US008642050B2

(12) United States Patent
Fontana et al.

(10) Patent No.: US 8,642,050 B2
(45) Date of Patent: Feb. 4, 2014

(54) GONOCOCCAL PROTEINS AND NUCLEIC ACIDS

(75) Inventors: Maria Rita Fontana, Sienna (IT); Mariagrazia Pizza, Siena (IT); Vega Masignani, Siena (IT); Elisabetta Monaci, Siena (IT)

(73) Assignee: Novartis AG, Basel (CH)

( * ) Notice: Subject to any disclaimer, the term of this patent is extended or adjusted under 35 U.S.C. 154(b) by 609 days.

(21) Appl. No.: 12/371,691

(22) Filed: Feb. 16, 2009

(65) Prior Publication Data

US 2009/0298099 A1 Dec. 3, 2009

Related U.S. Application Data

(63) Continuation of application No. 10/467,657, filed as application No. PCT/IB02/02069 on Feb. 12, 2002, now Pat. No. 7,504,111.

(30) Foreign Application Priority Data

Feb. 12, 2001 (GB) .................................. 0103424.8

(51) Int. Cl.
*A61K 39/095* (2006.01)
*C07K 14/22* (2006.01)
*C12P 21/06* (2006.01)
(52) U.S. Cl.
USPC ..................... 424/249.1; 424/190.1; 530/350; 435/69.1; 435/69.7
(58) Field of Classification Search
None
See application file for complete search history.

(56) References Cited

U.S. PATENT DOCUMENTS 6,627,204 B1 * 9/2003 Ruelle ......................... 424/250.1

FOREIGN PATENT DOCUMENTS

WO WO9802547 1/1998
WO WO0026375 5/2000

OTHER PUBLICATIONS

Houghten et al(Vaccines, 1986, Edited by Fred Brown: Cold Spring Harbor Laboratory).*
Roitt et al (Immunology, 1993, Mosby, St. Louis, p. 7.7-7.8).*
Holmes (Exp. Opin.Invest. Drugs, 2001, 10(3):511-519).*
Nachamkin et al Infection and Immunity May 1981; 32(2): 641-648.*
Tinsley et al., "Analysis of the genetic differences between *Neisseria meningitidis* and *Neisseria* gonorrhea: Two closely related bacteria expressing two different pathogenicities," Proceedings of the National Academy of Sciences of the USA, vol. 93 (Oct. 1, 1996), pp. 11109-1114.

Pizza et al., "Identification of vaccine candidates against serogroup B Meningococcus by whole-genome sequencing," Science, vol. 287, 2000, pp. 1816-1820.
Salzberg et al. "Microbial gene identification using interpolated Markov models," Nuecleic Acids Research, vol. 26, 1998, pp. 544-548.
Klee et al., "Molecular and biological analysis of eight genetic islands that distinguish *Neisseria meningitidis* from the closely related pathogen *Neisseria* gonorrhea," Infection and Immunity, vol. 68, (2000-2004), pp. 2082-2095.
Heckels et al., "Vaccination against gonorrhea: The potential protective effect of immunization with a synthetic peptide containing a conserved epitope of gonococcal outer membrane protein 1B," Vaccine, vol. 8 (Jun. 1, 1990), pp. 225-230.
Database EMBL 'Online! (Feb. 1, 1997) "Pilin gene inverting protein homolog PivNG" retrieved from EBI, accession No. P72078 Database accession No. P72078.
Database EMBL 'Online! (Oct. 1, 20001), "Hypothetical protein NMA2029" retrieved from EMBL, accession No. Q9JT17 Database accession No. Q9JT17.
Database EMBL 'Online! (May 1, 2000), "Trafficking protein B" retrieved from EMBL, accession No. Q9RF91 Database accession No. Q9RF91.
Database EMBL Online! (Nov. 1, 1999), "Hypothetical 12.2 kDA protein" retrieved from EBI, accession No. Q9XAZ8 Database accession No. Q9XAZ8.
Database EMBL 'Online! (Jul. 15, 1999), "DpcA protein precursor" retrieved from EBI, accession No. Q9XB00 Database accession No. Q9XB00.
Database EMBL 'Online! (Jan. 1, 1998), "Putative hemoglobin receptor component HpuA precursor," retrieved from EBI, accession No. 031179 Database accession No. 031179.
Database EMBL 'Online! (Oct. 1, 2000), "Putative integral membrane protein" retrieved from EBI, accession No. Q9JWE8 Database accession No. Q9JWE8.
Database EMBL 'Online! (Jul. 1, 1993, "Type III restriction enzyme NgoMIV (EC 3.1.21.4) (Endonuclease NgoMIV) (R.NgoMIV)" retrieved from EBI, accession No. P31032 Database accession No. P31032.
Database EMBL 'Online! (Oct. 1, 2000), "Hypothetical protein NMA0089" retrieved from EBI accession No. Q9JX27 Database accession No. Q9JX27.
Database EMBL 'Online! (Nov. 1, 1996), "NgoII cytosine methylase M. NgoII (EC 2.1.1.73) (Modified methylase) Cytosine-specific methyl transferase)" retrieved from EMBL, accession No. Q59604 Database accession No. Q59604.
Database EMBL 'Online! (Oct. 16, 2001), Stein et al., "Type II restriction enzyme NgoBI (EC 3.1.21.4) (Endonuclease NgoBI HR. NgoBI) (R. Ngol)" retrieved from EBI, accession No. Q50973 Database accession No. 050973.

(Continued)

*Primary Examiner* — Padma V Baskar
(74) *Attorney, Agent, or Firm* — Amy Hessler; Otis Littlefield

(57) ABSTRACT

The invention provides proteins from gonococcus (*Neisseria gonorrhoeae*), including amino acid sequences, the corresponding nucleotide sequences, expression data, and serological data. The proteins are useful antigens for vaccines, immunogenic compositions, and/or diagnostics. They are also useful for distinguishing between gonococcus and meningococcus and, in particular, between gonococcus and serogroup B meningococcus.

8 Claims, No Drawings

(56) References Cited

OTHER PUBLICATIONS

Database EMBL 'Online! (Mar. 1, 2001), "DNA cytosine methyl transferase M. NgoMIII (EC 2.1.1.73) (Modification methylase) (Cytosine-specific methyl transferase)" retrieved from EMBL, accession No. Q9F658 Database accession No. Q9F658.

Guymon et al., "Cell alterations in antibiotic-sensitive and -resistant strains of *Neisseria* gonorroheae," Department of Medicine, School of Medicine, University of North Carolina, Chapel Hill, Journal of Bacteriology, American Society for Microbiology, Oct. 1978, pp. 391-401.

Zhan et al., "Expression of the *Neisseria* gonorrhoeae major outer membrane protein P1 in *Escherichia coli*," World Journal of Microbiology and Biotechnology, vol. 22, No. 7 / Jul. 2006, pp. 693-700.

Nachamkin et al., "Monoclonal antibodies against *Neisseria* gonorrhoeae: production of antibodies directed against a Strain-Specific Cell Surface Antigen," Infection and Immunity May 1981; 32(2): 641-648.

Bowie et al., "Deciphering the message in protein sequences: tolerance to amino acid substitutions," Science, vol. 247: Mar. 1990 ; p. 1306; p. 1308.

Database EMBL 'Online! (Oct. 25, 2000), "*Neisseria meningitidis* BASB060 gene-encoded protein" retrieved from EBI, accession No. AAY95648 Database accession No. AAYK95648.

Database EMBL 'Online! (Jul. 15, 1999), "Carbonic anhydrase precursor" retrieved from EBI, accession No. Q50940 Database accession No. Q50940.

Database EMBL 'Online! (Mar. 21, 2000), "*Neisseria* gonorrhea ORF 122 protein sequence SEQ 10 NO:446" retrieved from EBI, accession No. AAYK74485 Database accession No. AAY74485.

\* cited by examiner

GONOCOCCAL PROTEINS AND NUCLEIC ACIDS

All documents cited herein are incorporated by reference in their entirety.

CROSS-REFERENCE TO RELATED APPLICATIONS

This application is a continuation of U.S. application Ser. No. 10/467,657, filed Dec. 20, 2004, now U.S. Pat. No. 7,504,111, which is a U.S. National Stage Application under 35 U.S.C. §371 of International Application No. PCT/IB02/02069, filed Feb. 12, 2002, which claims the benefit of priority to GB 0103424.8, filed Feb. 12, 2001, all of which are incorporated by reference in their entireties.

This application incorporates by reference the contents of a 11.2 MB text file labeled SEQLIST.TXT and created Feb. 16, 2009, which is the sequence listing for this application.

TECHNICAL FIELD

This invention relates to proteins from the bacterium *Neisseria gonorrhoeae*, and more particularly to such proteins which do not have corresponding homologs or orthologs in serogroup B *N. meningitidis*.

BACKGROUND ART

*Neisseria gonorrhoeae* is a bacterial pathogen. There is currently no effective vaccine against *N. gonorrhoeae* infection. It is an object of the invention to provide proteins and nucleic acid useful in vaccine study and/or manufacture.

*N. gonorrhoeae* is related to *N. meningitidis*. Sequence data are now available for serogroup B of meningococcus [e.g. WO99/24578; WO99/36544; WO99/57280; WO00/22430; WO00/66791; Tettelin et al. (2000) *Science* 287: 1809-1815] and also for serogroup A [Parkhill et al. (2000) *Nature* 404:502-506]. It is a further object of the invention to provide proteins and nucleic acid useful in distinguishing between gonococcus and meningococcus and, in particular, between gonococcus and serogroup B meningococcus.

DISCLOSURE OF THE INVENTION

The invention provides proteins comprising the *N. gonorrhoeae* amino acid sequences disclosed in the examples (the even-numbered SEQ IDS 2 to 8622). 159 of these have no homolog in serogroup B meningococcus and these have been given a name in the form "NGSn".

It also provides proteins comprising amino acid sequences having sequence identity to the *N. gonorrhoeae* amino acid sequences disclosed in the examples. Depending on the particular sequence, the degree of sequence identity is preferably greater than 50% (e.g. 60%, 70%, 80%, 90%, 95%, 99% or more). These proteins include homologs, orthologs, allelic variants and functional mutants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affine gap search with parameters gap open penalty=12 and gap extension penalty=1.

The invention further provides proteins comprising fragments of the *N. gonorrhoeae* amino acid sequences disclosed in the examples. The fragments should comprise at least n consecutive amino acids from the sequences and, depending on the particular sequence, n is 7 or more (e.g. 8, 10, 12, 14, 16, 18, 20, 30, 40, 50, 60, 70, 80, 90, 100 or more). Preferably the fragments comprise one or more epitopes from the sequence. Other preferred fragments are (a) the N-terminal signal peptides of the proteins disclosed in the examples, and (b) the proteins disclosed in the examples, but without their N-terminal signal peptides.

The proteins of the invention can, of course, be prepared by various means (e.g. recombinant expression, purification from *Neisseria*, chemical synthesis etc.) and in various forms (e.g. native, fusions etc.). They are preferably prepared in substantially pure form (i.e. substantially free from other *N. gonorrhoeae* or host cell proteins).

The proteins of the invention are preferably Neisserial proteins, more preferably *N. gonorrhoeae* proteins.

The invention provides antibodies which bind to these proteins. These may be polyclonal or monoclonal and may be produced by any suitable means. The antibodies may include a detectable label.

The invention provides nucleic acid comprising the *N. gonorrhoeae* nucleotide sequences disclosed in the examples. In addition, the invention provides nucleic acid comprising nucleotide sequences having sequence identity to the *N. gonorrhoeae* nucleotide sequences disclosed in the examples.

Furthermore, the invention provides nucleic acid which can hybridise to the *N. gonorrhoeae* nucleic acid disclosed in the examples, preferably under "high stringency" conditions (e.g. 65° C. in a 0.1×SSC, 0.5% SDS solution).

Nucleic acid comprising fragments of these sequences are also provided. These should comprise at least n consecutive nucleotides from the *N. gonorrhoeae* sequences and, depending on the particular sequence, n is 10 or more (e.g. 12, 14, 15, 18, 20, 25, 30, 35, 40, 50, 60, 70, 80, 90, 100, 150, 200 or more).

The invention also provides nucleic acid encoding the proteins and protein fragments of the invention.

The invention includes nucleic acid comprising sequences complementary to those described above (e.g. for antisense or probing purposes).

Nucleic acid according to the invention can be prepared in many ways (e.g. by chemical synthesis, from genomic or cDNA libraries, from the organism itself etc.) and can take various forms (e.g. single stranded, double stranded, vectors, probes etc.).

In addition, the term "nucleic acid" includes DNA and RNA, and also their analogues, such as those containing modified backbones, and also peptide nucleic acids (PNA) etc.

The invention provides vectors comprising nucleotide sequences of the invention (e.g. cloning or expression vectors) and host cells transformed with such vectors.

The invention provides compositions comprising protein, antibody, and/or nucleic acid according to the invention. These compositions may be suitable as immunogenic compositions, for instance, or as diagnostic reagents, or as vaccines.

The invention also provides nucleic acid, protein, or antibody according to the invention for use as medicaments (e.g. as vaccines) or as diagnostic reagents. It also provides the use of nucleic acid, protein, or antibody according to the invention in the manufacture of: (i) a medicament for treating or preventing infection due to *Neisseria*; (ii) a diagnostic reagent for detecting the presence of *Neisseria* or of antibodies raised against *Neisseria*; and/or (iii) a reagent which can raise antibodies against *Neisseria*. Said *Neisseria* may be any species, but is preferably *N. gonorrhoeae*.

The invention also provides a method of treating a patient, comprising administering to the patient a therapeutically effective amount of nucleic acid, protein, and/or antibody of the invention.

According to further aspects, the invention provides various processes.

A process for producing proteins of the invention is provided, comprising the step of culturing a host cell of to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridising conditions to form duplexes; and (b) detecting said duplexes.

A process for detecting proteins of the invention is provided, comprising the steps of: (a) contacting an antibody of the invention with a biological sample under conditions suitable for the formation of an antibody-antigen complexes; and (b) detecting said complexes.

A process for distinguishing *N. gonorrhoeae* from *N. meningitidis* is provided, comprising the steps of: (a) contacting an antibody of the invention with a biological sample under conditions suitable for the formation of an antibody-antigen complexes; and (b) detecting said complexes. Alternatively, the steps may be (a) contacting nucleic acid of the invention with a biological sample under conditions suitable for the nucleic acid hybridisation; and (b) detecting any such hybridisation. Alternatively, the steps may be (a) contacting a protein of the invention with a biological sample (e.g. blood or serum) under conditions suitable for the formation of an antibody-antigen complexes; and (b) detecting said complexes.

A summary of standard techniques and procedures which may be employed in order to perform the invention (e.g. to utilise the disclosed sequences for vaccination or diagnostic purposes) follows. This summary is not a limitation on the invention, but gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989) or *Third Edition* (2000); *DNA Cloning, Volumes I and II* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional e.g. X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a *Neisseria* sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (eg. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753, 235).

Expression Systems

The *Neisseria* nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual*, 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al (1989) "Expression of cloned genes in cultured mammalian cells." In *Molecular Cloning: A Laboratory Manual*].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers & Smith, *Texas Agricultural Experiment Station Bulletin No. 1555* (1987) ("Summers & Smith").

Prior to inserting the DNA sequence encoding the protein into the baculovirus genome, the above described components, comprising a promoter, leader (if desired), coding sequence, and transcription termination sequence, are usually assembled into an intermediate transplacement construct (transfer vector). This may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extra-chromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.,* 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers & Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91 The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers & Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers & Smith supra.

The modified insect cells may then be grown in an appropriate nutrient medium, which allows for stable maintenance of the plasmid(s) present in the modified insect host. Where the expression product gene is under inducible control, the host May be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, etc. As appropriate, the product may be further purified, as required, so as to remove substantially any insect proteins which are also present in the medium, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., *Nucleic Acids Research* 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology, Malcolm B. Wilkins, ed.,* 1984 Pitman Publishing Limited, London, pp. 21-52. References that describe other metabolically-regulated genes: Sheen, *Plant Cell,* 2:1027-1038 (1990); Maas et al., *EMBO J.* 9:3447-3452 (1990); Benkel and Hickey, *Proc. Natl. Acad. Sci.* 84:1337-1339 (1987).

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet*, 202:179-185, 1985. The genetic material may also be transferred into the plant cell by using polyethylene glycol, Krens, et al., *Nature,* 296, 72-74,1982. Another method of introduction of nucleic acid segments is high velocity ballistic penetration by small particles with the nucleic acid either within the matrix of small beads or particles, or on the surface, Klein, et al., *Nature,* 327,70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863,1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-lactamase (bla) promoter system [Weissmann (1981) "The cloning of interferon and other mistakes." In *Interferon* 3 (ed. 1. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the lac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli.*" In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: Experimental Manipulation of Gene Expression; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S, Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*" in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pCl/1 [Brake et al. (1984) Proc. Natl. Acad. Sci. USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.*, 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacterial.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying *Neisseria* proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to. (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as vetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be used [eg. Robinson & Torres (1997) *Seminars in Immunol* 9:271-283; Donnelly et al. (1997) *Annu Rev Immunol* 15:617-648; later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Pocus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC NoI VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO 93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) Human Gene Therapy 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO 95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC with accession numbers VR-977 and VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem L*401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) Vaccine 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Viral.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C & E, over time these lipoproteins lose A and acquire C & E. VLDL comprises A, B, C & E apoproteins, LDL comprises apoprotein B; and HDL comprises apoproteins A, C, & E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utermann (1984) Hum Genet. 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

*Neisseria* antigens of the invention can be used in immunoassays to detect antibody levels (or, conversely, anti-*Neisseria* antibodies can be used to detect antigen levels). Immunoassays based on well defined, recombinant antigens can be developed to replace invasive diagnostics methods. Antibodies to *Neisseria* proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of 24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\% (G+C)]-0.6 (\% \text{ formamide})-600/n-1.5 (\% \text{ mismatch}).$$

where Ci is the salt concentration (monovalent ions) and n is the length of the hybrid in base pairs (slightly modified from Meinkoth & Wahl (1984) *Anal. Biochem.* 138: 26.7-284).

In designing a hybridization experiment, some factors affecting nucleic acid hybridization can be conveniently altered. The temperature of the hybridization and washes and the salt concentration during the washes are the simplest to adjust. As the temperature of the hybridization increases (ie. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the *Neisseria* nucleotide sequences of the invention (including both sense and antisense strands). Though many different nucleotide sequences will encode the amino acid sequence, the native *Neisseria* sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the *Neisseria* sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional *Neisseria* sequence may also be helpful as a label to detect the formed duplex. For example, a non-complementary nucleotide sequence may be attached to the 5' end of the probe, with the remainder of the probe sequence being complementary to a *Neisseria* sequence. Alternatively, non-complementary bases or longer sequences can be interspersed into the probe, provided that the probe sequence has sufficient complementarity with the a *Neisseria* sequence in order to hybridize therewith and thereby form a duplex which can be detected.

The exact length and sequence of the probe will depend on the hybridization conditions (e.g. temperature, salt condition etc.). For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. see Agrawal & Iyer (1995) *Curr Opin Biotechnol* 6:12-19; Agrawal (1996) *TIBTECH* 14:376-387]; analogues such as peptide nucleic acids may also be used [eg. see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acid. The assay is described in Mullis et al. [*Meth. Enzymol.* (1987) 155:335-350] & U.S. Pat. Nos. 4,683,195 & 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired *Neisseria* sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the *Neisseria* sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF DRAWINGS

There are no drawings.

MODES FOR CARRYING OUT THE INVENTION

The following examples describe nucleic acid sequences which have been identified in *N. gonorrhoeae*, along with their inferred translation products.

The examples are generally in the following format:
- a nucleotide sequence which has been identified in *N. gonorrhoeae*. The strain used is FA1090 [Dempsey et al. (1991) *J. Bacteriol*. 173:5476-5486]
- the inferred translation product of this sequence
- a computer analysis (e.g. PSORT output) of the translation product, indicating antigenicity
- homologous sequences (where relevant)
- results of expression and purification (where relevant)

These examples typically include details of sequence homology between species and strains. Proteins that are similar in sequence are generally similar in both structure and function, and the homology often indicates a common evolutionary origin. Comparison with sequences of proteins of known function is widely used as a guide for the assignment of putative protein function to a new sequence and has proved particularly useful in whole-genome analyses.

Open reading frames (ORFs) within nucleotide sequences were predicted using the GLIMMER program [Salzberg et al. (1998) *Nucleic Acids Res* 26:544-8]. All predicted open-reading frames longer than 60 aa were screened against the meningococcus serotype B ('MenB') ORFs (accession NC002183) using the BLASTP algorithm [Altschul et al. (1990) *J. Mol. Biol.* 215:403-410]. ORFs were considered to be gonococcus-specific if they showed sequence identity to a MenB ORF lower than 60% over the whole protein length, or matching the MenB ORF over less than 30% of the length.

Open reading frames are usually shown with a N-terminal methionine. Where this is not the case (e.g. SEQ IDs 12, 18, 20, 32, 54, 62, 66, 84, 98, 102, 104, 112, 116, 118, 126, 128, 130, 134, 136, 138, 146, 152, 162, 186, 228, 238, 240, 278, 280, 288, 290, 298, 300, 308, 314), a non-ATG start codon is present, but the N-terminus amino acid will be methionine when translated using this start codon. If an upstream start codon is used, however, the "native" amino acid will be translated (e.g. if the sequence is expressed with N-terminus fusion sequences). Even where the first amino acid is not shown as methionine, the invention encompasses sequences in which the first amino acid is methionine.

Various tests can be used to assess the in vivo immunogenicity of the proteins identified in the examples. For example, the proteins can be expressed recombinantly and used to screen patient sera by immunoblot. A positive reaction between the protein and patient serum indicates that the patient has previously mounted an immune response to the protein in question i.e. the protein is an immunogen. This method can also be used to identify immunodominant proteins.

The recombinant protein can also be conveniently used to prepare antibodies e.g. in a mouse. These can be used for direct confirmation that a protein is located on the cell-surface. Labelled antibody (e.g. fluorescent labelling for FACS) can be incubated with intact bacteria and the presence of label on the bacterial surface confirms the location of the protein.

For protein expression of 14 antigens, sequences were amplified using the following primers:

|  | Sequences | Restriction site |
|---|---|---|
| NGS5 | Fwd CGCGGATCC<u>CATATG</u>-TGGGCAGAACAACCGGC | NdeI |
|  | Rev CCCG<u>CTCGAG</u>-GTTTTCAGCAGGGGATTG | XhoI |
| NGS7 | Fwd CGCGGATCC<u>CATATG</u>-GCCGGTAAAGAGCAATTTAC | NdeI |
|  | Rev CCCG<u>CTCGAG</u>-AGCCAAGAAGAACCCGTTAT | XhoI |
| NGS13 | Fwd CGCGGATCC<u>GCTAGC</u>-TGCGTTGCCGACCCCG | NheI |
|  | Rev CCCG<u>CTCGAG</u>-CATGTGCCGTGCGGCGT | XhoI |
| NGS36 | Fwd CGCGGATCC<u>GCTAGC</u>-GACACCCCGAACAATACC | NheI |
|  | Rev CCCG<u>CTCGAG</u>-AAACCTGCCCTTGATGCC | XhoI |
| NGS37 | Fwd CGCGGATCC<u>CATATG</u>-GTAGAAGTTAAAGGCGGGG | NdeI |
|  | Rev CCCG<u>CTCGAG</u>-TTTTTTCGCGCCGCCGAA | XhoI |
| NGS38 | Fwd CGCGGATCC<u>CATATG</u>-GCCGACGAACGCCGCC | NdeI |
|  | Rev CCCG<u>CTCGAG</u>-AAACCGATATTTAAAACCCAACAGCC | XhoI |
| NGS39 | Fwd CGCGGATCC<u>GCTAGC</u>-AACCAAGAAGGGATTACCG | NheI |
|  | Rev CCCG<u>CTCGAG</u>-TTTTTGAGCATAATGACTTTTGCCCT | XhoI |
| NGS67 | Fwd CGCGGATCC<u>CATATG</u>-CGTGCGCACGGACACG | NdeI |
|  | Rev CCCG<u>CTCGAG</u>-GGCGGCGAGTTTTTCGC | XhoI |
| NGS106 | Fwd CGCGGATCC<u>CATATG</u>-GCAAACAGCGGAACGATAG | NdeI |
|  | Rev CCCG<u>CTCGAG</u>-AAAATCCTGCGGGATCGGT | XboI |
| NGS115 | Fwd CGCGGATCC<u>CATATG</u>-GGGGGCGGCTCCGGC | NdeI |
|  | Rev CCCG<u>CTCGAG</u>-TTCGGCCAACAATGCTTCC | XhoI |
| NGSΔG115 | Fwd CGCGGATCC<u>CATATG</u>-GATGCCCAATCTTCACAAAG | NdeI |
|  | Rev CCCG<u>CTCGAG</u>-TTCGGCCAACAATGCTTCC | XhoI |
| NGS118 | Fwd CGCGGATCC<u>CATATG</u>-ACCGCCCTTCCCTCTGA | NdeI |
|  | Rev CCCG<u>CTCGAG</u>-CGGCTGCCATTCGCGTT | XhoI |

-continued

| Sequences | Restriction site |
|---|---|
| NGS122 Fwd CGCGGATCC<u>CATATG</u>-AACCCGAACGATGCGTTTT | NdeI |
| Rev CCCG<u>CTCGAG</u>-AGGGTAAAACTTATTCAAATCGGCAA | XhoI |
| NGS144 Fwd CGCGGATCC<u>CATATG</u>-GCTTCTGAAAATTCTGTAGC | NdeI |
| Rev CCCG<u>CTCGAG</u>-GAACACGCTTTTCATTACACCCA | XhoI |
| NGS151 Fwd CGCGGATCC<u>CATATG</u>-CACCGTATGCATAAGAGCA | NdeI |
| Rev CCCG<u>CTCGAG</u>-TTGCTGATGCGGCTTTATTCG | XhoI |

Example 1

A DNA sequence was identified in *N. gonorrhoeae* <SEQ ID 1> which encodes amino acid sequence<SEQ ID 2; NGS1>. Analysis of this protein sequence reveals the following:

GvH: Examining signal sequence (von Heijne)
Signal Score (−7.5): −5.47
Possible cleavage site: 36
>>> Seems to have no N-terminal signal seq.
Amino Acid Composition of Predicted Mature Form: calculated from 1
ALOM: Finding transmembrane regions (Klein et al.)
count: 0 value: 4.72 threshold: 0.0

PERIPHERAL        Likelihood = 4.72
modified ALOM score: −1.44
Rule: cytoplasmic protein

*** Reasoning Step: 2
Final Results bacterial cytoplasm --- Certainty = 0.326(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

The protein has homology with the following sequences in the databases:

Based on this analysis, it was predicted that this protein from *N. gonorrhoeae*, and its epitopes, could be useful antigens for vaccines or diagnostics.

Example 2

A DNA sequence was identified in *N. gonorrhoeae* <SEQ ID 3> which encodes amino acid sequence <SEQ ID 4; NGS2>. Analysis of this protein sequence reveals the following:

GvH: Examining signal sequence (von Heijne)
Signal Score (−7.5): −7.2
Possible cleavage site: 18
>>> Seems to have no N-terminal signal seq.
Amino Acid Composition of Predicted Mature Form: calculated from 1
ALOM: Finding transmembrane regions (Klein et al.)
count: 0 value: 5.89 threshold: 0.0

PERIPHERAL        Likelihood = 5.89
modified ALOM score: −1.68
Rule: cytoplasmic protein

*** Reasoning Step: 2
Final Results bacterial cytoplasm --- Certainty = 0.367(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

The protein has homology with the following sequences in the databases:

```
>sp|P45941|YQCF_BACSU HYPOTHETICAL 21.5 KD PROTEIN IN CWLA-CISA INTERGENIC
REGION
pir||E69949 hypothetical protein yqcF - Bacillus subtilis
dbj|BAA06963.1| (D32216) ORF95 [Bacillus subtilis]
dbj|BAA12427.1| (D84432) YqcF [Bacillus subtilis]
emb|CAB14528.1| (Z99117) yqcF [Bacillus subtilis]
Length = 192

Score = 35.5 bits (81), Expect = 0.45
Identities = 36/162 (22%), Positives = 77/162 (47%), Gaps = 5/162 (3%)

Query:  19 DSGSQYKLNIAAIPSSPNRDLKTYITLGLSKHDLNYK---SRFEILFVCSLKYDENQIFP    75
            D     ++I ++   P    + +Y TLGLS H +NY+    +    I V +++      +

Sbjct:  29 DDNKNSSIDILSVSDQPQEGITSYSTLGLSDHSINYEVNGTPLRIEIVAAMESASDIYAN   88

Query:  76 FLRWLAETIIENKKILLRGQVVYLPRSIVNS-TKMDALYVSAPFYFDDDFQVCYGEHYNI  134
            L  A II +      G +       S+ +  T M +      PF +++D ++    + N+

Sbjct:  89 VLSTCAFNIINSNFTCAPGVIFKNVISMYDQETDMKHIMFVPPFLWEEDLELLEFSNKNV  148

Query: 135 VFPLLVPLYKQEAELVEKKGWNAFEQFLLDNEVGNLSDMNRK                   176
            + + +P+ + E ++ EK G + + Q LL+++   ++ D+ R+

Sbjct: 149 TWLMALPISEGELQVAEKHG-SDYLQDLLESKQIDIFDIKRE                    189
```

```
>emb|CAC01359.1| (AL390975) hypothetical protein SCP8.21 [Streptomyces
coelicolor A3(2)]
Length = 198

Score =  37.1 bits (85), Expect = 0.15
Identities = 29/107 (27%), Positives = 51/107 (47%), Gaps = 3/107 (2%)

Query:  73 ETPEHIETLAMLASASMHYPDQFQLGKTVNIGRPWVEQSSFRHFLISLPYPYGQELEY--  130
           +T + +  LA+LA++            G +++G P    + F    L++ P    ++LE
Sbjct:  88 DTDKVLRPLAVLAASPQVEGVIAPGASLDVGEPLWPGAPFTSVLVAEPGGLVEDLELDA  147

Query: 131 -MDNVRFFWLLPITQTERLFLNTHSVEELETKFDEAGIDYLDINRAS              176
            +D VRF  LLP+T  E  +    H    L+ ++     G D   D +R S
Sbjct: 148 PLDPVRFLPLLPMTPNEAAWKRVHGAPALQERWLNHGTDLRDPSRRS              194
```

Based on this analysis, it was predicted that this protein from *N. gonorrhoeae*, and its epitopes, could be useful antigens for vaccines or diagnostics.

Example 3

A DNA sequence was identified in *N. gonorrhoeae* <SEQ ID 5> which encodes amino acid sequence <SEQ ID 6; NGS3>. Analysis of this protein sequence reveals the following:

| | |
|---|---|
| GvH: Examining signal sequence (von Heijne) | |
| Signal Score (–7.5): –1.69 | |
| Possible cleavage site: 32 | |
| >>> Seems to have a cleavable N-term signal seq. | |
| Amino Acid Composition of Predicted Mature Form: | |
| calculated from 33 | |
| ALOM: Finding transmembrane regions (Klein et al.) | |
| count: 5 value: –0.56 threshold: 0.0 | |

-continued

| | | | |
|---|---|---|---|
| INTEGRAL | Likelihood = –10.56 | Transmembrane | 182-198 (171-201) |
| INTEGRAL | Likelihood = –7.86 | Transmembrane | 251-267 (244-273) |
| INTEGRAL | Likelihood = –7.48 | Transmembrane | 142-158 (136-167) |
| INTEGRAL | Likelihood = –6.32 | Transmembrane | 55-71 (50-82) |
| INTEGRAL | Likelihood = –2.97 | Transmembrane | 100-116 (99-117) |
| PERIPHERAL | Likelihood = 4.72 | | |
| | modified ALOM score: 2.61 | | |
| | Rule: cytoplasmic membrane protein | | |

*** Reasoning Step: 2
Final Results

| | |
|---|---|
| bacterial inner membrane --- Certainty = | 0.522(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology with the following sequences in the databases:

```
>sp|P19845|NOSY_PSEST MEMBRANE PROTEIN NOSY PRECURSOR
pir||S13585 nosY protein precursor - Pseudomonas stutzeri
emb|CAA37717.1| (X53676) nosY [Pseudomonas stutzeri]
Length = 276

Score = 163 bits (413), Expect = 2e-39
Identities = 117/275 (42%), Positives = 174/275 (62%), Gaps = 2/275 (0%)

Query:   1 MNPVWIITGKEARDSLRNRWVLAAVLLLAALALSLGFLGSSPTGSVKVDPLTVTVVSLSS   60
             MN VW I  KE D LRINRW+LA  LL A LA+ + +LG++ +G +    +  T+ SL+S
Sbjct:   1 MNQVWNIARKELSDGLRNRWLLAISLLFAVLAVGIAWLGAAASGQLGFTSIPATIASLAS   60

Query:  61 LSIFLIPLIAMLLSYDALIGEIERGTMALLLSYPIWRNQILAGKFVGHLIILALATTAGY  120
           L+ FL+PLIA+LL+YDA++GE E GT+ LLL+YP+ R QIL GKFVGH +ILALA    G+
Sbjct:  61 LATFLMPLIALLLAYDAIVGEDEGGTLMLLLTYPLGRGQILLGKFVGHGLILALAVLIGF  120

Query: 121 GLAGITLQLANGGFDIAA-WKPFALLIAASVILGAAFLSMGYLISAKVKERGTAAGISIG  179
           G A + + L  G ++    + F    +S +LG  FL+   Y++S KV E+  +AAG+++G
Sbjct: 121 GCAALAIALLVEGVELGMLFWAFGRFMISSTLLGWVFLAFAYVLSGKVNEKSSAAGLALG  180

Query: 180 VWLFFVVIFDMALLGILVADSKQVITAPVVETVLLFNPTDIYRLLNLTGYENTAMYAGMA  239
           VW F V+  +L  L+ S+       ++  +LL NPTDIYRL+NL+G+E +     G+
Sbjct: 181 VW-FLFVLVFDLVLLALLVLSEGKFNPELLPWLLLLNPTDIYRLINLSGFEGSGSAMGVL  239

Query: 240 GLSGQIGLTVPVLLTAQVLWVIIPLVLAAGIFRKR                           274
              L   + +  VL   + W+ +  L+LA   IFR+R
Sbjct: 240 SLGADLPVPAAVLWLCLLAWTGVSLLLAYAIFRRR                           274
```

A homolog (amino acids 226-276) was found in serogroup A *N. meningitidis* but not in serogroup B, so NGS3 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 4

A DNA sequence was identified in *N. gonorrhoeae* <SEQ ID 7> which encodes amino acid sequence <SEQ ID 8; NGS4>. Analysis of this protein sequence reveals the following:

GvH: Examining signal sequence (von Heijne)
Signal Score (-7.5): 1.53
Possible cleavage site: 58
>>> Seems to have no N-terminal signal seq.
Amino Acid Composition of Predicted Mature Form:
calculated from 1
ALOM: Finding transmembrane regions (Klein et al.)
count: 0 value: 0.63 threshold: 0.0

PERIPHERAL    Likelihood = 0.63
modified ALOM score: -0.63
Rule: cytoplasmic protein

*** Reasoning Step: 2
Final Results bacterial cytoplasm --- Certainty =           0.103(Affirmative) < succ>
bacterial periplasmic space --- Certainty =   0.000(Not Clear) < succ>
bacterial outer membrane --- Certainty =      0.000(Not Clear) < succ>
bacterial inner membrane --- Certainty =      0.000(Not Clear) < succ>

The protein has homology with the following sequences in the databases:

```
>sp|Q59746|NOSZ_RHIME NITROUS-OXIDE REDUCTASE PRECURSOR (N(2)OR)
(N2O REDUCTASE)
gb|AAC44023.1| (U47133) nitrous-oxide reductase [Sinorhizobium meliloti]
prf||2209347B nitrous-oxide reductase [Rhizobium meliloti]
Length = 639

Score = 660 bits (1704), Expect = 0.0
Identities = 344/536 (64%), Positives 407/536 (75%), Gaps = 23/536 (4%)

Query:    1 MSDEKLEQNGLSRRSFLGTAA--ASGAGIAGAGLLGLAGCSKDGEQAAANASGAAPVAKA   58
            MS+E+ +   L+RR LGT A  A+   +   G L L+G                G A  A+A
Sbjct:    1 MSNEETKMR-LNRRQMLGTTAFMAAAGAVGAGGALTLSG-------------GTATPARA   46

Query:   59 QGESKPGQLSSEVGPGELDQYYGFLSGGQSGEMRLIGLPSMRELMRIPVFNNDSATGWGR  118
              Q S     S EV PGELD+YY F S GQSGE+R++G PSMRE+MRIPVFN  SATGWG+
Sbjct:   47 QETSGS---SYEVKPGELDEYYVFFSSGQSGEIRIVGAPSMREMMRIPVFNRCSATGWGQ  103

Query:  119 TNESLKVLNGNITEETRKFLKDSGLRCYPNGDLHHPHLSFTDQTYDGRYAYANDKANNRV  178
            TNES KV+  + ET +FLKD G   Y NGDLHHPH SFTD TYDGRY YANDK+N+RV
Sbjct:  104 TNESRKVMTEGLLPETVEFLKDQG-GLYLNGDLHHPHPSFTDGTYDGRYLYANDKSNSRV  162

Query:  179 CRVRLDVMKADKIIDIPNDSGIHGLRPQRYPKTGYVFANGEHITPVSGVGK-LDDAKTWN  237
            CR+RLDVMK DKII +PN  +HGLR Q+YPKTGYVF NGE   PV  GK + D   ++
Sbjct:  163 CRIRLDVMKCDKIIQLPNQHTVHGLRVQKYPKTGYVFCNGEDAVPVPNDGKTMGDKNSYQ  222

Query:  238 AVYTAIDGETMEIAWQVLVDGNLDNGDADYQGKYSFATCYNSERALTVQGASSNEQDWCV  297
            A++TA+DGETME+AWQV+VDGNLDN DADYQGKY FATCYNSE   T+    ++EQDW V
Sbjct:  223 AIFTAVDGETMEVAWQVMVDGNLDNVDADYQGKYCFATCYNSEEGFTLADMMASEQDWVV  282

Query:  298 VFDLKAIEEGIKAGDFKEVNGVKMLDGRAEAKSKYTRYIPVPNSPHGCNASPDGKYIMPN  357
            +F+LK IEE +  GD+KE+ GV +LDGR    S YTRY+PVPNSPHG N +PDG +++ N
Sbjct:  283 IFNLKRIEEAVAKGDYKEIGGVPVLDGR--KGSPYTRYVPVPNSPHOINTAPDGIHVVAN  340

Query:  358 GKLPPTVTVLDVSKLDDLFAGKIKERDVVVAEPQLGLGPLHTAFDGRGNAYTTLFTDSQM  417
            GKL PTVTV DV K DDLF  KI+ RD VVAEP+LGLGPLETA+DG+GNAYTTLFIDSQ+
Sbjct:  341 GKLSPTVTVFDVRKFDDLFDDKIQARDTVVAEPELGLGPLHTAYDGKGNAYTTLFIDSQV  400

Query:  418 VKWNIDDAIKAYKGEKIDPIKQKLDVHYQPGHNHTTMGETKEADGQWLVSLNKFSKDRFL  477
              KWNI+DA +AY GEK+DPI+ KLDVHYQPGHNHT+MG+TKEADG+WL+SLNKFSKDR+L
Sbjct:  401 CKWNIEDAKRAYAGEKVDPIRHKLDVHYQPGHNHTSMGQTKEADGKWLISLNKFSKDRYL  460

Query:  478 NAGPLKPECDQLIGISGDEMRLVHDNPTFAEPHDLCLVAASKLNPGKTWDRKDPWF      533
            N GPLKPE DQLI ISGDEM LVHDNPTFAEPHD +V ASK+NP    W+R DP+F
Sbjct:  461 NVGPLKPENDQLIDISGDEMVLVHDNPTFAEPHDATIVHASKINPVHVWNRDDPFF      516
```

Based on this analysis, it was predicted that this protein from *N. gonorrhoeae*, and its epitopes, could be useful antigens for vaccines or diagnostics.

Example 5

A DNA sequence was identified in *N. gonorrhoeae* <SEQ ID 9> which encodes amino acid sequence <SEQ ID 10; NGS5>. Analysis of this protein sequence reveals the following:

GvH: Examining signal sequence (von Heijne)
Signal Score (−7.5): 1.09
Possible cleavage site: 19
>>> Seems to have a cleavable N-term signal seq.
Amino Acid Composition of Predicted Mature Form:
calculated from 20
ALOM: Finding transmembrane regions (Klein et al.)
count: 0 value: 7.43 threshold: 0.0

PERIPHERAL  Likelihood = 7.43
modified ALOM score: −1.99
Score for OM-PP discrimination: 4.97
Rule: outer membrane or periplasmic protein
Score for OM-PP discrimination: 4.97
Rule: outer membrane or periplasmic protein

*** Reasoning Step: 2
Outer membrane? Score: 0.496525
Final Results

| | |
|---|---|
| bacterial outer membrane --- Certainty = | 0.781(Affirmative) < succ> |
| bacterial periplasmic space --- Certainty = | 0.138(Affirmative) < succ> |
| bacterial inner membrane --- Certainty = | 0.000(Not Clear) < succ> |
| bacterial cytoplasm --- Certainty = | 0.000(Not Clear) < succ> |

The protein has no homology with sequences in the databases.

The protein was expressed in *E. coli* as an insoluble 43.56 kDa His-fusion product and then purified.

Based on this analysis, it was predicted that this protein from *N. gonorrhoeae*, and its epitopes, could be useful antigens for vaccines or diagnostics.

Example 6

A DNA sequence was identified in *N. gonorrhoeae* <SEQ ID 11> which encodes amino acid sequence <SEQ ID 12; NGS6>. Analysis of this protein sequence reveals the following:

GvH: Examining signal sequence (von Heijne)
Signal Score (−7.5): −3.93
Possible cleavage site: 36
>>> Seems to have no N-terminal signal seq.

Amino Acid Composition of Predicted Mature Form:
calculated from 1
ALOM: Finding transmembrane regions (Klein et al.)
count: 0 value: 6.42 threshold: 0.0

PERIPHERAL  Likelihood = 6.42
modified ALOM score: −1.78
Rule: cytoplasmic protein

*** Reasoning Step: 2
Final Results

| | |
|---|---|
| bacterial cytoplasm --- Certainty = | 0.447(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||F83173 outer membrane protein OprC PA3790 [imported] - Pseudomonas
aeruginosa (strain PAO1)
dbj|BAA05664.1|(D28119) outer membrane protein C [Pseudomonas aeruginosa]
gb|AAG07177.1|AE004797_12 (AE004797) outer membrane protein OprC
[Pseudomonas aeruginosa]
Length = 723

Score = 77.9 bits (191), Expect = 1e-13
Identities = 58/188 (30%), Positives = 89/188 (46%), Gaps = 13/188 (6%)

Query:  49 VKDLIIFDRAHGQSGTASKDGGIITRNVDARLFTAQAYARYNFNPHWAAGIKAAYNYGHN 108
           V+D I+F     G   G++++      NVDAR+   + A Y    +W      AY +G N
Sbjct: 546 VQDFILFSYREGMMGSSTQ-----ATNVDARIMGGELGASYQLTGNWKTDASLAYAWGKN 600

Query: 109 ETDGRPPYQIRPFEAAVQADYKNYFAHGSYNIGAATRFVAKQTRGDFDMASGLGIDKREA 168
           +D R    QI P EA      Y+    G ++ G+  R VA Q R    D    +G D  ++
Sbjct: 601 SSDDRALPQIPPLEARFGLTYE----EGDWSAGSLWRVVAPQNRIARDQGNVVGKDFDKS 656

Query: 169 AKGFTVADVYAGVNIKDKYGLRLGVNNVFNKKYVEYI--SGDHVLALSPS-VVYAPGRTY 225
           A GF V +    +   L  GV+N+F+K Y E++    +GD     S +  V  PGRT+
Sbjct: 657 A-GFGVFSLNGAYRVTRNVKLSAGVDNLFDKDYTEHLNKAGDAGFGFSANETVPEPGRTF 715

Query: 226 WLSLHAAF                                                     233
           W   +  +F
Sbjct: 716 WTKVDFSF                                                     723
```

Based on this analysis, it was predicted that this protein from *N. gonorrhoeae*, and its epitopes, could be useful antigens for vaccines or diagnostics.

Example 7

A DNA sequence was identified in *N. gonorrhoeae* <SEQ ID 13> which encodes amino acid sequence <SEQ ID 14; NGS7>. Analysis of this protein sequence reveals the following:

GvH: Examining signal sequence (von Heijne)
Signal Score (−7.5): 4.94
Possible cleavage site: 26
>>> Seems to have a cleavable N-term signal seq.
Amino Acid Composition of Predicted Mature Form:
calculated from 27

| ALOM: Finding transmembrane regions (Klein et al.) count: 0 value: 0.79 threshold: 0.0 |
| --- |
| PERIPHERAL         Likelihood = 0.79<br>modified ALOM score: −0.66<br>Score for OM-PP discrimination: −18.85<br>Rule: outer membrane or periplasmic protein<br>Score for OM-PP discrimination: −18.85<br>Rule: outer membrane or periplasmic protein |
| \*\*\* Reasoning Step: 2<br>Periplasmic space? Score: 1.8846<br>Final Results |
| bacterial periplasmic space --- Certainty = 0.929(Affirmative) < succ ><br>bacterial outer membrane --- Certainty = 0.211(Affirmative) < succ ><br>bacterial inner membrane --- Certainty = 0.000(Not Clear) < succ ><br>bacterial cytoplasm --- Certainty = 0.000(Not Clear) < succ > |

The protein has homology with the following sequences in the databases:

```
>pir||D72405 hypothetical protein - Thermotoga maritima (strain MSB8)
gb|AAD35294.1|AE001705_5 (AE001705) hypothetical protein
[Thermotoga maritima]
Length = 300

Score = 81.8 bits (201), Expect = 1e-14
Identities = 72/289 (24%), Positives = 124/289 (41%), Gaps = 17/289 (5%)

Query:  38 PAMPSVTIAVAALQGKLAKQADVSLKIWRSPDQLRAGVASGQFKVMMSPSNVGVNLRNQG   97
              P  P++   V  + GK+    DV ++IW++P++  A + S +      + P  VG NL  +G
Sbjct:  24 PLGPALIPVVPIMDGKIP--TDVKIEIWKNPEEAVAKIVSKEVDFAVLPVTVGANLYGKG   81

Query:  98 QKVGMVNILTNGITQLVCKGSAIASP-QDLVGKKILVPF-KNDMPDIVLQALLKKLKIDA  155
              ++ +V +    + LV  A       + L G+++  P  +     D++++  L K  +
Sbjct:  82 VRIKLVGVHEWKVFYLVASDDATFDGWESLRGQEVYTPHGRGQTVDVLMRYFLSKAGLTL  141

Query: 156 HK-VSITYAATPPEAVGLFPSKGYHAVILPEPMATASLLKGKTIGINVVHGFDLVKAWGQ  214
              +  V I YA   P E V LF S        LPEP  + L +GK +       D  K WG+
Sbjct: 142 DRDVKILYAP-PQEIVALFKSGKVKYAALPEPFVSMCLDRGKVV-------LDFQKEWGK  193

Query: 215 AFDTKPLIPMAGIIANEEYFHAHKAQFDIFHQDLKNALNWILANRQNAAKIGKNYLPAPE  274
                       IP+AG+   E      K   +   + L +++ W+ N     ++    L  P
Sbjct: 194 ELGVPGRIPIAGLFVRE---GVDKETVEKVEKALIDSIRWMKENLDETVQLSSEKLGIPA  250

Query: 275 PALVMGLDGARLTVSKGSEVKNEILKFYEILMQFNPELLGGKLPDNGFF            323
                L   L+          + + E+  F + L +   PE    K+PD GF+
Sbjct: 251 KILKSSLERIEFEYVPVEKCREEVETFLKKLNELYPEGF-EKIPDEGFY            298
```

The protein was expressed in *E. coli* as an insoluble 32.89 kDa His-fusion product and then purified.

Based on this analysis, it was predicted that this protein from *N. gonorrhoeae*, and its epitopes, could be useful antigens for vaccines or diagnostics.

Example 8

A DNA sequence was identified in *N. gonorrhoeae* <SEQ ID 15> which encodes amino acid sequence <SEQ ID 16; NGS8>. Analysis of this protein sequence reveals the following:

| GvH: Examining signal sequence (von Heijne)<br>Signal Score (−7.5): 2.39<br>Possible cleavage site: 15<br>>>> Seems to have a cleavable N-term signal seq.<br>Amino Acid Composition of Predicted Mature Form:<br>calculated from 16<br>ALOM: Finding transmembrane regions (Klein et al.)<br>count: 4 value: −8.23 threshold: 0.0 | | | |
| --- | --- | --- | --- |
| INTEGRAL | Likelihood = −8.23 | Transmembrane | 49-65 (41-73) |
| INTEGRAL | Likelihood = −7.38 | Transmembrane | 83-99 (75-106) |
| INTEGRAL | Likelihood = −7.06 | Transmembrane | 110-126 (100-133) |
| INTEGRAL | Likelihood = −4.41 | Transmembrane | 164-180 (163-187) |
| PERIPHERAL | Likelihood = 5.89<br>modified ALOM score: 2.15<br>Rule: cytoplasmic membrane protein | | |

-continued

| \*\*\* Reasoning Step: 2<br>Final Results |
| --- |
| bacterial inner membrane --- Certainty = 0.429(Affirmative) < succ ><br>bacterial periplasmic space --- Certainty = 0.000(Not Clear) < succ ><br>bacterial outer membrane --- Certainty = 0.000(Not Clear) < succ ><br>bacterial cytoplasm --- Certainty = 0.000(Not Clear) < succ > |

The protein has homology with the following sequences in the databases:

```
>sp|P38044|NRTB_SYNP7 NITRATE TRANSPORT PERMEASE PROTEIN NRTB
pir||S30892 nitrate transport protein nrtB - Synechococcus sp. (strain PCC
7942)
emb|CAA43810.1|(X61625) nitrate transporter [Synechococcus sp.]
prf||1908370A nitrate transporter [Synechococcus sp.]
Length = 279

Score = 67.5 bits (164), Expect = 1e-10
Identities = 54/202 (26%), Positives = 96/202 (46%), Gaps = 7/202 (3%)

Query:    4 VALWAWGSAVFGEFMLPAPVEVFQKSL--DLLKHFQEN-----EIGISLWRSVVGISVAL   56
            +A+W    SA+ G+  LP P+ V       +++ F +N     +G+ +  S+  +++
Sbjct:   36 LAIWQVISAILGQDRLPGPINVVANTWMPYIVEPFFDNGGTSKGLGLQILISLQRVAIGY   95

Query:   57 IAGLAAGLVAGLVAGSFKTAMALLKPVITILLAMPPIIWVVMALFWFGFGNPSVLFTIIV  116
              +   G++ G V G  K      L PVI +L +PP+ W  ++L  F   N S +F I +
Sbjct:   96 LLAACTGILVGGVLGMSKFLGKGLDPVIQVRTVPPLAWFPISLMVFQDANTSAIFVIFI   155

Query:  117 LVAPLTFASAAVGMASVNKQHEELFDAYKLGRLKKIRYLYIPHLTGYVISSVGVAVAMGV  176
                      + AVG+  +  +  +    KL +   I   + IP    YV + + +AV +
Sbjct:  156 TAIWPIIINTAVGINQIPDDYNNVARVLKLSKKDYILNILIPSTVPYVFAGLRIAVGLAW  215

Query:  177 KAVIMAELLGASKGVGARIADA                                        198
             A++ AE+L A   G+G   I DA
Sbjct:  216 LAIVAAEMLKADGGIGYFIWDA                                        237
```

Based on this analysis, it was predicted that this protein from *N. gonorrhoeae*, and its epitopes, could be useful antigens for vaccines or diagnostics.

Example 9

A DNA sequence was identified in *N. gonorrhoeae* <SEQ ID 17> which encodes amino acid sequence <SEQ ID 18; NGS9>. Analysis of this protein sequence reveals the following:

GvH: Examining signal sequence (von Heijne)
Signal Score (−7.5): −5.07
Possible cleavage site: 29
>>> Seems to have no N-terminal signal seq.
Amino Acid Composition of Predicted Mature Form:
calculated from 1

| | | | |
|---|---|---|---|
| ALOM: Finding transmembrane regions (Klein et al.) count: 1 value: −1.81 threshold: 0.0 | | | |
| INTEGRAL | Likelihood = −1.81 | Transmembrane | 97-113 (96-113) |
| PERIPHERAL | Likelihood = 4.24 modified ALOM score: 0.86 Rule: cytoplasmic membrane protein | | |

*** Reasoning Step: 2
Final Results

| | |
|---|---|
| bacterial inner membrane --- Certainty = | 0.172(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology with the following sequences in the databases:

```
>sp|P97027|SSUB_BACSU PUTATIVE ALIPHATIC SULFONATES
TRANSPORT ATP-BINDING PROTEIN SSUB
pir||G69816 nitrate ABC transporter (binding protein) homolog ygaL -
B. subtilis
emb|CAB07520.1|(Z93102) hypothetical 30.6 kd protein [Bacillus subtilis]
emb|CAB12711.1|(Z99108) similar to nitrate ABC transporter (binding protein)
[Bacillus subtilis]
Length = 274

Score = 99.5 bits (247), Expect = 3e-20
Identities = 68/181 (37%), Positives = 102/181 (55%), Gaps = 9/181 (4%)

Query:    4 LFGPSGCGKTTVLRLIAGLETPKSGTIRNTFH-------KTGFLFQENRLPENLTAMQNI   56
            L GPSGCGK+T+L++IAGL++    G++      + GF+FQE+RL   LT  QNI
Sbjct:   56 LIGPSGCGKSTLLKIIAGLDSEYDGSVEINGRSVTAPGIQQGFIFQEHRLFPWLTVEQNI  115

Query:   57 A--IFMDNPDEGEIVALAAKVGLTAGDLNKYPTELSGGMAKRVAFLRLLLCGCDLALLDE  114
            A    + +P  + V    ++ G       YP ELSGGM++RVA  R LL    ++ LLDE
Sbjct:  116 AADLNLKDPKVKQKVDELIEIVRLKGSEKAYPRELSGGMSQRVAITRALLREPEVLLLDE  175

Query:  115 PFVGLDRDLRDILVAMLVEKIERQGMACILVTHDRFEAARLSHEIMLLSAKGMNVQNVIT  174
            PF  LD   R L +L++   ++       ILVTHD  E+  L +E+ +L AK     + +
Sbjct:  176 PFGALDAFTRKHLQDVLLDIWRKKKTTMILVTHDIDESVYLGNELAILKAKPGKIHKLMP  235

Query:  175 L                                                            175
            +
Sbjct:  236 I                                                            236
```

Based on this analysis, it was predicted that this protein from *N. gonorrhoeae*, and its epitopes, could be useful antigens for vaccines or diagnostics.

Example 10

A DNA sequence was identified in *N. gonorrhoeae* <SEQ ID 19> which encodes amino acid sequence <SEQ ID 20; NGS10>. Analysis of this protein sequence reveals the following:

GvH: Examining signal sequence (von Heijne)

Signal Score (−7.5): 2.27

Possible cleavage site: 26

>>> Seems to have no N-terminal signal seq.

Amino Acid Composition of Predicted Mature Form:

calculated from 1

ALOM: Finding transmembrane regions (Klein et al.)

count: 0 value: 5.14 threshold: 0.0

| PERIPHERAL | Likelihood = 5.14 |
|---|---|
| modified ALOM score: −1.53 | |

*** Reasoning Step: 2
imb2 HYPID: 2 CFP: 0.1
Final Results

| | |
|---|---|
| bacterial inner membrane --- Certainty = | 0.100(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology with the following sequences in the databases:

```
>pir||A82615 surface protein XF1981 [imported] - Xylella fastidiosa (strain
9a5c)
gb|AAF84783.1|AE004017_6 (AE004017) surface protein [Xylella fastidiosa]
Length = 1190

Score = 50.2 bits (119), Expect = 2e-05
Identities = 59/210 (28%), Positives = 92/210 (43%), Gaps = 5/210 (2%)

Query:    17 SIGTSAEANAPGALALGGSSEASKKFSIAEGYLASSDGYGAIAIGSAAKI-KQLEKGTIN    75
                ++G    A+A GA A+G   + AS K S A G  A+   G++A+G  AK    +   +
Sbjct:   876 AVGVGTLASAEGATAVGSGAAASGKGSTAIGRNAVASADGSVALGDGAKDGARGAESYTG   935

Query:    76 HIVGNDNKGLYVDADGNVTKITVRTESEKDILSRYGQTYGAVALGFRSSSHNLFA----S   131
                  G  N  +   + G+ +K    RT S                L   +   N +
Sbjct:   936 KYSGLQNNTVGTVSVGDASKGETRTVSNVADAKEATDAVNLRQLDRVAQDANRYVDNKIE   995

Query:   132 SFGAFSTATAIESLAVGDSSQSTGYRSATFGSHSRALAEESLALGYETRANAYGSVALGA   191
                S     T    + SL    +  + G  +    G  + A    +S+A+G  +  A+A   +VA+G
Sbjct:   996 SLSEGQTFVKVNSLNNSATPIAAGVDATAIGVGATASGADSIAMGNKASASADNAVAIGN  1055

Query:   192 ESVANEENTVSVSSDTLKRKIVNVADGTED   221
                SVA+   NTVSV S    +R++ NVA GT D
Sbjct:  1056 HSVADRANTVSVGSAGSERQVTNVAAGTAD  1085

>sp|P10858|YADA_YERPS INVASIN PRECURSOR (OUTER MEMBRANE ADHESIN)
pin||S04534 invasin precursor - Yersinia pseudotuberculosis plasmid pIBI
emb|CAA32088.1|(x13883) Yop1 preprotein (AA 1-434) [Yersinia
pseudotuberculosis]
prf||1411295A invasin [Yersinia pseudotuberculosis]
Length = 434

Score = 42.1 bits (98), Expect = 0.006
Identities = 35/134 (26%), Positives = 68/134 (50%), Gaps = 28/134 (20%)

Query:   116 AVALGFRSSSHNLFASSFGAFSTATAIESLAVGDSSQSTGYRSATFGSHSRA--------   167
                ++A+G  + +      A + G+ S AT + S+A+G  S++ G   + T+G+ S A
Sbjct:   107 SIAIGATAEAAKPAAVAVGSGSIATGVNSVAIGPLSKALGDSAVTYGASSTAQKDGVAIG   166

Query:   168 ----LAEESLALGYETRANAYGSVALGA----------------ESVANEENTVSVSSDT   207
                     ++  +A+G+ ++ +A  SVA+G                   S   + EN+VS+  ++
Sbjct:   167 ARASASDTGVAVGFNSKVDAQNSVAIGHSSHVAADHGYSIAIGDHSKTDRENSVSIGHES   226

Query:   208 LKRKIVNVADGTED   221
                L R++ ++A GTED
Sbjct:   227 LNRQLTHLAAGTED   240
```

Based on this analysis, it was predicted that this protein from *N. gonorrhoeae*, and its epitopes, could be useful antigens for vaccines or diagnostics.

Example 11

A DNA sequence was identified in *N. gonorrhoeae* <SEQ ID 21> which encodes amino acid sequence <SEQ ID 22; NGS11>. Analysis of this protein sequence reveals the following:

GvH: Examining signal sequence (von Heijne)
Signal Score (−7.5): −0.16
Possible cleavage site: 60
>>> Seems to have no N-terminal signal seq.

-continued

| Amino Acid Composition of Predicted Mature Form: calculated from 1 |  |
| --- | --- |
| ALOM: Finding transmembrane regions (Klein et al.) count: 0 value: 4.67 threshold: 0.0 |  |

| PERIPHERAL | Likelihood = 4.67 |
| --- | --- |
| modified ALOM score: −1.43 |  |
| Rule: cytoplasmic protein |  |

| *** Reasoning Step: 2 Final Results | |
| --- | --- |
| bacterial cytoplasm --- Certainty = | 0.297(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>sp|P10858|YADA_YERPS INVASIN PRECURSOR (OUTER MEMBRANE ADHESIN)
pir||S04534 invasin precursor - Yersinia pseudotuberculosis plasmid pIBI
emb|CAA32088.1|(X13883) Yop1 preprotein (AA 1-434) [Yersinia
pseudotuberculosis]
prf||1411295A invasin [Yersinia pseudotuberculosis]
Length = 434

Score = 41.3 bits (96), Expect = 0.007
Identities = 27/71 (38%), Positives = 48/71 (67%), Gaps = 4/71 (5%)

Query:   16 QLNRLSKRTNRVGASAAALASL-KPAQLGKNDKFAFSLGFGSYKNAQAVAMGAVFKPAEN    74
            +L++L KR ++  AS+AAL SL +P  +GK +   F+ G G Y+++QA+A+G+ ++  E+
Sbjct:  353 RLDKLDKRVDKGLASSAALNSLFQPYGVGKVN---FTAGVGGYRSSQALAIGSGYRVNES  409

Query:   75 VLLNVAGSFAG    85
            V L    ++AG
Sbjct:  410 VALKAGVAYAG   420
```

Based on this analysis, it was predicted that this protein from *N. gonorrhoeae*, and its epitopes, could be useful antigens for vaccines or diagnostics.

Example 12

A DNA sequence was identified in *N. gonorrhoeae* <SEQ ID 23> which encodes amino acid sequence <SEQ ID 24; NGS12>. Analysis of this protein sequence reveals the following:

| GvH: Examining signal sequence (von Heijne) |
| --- |
| Signal Score (−7.5): −1.29 |
| Possible cleavage site: 61 |
| >>> Seems to have a cleavable N-term signal seq. |
| Amino Acid Composition of Predicted Mature Form: calculated from 62 |
| ALOM: Finding transmembrane regions (Klein et al.) count: 0 value: 6.36 threshold: 0.0 |

| PERIPHERAL | Likelihood = 6.36 |
| --- | --- |
| modified ALOM score: −1.77 | |
| Score for OM-PP discrimination: 6.03 | |
| Rule: outer membrane or periplasmic protein | |
| Score for OM-PP discrimination: 6.03 | |
| Rule: outer membrane or periplasmic protein | |

| *** Reasoning Step: 2 Outer membrane? Score: 0.602784 Final Results | |
| --- | --- |
| bacterial outer membrane --- Certainty = | 0.867(Affirmative) < succ> |
| bacterial periplasmic space --- Certainty = | 0.158(Affirmative) < succ> |

| bacterial inner membrane --- Certainty = | 0.000(Not Clear) < succ> |
| --- | --- |
| bacterial cytoplasm --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 13

A DNA sequence was identified in *N. gonorrhoeae* <SEQ ID 25> which encodes amino acid sequence <SEQ ID 26; NGS13>. Analysis of this protein sequence reveals the following:

| GvH: Examining signal sequence (von Heijne) |
| --- |
| Signal Score (−7.5): −3.64 |
| Possible cleavage site: 51 |
| >>> May be a lipoprotein |
| Amino Acid Composition of Predicted Mature Form: calculated from 21 |
| ALOM: Finding transmembrane regions (Klein et al.) count: 1 value: −1.01 threshold: 0.0 |

| INTEGRAL | Likelihood = −1.01 | Transmembrane 36-52 (36-52) |
| --- | --- | --- |
| PERIPHERAL | Likelihood = 5.14 | |
| | modified ALOM score: 0.70 | |
| | Rule: inner or outer membrane protein | |
| | Rule: inner or outer membrane protein | |
| | Rule: cytoplasmic membrane protein | |

| *** Reasoning Step: 2 Lipoprotein? Inner membrane? Final Results | |
| --- | --- |
| bacterial outer membrane --- Certainty = | 0.790(Affirmative) < succ> |
| bacterial inner membrane --- Certainty = | 0.742(Affirmative) < succ> |
| bacterial periplasmic space --- Certainty = | 0.000(Not Clear) < succ> |
| bacterial cytoplasm --- Certainty = | 0.000(Not Clear) < succ> |

The protein has homology with the following sequences in the databases:

```
>gb|AAC33455.1|(AF067083) outer membrane protein homolog [Vitreoscilla sp.]
Length = 217

Score = 236 bits (602), Expect = 2e-61
Identities = 134/217 (61%), Positives = 166/217 (75%)

Query:     1 MTFFKPSTVVLTASALALSGCVADPVTGQQSPNKSAMYGLGGAAVCGIVGALTHSGKGAR     60
             M  +K  +++ T +A+ALS C  DP+TGQ    N + +  LGGAA CGIVGALTH  KGAR
Sbjct:     1 MKAWKKFSLMATVAAVALSACATDPMTGQVDRNNTVLGALGGAATCGIVGALTHGSKGAR     60

Query:    61 NSALACGAIGAGVGGYMDYQEQRLRQNLAGTQIEIQRQGNQIRLVMPESVTFATGSAALG    120
             NSALACGAIGAGVG YMD+QE++LRQ+LA TQ+E+ R G++IRLVMPES+TFATGS  L
Sbjct:    61 NSALACGAIGAGVGAYMDHQERQLRQSLANTQVEVNRVGDEIRLVMPESITFATGSYQLN    120

Query:   121 GSAQYALNTAAQTLVQYPDTTLTINGHTDNTGSDAVNNPLSQHRAQAVAYYLQTRGVAAS    180
              SA  +LN+ +  L QY DTT+ I GHTD+TGSDA+N PLS++RA AVA YL +R VA++
Sbjct:   121 SSASTSLNSVSSVLAQYTDTTINIVGHTDSTGSDAINEPLSRNARSAVANYLVSRNVASN    180

Query:   181 RLTVYGYGSHMPVASNATVEGRAQNRRVEILINPDQR                         217
             R+T  G G   PVASN TV GRA+NRRVEI +NP QR
Sbjct:   181 RITTVGAGCRQPVASNNTVAGRAENRRVEITVNPIQR                         217

>gb|AAD40344.1|U88088_22 (U88088) OmpA [Pseudomonas alcaligenes]
Length = 220

Score = 130 bits (328), Expect = 1e-29
Identities = 90/219 (41%), Positives = 127/219 (57%), Gaps = 6/219 (2%)

Query:     7 STVVLTASALALSGCVA---DPVTGQQSPNKSAMYGLGGAAVCGIVGALTHSGKGARNSA     63
             S + +    L+GC +   + T + +   A   L GA   ++G  +  +GA   A
Sbjct:     3 SVIAASLVIFTLTGCASIQNEDGTTKNTALYGAGGALAGAVAGALIGK-ENRAQGALIGA     61

Query:    64 LACGAIGAGVGGYMDYQEQRLRQNLAGTQIEIQRQGNQIRLVMPESVTFATGSAALGGSA    123
               G++GAG Y D QE   LR+ + G+ ++++RQG++I +VMP ++TFATG A + +
Sbjct:    62 AVAGSLGAGYGYYADKQEAELREQMKGSGVQVERQGDEIVIVMPGAITFATGKAEIQPNF    121

Query:   124 QYALNTAAQTLVQYPDTTLTINGHTDNTGSDAVNNPLSQHRAQAVAYYLQTRGVAASRLT    183
               LN A +   YPD+ L + GHTD+ GS  N  LSQ RAQ+VA +L+ GV R+
Sbjct:   122 ANTLNQLAGSFRNYPDSRLIVTGHTDSVGSYEANELLSQRRAQSVAQFLRGNGVQTDRIE    181

Query:   184 VYGYGSHMPVASNATVEGRAQNRRVEILINPDQRAVNAA                       222
             V G G + PVASNAT EGRAQNRRVEI + P  RAV  A
Sbjct:   182 VIGAGPNQPVASNATAEGRAQNRRVEIKLAP--RAVQQA                       218
```

The protein was expressed in *E. coli* as a soluble 22.55 kDa His-fusion product and then purified.

Based on this analysis, it was predicted that this protein from *N. gonorrhoeae*, and its epitopes, could be useful antigens for vaccines or diagnostics.

Example 14

A DNA sequence was identified in *N. gonorrhoeae* <SEQ ID 27> which encodes amino acid sequence <SEQ ID 28; NGS14>. Analysis of this protein sequence reveals the following:

---

GvH: Examining signal sequence (von Heijne)
Signal Score (−7.5): −5.32
Possible cleavage site: 40
>>> Seems to have no N-terminal signal seq.
Amino Acid Composition of Predicted Mature Form:
calculated from 1
ALOM: Finding transmembrane regions (Klein et al.)
count: 0 value: 3.39 threshold: 0.0

---

-continued

| | |
|---|---|
| PERIPHERAL | Likelihood = 3.39 |
| modified ALOM score: −1.18 | |
| Rule: cytoplasmic protein | |

*** Reasoning Step: 2
Final Results

| | |
|---|---|
| bacterial cytoplasm --- Certainty = | 0.254(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 15

A DNA sequence was identified in *N. gonorrhoeae* <SEQ ID 29> which encodes amino acid sequence <SEQ ID 30; NGS15>. Analysis of this protein sequence reveals the following:

GvH: Examining signal sequence (von Heijne)
Signal Score (-7.5): -1.75
Possible cleavage site: 45
>>> Seems to have no N-terminal signal seq.
Amino Acid Composition of Predicted Mature Form:
calculated from 1
ALOM: Finding transmembrane regions (Klein et al.)
count: 0 value: 5.89 threshold: 0.0

| PERIPHERAL | Likelihood = 5.89 |
|---|---| modified ALOM score: -1.68
Rule: cytoplasmic protein

*** Reasoning Step: 2
Final Results bacterial cytoplasm --- Certainty = 0.232(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

The protein has homology with the following sequences in the databases:

```
>sp|P10487|RCI1_ECOLI SHUFFLON-SPECIFIC DNA RECOMBINASE
pir||S03815 probable integrase - Escherichia coli
dbj|BAA77989.1|(AB027308) shufflon-specific DNA recombinase [Plasmid R64]
Length = 384

Score = 67.1 bits (163), Expect = 3e-10
Identities = 75/301 (24%), Positives = 125/301 (40%), Gaps = 34/301 (11%)

Query:  68 KVKMMTLSEAMRKYLNETLGAGRSKKMGL---RFLMEFPIGGIGIDKLKRSDFAEHVMQR   124
           +++ M+LS A+ KYL         + +      + +PI   +D++   D A +   R Sbjct:   5 RIRKMSLSRALDKYLKTVSVHKKGHQQEFYRSNVIKRYPIALRNMDEITTVDIATYRDVR    64

Query: 125 RRGIPELDIAPIAASTALQELQYIRSVLKHAFYVWGLEIGWQELDFAANGLKRSNMVAKS   184
             I    PI +T  EL + S+  A   WG         N ++          S Sbjct:  65 LAEINPRTGKPITGNTVRLELALLSSLFNIARVEWG--------TCRTNPVELVRKPKVS   116

Query: 185 AIRDRLPTTEELQTLTTYFLRQWQSRKSSIPMHLIMWLAIYTSRRQDEICRLLFDDWHKN   244
           + RDR  T+ E + L+ YF       R+ ++ +++I   LA+ T+ RQ EI   L    W Sbjct: 117 SGRDRRLTSSEERRLSRYF------REKNLMLYVIFHLALETAMRQGEILAL---RWEHI   167

Query: 245 DCTRPVRDLKNPNGSTGNNKEFDILPMALPVIDELPEESVRKRMLANKGIADSLVPCNGK   304
            D    V L  P  G++++   +  A   +P          +  ++

Sbjct: 168 DLRHGVAHL--PETKNGHSRDVPLSRRARNFLQMMP----------VNLHGNVFDYTAS   214

Query: 305 SVSAAWTRACKVLGIKDLRFHDLRHEAATRMAEDG-FTIPQMQRVTLHDGWNSLQRYVSVR   364
                  AW   A + L I+DL FHDLRHEA +R  E G  + ++  ++  H   N L+RY   +R Sbjct: 215 GFKNAWRIATQRLRIEDLHFHDLRHEAISRFFELGSLNVMEIAAISGHRSMNMLKRYTHLR   275
```

Based on this analysis, it was predicted that this protein from *N. gonorrhoeae*, and its epitopes, could be useful antigens for vaccines or diagnostics.

Example 16

A DNA sequence was identified in *N. gonorrhoeae* <SEQ ID 31> which encodes amino acid sequence <SEQ ID 32; NGS16>. Analysis of this protein sequence reveals the following:

GvH: Examining signal sequence (von Heijne)
Signal Score (-7.5): -3.64
Possible cleavage site: 20
>>> Seems to have no N-terminal signal seq.
Amino Acid Composition of Predicted Mature Form:
calculated from 1
ALOM: Finding transmembrane regions (Klein et al.)
count: 0 value: 4.67 threshold: 0.0

| PERIPHERAL | Likelihood = 4.67 |
|---|---| modified ALOM score: -1.43
Rule: cytoplasmic protein

*** Reasoning Step: 2
Final Results bacterial cytoplasm --- Certainty = 0.262(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

The protein has homology with the following sequences in the databases:

```
>sp|P10484|T1M1_ECOLI TYPE I RESTRICTION ENZYME ECOR124II M
PROTEIN (M.ECOR124II)
pir||S02166 type I site-specific deoxyribonuclease (EC 3.1.21.3) EcoR124/3
chain hsdM - Escherichia coli plasmid R124/3
emb|CAA31541.1|(X13145) hsdM protein (AA 1-520) [Escherichia coli]
Length = 520

Score = 44.4 bits (104), Expect = 0.002
Identities = 65/235 (27%), Positives = 99/235 (41%), Gaps = 55/235 (23%)

Query: 107 NRKKAGGYAEYITGGSLRRLVAAKVRRYCGEHPGVFDGAAGSG--------QLEQYIEPS 158
            N K+GG   E+ T   + +L+A          ++D AAGSG          Q +  +I
Sbjct: 191 NAGKSGG--EFFTPQHVSKLIAQLAMHGQTHVNKIYDPAAGSGSLLLQAKKQFDNHIIEE 248

Query: 159 DFRAVEIQAEACKALLQNYPAAKVYNTSLFL--------------------YTDGEPQDC 198
              F   EI          N+    + ++FL                    + D +P D
Sbjct: 249 GFFGQEI----------NHTTYNLARMNMFLHNINYDKFDIKLGNTLTEPHFRDEKPFDA 298

Query: 199 TVMNPPFSIKLKDLSEDEKSRIAQEYPWKKSGV------ADEIFVLKGLE--NARRFGFF 250
            V NPP+S+K   D+ + I   E  +GV         AD  FVL L    +A+
Sbjct: 299 IVSNPPYSVKW--IGSDDPTLINDER-FAPAGVLAPKSKADFAFVLHALNYLSAKGRAAI 355

Query: 251 ILFPGIAYR-KSEQRFRE-IIGNRLAE--LNRIQNAFEDTPIEVLLLVIDKDKTD      301
            + FPGI YR  +EQ+ R+ ++ N   E  ++    N F   T I V +LV+ K KTD
Sbjct: 356 VCFPGIFYRGGAEQKIRQYLVDNNYVETVISLAPNLFFGTTIAVNILVLSKHKTD      410
```

Based on this analysis, it was predicted that this protein from *N. gonorrhoeae*, and its epitopes, could be useful antigens for vaccines or diagnostics.

Example 17

A DNA sequence was identified in *N. gonorrhoeae* <SEQ ID 33> which encodes amino acid sequence <SEQ ID 34; NGS17>. Analysis of this protein sequence reveals the following:

| | |
|---|---|
| GvH: Examining signal sequence (von Heijne) | |
| Signal Score (−7.5): −5.29 | |
| Possible cleavage site: 16 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 2.60 threshold: 0.0 | |

| PERIPHERAL | Likelihood = 2.60 |
|---|---|
| modified ALOM score: −1.02 | |
| Rule: cytoplasmic protein | |

*** Reasoning Step: 2
Final Results

| | |
|---|---|
| bacterial cytoplasm --- Certainty = | 0.284(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>ref|NP_052389.1|translocator YopD [Yersinia enterocolitica]
sp|P37132|YOPD_YEREN YOPD PROTEIN
gb|AAD16812.1|(AF102990) translocator YopD [Yersinia enterocolitica]
Length = 306

Score = 32.1 bits (72), Expect = 8.2
Identities = 29/93 (31%), Positives = 43/93 (46%), Gaps = 17/93 (18%)

Query:  13 MLAAKRAAKESTRQERAVKRAGTVRNVDRNRLSARSKAQKENIARMLSGAKVSEDEALTC  72
            +L   R A+E   Q+R ++    T+              AQKE +A M+SGAK+    A+
Sbjct:  89 LLELARKAREMGLQQRDIENKATI-----------SAQKEQVAEMVSGAKLMIAMAVVS 136

Query:  73 GIMMRLSLQDMRYACNQELINFAEHIVKQVQRL                            105
            GIM  S    ++  +E+      IVKQ Q L
Sbjct: 137 GIMAATSTVASAFSIAKEV-----KIVKQEQIL                            164
```

Based on this analysis, it was predicted that this protein from *N. gonorrhoeae*, and its epitopes, could be useful antigens for vaccines or diagnostics.

Example 18

A DNA sequence was identified in *N. gonorrhoeae* <SEQ ID 35> which encodes amino acid sequence <SEQ ID 36; NGS18>. Analysis of this protein sequence reveals the following:

| | |
|---|---|
| GvH: Examining signal sequence (von Hejine) | |
| Signal Score (−7.5): −2.56 | |
| Possible cleavage site: 38 | |
| >>> Seems to have no N-terminal signal seq. | |
| Amino Acid Composition of Predicted Mature Form: calculated from 1 | |

-continued

| ALOM: Finding transmembrane regions (Klein et al.) count: 0 value: 4.56 threshold: 0.0 | |
|---|---|
| PERIPHERAL modified ALOM score: −1.41 Rule: cytoplasmic protein | Likelihood = 4.56 |
| *** Reasoning Step: 2 Final Results | |
| bacterial cytoplasm --- Certainty = | 0.397(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 19

A DNA sequence was identified in *N. gonorrhoeae* <SEQ ID 37> which encodes amino acid sequence <SEQ ID 38; NGS19>. Analysis of this protein sequence reveals the following:

| GvH: Examining signal sequence (von Heijne) Signal Score (−7.5): −4.12 Possible cleavage site: 43 >>> Seems to have no N-terminal signal seq. Amino Acid Composition of Predicted Mature Form: calculated from 1 ALOM: Finding transmembrane regions (Klein et al.) count: 0 value: 8.49 threshold: 0.0 | |
|---|---|
| PERIPHERAL modified ALOM score: −2.20 Rule: cytoplasmic protein | Likelihood = 8.49 |
| *** Reasoning Step: 2 Final Results | |
| bacterial cytoplasm --- Certainty = | 0.250(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>ref|NP_043483.1|orf14 [Bacteriophage HP1]
sp|P51716|YO14_BPHP1 HYPOTHETICAL 14.9 KD PROTEIN IN REP-HOL
INTERGENIC REGION (ORF14)
pir||S69520 hypothetical protein 14 - phage HP1
gb|AAB09199.1|(U24159) orf14 [Bacteriophage HP1]
          Length = 133

Score = 73.3 bits (179), Expect = 1e-12
 Identities = 44/129 (34%), Positives = 74/129 (57%), Gaps = 6/129 (4%)

Query:    1 MFIPAALHKDEHSAYGVTIPDLPGCFSCGDTVEEAVANARSAAYMHIDGMIEDGGFKNLA    60
            M  P  + K  +   Y V++PD+PGCFS GDT+ EA+ NA+ A   HI+GM+ED   + L
Sbjct:    1 MLYPICIEK-VNDGYVVSVPDVPGCFSAGDTLSEAMLNAKEAISFHIEGMLEDD--EELP    57

Query:   61 VSS-IADLSQEPDYHGATWVMIEIDPAKISRQQIRFNVSWPQYLLDRVDEY--TSANHET   117
             S+ I    +P+Y    ++++D   +  + N++ P  LL R+D++   T    ++
Sbjct:   58 KSNPIEQYINQPEYKDFIVTVVDVDLTHLMGKAEKINITVPALLLHRIDQFIATHPEYKN   117

Query:  118 RSGFLAKAA                                                    126
            RS FL++ A
Sbjct:  118 RSNFLSQLA                                                    126
```

Based on this analysis, it was predicted that this protein from *N. gonorrhoeae*, and its epitopes, could be useful antigens for vaccines or diagnostics.

Example 20

A DNA sequence was identified in *N. gonorrhoeae* <SEQ ID 39> which encodes amino acid sequence <SEQ ID 40; NGS20>. Analysis of this protein sequence reveals the following:

| GvH: Examining signal sequence (von Heijne) Signal Score (−7.5): −0.1 Possible cleavage site: 19 >>> Seems to have no N-terminal signal seq. Amino Acid Composition of Predicted Mature Form: calculated from 1 ALOM: Finding transmembrane regions (Klein et al.) count: 0 value: 7.58 threshold: 0.0 | |
|---|---|
| PERIPHERAL modified ALOM score: −2.02 Rule: cytoplasmic protein | Likelihood = 7.58 |
| *** Reasoning Step: 2 Final Results | |
| bacterial cytoplasm --- Certainty = | 0.057(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 21

A DNA sequence was identified in *N. gonorrhoeae* <SEQ ID 41> which encodes amino acid sequence <SEQ ID 42; NGS21>. Analysis of this protein sequence reveals the following:

| GvH: Examining signal sequence (von Heijne) | |
|---|---|
| Signal Score (−7.5): −3.52 | |
| Possible cleavage site: 52 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 5.83 threshold: 0.0 | |
| PERIPHERAL | Likelihood = 5.83 |
| modified ALOM score: −1.67 | |
| Rule: cytoplasmic protein | |

| *** Reasoning Step: 2 Final Results | |
|---|---|
| bacterial cytoplasm --- Certainty = | 0.311(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>ref|NP_040628.1|cI (repressor; 237) [bacteriophage lambda]
ref|NP_061378.1|phage lambda repressor protein CI [Escherichia coli]
sp|P03034|RPC1_LAMBD REPRESSOR PROTEIN CI
pir||RPBPL repressor protein cI - phage lambda
emb|CAA24991.1|(X00166) coding sequence cI gene [bacteriophage lambda]
gb|AAA96581.1|(J02459) cI (repressor; 237) [bacteriophage lambda]
emb|CAB96428.1|(AJ277653) phage lambda repressor protein CI [Escherichia-
  coli]
Length = 237

Score = 62.5 bits (151), Expect = 5e-09
Identities = 36/85 (42%), Positives = 51/85 (59%)

Query:   2 KKRELNEIETAECAELKRIFNSKKEELKLTQYKLAEAVGVTQSAVNHYLNGTNALNASIA   61
            KK+ L + +   +   LK I+  KK EL L+Q  +A+ +G+ QS V   NG NALNA  A
Sbjct:   4 KKKPLTQEQLEDARRLKAIYEKKKNELGLSQESVADKMGMGQSGVGALFNGINALNAYNA   63

Query:  62 SQFAKILQIPVSDFSLRLAEEISSM                                     86
           +  AKIL++ V +FS  +A EI  M
Sbjct:  64 ALLAKILKVSVEEFSPSIAREIYEM                                     88
```

Based on this analysis, it was predicted that this protein from *N. gonorrhoeae*, and its epitopes, could be useful antigens for vaccines or diagnostics.

Example 22

A DNA sequence was identified in *N. gonorrhoeae* <SEQ ID 43> which encodes amino acid sequence <SEQ ID 44; NGS22>. Analysis of this protein sequence reveals the following:

| GvH: Examining signal sequence (von Heijne) | |
|---|---|
| Signal Score (−7.5): −2.6 | |
| Possible cleavage site: 43 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 7.74 threshold: 0.0 | |
| PERIPHERAL | Likelihood = 7.74 |
| modified ALOM score: −2.05 | |
| Rule: cytoplasmic protein | |

| *** Reasoning Step: 2 Final Results | |
|---|---|
| bacterial cytoplasm --- Certainty = | 0.072(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||S30432 hypothetical protein - Streptomyces clavuligerus plasmid pSCL
Length = 307
```

```
Score = 43.6 bits (102), Expect = 0.002
Identities = 25/86 (29%), Positives = 49/86 (56%), Gaps = 2/86 (2%)

Query:   6 MGMAFKT-GIPRGQRFVLVKLCDCANDDGLCYPSQETLAEDTGFAETAVRQHIKWLKDNN  64
           MGM F   G+   ++ +L+   +  + G C+PS++ L +D G + + V++   + L    N
Sbjct:   1 MGMVFAAEGLDGSEKLLLLGYTNWTDPYGYCWPSEDRLVDDCGTSRSTVQRTKRKLVKKN  60

Query:  65 FIKSARRQRGR-ERKSDIYRINVALL  89
           ++S RR+  + E  S++ R+N+ LL
Sbjct:  61 LLRSVRRKNSKGEPISNLSRVNLPLL  86
```

Based on this analysis, it was predicted that this protein from *N. gonorrhoeae*, and its epitopes, could be useful antigens for vaccines or diagnostics.

Example 23

A DNA sequence was identified in *N. gonorrhoeae* <SEQ ID 45> which encodes amino acid sequence <SEQ ID 46; NGS23>. Analysis of this protein sequence reveals the following:

| GvH: Examining signal sequence (von Heijne) |
| --- |
| Signal Score (−7.5): −2.8 |
| Possible cleavage site: 59 |
| >>> Seems to have no N-terminal signal seq. |
| Amino Acid Composition of Predicted Mature Form: calculated from 1 |
| ALOM: Finding transmembrane regions (Klein et al.) count: 0 value: 0.05 threshold: 0.0 |

| PERIPHERAL | Likelihood = 0.05 |
| --- | --- |
| modified ALOM score: −0.51 | |
| Rule: cytoplasmic protein | |

*** Reasoning Step: 2
Final Results

| bacterial cytoplasm --- Certainty = | 0.195(Affirmative) < succ> |
| --- | --- |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

Based on this analysis, it was predicted that this protein from *N. gonorrhoeae*, and its epitopes, could be useful antigens for vaccines or diagnostics.

Example 24

A DNA sequence was identified in *N. gonorrhoeae* <SEQ ID 47> which encodes amino acid sequence <SEQ ID 48; NGS24>. Analysis of this protein sequence reveals the following:

| GvH: Examining signal sequence (von Heijne) |
| --- |
| Signal Score (−7.5): −5.76 |
| Possible cleavage site: 26 |
| >>> Seems to have no N-terminal signal seq. |
| Amino Acid Composition of Predicted Mature Form: calculated from 1 |
| ALOM: Finding transmembrane regions (Klein et al.) count: 0 value: 1.43 threshold: 0.0 |

| PERIPHERAL | Likelihood = 1.43 |
| --- | --- |
| modified ALOM score: −0.79 | |
| Rule: cytoplasmic protein | |

*** Reasoning Step: 2
Final Results

| bacterial cytoplasm --- Certainty = | 0.112(Affirmative) < succ> |
| --- | --- |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>sp|P07905|DNAC_ECOLI DNA REPLICATION PROTEIN DNAC
pir||XMECNC DNA replication protein dnaC - Escherichia coli (strain K-12)
Length = 245

Score = 110 bits (275), Expect = 2e-23
Identities = 75/224 (33%), Positives = 116/224 (51%), Gaps = 23/224 (10%)

Query:  50 EAADEMAAYAETLRRGAMRDA----------LEKRIGRSGIAPRFRNCRIENYAV--SDS   97
           +  +E+ A+ +    +GA+R A           +++  RSGI P  +NC   ENY V
Sbjct:  24 KTGEELLAWQK--EQGAIRSAALERENRAMKMQRTFNRSGIRPLHQNCSFENYRVECEGQ   81

Query:  98 IPGMARAKAAAAEYAANFADVLQTGRSMIFSGRRGTGKNHLACGIAREVIAAGKSALVIT  157
           +   +++A+    E+   N A     S IFSG+ GTGKNHLA  I   E++  GKS L+IT
Sbjct:  82 MNALSKARQYVEEFDGNIA-------SFIFSGKPGTGKNHLAAAICNELLLRGKSVLIIT  134

Query: 158 VGDMLRTVKDSF--GGGGEAGAVGIFVKPDLLVLDEFGAGSLSETDGRILFSVVNARYER  215
           V D++   +KD+F   G  E        +  DLLV+DE G  + S+ +   I+    +V+ R
Sbjct: 135 VADIMSAMKDTFRNSGTSEEQLLNDLSNVDLLVIDEIGVQTESKYEKVIINQIVDRRSSS  194

Query: 216 LMPMLVLTNLTAEAFRENTDARIRDRLRDGGGKLIPFDWESYRA                 259
                 P  +LTN   E    +   R+ DR+R G      + F+W+SYR+
Sbjct: 195 KRPTGMLTNSNMEEMTKLLGERVMDRMRLGNSLWVIFNWDSYRS                 238
```

```
>ref|NP_053228.1|pXO2-73 [Bacillus anthracis]
gb|AAF13678.1|AF188935_76 (AF188935) pXO2-73 [Bacillus anthracis]
Length = 541

Score = 125 bits (315), Expect = 9e-28
Identities = 139/535 (25%), Positives = 254/535 (46%), Gaps = 70/535 (13%)

Query:  14 PVLFIGTGMSLRYLDNSYTWDGLLSKIAIDLFGDDREYLNIKSRYCEDGRFQYEEIAEEL   73
           P LFIG+G S RYL N   W GL+ K + +L   + EY      Y       + E+AE +
Sbjct:  19 PFLFIGSGFSKRYL-NLEDWAGLMKKFS-NLMPYEFEY------YSSTANKDWAEVAELM   70

Query:  74 QSKFDKVL--ENDPDGRFKEINDKFFENMRAGNTLSRFKIYISTLLSQLNYK----DNSN  127
             F  +   E   +   KE  D      R  +  S  K+ ++  L+ + YK    + ++
Sbjct:  71 AKDFHPIWWKEQQFENNRKEFKD------RISSKQSPLKVEVAKYLNSIEYKYGLDEKND  124

Query: 128 TELSELKKARKNVGSIITTNYDKLAQDIFEFNPL---IGN-DILLSNPY--GSVYKIHGC  181
            E++ LKK    +  IITTN+D L + IFE    +   IG  ++L S+P     +YKIHGC
Sbjct: 125 KEIAALKKIV--IDGIITTNWDLLLEQIFEEQEMQVYIGQKELLFSHPLEINEIYKIHGC  182

Query: 182 VDDPSKIIITKKDYEKFKEKYELIRAQLLSLFIHNPIIFLGYNVGDENIKEILKTIFTYV  241
             P  +++T  DY+ + EK    + A+LL++FI +P+IFLGY++ D+NI++ILK I   +
Sbjct: 183 SSIPDSLVLTTSDYKGYNEKNAYLAAKLLTVFIEHPVIFLGYSISDDNIQQILKAITRCL  242

Query: 242 EQNSPSANKIRRNFLLVEYEPESNNEDIVEHDIDIT-GFSTIRINKIKTDNFSQIYKALA  300
           +Q++    K R    L+  E     ED  E++  +T G  T+ I ++KT+++ +IY ALA
Sbjct: 243 DQDNIHKLKDR----LIFVERAGQEEDSFENNSSLTIGKITVPITRVKTNDYEKIYNALA  298

Query: 301 ELTLPISAMDVRKFQSIAKEIYTGGNIKVSF---TEDMDNLNNSDKVVAIGSTKTISYNF  357
           +     S   +R+ +S   E+    + +         + D+  + + V+ +G  K +
Sbjct: 299 QNKRKFSMKMMRQMKSQIYELVKTNDPEEKIYVVDGEYDDTQDIEFVIGLG-VKNVVEEM  357

Query: 358 QTTSEMMSN----------------YFKIIEEENS----QLLKLIDKHSIASTQYFPI--  395
           Q+  E+ ++                  + +++ +E        ++K+      + S QY P+
Sbjct: 358 QSNHEISASKELSEHGYGGISDIELFNELLSDEPKYDYDSIVKISLPQILRSNQYVPLFR  417

Query: 396 YGFSRICSDIHKEAVLKRQQKEKLDHFIEEINRRCKNNHSSIQSILDDENISDTYKNDAI  455
           Y        D    ++ +K + K +    F+ E  ++    N S       + + +   + +  +
Sbjct: 418 YVLESSVEDELLDSKIKNKLKMRYTDFLTETQKKNIKNLSWDWQFKNLDEVLKGFPDIKV  477

Query: 456 AWG----IWNNQLSEDEVENYL---KNFVNKKN----THYKRLLCMFDYKKYADT      499
           A       +       L+ D+++++L      FV +KN     T  +RL  ++D+ KY  +
Sbjct: 478 AIEQIPLLGQKNLNCDDLKDFLIKNSKFVKEKNTPERTGIRRLFRIYDWLKYGQS      532
```

Based on this analysis, it was predicted that this protein from *N. gonorrhoeae*, and its epitopes, could be useful antigens for vaccines or diagnostics.

Example 25

A DNA sequence was identified in *N. gonorrhoeae* <SEQ ID 49> which encodes amino acid sequence <SEQ ID 50; NGS25>. Analysis of this protein sequence reveals the following:

GvH: Examining signal sequence (von Heijne)
Signal Score (−7.5): 4.76837e−07
Possible cleavage site: 56
>>> May be a lipoprotein
Amino Acid Composition of Predicted Mature Form:
calculated from 21

-continued

ALOM: Finding transmembrane regions (Klein et al.)
count: 0 value: 6.68 threshold: 0.0

PERIPHERAL Likelihood = 6.68
modified ALOM score: −1.84
Rule: inner or outer membrane protein
Rule: inner or outer membrane protein

*** Reasoning Step: 2
Lipoprotein?
Inner membrane?
Final Results

| | |
|---|---|
| bacterial outer membrane --- Certainty = | 0.790(Affirmative) < succ> |
| bacterial inner membrane --- Certainty = | 0.700(Affirmative) < succ> |
| bacterial periplasmic space --- Certainty = | 0.000(Not Clear) < succ> |
| bacterial cytoplasm --- Certainty = | 0.000(Not Clear) < succ> |

The protein has homology with the following sequences in the databases:

```
>gi|7433005|pir||B70313 cytochrome-c peroxidase (EC 1.11.1.5) -
Aquifex aeolicus
gi|2982865|gb|AAC06485.1|(AE000675) cytochrome c peroxidase
[Aquifex aeolicus]
Length = 355

Score = 345 bits (885), Expect = 7e-94
Identities = 180/336 (53%), Positives = 237/336 (69%), Gaps = 12/336 (3%)

Query:  59 EDQDLLKRAQGVFQPLPTVEEMQKIRPFTEEQVKLGHQLWYEPRLSKGNTVSCNSCHNLA   118
           +D++LLK A+   F+PLP V E   +   P T E+VKLG  L+Y+PRLSK    +SCN+CHNLA
```

```
Sbjct:  22 DDKELLKMARQYFKPLPKVAENPQ-NPVTPEKVKLGKMLYYDPRLSKSGLISCNTCHNLA    80

Query: 119 SAGVDNMPTSQGHKGQFGGRNSPTALNAALLGSQFWDGRAADVEEQAGGPLVNPVEMAND    178
           GVDN+PTS GH+   G RN+PT  NAA+  +QFWDGRA DVEEQA GP+VNP+EMAN
Sbjct:  81 RYGVDNLPTSIGHRWAIGPRNAPTVYNAAIHIAQFWDGRAKDVEEQALGPIVNPIEMAN-    139

Query: 179 SQEAAAAKIAKVPEYQEMFKKAFP-EDGAVSFKNITTALGAFERTLLTPTKWDEYLKGNV    237
           ++E A    +  +PEY E+FKKAFP E   V ++NI   A+GAFERTL+TP+++DE+LKGN
Sbjct: 140 TEENAVKTLKSIPEYVELFKKAFPNEKDPVKYENIGKAIGAFERTLMTPSRFDEFLKGNT    199

Query: 238 NALSEQERKGVRAFMDNGCIACHNGVNLGGTTFQKFGLVQGPYWK------FIEDP--KR    289
           AL+EQE++G++ F++ GC+ACHNG  +GG  F KFG++    YWK          +  P  K
Sbjct: 200 KALTEQEKRGLKTFIEVGCVACHNGPGVGGNMFAKFGMIT-EYWKVTYPYVLVGKPAIKV    258

Query: 290 DKGRADVTKKTEDEFFFRVPGLRNVAKTYPYFHNGSVWELDKAVTIMGKAQLGKDIPKED    349
           D GR  VTKK ED F F+VP LRN+   TYPYFH+GSVW L+ AV IM K QLGK++   +
Sbjct: 259 DFGRFGVTKKEEDMFVFKVPSLRNIEHTYPYFHDGSVWSLEDAVRIMAKTQLGKELTDQQ    318

Query: 350 VDNIVVFLNALSGNVSESARTMPELPLTAPMESKPD                           385
           V +IV FL AL+G + + A  +PELP +     KP+
Sbjct: 319 VKDIVAFLKALTGKIPKHALEVPELPPSTDKTPKPE                           354
```

Based on this analysis, it was predicted that this protein from *N. gonorrhoeae*, and its epitopes, could be useful antigens for vaccines or diagnostics.

Example 26

A DNA sequence was identified in *N. gonorrhoeae* <SEQ ID 51> which encodes amino acid sequence <SEQ ID 52; NGS26>. Analysis of this protein sequence reveals the following:

GvH: Examining signal sequence (von Heijne)
Signal Score (−7.5): 0.610001
Possible cleavage site: 15
>>> Seems to have no N-terminal signal seq.
Amino Acid Composition of Predicted Mature Form:
calculated from 1
ALOM: Finding transmembrane regions (Klein et al.)
count: 0 value: 5.04 threshold: 0.0

| PERIPHERAL | Likelihood = 5.04 |
|---|---|
| modified ALOM score: −1.51 | |
| Rule: cytoplasmic protein | |

*** Reasoning Step: 2
Final Results

| | |
|---|---|
| bacterial cytoplasm --- Certainty = | 0.127(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||T13296 hypothetical protein 8 - Streptococcus phage phi-O1205
gb|AAC79524.1|(U88974) ORF8 [Streptococcus thermophilus temperate
bacteriophage O1205]
Length = 157

Score = 62.5 bits (151), Expect = 2e-09
Identities = 53/161 (32%), Positives = 86/161 (52%), Gaps = 8/161 (4%)

Query:   5 TLYRCAADVQAALDYYFDSETEREDTLEAV--IGQFEVKAQSVIAYIKNQEITEKMLEGH    62
           TLY     +    + D ET + DTLEA+     +E K+    + IK+ E    +   +
Sbjct:   3 TLYELTDQLLEIYNMDVDDET-KLDTLEAIDWTTDYENKVEGYVKVIKSLEADIEARKNE    61

Query:  63 IRQMTGKLKAAKARNQSLKDYLARNMQAAGITEIKADDGTFKASFRKSEAVVILDEAQIP    122
           +++  G  K+ +++    LK   LA +M   G T +   D    FK  FRKSEAVV+ +E ++P
Sbjct:  62 KKRLDGLNKSDQSKIDKLKTALAVSMAETGQTRV--DTTLFKVGFRKSEAVVV-NEEKLP    118

Query: 123 AEFMREAVKTEPDKTAIRKAIESGRQVAGAKIEGRKNLQIR                       163
           E+    K  PDK  +++  ++SG+  + GA +E R+NL IR
Sbjct: 119 KEYQIATYK--PDKKTLKELLKSGKHIEGATLEERRNLNIR                       157
```

Based on this analysis, it was predicted that this protein from *N. gonorrhoeae*, and its epitopes, could be useful antigens for vaccines or diagnostics.

Example 27

A DNA sequence was identified in *N. gonorrhoeae* <SEQ ID 53> which encodes amino acid sequence <SEQ ID 54; NGS27>. Analysis of this protein sequence reveals the following:

```
            GvH: Examining signal sequence (von Heijne)
            Signal Score (−7.5): −5.45
            Possible cleavage site: 49
            >>> Seems to have no N-terminal signal seq.
            Amino Acid Composition of Predicted Mature Form:
            calculated from 1
            ALOM: Finding transmembrane regions (Klein et al.)
            count: 0 value: 1.80 threshold: 0.0

PERIPHERAL              Likelihood = 1.80
         modified ALOM score: −0.86
         Rule: cytoplasmic protein

*** Reasoning Step: 2
                        Final Results bacterial cytoplasm --- Certainty =    0.559(Affirmative) < succ>
motifs:
Subtilase_Asp   (S, T, A, I, V)x(L, I, V, M, F) (L, I, V, M)D(D, S, T, A)G(L, I, V, M, F, C)x)
                                (A)x(L) (I)D(D)G(I)x{2}(D)
       79: DDDFL                        AALIDDGIVFD              V
```

A homolog was found in serogroup A *N. meningitidis* but not in serogroup B, so NGS27 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 28

A DNA sequence was identified in *N. gonorrhoeae* <SEQ ID 55> which encodes amino acid sequence <SEQ ID 56; NGS28>. Analysis of this protein sequence reveals the following:

```
>prf||1306286A mobilization protein B [Escherichia coli]
Length = 529

Score = 34.7 bits (78), Expect = 2.4
Identities = 24/69 (34%), Positives = 31/69 (44%), Gaps = 12/69 (17%)

Query: 344 QLRARQQEIPVDYARTAVCGRIPFRRHSRPTLRSRTLGAQRRRIVPNVGQAGGIRAD---  400
               +LRA  Q++P D+ +T V    P R   +    GA       GQ G IR D
Sbjct: 440 RLRAAGQDLPADFVKTTVLDNTPIRWFYRAASQESRSGA---------GQTGEIRVDVER  490

Query: 401 RTPNTQRGT                                                    409
             R P  +RGT
Sbjct: 491 RGPAGRRGT                                                    499
```

```
            GvH: Examining signal sequence (von Heijne)
            Signal Score (−7.5): −0.19
            Possible cleavage site: 61
            >>> Seems to have a cleavable N-term signal seq.
            Amino Acid Composition of Predicted Mature Form:
            calculated from 62
            ALOM: Finding transmembrane regions (Klein et al.)
            count: 0 value: 0.69 threshold: 0.0

PERIPHERAL              Likelihood = 0.69
         modified ALOM score: −0.64
         Score for OM-PP discrimination: −24.78
         Rule: outer membrane or periplasmic protein
         Score for OM-PP discrimination: −24.78
         Rule: outer membrane or periplasmic protein
```

```
                    -continued

*** Reasoning Step: 2
            Periplasmic space? Score: 2.47798
            Periplasmic space? Score: 2.47798
                        Final Results bacterial periplasmic space --- Certainty =    0.916(Affirmative) < succ>
```

The protein has homology with the following sequences in the databases:

A homolog was found in serogroup A *N. meningitidis* but not in serogroup B, so NGS28 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 29

A DNA sequence was identified in *N. gonorrhoeae* <SEQ ID 57> which encodes amino acid sequence <SEQ ID 58; NGS29>. Analysis of this protein sequence reveals the following:

GvH: Examining signal sequence (von Heijne)
Signal Score (-7.5): -3.61
Possible cleavage site: 31
>>> Seems to have no N-terminal signal seq.
Amino Acid Composition of Predicted Mature Form:
calculated from 1
ALOM: Finding transmembrane regions (Klein et al.)
count: 0 value: 4.03 threshold: 0.0

-continued

PERIPHERAL Likelihood = 4.03
modified ALOM score: -1.31
Rule: cytoplasmic protein

*** Reasoning Step: 2
Final Results bacterial cytoplasm --- Certainty =   0.106(Affirmative) < succ>

The protein has homology with the following sequences in the databases:

```
emb|CAB83930.1|(AL162753) hypothetical protein NMA0640
[Neisseria meningitidis Z2491]
Length = 387

Score = 653 bits (1685), Expect = 0.0
Identities = 324/388 (83%), Positives = 351/388 (89%), Gaps = 1/388 (0%)

Query:    1 MNITIAAPYCSLPSEPHFNRFWYLAELLSQSHDVLLITSNFKHYDKSFRRPEDAKAASQG    60
            MNITI APYCSLPSEP+FNRFWYLAE LSQSHDVLLITS F+HYDKSFRR EDA A S G
Sbjct:    1 MNITIVAPYCSLPSEPYFNRFWYLAERLSQSHDVLLITSRFRHYDKSFRRHEDAAATSNG   60

Query:   61 RLKVMLLEESGYSKNVSLGRVTSHHRFVKHFEKWLENCRPGEQDVVYSAYPLIATNLLLG  120
            RL+V LL+E GY KNVSL RV SH  FV++  +WL + +  EQD+VYSAYPL+ATNLLLG
Sbjct:   61 RLRVKLLDEPGYRKNVSLARVASHRVFVRNLARWLHSPQAAEQDIVYSAYPLMATNLLLG  120

Query:  121 KHKARLGYKLIVDVQDVWPESFSSVVPFLKKIPHNLLPFASRANRAYRYADALVAVSQTY  180
            KHKARLGYKLIVDVQDVWPESFSSVVPFLKK+PH LLPFASRANRAYR ADAL+AVSQTY
Sbjct:  121 KHKARLGYKLIVDVQDVWPESFSSVVPFLKKVPHKLLPFASRANRAYRCADALIAVSQTY  180

Query:  181 LDRAKEANPNVPGEVVYIGADFAAIAPPPRFRSKTVRFFYLGTLSYNYDVETVCKGVRKL  240
            LDRAKEANPNVPGE VYIG DFAAIA PPRFRSKTVR FYLGTLSY+YDVETVCKGVRKL
Sbjct:  181 LDRAKEANPNVPGETVYIGTDFAAIA-PPRFRSKTVRLFYLGTLSYSYDVETVCKGVRKL  239

Query:  241 LDDGENVELHIMGGGPDLDRLKQYACDGIKFYGYIPYAEMMSVAKGCDIAVNAIHSYAMQ  300
            LDDGENVELHIMGGGPDL++LKQY    IKFYGY+PY+EMMS+AK CDIAVNAIHS+AMQ
Sbjct:  240 LDDGENVELHIMGGGPDLEKLKQYENRAIKFYGYLPYSEMMSIAKACDIAVNAIHSHAMQ  299

Query:  301 SITNKLSDYMALQKPILNSQVHDEVAEVLTLLPHENYRSGDVDGFVQAAKDILKRKNDPV  360
            S+TNKLSDYMALQKPILNSQ + EV ++L LLPHENYRSGDVD FVQAAK+ILKRK+DPV
Sbjct:  300 SVTNKLSDYMALQKPILNSQNNAEVLDLLNLLPHENYRSGDVDSFVQAAKNILKRKDDPV  359

Query:  361 QSDEIVRRFRHDISYRKIVNLIERLANE                                 388
            QSDEIVRRFR DISYRKIVNLIERLA+E
Sbjct:  360 QSDEIVRRFRRDISYRKIVNLIERLAHE                                 387

>emb|CAB58324.1|(AL121855) hypothetical protein SCF62.09
[Streptomyces coelicolor A3(2)]
Length = 407

Score = 54.7 bits (130), Expect = 2e-06
Identities = 57/243 (23%), Positives = 105/243 (42%), Gaps = 24/243 (9%)

Query:   99 RPGEQDVVYSAYP---LIATNLLLGKHKARLGYKLIVDVQDVWPESFSSVVPFLKKIPHN  155
            R G  DVV++  P    L    LL   RG + +D  D+ PE S        K + +
Sbjct:   81 RVGPVDVVHACNPPDLLFLPALWL----KRRGARFVFDQHDLIPELYLSRFGRGKDLLYR  136

Query:  156 LLPFASRANRAYRYADALVAVSQTYLDRAKEANPNVPGEVVYIGA-----DFAAIAPPPR  210
               +    R      YR AD ++A +++Y D A       P +V + +       F + P P
Sbjct:  137 AVCALERWT--YRAADVVLATNESYKDVAIRRGGRRPDDVFVVRSAPATDRFQPVPPEPE  194

Query:  211 F-RSKTVRFFYLGTLSYNYDVETVCKGVRKLLDDGENVELH--IMGGGPDLDRLKQYA--  265
              R K      YLG +     V+   + + KL D+   + H  +G G D + +
Sbjct:  195 LKRGKPHLLCYLGVMGPQDGVDYALRALAKLRDEVGRTDWHAVFVGSGDAFDAMVELSRS  254

Query:  266 ---CDGIKFYGYIPYAEMMSVAKGCDIAVNAIHSYAMQSIT--NKLSDYMALQKPILNSQ  320
               + ++F G IP A+++      D+ ++       +  ++    NK+  +YMA+  +PI++
Sbjct:  255 LGLDEQVRFTGRIPDADLVRHLSTADVCLSPDPRNPLNDVSTMNKVLEYMAMGRPIVSFD  314

Query:  321 VHD                                                          323
            + +
Sbjct:  315 LRE                                                          317
```

As a homolog was found in serogroup A *N. meningitidis* but not in serogroup B, NGS29 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 30

A DNA sequence was identified in *N. gonorrhoeae* <SEQ ID 59> which encodes amino acid sequence <SEQ ID 60; NGS30>. Analysis of this protein sequence reveals the following:

Signal Score (−7.5): −4.8
Possible cleavage site: 46
>>> Seems to have no N-terminal signal seq.
Amino Acid Composition of Predicted Mature Form:
calculated from 1
ALOM: Finding transmembrane regions (Klein et al.)
count: 0 value: 1.54 threshold: 0.0

PERIPHERAL      Likelihood = 1.54
modified ALOM score: −0.81
Rule: cytoplasmic protein \*\*\* Reasoning Step: 2
Final Results bacterial cytoplasm --- Certainty =      0.113(Affirmative) < succ>

The protein has homology with the following sequences in the databases:

A homolog was found in serogroup A *N. meningitidis* but not in serogroup B, so NGS30 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 31

A DNA sequence was identified in *N. gonorrhoeae* <SEQ ID 61> which encodes amino acid sequence <SEQ ID 62; NGS31>. Analysis of this protein sequence reveals the following:

GvH: Examining signal sequence (von Heijne) Signal Score (−7.5): −5.36
Possible cleavage site: 16
>>> Seems to have no N-terminal signal seq.
Amino Acid Composition of Predicted Mature Form:
calculated from 1
ALOM: Finding transmembrane regions (Klein et al.)
count: 0 value: 3.50 threshold: 0.0

PERIPHERAL      Likelihood = 3.50
modified ALOM score: −1.20
Rule: cytoplasmic protein \*\*\* Reasoning Step: 2
Final Results bacterial cytoplasm --- Certainty =      0.299(Affirmative) < succ>

The protein has homology with the following sequences in the databases:

```
fastidiosa (strain 9a5c)
gb|AAF84279.1|AE003977_2 (AE003977) conserved hypothetical protein
[Xylella fastidiosa]
Length = 376

Score = 73.6 bits (179), Expect = 3e-12
Identities = 82/354 (23%), Positives = 143/354 (40%), Gaps = 35/354 (9%)

Query:    1 MKIILTTSMSGLGGTETATVRLGRLLKRHGHDIILASSDG-PFVGEAQASGIRWQPVDFY    59
            MKI+ T + +G GG E    R    ++ GH + L   G P    A+ +G+    ++ +
Sbjct:    1 MKILHTEAATGCGGEEIYIYRHMLSMQAQGHHMALLCQPGAPLSTMARNAGLPVYHINMH   60

Query:   60 RGGLAGYLKSTFAYARMLRREQPDIIDCQMARVVPACALAAKIVSPKTKIICHSHGLDAA  119
               G    L     +L+RE D+++          A AA++    +T++I   S  L A
Sbjct:   61 --GPWRVLNGIHTVQHLLQRETFDVVNTTSHVDTLIAAAAARLT--RTRLIVRSRHLMAP  116

Query:  120 TYPKTAKLFDKLGAYIIGNCKHEREKLIRHGFPAGRIAYA---------YNTPPEFHFRK  170
              K+   + L   +I   +H R+ LI+ G      RI             +T PE +++
Sbjct:  117 I--KSQLTYTYLPHRVITVSQHVRDLLIKQGIQPTRIGIVPPITAQPPWMDTDPEHAWQR  174

Query:  171 TEK-------------ECAVLGTLSRLDTVRAVHLMLDILKKMVGRNIPVRLNMAGIGEE  217
             ++              ++G  ++ L  +    +LD + +   N  + L +AG GE
Sbjct:  175 LQQTRHVVRTELGFNDNDIIVGCVAVLREAKGHRELLDAIAPLCQANPRLHLVIAGDGEP  234

Query:  218 -MDNLKAQAKRLGIEDKVTFLGGVRDLTGYFKEVDILVNTPHCVGDHGAGVGNNILEAGL  276
             M +L A  K L +E ++     LG    D        DI   +    G    LEA
Sbjct:  235 VMQHLLAHRKTLTLETQIHLLGYRHDAPRLMSGFDIFA-----LATQKEAAGTVFLEAAQ  289

Query:  277 YDTPVVTYNMAGISEMVITGQTGYCIPFGDDEAFIEAVDTLIKHPELRSQMGKA        330
             P++    + G+ EM+   G     +   G+  A  A+ TL+ + + R  MG+A
Sbjct:  290 AGIPIIATRVGGVPEMLQEGTNAILVTPGNQTALTNALHTLVTNNQQRHSMGRA        343
```

```
gb|AAB49297.1|(U84350) hypothetical hydroxylase a
[Amycolatopsis orientalis]
Length = 491

Score = 111 bits (278), Expect = 1e-23
Identities = 87/269 (32%), Positives = 123/269 (45%), Gaps = 15/269 (5%)

Query:    1 LKNGAAFSWGSRYTEFDF----TDKFSDGPGTVYQVRRAVFDKILIEEAAKQGVEVRFGH   56
            +K G  F WG+R   + F    + K +    YQV RA FD IL++ A  +GV VR  G
Sbjct:   73 IKRGGTFRWGARPEPWTFHFGISAKMAGSTSHAYQVERAKFDDILLKNAKSKGVVVREGC  132

Query:   57 GVTAFDNSGDFARLNIETDT-GESYELTAKFVLDASGY-GRVLPRLLNLETPSHLPPRQT  114
               V     G+       TD G ++E++A+FV+DASG  R+   ++       S
Sbjct:  133 SVNDVVEDGERVTGARYTDADGNAHEVSARFVIDASGNKSRLYTKVNGSRNYSEFFRSLA  192

Query:  115 HFTHIDDNITHPKFDRNKILITTHPQHRDVWIWLIPFGDNRCSVGVV---GTPDKLAGES  171
              F + +   P+       IL          W W IP  D   SVG V    DK+ G+
Sbjct:  193 LFGYFEGGKRLPEPVSGNILSVAFDSG---WFWYIPLSDTLTSVGAVVRREDADKIQGDR  249

Query:  172 ETVLKKFVYECPMLSEILDKAVWENDFPFRSIQ---GYSANVKSLHGRHFALLGNAAEFL  228
              E   L   + ECP++SE L  A      +  ++    YS  S       L+G+AA F+
Sbjct:  250 EKALNTLIAECPLISEYLSNATRVTTGRYGELRVRKDYSYQQDSYWRPGMVLVGDAACFV  309

Query:  229 DPVFSSGVTIALHSAELAADLLTKQLKGE                                257
            DPVFSSGV +A +SA LAA +   L G+
Sbjct:  310 DPVFSSGVHLATYSALLAARSINSVLAGD                                338
```

A homolog (amino acids 280-341) was found in serogroup A *N. meningitidis* but not in serogroup B, so NGS31 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 32

A DNA sequence was identified in *N. gonorrhoeae* <SEQ ID 63> which encodes amino acid sequence <SEQ ID 64; NGS32>. Analysis of this protein sequence reveals the following:

Signal Score (−7.5): −3.49
Possible cleavage site: 38
>>> Seems to have no N-terminal signal seq.
Amino Acid Composition of Predicted Mature Form:

-continued calculated from 1
ALOM: Finding transmembrane regions (Klein et al.)
count: 0 value: 7.80 threshold: 0.0

PERIPHERAL    Likelihood = 7.80
modified ALOM score: −2.06
Rule: cytoplasmic protein

*** Reasoning Step: 2
Final Results bacterial cytoplasm --- Certainty =    0.278(Affirmative) < succ>

The protein has homology with the following sequences in the databases:

```
fastidiosa (strain 9a5c)
gb|AAF83310.1|AE003899_2 (AE003899) phage-related repressor protein
[Xylella fastidiosa]
Length = 143

Score = 87.0 bits (214), Expect = 2e-16
Identities = 40/71 (56%), Positives = 54/71 (75%)

Query:    1 MFSGEQLGQAISEAIKRKNVSQKEVADHFGVKQPSVSGWIKNGRIDKKHLDKLIDYFSDV   60
            M +GEQLG+AI +A++  K V+  ++A+HFGVK PSV GWIK GRI K+ L   L YFSDV
Sbjct:    1 MLTGEQLGRAIKQAMQLKGVTPTKMAEHFGVKAPSVYGWIKEGRISKEKLPSLWSYFSDV   60

Query:   61 VTPSHFGIETF                                                  71
             V P+H+G+E +
Sbjct:   61 VGPTHWGLEAW                                                  71

>sp|P18680|RPC1_BPHK0 26 KD REPRESSOR PROTEIN (REGULATORY PROTEIN CI)
emb|CAA34222.1|(X16093) cI gene product (AA 1-208) [Bacteriophage HK022]
Length = 235

Score = 80.5 bits (197), Expect = 2e-14
Identities = 60/200 (30%), Positives = 99/200 (49%), Gaps = 15/200 (7%)

Query:   22 QKEVADHFGVKQPSVSGWIKNGRIDKKHLDKLIDYFSDVVTPSHF--------GIETFRV   73
               Q ++A    V    ++S W     I +K DK+    S + +  +         GI  +
```

```
Sbjct:  29 QADLAVRLKVTPKAISKWFNGESIPRK--DKMESLASVLGTTAAYLHGYADDDGITVNHL   86

Query:  74 LKSNEQSSIRFPRLNAEATCGAGT-INDHYIEVVDYVTVAAAWAREKLGGNLNK-IQVIT  131
           +SN+      R   L+ +A+ G GT +++ +IE + +       AR    G   + ++VIT Sbjct:  87 SRSNDY--YRVDVLDVQASAGPGTMVSNEFIEKIRAIEYTTEQARILFNGRPQESVKVIT  144

Query: 132 ARGDSMEPTIENGDVMFVDTAVEAFDGDGLYLLWYIDGLKAKRLQSTVGGGLMIISDNSS  191
           RGDSME TI  GD +FVD ++   FDGDG+Y+ Y   +   KRLQ       L +ISDN++

Sbjct: 145 VRGDSMEGTINPGDEIFVDVSITCFDGDGIYVFVYGKTMHVKRLQMQ-KNRLAVISDNAA  203

Query: 192 YRTETVRGEDLNAVRIIGRI                                         211
           Y    +      +  +I+ ++

Sbjct: 204 YDRWYIEEGEEEQLHILAKV                                         223
```

Based on this analysis, it was predicted that this protein from *N. gonorrhoeae*, and its epitopes, could be useful antigens for vaccines or diagnostics.

Based on this analysis, it was predicted that this protein from *N. gonorrhoeae*, and its epitopes, could be useful antigens for vaccines or diagnostics.

Example 33

A DNA sequence was identified in *N. gonorrhoeae* <SEQ ID 65> which encodes amino acid sequence <SEQ ID 66; NGS33>. Analysis of this protein sequence reveals the following:

| |
|---|
| GvH: Examining signal sequence (von Heijne) |
| Signal Score (-7.5): -4.87 |
| Possible cleavage site: 31 |
| >>> Seems to have no N-terminal signal seq. |
| Amino Acid Composition of Predicted Mature Form: calculated from 1 |
| ALOM: Finding transmembrane regions (Klein et al.) |
| count: 0 value: 4.88 threshold: 0.0 |

| | |
|---|---|
| PERIPHERAL | Likelihood = 4.88 |
| modified ALOM score: -1.48 | |
| Rule: cytoplasmic protein | |

*** Reasoning Step: 2
Final Results

| | |
|---|---|
| bacterial cytoplasm --- Certainty = | 0.313(Affirmative) < succ> |

The protein has homology with the following sequences in the databases:

Example 34

A DNA sequence was identified in *N. gonorrhoeae* <SEQ ID 67> which encodes amino acid sequence <SEQ ID 68; NGS34>. Analysis of this protein sequence reveals the following:

| |
|---|
| GvH: Examining signal sequence (von Heijne) |
| Signal Score (-7.5): -5.65 |
| Possible cleavage site: 50 |
| >>> Seems to have no N-terminal signal seq. |
| Amino Acid Composition of Predicted Mature Form: calculated from 1 |
| ALOM: Finding transmembrane regions (Klein et al.) |
| count: 0 value: 3.76 threshold: 0.0 |

| | |
|---|---|
| PERIPHERAL | Likelihood = 3.76 |
| modified ALOM score: -1.25 | |
| Rule: cytoplasmic protein | |

*** Reasoning Step: 2
Final Results

| | |
|---|---|
| bacterial cytoplasm --- Certainty = | 0.310(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
gb|AAF31132.1|(AF069529) Gp54 [Bacteriophage HK97]
Length = 273

Score = 47.4 bits (111), Expect = 3e-04
Identities = 33/123 (26%), Positives = 52/123 (41%), Gaps = 20/123 (16%)

Query: 221 NGGLSGKPKNANVPRRRKTHGVPLQEIADLYNEVLGGRLPSVQVLNDTRKRAIANRWCEM  280
           NGG  G+ K   P RRK   +  +   + YN +G RLP    +N+ RKR +   +
Sbjct: 160 NGGGDGQVK----PERRKAERIDYESFLNAYNTEVGDRLPHAVAVNEKRKRRL-KKIIPQ  214

Query: 281 LGTAAPNGKVRFGDKETGLAWFAGFFRKVA--MNPFWMGENQTGFAVGFDWIFKAGNFVK  338
           L T   +G        F   R       PF+ G+N TG+   FD++ +    +
Sbjct: 215 LKTPNVDG-------------FRAYVRAFVHQAKPFYFGDNDTGWTADFDYLLREDSLTG  261

Query: 339 ILE                                                         341
           + E
Sbjct: 262 VRE                                                         264
```

```
>pir||H82649 hypothetical protein XF1674 XF1569 [imported] -
Xylella fastidiosa (strain 9a5c)
gb|AAF84378.1|AE003986_8 (AE003986) hypothetical protein
[Xylella fastidiosa]
gb|AAF84483.1|AE003993_2 (AE003993) hypothetical protein
[Xylella fastidiosa]
Length = 316

Score =  167 bits (424), Expect = 2e-40
Identities = 108/308 (35%), Positives = 152/308 (49%), Gaps = 30/308 (9%)

Query:   10 ETSVIRSLSSASLYMFTRRMFYQRRGYVWQRANHHAPICNALERVFNGETKRLIINIPPR   69
            E +VI++    A    FTR  F QR+   ++   HH  I   ++ V  G  K ++IN+PP
Sbjct:   10 EQAVIKARCEADHLFFTRYFFKQRQQLRFRVNWHHHVIAGVVDDVIAGRRKDVVINVPPG   69

Query:   70 YSKTEIAVVNFIAWAMGRVPDCEFIHASYSAALAVNNSVQIRNLVQHEEYRAIFP-DLAL  128
            SKTE+  +N +A +    P   F+H SYS  LA+ NS    R +VQ +EYRA++P  ++A
Sbjct:   70 SSKTELVAINVMARGLALNPYARFLHISYSDDLALLNSETAREIVQSDEYRALWPLEIAD  129

Query:  129 AGESGHHWKTT-----AGGVMYXXXXXXXXXXXXXXXRHREGFGGCIIIDDPHKADEARSE  183
            +S   W          AGGV Y                G+ G IIIDDP K ++A S+
Sbjct:  130 DAKSKKRWNVVVDGKKAGGV-YAVSLGGQVTGFRAGHMAPGWQGAIIIDDPLKVEDAYSK  188

Query:  184 VRRQNVIDWFQNTVESRKNSPDTPIILIMQRLHEKDLAGWLLDGGNGEEWEHLCLPAIQE  243
            R           +TV+SRK SPDTPII+IMQRL + D  G++   GG    WE +  +PA+ +
Sbjct:  189 TGRSKANRKLVSTVKSRKASPDTPIIVIMQRLAQDDPTGFIQSGGFPGAWECIEIPALID  248

Query:  244 DG---------------------TALWPEKHDIETLRRMEQAAPYVFAGQYLQKPAPP  280
            D                      + WP K  +  L  +E    YVF+GQY Q+P+P
Sbjct:  249 DAYVSRLPEHVQGQVVRDAQDQDGRYSYWPYKEPLAELLALEATDRYVFSGQYQQRPSPL  308

Query:  281 DGGTFKPD                                                     288
            GG   K D
Sbjct:  309 GGGIIKGD                                                     316
```

Based on this analysis, it was predicted that this protein from *N. gonorrhoeae*, and its epitopes, could be useful antigens for vaccines or diagnostics.

Example 35

A DNA sequence was identified in *N. gonorrhoeae* <SEQ ID 69> which encodes amino acid sequence <SEQ ID 70; NGS35>. Analysis of this protein sequence reveals the following:

GvH: Examining signal sequence (von Heijne)
Signal Score (−7.5): −1.07
Possible cleavage site: 40
>>> Seems to have no N-terminal signal seq.

Amino Acid Composition of Predicted Mature Form: calculated from 1
ALOM: Finding transmembrane regions (Klein et al.)
count: 0 value: 1.64 threshold: 0.0

PERIPHERAL   Likelihood = 1.64
modified ALOM score: −0.83
Rule: cytoplasmic protein

*** Reasoning Step: 2
Final Results bacterial cytoplasm --- Certainty =   0.020(Affirmative) < succ>

The protein has homology with the following sequences in the databases:

```
>ref|NP_047925.1|gp34 [Bacteriophage phi-C31]
emb|CAA07104.1|(AJ006589) gp34 [Bacteriophage phi-C31]
Length = 457

Score =  59.7 bits (143), Expect = 1e-07
Identities = 68/272 (25%), Positives = 117/272 (43%), Gaps = 49/272 (18%)

Query:  226 GYSPVEQIIMTVNIALKRQVHALEYYTAGSVPDALVGVPETWSADDIRRFQEYWDLLLSG  285
            G SP+    ++ +AL  Q +    +++  G++P A+V VP T S + + R  +E W     SG
Sbjct:  192 GCSPISYARESIGLALAAQKYGSKFFANGAMPGAVVPEVPGTMSEEGLARAREAWRAANSG  251

Query:  286 -----------ETAQRRKMRFVPGELSRNFRETKQPPLKDVYDEWLARVVCFAFSVEPTP  334
                        E A+  K+   P E   F +T+Q  + ++      AR+     F V P
Sbjct:  252 VDNAHRVALLTEGAKFSKVAMSPDEAQ--FLQTRQFQVPEI-----ARI----FGVPPH-  299

Query:  335 FVAQVNRSVAETS--REQSLSDGMGSLKNWVKALIDDVLARYMDMAA--YEFVWKGEESL  390
                 ++    S + S    EQ+++   M SL+ W++ +          A    + FV    + +
Sbjct:  300 LISDATNSTSWGSGLAEQNIAFTMFSLRPWLERIEAGFNRLLFAETADRFRFVKFNLDEI  359

Query:  391 N---PKEQAEIYAIYKNAGILTADEIRAELGKEPLP-GQG--------------QPEPDK  432
                 PKE+ E++++    GI + DE+RA   PLP G G                +PEP+
```

```
Sbjct:  360 KRGAPKERMELWSLGLQNGIYSIDEVRAAEDMTPLPDGLGEKYRVPLNLGEVGEEPEPEP   419

Query:  433 QDG----RKPEEPPNQGAEKLGKSESPMSEDE                              460
                P E P++  E  GK +    + +E
Sbjct:  420 APAPPAIEPPAEEPDEEPEPEGKPDDEGATEE                              451
```

A homolog (amino acids 641-700) was found in serogroup A *N. meningitidis* but not in serogroup B, so NGS35 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 36

A DNA sequence was identified in *N. gonorrhoeae* <SEQ ID 71> which encodes amino acid sequence <SEQ ID 72; NGS36>. Analysis of this protein sequence reveals the following:

GvH: Examining signal sequence (von Heijne)
Signal Score (-7.5): 4.3
Possible cleavage site: 26
>>> Seems to have a cleavable N-term signal seq.

Amino Acid Composition of Predicted Mature Form: calculated from 27
ALOM: Finding transmembrane regions (Klein et al.)
count: 0 value: 1.70 threshold: 0.0

PERIPHERAL   Likelihood = 1.70
modified ALOM score: −0.84
Score for OM-PP discrimination: 0.02
Rule: outer membrane or periplasmic protein
Score for OM-PP discrimination: 0.02
Rule: outer membrane or periplasmic protein

*** Reasoning Step: 2
Outer membrane? Score: 0.00213559
Outer membrane? Score: 0.00213559
Final Results bacterial outer membrane --- Certainty =   0.232(Affirmative) < succ>

The protein has homology with the following sequences in the databases:

```
>pir||D82437 TonB receptor-related protein VCA0625 [imported] -
Vibrio cholerae
(group O1 strain N16961)
gb|AAF96526.1|(AE004392) TonB receptor-related protein [Vibrio cholerae]
Length = 784

Score = 103 bits (256), Expect = 2e-20
Identities = 104/427 (24%), Positives = 162/427 (37%), Gaps = 100/427 (23%)

Query:   31 NTEQQKELNTIVVHGKRS-ADQKGADDVYYKNVSNAYVGKEYLERYRVQSAGDVLKGLNG    89
            NTEQ   +  T+ VHG+    DQ+    D            L++ R  + D+   G+
Sbjct:   57 NTEQAVD-ETVTVHGQSILTDQRTRSD---------------LDKVRGIANADIFSGITS   100

Query:   90 VYNMNTRTAGGAITPNIRGITGKGRIPVTIDGTEQTIDVWMNNYGVGDRNYLDPALFRSI   149
            V + N      GA+   IRG+ G+GR+P+ IDG+  Q+         GV DR Y+D L  S+
Sbjct:  101 VQSNNMHNEAGALDIGIRGVQGEGRVPIFIDGSLQSTHTSRGYQGVSDRTYIDTDLLSSL   160

Query:  150 AVEKSPALTRG--VKSGVGGAMSIRTIEPSDIIPEGRNWGIEVKTEFSGNTVAQKNDLRQ   207
              V K   +      VGG  ++    T+   DII + +  +G+  +K
Sbjct:  161 TVNKGATIESSPYASGAVGGVVNATTLGIKDIIKDDQAFGVVLK----------------   204

Query:  208 FLGRDYRTLSPIGATADGVSGMPDVLTGYTGKPSPTALLLDEGIADTKFSGGKSHTNFKD   267
                         A A+   +   PDV   Y+  +        LDE    + F  G
Sbjct:  205 -------------ARANNHNRTPDVSGDYSEQGQ---YALDERGEHSAFKHG--------   240

Query:  268 DRQLMLSAAFKTDITDGLAAYSHRQKGNYYAGKRGYQSYLNNPI--YGADACYDQYPDKS   325
                LML   ++ +  +  + AYS R KGN++AGK GY+ Y     P+   G  +       + S
Sbjct:  241 --SLMLGLGYQAESFNTVLAYSKRSKGNHFAGKKGYEEY-QEPVVGQGQEVVNTSFESDS   297

Query:  326 WREKDILCKSSASLVPNMAVLFRPGEEIMNSHTDTKILLLKNNWYLPDNQKISLQYMDNK   385
            W K   S   N   +R      H     +L    WY       Y D K
Sbjct:  298 WLFK---LASDTGTAHNADFNYR-------HHAQKAGEVLMAYWYKSSEDWEGNPYPDGK   347

Query:  386 IGFGEINPLITAWILGFAEQSLNEPVQQAPGIGTKIDSKTYKIGYEWKPQNNKWIDLQAD   445
             +  W LG A+ +                          TY   Y ++P ++ W++L A+
Sbjct:  348 -------DRMPQWGLGTAKVN-----------------TYSANYYYQP-DHPWLNLNAN   381

Query:  446 MWRVKTD   452
            W  + D
Sbjct:  382 FWYTEAD   388

Score = 94.7 bits (234), Expect = 5e-18
Identities = 80/290 (27%) , Positives = 126/290 (42%), Gaps = 37/290 (12%)

Query:  929 SYDLADNHRLFARYARMSRFPSLYELTAATGSGGLYGSETVAEYS----LKPEKSTNWEV   984
            +Y L  +LF  + +R   R PSLYE T      S   V Y+     +KPE++ N EV
```

-continued

```
Sbjct:  514 TYALTPSTQLFLKSSRTYRMPSLYETTL---------SNEVFSYNPYNPIKPEQAWNNEV  564

Query:  985 GYNFNFAPHFAKLRQGDLRLTYYSNKIKNQIDTSN--EDGGMIQ---------YDKAVSK 1033
            G  F  +     +  + +L ++Y+ N IK+ I      + GM  +          YDK
Sbjct:  565 GVQFMASNSVLQDDRLNLSVSYFRNSIKDFISGGRLAKTPGMSEWQANFTFTNYDKLQLS  624

Query: 1034 GVELQSRLDSGRFFASFGGTYRLKHMVCDKGIAFKFDYYLQRVPECLEGGFGLSRFFQSL 1093
            G EL +      + F T   +  +C   A           C    GF          +
Sbjct:  625 GWELGAHYQYAWLYTHFAATLYSETKICSVQQA-----QYAESDTCNSLGFAWGLTPTRI  679

Query: 1094 QPKYSLTLDVGTRFFNEKLELGMRAIHHSKAERRNYDKLIADGAGQVYARNGKPYGWHAA 1153
            PK  +L L+VGT+FFN+ L+ G++   +HS    + N     +A  A            Y
Sbjct:  680 PPKQNLYLNVGTKFFNDTLDSGVKVSYHSG--KSNPSDWLAGTAANPILEIPSDY-----  732

Query: 1154 TLLDAYARYRIGKHIDLNFSVTNLANRYYLDPMSSTPVPGPGRTITFGIK           1203
            +D Y++Y +   +  L F++ N+ +RY + P  S    +P PGRTIT G  +
Sbjct:  733 -TIDLYSQYELNANTQLFFAINNVTDRYQVRPGSVVSMPDPGRTITLGFE            781
```

Based on this analysis, it was predicted that this protein from *N. gonorrhoeae*, and its epitopes, could be useful antigens for vaccines or diagnostics.

Example 37

A DNA sequence was identified in *N. gonorrhoeae* <SEQ ID 73> which encodes amino acid sequence <SEQ ID 74; NGS37>. Analysis of this protein sequence reveals the following:

GvH: Examining signal sequence (von Heijne)
Signal Score (−7.5): 4.47
Possible cleavage site: 21
>>> Seems to have a cleavable N-term signal seq.
Amino Acid Composition of Predicted Mature Form:
calculated from 22
ALOM: Finding transmembrane regions (Klein et al.)
count: 0 value: 7.21 threshold: 0.0

PERIPHERAL        Likelihood = 7.21
modified ALOM score: −1.94
Score for OM-PP discrimination: 16.42
Rule: outer membrane or periplasmic protein
Score for OM-PP discrimination: 16.42
Rule: outer membrane or periplasmic protein

*** Reasoning Step: 2
Outer membrane? Score: 1.64214
Outer membrane? Score: 1.64214
Final Results bacterial outer membrane --- Certainty =    0.938(Affirmative) < succ>

The protein has homology with the following sequences in the databases:

The protein was expressed in *E. coli* as an insoluble 32.45 kDa His-fusion product and then purified.

Based on this analysis, it was predicted that this protein from *N. gonorrhoeae*, and its epitopes, could be useful antigens for vaccines or diagnostics.

Example 38

A DNA sequence was identified in *N. gonorrhoeae* <SEQ ID 75> which encodes amino acid sequence <SEQ ID 76; NGS38>. Analysis of this protein sequence reveals the following:

GvH: Examining signal sequence (von Heijne)
Signal Score (−7.5): 0.34
Possible cleavage site: 24
>>> Seems to have a cleavable N-term signal seq.
Amino Acid Composition of Predicted Mature Form:
calculated from 25
ALOM: Finding transmembrane regions (Klein et al.)
count: 0 value: 3.98 threshold: 0.0

PERIPHERAL        Likelihood = 3.98
modified ALOM score: −1.30
Score for OM-PP discrimination: 2.87
Rule: outer membrane or periplasmic protein
Score for OM-PP discrimination: 2.87
Rule: outer membrane or periplasmic protein

*** Reasoning Step: 2
Outer membrane? Score: 0.287446
Outer membrane? Score: 0.287446
Final Results bacterial outer membrane --- Certainty =    0.607(Affirmative) < succ>

The protein has homology with the following sequences in the databases:

```
>sp|Q03155|AIDA_ECOLI ADHESIN AIDA-I PRECURSOR
piR||S28634 adhesin AIDA-I precursor - Escherichia coli plasmid pIB6
emb|CAA46156.1|(X65022) AIDA-I [Escherichia coli]
Length = 1286

Score = 35.8 bits (81), Expect = 0.67
Identities = 34/138 (24%), Positives = 62/138 (44%), Gaps = 16/138 (11%)

Query:   3 ASQLTLAVLLAAAFGSAYAVEVKGGDSSKGQLIQAAESDFLPFGSGAADIKVSTGNGLSK   62
           A   L + +    G+A+AV + G  SS G  + E+   +  G G ++   V++G    ++
Sbjct:  31 AKNTLLVLAVVSTIGNAFAVNISGTVSS-GGTVSSGETQIVYSGRGNSNATVNSGG--TQ   87

Query:  63 SINLEAGPAQRIRNKYGNAPINGGNQNTNVNGAANSRYLQPGDINPIA--GWFSKTRLA-  119
           +N             N     + G+QN    +GA  S    +   GI  ++  G ST L+
Sbjct:  88 IVNNGGKTTATTVN-------SSGSQNVGTSGATISTIVNSGGIQRVSSGGVASATNLSG  140

Query: 120 ---QVWYEKRANNTEVFS                                           134
              ++     A+NT +FS
Sbjct: 141 GAQNIYNLGHASNTVIFS                                           158
```

```
>sp|Q03155|AIDA_ECOLI ADHESIN AIDA-I PRECURSOR
pir||S28634 adhesin AIDA-I precursor - Escherichia coli plasmid pIB6
emb|CAA46156.1|(X65022) AIDA-I [Escherichia coli]
        Length = 1286

Score = 35.8 bits (81), Expect = 0.67
 Identities = 34/138 (24%), Positives = 62/138 (44%), Gaps = 16/138 (11%)

Query:   3 ASQLTLAVLLAAAFGSAYAVEVKGGDSSKGQLIQAAESDFLPFGSGAADIKVSTGNGLSK    62
           A   L +++  G+A+AV + G SS G + + E+ +  GG ++  V++G   ++
Sbjct:  31 AKNTLLVLAVVSTIGNAFAVNISGTVSS-GGTVSSGETQIVYSGRGNSNATVNSGG--TQ   87

Query:  63 SINLEAGPAQRIRNKYGNAPINGGNQNTNVGAANSRYLQPGDINPIA--GWFSKTRLA-   119
            +N        N       + G+QN  +GA S  + GI ++  G ST L+
Sbjct:  88 IVNNGGKTTATTVN-------SSGSQNVGTSGATISTIVNSGGIQRVSSGGVASATNLSG  140

Query: 120 ---QVWYEKRANNTEVFS                                            134
              ++      A+NT +FS
Sbjct: 141 GAQNIYNLGHASNTVIFS                                            158

>pir||G81213 conserved hypothetical protein NMB0313 [imported] - Neisseria
meningitidis (group B strain MD58)
gb|AAF40758.1|(AE002388) conserved hypothetical protein
[Neisseria meningitidis MC58]
        Length = 488

Score = 84.3 bits (207), Expect = 3e-15
 Identities = 111/498 (22%), Positives = 185/498 (36%), Gaps = 35/498 (7%)

Query:   7 LLFLPLCTVCLAAPSNDAADERRRLLDEGSRQTQQYRESGW--LDTEQARGEVEENDGYI   64
           +L LPL       S   A+E  R  D SR + E+   +D E+  G+V E   +
Sbjct:  19 MLLLPLLA------SAAYAEETPREPDLRSRPEFRLHEAEVKPIDREKVPGQVREKGKVL   72

Query:  65 SIGGEIYQVGDTAEELESAIYHALNARQWHKVRQFAARYAKLPRHKPALIHLADALQKRD  124
            I GE      E L  A+Y A+ +   +R    Y  +    L  A +
Sbjct:  73 QIDGETLL--KNPELLSRAMYSAVVSNNIAGIRVILPIYLQQAQQDKMLALYAQGILAQA  130

Query: 125 EGDFRAAGNSFQTALEAEPDNPRLLLEAGRFYAEDNQNKESAAAFEKVLKTDIPAETRPI  184
            +G   A  +   + A+PD P + +       E+ QN+ +A F +++ ++P+
Sbjct: 131 DGRVKEAISHYRELIAAQPDAPAVRMRLAAALFENRQNEAAADQFDRLKAENLPPQLMEQ  190

Query: 185 VENYLSELGKRRRWHGQISLGYGYNSNVNQGNGINQCVWEIAGMCLMERTLPAPTDSTFS  244
           VE Y   L +R W        N+NQ  Q          + T P     D T
Sbjct: 191 VELYRKALRERDAWKVNGGFSVTREHNINQAPKRQQ---------YGKWTFPKQVDGTAV  241

Query: 245 SYSATAEKTVPLKGNHGVQVRGVLYGNRYTEKDKDSAAMPDYGYRNGSLYAGYAYADARS  304
           +Y  AEK    LK    G +   Y    K       +         +  G  +AD R
Sbjct: 242 NYRLGAEKKWSLKNGWYTTAGGDVSGRVYPGNKK-------FNDMTAGVSGGIGFADRRK  294

Query: 305 SFSLLPYFEYDFRNRHTHYRAWGADADWSRTLSPHWRINSHAGAKKTGYGGQSKTYFADF  364
            +         L   E   +      GA   ++R  +P W+ S A    +G     ++D
Sbjct: 295 DAGLAVFHERRTYGNDAYSYTNGARLYFNRWQTPKWQTLSSA---EWGRLKNTRRARSDN  351

Query: 365 KQYELGAGAEFSITLKSGLLVNFDAARKAYP-EKSSSSKEYTARLGAYRLFSGGTYLNAV  423
                        ++     F + +  D R+ P ++    + Y R  A+   GG+ L+++
Sbjct: 352 THLQISNSLVFYRNARQYWMGGLDFYRERNPADRGDNFNRYGLRF-AWGQEWGGSGLSSL  410

Query: 424 LLY--RRSLYDAASFVSDNK--RRRDKQYIMMAAAGFPQWNIKGVYPELRFRRTIAHSNA  479
           L    +  Y+  F S K    RRRDK+      +    +    + KG+  P L    SN
Sbjct: 411 LRLGAAKRHYEKPGFFSGFKGERRRDKELNTSLSLWHRALHFKGITPRLTLSHRETRSND  470

Query: 480 VYYRYRQNEWLLGFKYRF                                            497
           V+  Y +N   + F  F
Sbjct: 471 VFNEYEKNRAFVEFNKTF                                            488

>pir||C81790 conserved hypothetical protein NMA2174 [imported] -
Neisseria meningitidis (group A strain Z2491)
emb|CAB85386.1|(AL162758) conserved hypothetical protein
[Neisseria meningitidis Z2491]
        Length = 490

Score = 84.0 bits (206), Expect = 4e-15
 Identities = 111/498 (22%), Positives = 185/498 (36%), Gaps = 35/498 (7%)

Query:   7 LLFLPLCTVCLAAPSNDAADERRRLLDEGSRQTQQYRESGW--LDTEQARGEVEENDGYI   64
           +L LPL       S   A+E  R  D SR + E+   +D E+  G+V E   +
Sbjct:  21 MLLLPLLA------SAAYAEETPREPDLRSRPEFRLHEAEVKPIDREKVPGQVREKGKVL   74

Query:  65 SIGGEIYQVGDTAEELESAIYHALNARQWHKVRQFAARYAKLPRHKPALIHLADALQKRD  124
            I GE      E L  A+Y A+ +   +R    Y  +    L  A +
Sbjct:  75 QIDGETLL--KNPELLSRAMYSAVVSNNIAGIRVILPIYLQQAQQDKMLALYAQGILAQA  132
```

-continued

```
Query: 125 EGDFRAAGNSFQTALEAEPDNPRLLLEAGRFYAEDNQNKESAAAFEKVLKTDIPAETRPI    184
            +G   + A + ++   + A+PD P + +           E+ QN+ +A  F+++    ++P +
Sbjct: 133 DGRVKEAISHYRELIVAQPDAPAVRMRLAAALFENRQNEAAADQFDRLKAENLPPQLMEQ    192

Query: 185 VENYLSELGKRRRWHGQISLGYGYNSNVNQGNGINQCVWEIAGMCLMERTLPAPTDSTFS    244
            VE Y   L +R W              N+NQ     Q              + T P   D T
Sbjct: 193 VELYRKALRERDAWKVNGGFSVTREHNINQAPKRQQ---------YGKWTFPKQVDGTAV    243

Query: 245 SYSATAEKTVPLKGNHGVQVRGVLYGNRYTEKDKDSAAMPDYGYRNGSLYAGYAYADARS    304
            +Y    AEK     LK      G + G  Y      K         +       + G +AD R
Sbjct: 244 NYRLGAEKKWSLKNGWYTTAGGDVSGRVYPGNKK-------FNDMTAGVSGGIGFADRRK    296

Query: 305 SFSLLPYFEYDFRNRHTHYRAWGADADWSRTLSPHWRINSHAGAKKTGYGGQSKTYFADF    364
                 L + E         +    GA   ++R  +P W+    S A    + G        ++    +D
Sbjct: 297 DAGLAVFHERRTYGNDAYSYTNGARLYFNRWQTPKWQTLSSA---EWGRLKNTRRARSDN    353

Query: 365 KQYELGAGAEFSITLKSGLLVNFDAARKAYP-EKSSSSKEYTARLGAYRLFSGGTYLNAV    423
                ++     F   +  +  D  R+  P ++  +     Y   R A+    GG+ L+++
Sbjct: 354 THLQISNSLVFYRNARQYWMGGLDFYRERNPADRGDNFNRYGLRF-AWGQEWGGSGLSSL    412

Query: 424 LLY--RRSLYDAASFVSDNK--RRRDKQYIMMAAAGFPQWNIKGVYPELRFRRTIAHSNA    479
            L     + Y+   F S  K    RRRDK+    +          + KG+ P L              SN
Sbjct: 413 LRLGAAKRHYEKPGFFSGFKGERRRDKELNTSLSLWHRALHFKGITPRLTLSHRETRSND    472

Query: 480 VYYRYRQNEWLLGFKYRF    497
            V+  Y +N    + F    F
Sbjct: 473 VFNEYEKNRAFVEFNKTF    490
```

The protein was expressed in *E. coli* as an insoluble 52.03 kDa His-fusion product and then purified.

Based on this analysis, it was predicted that this protein from *N. gonorrhoeae*, and its epitopes, could be useful antigens for vaccines or diagnostics.

Example 39

A DNA sequence was identified in *N. gonorrhoeae* <SEQ ID 77> which encodes amino acid sequence <SEQ ID 78; NGS39>. Analysis of this protein sequence reveals the following:

GvH: Examining signal sequence (von Heijne)
Signal Score (-7.5): -5.38

Possible cleavage site: 18
>>> Seems to have no N-terminal signal seq.
Amino Acid Composition of Predicted Mature Form:
calculated from 1
ALOM: Finding transmembrane regions (Klein et al.)
count: 0 value: 7.16 threshold: 0.0

| PERIPHERAL | Likelihood = 7.16 |
|---|---|
| modified ALOM score: -1.93 | |
| Rule: cytoplasmic protein | |

*** Reasoning Step: 2
Final Results bacterial cytoplasm --- Certainty =      0.325(Affirmative) < succ>

The protein has homology with the following sequences in the databases:

```
>ref|NP_052685.1|serine protease EspP [Escherichia coli]
pir||T00317 probable serine proteinase espP, extracellular - Escherichia coli
plasmid pO157
pir||T42120 probable serine proteinase espP, extracellular - Escherichia coli
plasmid pO157
emb|CAA66144.1|(X97542) putative exoprotein-precursor [Escherichia coli]
dbj|BAA31836.1|(AB011549) serine protease EspP [Escherichia coli]
gb|AAC70088.1|(AF074613) putative exoprotein-precursor [Escherichia coli
O157:H7]
Length = 1300

Score = 58.9 bits (141), Expect = 2e-07
Identities = 153/687 (22%), Positives = 248/687 (35%), Gaps = 106/687 (15%)

Query:  194 DLTVENKNTLSDA---EFGVYALNTSMVNLSSKDNNEVKSTQVGLYSQDGGSINVDR---    247
            D        +NT +DA        Y N ++ +LS  D  E    + +G     +       +V R
Sbjct:  595 DYVAGMQNTEADAVKQNGNAYKTNNAVSDLSQPDW-ETGTFRFGTLHLENSDFSVGRNAN    653

Query:  248 --------KDNIIEGDAVALVGKGGSQNIRAS----RTNLISSKSLGIHAEQAAKIAITG    295
                    K NI  GD  A +       +NI         R N++      S G    E        IT
Sbjct:  654 VIGDIQASKSNITIGDTTAYIDLHAGKNITGDGFGFRQNIVRGNSQG---ETLFTGGITA    710

Query:  296 ASNTIHASNAAIRSLDKSEVKIDGQITIDSNVANLARQDGSIH---LNYKDDTRITGATV    352
            +TI     + A             ++ + TI+ N A++   Q G             ++     + +TG
Sbjct:  711 EDSTIVIKDKAKALFSNYVYLLNTKATIE-NGADVTTQSGMFSTSDISISGNLSMTGNPD    769

Query:  353 SDKGLVAIKPLNNTNIVADTIHYKGDVLAVNKGKVELDF----TPNILLAGRLDNFSGLT    408
            D          LN+ + +        + +++A NK V D       + +I+        + S L+
```

```
                                -continued
Sbjct:    770 KDNKFEPSIYLNDASYLLTDDSAR--LVAKNKASVVGDIHSTKSASIMFGHDESDLSQLS    827

Query:    409 DSKHKNLFENYVANLDSKSAGEINFNLAKDAL----WTMTGQSWLDKLEGQGTIDFNNDA    464
              D  KL    +  D    G +N  A   +  W +TG S L  L+    ++ +  D+
Sbjct:    828 DRTSKGLALGLLGGFDVSYRGSVNAPSASATMNNTWWQLTGDSALKTLKSTNSMVYFTDS    887

Query:    465 KTSGR--ALHIGELAGANK-FLMHLNKDGIHSDMLYVKKGTSTPQEVVVKNLSEVLDSMN    521
               + +   L + ELA +N +  M  N     SD L VKK S     ++     L + L
Sbjct:    888 ANNKKFHTLTVDELATSNSAYAMRTNLS--ESDKLEVKKHLSGENNIL---LVDFLQKPT    942

Query:    522 YGERLRFATVTNSKNEFVNGKKYIDDTHLMEDALTVEYSAHNGXXXXXXXXXXXSFNGSEM    581
              ++L   V+  K+   N  K       T    D   V
Sbjct:    943 PEKQLNIELVSAPKDTNENVFKASKQTIGFSDVTPV-----------------------    978

Query:    582 TAEKAGDDYVNKTYTDNRQNVYLVKQATGNPSRNVKNINDMFDSTAHYAFT--LDTYAKR    639
                + DD +  T++    N  K+AT N +            S  + AF  ++    KR
Sbjct:    979 ITTRETDDKI--TWSLTGYNTVANKEATRNAAA--------LFSVDYKAFLNEVNNLNKR    1028

Query:    640 EGERAFSTLDKKEGDWIRLTHTRVIQSNAFRFHNNDFEIGYDRFSLNEQEKKRKWGISLD    699
               G+    ++ +  G W R+       S  F  +   ++G D+      K    G+ L
Sbjct:    1029 MGD--LRDINGEAGAWARIMSGTGSASGGFSDNYTHVQVGVDK-------KHELDGLDLF    1079

Query:    700 YGHGRTSLWNTFGKD----KIRKYELALYNTTQYIDKEGDETGYIDNVLKIGKLRNRVIA    755
               G T   ++   D    K+    LY + +   D   YID + K   N   A
Sbjct:    1080 TGFTVTHTDSSASADVFSGKTKSVGAGLYASAMF-----DSGAYIDLIGKYVHHDNEYTA    1134

Query:    756 RNHMGQLWGKGKYSNTLFSISTEYGRRKFLDDDKLWRITPQVQLQYSYLRGTGYRI-DNG    814
                  G   G  YS +    E GR   ++D  W I PQ +L Y   + G +    D G
Sbjct:    1135 -TFAGL--GTRDYSTHSWYAGAEAGYRYHVTEDA-W-IEPQAELVYGSVSGKQFAWKDQG    1189

Query:    815 INVNLSHA--NSLIGRLGLDVVRKFDG                                   839
              +++++       N LIGR G+DV + F G
Sbjct:    1190 MHLSMKDKDYNPLIGRTGVDVGKSFSG                                   1216

Score = 36.6 bits (83), Expect = 1.2
Identities = 97/412 (23%), Positives = 164/412 (39%), Gaps = 83/412 (20%)

Query:     63 DNIVTMKSGDADADYVNNSKVLTETPYYKSKRGSNGIFAYGDKSLVKLIGENNIVK--SE    120
              D   V    G    +  ++ SK    Y  +G   + A+    S V   +N  +   +E
Sbjct:    163 DKFVVETRGATEGADISLSKQQALERYGVNYKGEKKLIAFRAGSGVVSVKKNGRITPFNE    222

Query:    121 ISEKSKALNGGFRHIGIYS-W---QNAKVE----LSAKSDN---------------IVQGG    158
              +S K + LNG F HI +S W   N  + +     ++++  D+                +V G
Sbjct:    223 VSYKPEMLNGSFVHIDDWSGWLILTNNQFDEFNNIASQGDSGSALFVYDNQKKKWVVAGT    282

Query:    159 IWGLYS----NNSSISLKGKNNVISNPKYNVFAYKKAKVDLTVENKNTLSDAEFGVYALN    214
              +WG+Y+    N  + K     I N K N ++Y     VD++   T + + +
Sbjct:    283 VWGIYNYANGKNHAAYSKWNQTTIDNLK-NKYSY---NVDMSGAQVATIENGK--LTGTG    336

Query:    215 TSMVNLSSKDNNEVKSTQVGLYSQ----DGGSINVDRKDNIIEGDAVALVGKG-----GS    265
              +   ++ +KD         + L S     GG +  D+K   + GD     G G     GS
Sbjct:    337 SDTTDIKNKDLIFTGGGDILLKSSFDNGAGGLVFNDKKTYRVNGDDFTFKGAGVDTRNGS    396

Query:    266 Q---NIR-ASRTNL--ISSKSLGIHAEQAAK------IAITGASNTIHASNAAIRSLDKS    313
                  NIR  ++ NL  I    +L  +   Q        + I GA  T   +N   I S D
Sbjct:    397 TVEWNIRYDNKDNLHKIGDGTLDVRKTQNTNLKTGEGLVILGAEKTF--NNIYITSGD-G    453

Query:    314 EVKIDGQITIDSNVAN--LARQDGSIHLN-YKDDTRITGATVSDKGLV--------AIK    361
              V+++ +  +    N    A+  G++ LN Y          AT  D G V         +I
Sbjct:    454 TVRLNAENALSGGEYNGIFFAKNGGTLDLNGYNQSFNKIAAT--DSGAVITNTSTKKSIL    511

Query:    362 PLNNTNIVADTIHYKG-----DVLAVNKGKVELDFTPNILLAGRLDNFSGLT         408
                LNNT   AD I++      DVL ++ K E     ++L G +D    + ++
Sbjct:    512 SLNNT---ADYIYHGNINGNLDVLQHHETKKE---NRRLILDGGVDTTNDIS         557
```

The protein was expressed in *E. coli* as an insoluble 95.92 kDa His-fusion product and then purified.

Based on this analysis, it was predicted that this protein from *N. gonorrhoeae*, and its epitopes, could be useful antigens for vaccines or diagnostics.

Example 40

A DNA sequence was identified in *N. gonorrhoeae* <SEQ ID 79> which encodes amino acid sequence <SEQ ID 80; NGS40>. Analysis of this protein sequence reveals the following:

GvH: Examining signal sequence (von Heijne)
Signal Score (−7.5): −4.18
Possible cleavage site: 17
>>> Seems to have no N-terminal signal seq.
Amino Acid Composition of Predicted Mature Form: calculated from 1
ALOM: Finding transmembrane regions (Klein et al.)
count: 0 value: 7.05 threshold: 0.0

-continued

| | |
|---|---|
| PERIPHERAL | Likelihood = 7.05 |
| modified ALOM score: −1.91 | |
| Rule: cytoplasmic protein | |

*** Reasoning Step: 2
Final Results

| | |
|---|---|
| bacterial cytoplasm --- Certainty = | 0.108(Affirmative) < succ> |

The protein has no homology with sequences in the databases.

Based on this analysis, it was predicted that this protein from *N. gonorrhoeae*, and its epitopes, could be useful antigens for vaccines or diagnostics.

Example 41

A DNA sequence was identified in *N. gonorrhoeae* <SEQ ID 81> which encodes amino acid sequence <SEQ ID 82; NGS41>. Analysis of this protein sequence reveals the following:

GvH: Examining signal sequence (von Heijne)
Signal Score (−7.5): −2.47
Possible cleavage site: 17
>>> May be a lipoprotein
Amino Acid Composition of Predicted Mature Form:
calculated from 16
ALOM: Finding transmembrane regions (Klein et al.)
count: 0 value: 7.37 threshold: 0.0

| | |
|---|---|
| PERIPHERAL | Likelihood = 7.37 |
| modified ALOM score: −1.97 | |
| Rule: inner or outer membrane protein | |
| Rule: inner or outer membrane protein | |

*** Reasoning Step: 2
Lipoprotein?
Inner membrane?
Final Results

| | |
|---|---|
| bacterial outer membrane --- Certainty = | 0.790(Affirmative) < succ> |

The protein has no homology sequences in the databases.

Based on this analysis, it was predicted that this protein from *N. gonorrhoeae*, and its epitopes, could be useful antigens for vaccines or diagnostics.

Example 42

A DNA sequence was identified in *N. gonorrhoeae* <SEQ ID 83> which encodes amino acid sequence <SEQ ID 84; NGS42>. Analysis of this protein sequence reveals the following:

GvH: Examining signal sequence (von Heijne)
Signal Score (−7.5): −5.2
Possible cleavage site: 14
>>> Seems to have no N-terminal signal seq.
Amino Acid Composition of Predicted Mature Form:
calculated from 1
ALOM: Finding transmembrane regions (Klein et al.)
count: 0 value: 6.58 threshold: 0.0

| | |
|---|---|
| PERIPHERAL | Likelihood = 6.58 |
| modified ALOM score: −1.82 | |
| Rule: cytoplasmic protein | |

*** Reasoning Step: 2
Final Results

| | |
|---|---|
| bacterial cytoplasm --- Certainty = | 0.514(Affirmative) < succ> |

The protein has no homology with sequences in the databases.

Based on this analysis, it was predicted that this protein from *N. gonorrhoeae*, and its epitopes, could be useful antigens for vaccines or diagnostics.

Example 43

A DNA sequence was identified in *N. gonorrhoeae* <SEQ ID 85> which encodes amino acid sequence <SEQ ID 86; NGS43>. Analysis of this protein sequence reveals the following:

GvH: Examining signal sequence (von Heijne)
Signal Score (−7.5): −4.34
Possible cleavage site: 39
>>> Seems to have no N-terminal signal seq.
Amino Acid Composition of Predicted Mature Form:
calculated from 1
ALOM: Finding transmembrane regions (Klein et al.)
count: 2 value: −4.78 threshold: 0.0

| | | | |
|---|---|---|---|
| INTEGRAL | Likelihood = −4.78 | Transmembrane | 1881-1897 |
| INTEGRAL | Likelihood = −1.01 | | (1876-1898) |
| PERIPHERAL | Likelihood = 1.91 | Transmembrane | 1966-1982 |
| | | | (1966-1982) |
| modified ALOM score: 1.46 | | | |
| Rule: cytoplasmic membrane protein | | | |

*** Reasoning Step: 2
Final Results

| | |
|---|---|
| bacterial inner membrane --- Certainty = | 0.291(Affirmative) < succ> |

The protein has no homology with sequences in the databases.

Based on this analysis, it was predicted that this protein from *N. gonorrhoeae*, and its epitopes, could be useful antigens for vaccines or diagnostics.

Example 44

A DNA sequence was identified in *N. gonorrhoeae* <SEQ ID 87> which encodes amino acid sequence <SEQ ID 88; NGS44>. Analysis of this protein sequence reveals the following:

GvH: Examining signal sequence (von Heijne)
Signal Score (−7.5): −3.49
Possible cleavage site: 58
>>> Seems to have no N-terminal signal seq.
Amino Acid Composition of Predicted Mature Form:
calculated from 1
ALOM: Finding transmembrane regions (Klein et al.)
count: 1 value: −1.33 threshold: 0.0

| | | | |
|---|---|---|---|
| INTEGRAL | Likelihood = −1.33 | Transmembrane | 141-157 |
| PERIPHERAL | Likelihood = 2.54 | | (140-157) |
| modified ALOM score: 0.77 | | | |
| Rule: cytoplasmic membrane protein | | | |

*** Reasoning Step: 2
Final Results

| | |
|---|---|
| bacterial inner membrane --- Certainty = | 0.153(Affirmative) < succ> |

The protein has no homology with sequences in the databases.

Based on this analysis, it was predicted that this protein from *N. gonorrhoeae*, and its epitopes, could be useful antigens for vaccines or diagnostics.

Example 45

A DNA sequence was identified in *N. gonorrhoeae* <SEQ ID 89> which encodes amino acid sequence <SEQ ID 90; NGS45>. Analysis of this protein sequence reveals the following:

GvH: Examining signal sequence (von Heijne)
Signal Score (-7.5): -4.07
Possible cleavage site: 46
>>> Seems to have no N-terminal signal seq.
Amino Acid Composition of Predicted Mature Form:
calculated from 1

ALOM: Finding transmembrane regions (Klein et al.)
count: 0 value: 2.07 threshold: 0.0

PERIPHERAL    Likelihood = 2.07
modified ALOM score: -0.91
Rule: cytoplasmic protein

*** Reasoning Step: 2
Final Results bacterial cytoplasm --- Certainty =    0.333(Affirmative) < succ>

The protein has homology with the following sequences in the databases:

```
>ref|NP_049512.1|putative portal protein [Bacteriophage 933W]
ref|NP_050550.1|hypothetical protein [Bacteriophage VT2-Sa]
gb|AAD25457.1|AF125520_52 (AF125520) putative portal protein
[Bacteriophage 933W]
dbj|BAA84334.1|(AP000363) hypothetical protein [Bacteriophage VT2-Sa]
dbj|BAA94158.1|(AP000422) portal protein [Escherichia coli O157:H7]
Length = 714

Score = 314 bits (805), Expect = 2e-84
Identities = 213/658 (32%), Positives = 327/658 (49%), Gaps = 22/658 (3%)

Query:    7 ETGVLPDKNGEPLTIG----EYRLFVGEMMNQPAWRAVADKEMDYADGRQLDNELLQKQR   62
            ET + KN   T      + +    ++ +QP WR  A+K    Y DG QL  E+LQ +
Sbjct:    4 ETNTMATKNDNGATPRFSQRQLQALCSDIDSQPKWRDAANKACAYYDGDQLPPEVLQVLK   63

Query:   63 ELGLPPAVENLITPTLLSVQGYEATIRTDWRVTADGETGGRD-VADALNFKLNRAERQSR  121
            + G P  + NLI PT+   V G EA  RTD V +D        + +A+A+N +    A R
Sbjct:   64 DRGQPMTIHNLIAPTVDGVLGMEAKTRTDLVVMSDEPDDETEKLAEAINAEFADACRLGN  123

Query:  122 ADKACSDAFRGQIACGIGWVEVTRNPNPFEFPYECGVIHRNAIHWDMKSYKYDLSDARWL  181
               KA SDA+  QI  G+ WVEV RN +PF   ++  + RN +WD  S + DLSD RWL
Sbjct:  124 MNKARSDAYAEQIKAGLSWVEVRRNSDPFGPEFKVSTVSRNEVFWDWLSREADLSDCRWL  183

Query:  182 IRRRWLLPERLAQFFPEYAGHFKAMGRGGSDWR-ISGEMLDGGGNTGLADAWGISGRNTV  240
            +RRRW+  +         FP    G   + + DWR   +   G + G    AW
Sbjct:  184 MRRRWMDTDEAKATFP---GMAQVIDYAIDDWRGFVDTTVTEGQPSPLMSAWEEYQSWDR  240

Query:  241 SEEFWFNETTRELAVAEVWYRRWVTADCLRDKKTGRTVEFDGANPNHREMAANGAV-LFA  299
            +    W   R + + V+YR +     + +   GR V FD N       A+G V +
Sbjct:  241 QQNEWLQRERRRVLLQVVYYRTFERLPVI-ELSNGRVVAFDKNNLMQAVAVASGRVQVKV  299

Query:  300 ASVPRMRRAFVVGDLVVRDEPTPYPHQKFPYVPFFGFREDNTGIPYGYVRNMKYAQDNLN  359
             V R+R A+ VG   + D P   P    FP VPF+G+R+D TG PYG  +    AQD +N
Sbjct:  300 GRVSRIREAWFVGPHFIVDRPCSAPQGMFPLVPFWGYRKDKTGEPYGLISRAIPAQDEVN  359

Query:  360 STNSKLRWGLSAIRTVRTKGIVDMSDEQFRRNIARVDADIVLNKIEAAQPGAR--FDVSR  417
                KL W L A R+ +    +SD    I R D I LN+    Q         F V +
Sbjct:  360 FRRIKLTWLLQAKRVIMDEDATQLSDNDLMEQIERPDGIIKLNPVRKNQKSVADVFRVEQ  419

Query:  418 DFELSAQHWQMLQDSRATIRQISGITPSFMGNRGNATSGRQESIQVEQSNQSLGLVMDNF  477
            DF++++ +Q++Q+S   I+   G+    +F+G    ATSG   S  VEQ   +L  + DN+
Sbjct:  420 DFQVASQQFQVMQESEKLIQDTMGVYSAFLGQDSGATSGVAISNLVEQGATTLAEINDNY  479

Query:  478 RQSRSLVGELLLAMIIEDLGS-DEQTVVIEGDAVTQGRTVVINRPETDPVTGKAYLSNDL  536
            + +      VG LLLA +++DL       VVI D    + +T+V+N  E D         L+ND+
Sbjct:  480 QFACQQVGRLLLAYLLDDLKKRRNHAVVINRDDRQRRQTIVLN-AEGD----NGELTNDI  534

Query:  537 QNIRLKVALEDVPSTNSYRSQQLGAMSEAVKSLPPEYQAAVLPFMVSLMDIPFKDKVIEK  596
            +    +AL V T ++++Q      MSE ++ LPP+ QA VL    V+L+D+P+ K + E+
Sbjct:  535 SRLNTHIALAPVQQTPAFKAQLAQRMSEVIQGLPPQVQAVVLDLWVNLLDVPQKQEFVER  594

Query:  597 IK-EVRVQETPEQI--EARIAQAVQDALAKSGNDIKRRELALKEQRTASEIKAIEARA   651
            I+ +  ++P+++   E +     A Q  AL +    +++ RE+A  +  +  ++     A  A
Sbjct:  595 IRAALGTPKSPDEMTPEEQEVAAQQQALQQQQAELQMREMAGRVAKLEADAARAHAAA    652
```

Based on this analysis, it was predicted that this protein from *N. gonorrhoeae*, and its epitopes, could be useful antigens for vaccines or diagnostics.

Example 46

A DNA sequence was identified in *N. gonorrhoeae* <SEQ ID 91> which encodes amino acid sequence <SEQ ID 92; NGS46>. Analysis of this protein sequence reveals the following:

```
GvH: Examining signal sequence (von Heijne)
Signal Score (-7.5): -3.25
Possible cleavage site: 37
>>> Seems to have no N-terminal signal seq.
Amino Acid Composition of Predicted Mature Form:
calculated from 1
ALOM: Finding transmembrane regions (Klein et al.)
count: 0 value: 4.77 threshold: 0.0

PERIPHERAL              Likelihood = 4.77
modified ALOM score: -1.45
Rule: cytoplasmic protein

*** Reasoning Step: 2
                Final Results bacterial cytoplasm --- Certainty =    0.281(Affirmative) < succ>
```

The protein has homology with the following sequences in the databases:

Based on this analysis, it was predicted that this protein from *N. gonorrhoeae*, and its epitopes, could be useful antigens for vaccines or diagnostics.

Example 47

A DNA sequence was identified in *N. gonorrhoeae* <SEQ ID 93> which encodes amino acid sequence <SEQ ID 94; NGS47>. Analysis of this protein sequence reveals the following:

```
GvH: Examining signal sequence (von Heijne)
Signal Score (-7.5): -4.87
Possible cleavage site: 31
>>> Seems to have no N-terminal signal seq.
Amino Acid Composition of Predicted Mature Form:
calculated from 1
ALOM: Finding transmembrane regions (Klein et al.)
count: 0 value: 4.88 threshold: 0.0

PERIPHERAL              Likelihood = 4.88
modified ALOM score: -1.48
Rule: cytoplasmic protein

*** Reasoning Step: 2
                Final Results bacterial cytoplasm --- Certainty =    0.313(Affirmative) < succ>
```

The protein has homology with the following sequences in the databases:

```
>sp|P44184|YE10_HAEIN HYPOTHETICAL PROTEIN HI1410
pir||E64028 hypothetical protein HI1410 - Haemophilus influenzae (strain Rd
KW20)
gb|AAC23058.1|(U32820) H. influenzae predicted coding region HI1410
[Haemophilus influenzae Rd]
Length = 394

Score = 150 bits (379), Expect = 3e-35
Identities = 75/168 (44%), Positives = 114/168 (67%), Gaps = 2/168 (1%)

Query:  57 REIQKSMRDSVHRLLKDKVAQLGLGHFYEITDFEIRGANGTLFVFSGLQSHTVDSIKSFE    116
           REIQKS+ DSV ++L D++   L L  F+++    I G NG+ F F+GL+++ + SIKS
Sbjct:   3 REIQKSISDSVIQMLADQIEMLSLQAFFDVQKTQIIGQNGSRFTFAGLKTN-ITSIKSMT   61

Query: 117 GIDIVWVEEGHGVSKKSWDVLTPTIRKEGSEIWITLNPDMETDETYRRFIAMPSEDTWLC    176
           GID+VWVEEG  VSK+SWD+L PTIR++GS+I ++ NP     D+TY+RF+    P E
Sbjct:  62 GIDVVWVEEGENVSKESWDILIPTIREDGSQIIVSFNPKNILDDTYQRFVIHPPERCKSV   121

Query: 177 EINWRDNPWFPEALNRERLKAQRSMNKEDYGNIWEGRPRMVSEGAVYR               224
           +NW+DNP+FP+ L  E ++  R  + E Y +++EG P    S+ A+ +
Sbjct: 122 LVNWQDNPYFPKEL-MEDMEQMRERDYELYRHVYEGEPVADSDLAIIK               168

>ref|NP_050979.1|P18 [Bacteriophage APSE-1]
gb|AAF03961.1|AF157835_18 (AF157835) P18 [Bacteriophage APSE-1]
Length = 469

Score = 117 bits (294), Expect = 2e-25
Identities = 72/233 (30%), Positives = 110/233 (46%), Gaps = 13/233 (5%)

Query:  17 LFKPCRYKVMYXXXXXXXXXXXXXXXXXXXXXXXQRPLRILCAREIQKSMRDSVHRLLKDKVA    76
           +FKP R KV +                         R LC RE   S+ DS H +L+ +V
Sbjct:   1 MFKPKRIKVYFGGRGGMKTVSFAKIALITASMHKRRFLCLREFMNSIEDSGHAVLQAEVE    60

Query:  77 QLGLGHFYEITDFEIRGANGTLFVFSGLQSHTVDSIKSFEGIDIVWVEEGHGVSKKSWDV   136
            LGL + + I +   I G N++F + L +  + SIKS    D+ WVEE   VS+KS D
Sbjct:  61 TLGLQNRFRILNTYIEGINDSIFKYGQL-ARNIASIKSKHDFDVAWVEEAETVSEKSLDS   119

Query: 137 LTPTIRKEGSEIWITLNPDMETDETYRRFIA-----------MPSEDTWLCEINWRDNPW   185
           L PTIRK GSE+W + NP E     Y+RF+             +D ++   ++++ DNPW
Sbjct: 120 LIPTIRKPGSELWFSFNPAEEDGAVYKRFVKPYKELIDTQGYYEDDDLYVGKVSYLDNPW   179

Query: 186 FPEALNRERLKAQRSMNKEDYGNIWEGRPPMVSEGAVYRHEIQDAFHSGRVTL          238
                P L + K +R N + +   G    E A+ + E  +A    + L
Sbjct: 180 LPAELKNDAQKMKRE-NYKKWRHVYGGECDANYEDALIQPEWVEAAIDAHIKL          231
```

```
>ref|NP_37739.1|Gp54 [Bacteriophage HK97]
gb|AAF31132.1|(AF069529) Gp54 [Bacteriophage HK97]
Length = 273

Score = 47.4 bits (111), Expect = 3e-04
Identities = 33/123 (26%), Positives = 52/123 (41%), Gaps = 20/123 (16%)

Query: 242 NGGLSGKPKNANVPRRRKTHGVPLQEIADLYNEVLGGRLPSVQVLNDTRKRAIANRWCEM  301
           NGG  G+ K    P RRK    +  +  + YN +G RLP   +N+ RKR + +
Sbjct: 160 NGGGDGQVK----PERRKAERIDYESFLNAYNTEVGDRLPHAVAVNEKRKRRL-KKIIPQ 214

Query: 302 LGTAAPNGKVRFGDKETGLAWFAGFFRKVA--MNPFWMGENQTGFAVGFDWIFKAGNFVK  359
           L T   +G            F + R       PF+ G+N TG+    FD++ + +
Sbjct: 215 LKTPNVDG------------FRAYVRAFVHQAKPFYFGDNDTGWTADFDYLLREDSLTG  261

Query: 360 ILE  362
           + E
Sbjct: 262 VRE  264
```

Based on this analysis, it was predicted that this protein from *N. gonorrhoeae*, and its epitopes, could be useful antigens for vaccines or diagnostics.

Example 48

A DNA sequence was identified in *N. gonorrhoeae* <SEQ ID 95> which encodes amino acid sequence <SEQ ID 96; NGS48>. Analysis of this protein sequence reveals the following:

GvH: Examining signal sequence (von Heijne)
Signal Score (-7.5): -6.85
Possible cleavage site: 15

-continued

>>> Seems to have no N-terminal signal seq.
Amino Acid Composition of Predicted Mature Form:
calculated from 1
ALOM: Finding transmembrane regions (Klein et al.)
count: 0 value: 7.16 threshold: 0.0

| PERIPHERAL | Likelihood = 7.16 |
|---|---|
| modified ALOM score: -1.93 | |
| Rule: cytoplasmic protein | |

*** Reasoning Step: 2
Final Results bacterial cytoplasm --- Certainty =      0.379(Affirmative) < succ>

The protein has homology with the following sequences in the databases:

```
>dbj|BAA36059.1|(D90754) Outer membrane protein P.69 precursor
[Escherichia coli]
Length = 762

Score = 64.7 bits (156), Expect = 1e-09
Identities = 79/292 (27%), Positives = 121/292 (41%), Gaps = 55/292 (18%)

Query:    3 NGARWTVTNDSMLKELDLSEDAQVEFSDNNK----FVKVSVSKLKGDGGVFKMYGDIV--  56
            N + W VT++S L   L LS    V+F+ +        F  ++V  L G+    F M  D+V
Sbjct:  289 NNSVWNVTSNSNLDTLALSHST-VDFASHGSTAGTFATLNVENLSGNS-TFIMRADVVGE 346

Query:   57 ----KGESDKLITRKGSEGTHIIEYMDDAKAKTTGREYLKLVENKGNQEDNKASNKASYK  112
                + D L    S G H++   +     TTG E L +V+      D   AS   AS +
Sbjct:  347 GNGNNNKGDLLNISGSSAGNHVLAIRNQGSEATTGNEVLTVVKTT----DGAASFSASSQ 402

Query:  113 LNVRCTEQGGWCFALGESG------ASKKVNISTDGKRDF-------YLYPD--------  151
            +    E GG+ + + ++G           AS V   T            + PD
Sbjct:  403 V-----ELGGYLYDVRKNGTNWELYASGTVPEPTPNPEPTPAPAQPPIVNPDPTPEPAPT 457

Query:  152 ---TLTPGASSSVLFGEALYQLNAVSDETLVQRMGEIHADGMPQEDNNVWIKRVGGKFSG  208
               T T A  + L     Y LN V + TL+QRMG++         +D N+W++   GG
Sbjct:  458 PKPTTTADAGGNYL--NVGYLLNYVENRTLMQRMGDLRNQ---SKDGNIWLRSYGGSLDS 512

Query:  209 SRSDYRVGGYGNRYWGFAGGFNRTGFGDKWIHYKGLMLRHLQSSYASEDYVG         260
            S   ++ G+    Y G  ++     D      Y GL    ++ S++AS DY G
Sbjct:  513 FASG-KLSGFDMGYSGIQFGGDKR-LSDVMPLYVGL---YIGSTHASPDYSG         559
```

Based on this analysis, it was predicted that this protein from *N. gonorrhoeae*, and its epitopes, could be useful antigens for vaccines or diagnostics.

Example 49

A DNA sequence was identified in *N. gonorrhoeae* <SEQ ID 97> which encodes amino acid sequence <SEQ ID 98; NGS49>. Analysis of this protein sequence reveals the following:

GvH: Examining signal sequence (von Heijne)
Signal Score (−7.5): −8.37
Possible cleavage site: 15
>>> Seems to have no N-terminal signal seq.
Amino Acid Composition of Predicted Mature Form: calculated from 1
ALOM: Finding transmembrane regions (Klein et al.)
count: 0 value: 4.93 threshold: 0.0

PERIPHERAL    Likelihood = 4.93
modified ALOM score: −1.49
Rule: cytoplasmic protein

*** Reasoning Step: 2
Final Results

| | |
|---|---|
| bacterial cytoplasm --- Certainty = | 0.355(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

Based on this analysis, it was predicted that this protein from *N. gonorrhoeae*, and its epitopes, could be useful antigens for vaccines or diagnostics.

Example 50

A DNA sequence was identified in *N. gonorrhoeae* <SEQ ID 99> which encodes amino acid sequence <SEQ ID 100; NGS50>. Analysis of this protein sequence reveals the following:

GvH: Examining signal sequence (von Heijne)
Signal Score (−7.5): −6.6
Possible cleavage site: 50
>>> Seems to have no N-terminal signal seq.
Amino Acid Composition of Predicted Mature Form: calculated from 1
ALOM: Finding transmembrane regions (Klein et al.)
count: 0 value: 7.80 threshold: 0.0

PERIPHERAL    Likelihood = 7.80
modified ALOM score: −2.06
Rule: cytoplasmic protein

*** Reasoning Step: 2
Final Results

| | |
|---|---|
| bacterial cytoplasm --- Certainty = | 0.398(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
gi|11282647|pir||H81959 patch repair protein (EC 3.1.-.-) NMA0429
[imported] - Neisseria meningitidis (group A strain Z2491)
gi|7379179|emb|CAB83728.1|(AL162753) patch repair protein [Neisseria
meningitidis Z2491]
Length = 140

Score = 256 bits (628), Expect = 8e-68
Identities = 131/140 (93%), Positives = 132/140 (93%)

Query:   1 MTDIFTPSKRSFVMSKIHSKETKPEVLVRKFLFSQGFRYRKNDKRYAGKPDIVLPKYKTV    60
           MTDIFT SKRSFVM KIHSKETKPEVLVRKFLF QGFRYRKNDKRY GRPDIVL KYKTV Sbjct:   1 MTDIFTTSKRSFVMLKIHSKETKPEVLVRKFLFFQGFRYRKNDKRYVGKPDIVLSKYKTV    60

Query:  61 VFIHGCFWHGHSCNKGHIPKSNMDFWLEKITKNRERDIKNETELEKIGFKVIVVWECELK   120
           VFIHGCFW+GHSCNKGHIPKSN DFWLEKITKN ERDIKNETELEKIGFKVIVVWECELK Sbjct:  61 VFIHGCFWYGHSCNKGHIPKSNTDFWLEKITKNCERDIKNETELEKIGFKVIVVWECELK   120

Query: 121 NKAICRERLNRLVEEIKDAV                                          140
           NKAICRERLNRLV EIKDAV Sbjct: 121 NKAICRERLNRLVREIKDAV                                          140
```

```
>gi|11352963|pir||G81959 conserved hypothetical protein NMA0428
[imported] - Neisseria meningitidis (group A strain Z2491)
gi|7379178|emb|CAB83727|(AL162753) conserved hypothetical protein
[Neisseria meningitidis Z2491]
Length = 548

Score = 371 bits (954), Expect = e-102
Identities = 189/197 (95%) , Positives = 194/197 (97%)

Query:    1 VKGESGVDIENWKNKLPEKEREPVEVILNRLEDSELTNKEQAEVISALHSIIPEYPYYHW    60
            VKGESGVDIE+WKNKLPEKEREPVEVILNRLEDSELTNKEQAEVISALHSIIPEYPYYHW
Sbjct:  350 VKGESGVDIEDWKNKLPEKEREPVEVILNRLEDSELTNKEQAEVISALHSIIPEYPYYHW   409

Query:   61 RHLHQDLHTACNDFYNEKKDYLSAAIEAVKVFEDKVQKQTGLHSIDGRELIEKAFGSKKS   120
            RHLHQDLHTACNDFYNEKKDYLSAAIEAVKVFEDKVQKQTGLHSIDGRELIE+AFGSK S
Sbjct:  410 RHLHQDLHTACNDFYNEKKDYLSAAIEAVKVFEDKVQKQTGLHSIDGRELIEQAFGSKNS   469

Query:  121 MLLLTNNKTQAEQNLEDGLEQLACGTWTGFRNPVQHELRANLSPSIFNDKDALDLISLVS   180
            +LLLTNNKT+AEQNLEDGLEQLACGTWTGFRNPVQHELRANLSPSIFNDKDALDLISLVS
Sbjct:  470 ILLLTNNKTKAEQNLEDGLEQLACGTWTGFRNPVQHELRANLSPSIFNDKDALDLISLVS   529

Query:  181 YLLRKVEQTKKRAKPTS                                              197
            YLLRKVEQTKKR+K  S
Sbjct:  530 YLLRKVEQTKKRSKVVS                                              546

>gi|10955124|ref|NP_059780.1|ymh [Agrobacterium tumefaciens]
gi|5738274|gb|AAB91582.2|(AF242881) ymh [Agrobacterium tumefaciens]
Length = 266

Score = 58.7 bits (141), Expect = 5e-08
Identities = 40/127 (31%), Positives = 69/127 (53%), Gaps = 5/127 (3%)

Query:   61 RHLHQDLHTACNDFYNEKKDYLSAAIEAVKVFEDKVQKQTGLHSIDGRELIEKAFGSKKS   120
            R +H D+    C +       +Y  A +EAVK    DK++++TGL + DG  L+++AF
Sbjct:  137 RGVHPDVLRFCREEL-LVDNYFHAVLEAVKSVADKIRQRTGL-TDDGAVLVDRAFSGDAP   194

Query:  121 MLLLTNNKTQAEQNLEDGLEQLACGTWTGFRNPVQHELRANLSPSIFNDKDALDLISLVS   180
            ML +   ++++E+  + G   L   GT++ FRN    H R +    S    +DA DL S+ S
Sbjct:  195 MLAINELQSESEKGEQRGFSNLVKGTFSMFRNTTAHAPRIHWQMS---KEDAEDLFSMFS   251

Query:  181 YLLRKVE                                                        187
              + R+++
Sbjct:  252 LMHRRID                                                        258
```

As a homolog was found in serogroup A *N. meningitidis* but not in serogroup B, NGS50 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 51

A DNA sequence was identified in *N. gonorrhoeae* <SEQ ID 101> which encodes amino acid sequence <SEQ ID 102; NGS51>. Analysis of this protein sequence reveals the following:

GvH: Examining signal sequence (von Heijne)
Signal Score (-7.5): 0.14
Possible cleavage site: 42

>>> Seems to have no N-terminal signal seq.
Amino Acid Composition of Predicted Mature Form:
calculated from 1
ALOM: Finding transmembrane regions (Klein et al.)
count: 0 value: 5.67 threshold: 0.0

| PERIPHERAL | Likelihood = 5.67 |
|---|---|
| modified ALOM score: −1.63 | |
| Rule: cytoplasmic protein | |

*** Reasoning Step: 2
Final Results

| | |
|---|---|
| bacterial cytoplasm --- Certainty = | 0.145(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||G81959 conserved hypothetical protein NMA0428 [imported] -
Neisseria meningitidis (group A strain Z2491)
emb|CAB83727.1|(AL162753) conserved hypothetical protein [Neisseria
meningitidis Z2491]
Length = 548

Score = 532 bits (1371), Expect = e-150
Identities = 272/285 (95%), Positives = 280/285 (97%)
```

```
-continued
Query:   1 MSEEKLKMSFEPTVIEHLGVKMYSHTVPAIAELIANAYDACATEVEVRLFDKPEHKIVIK  60
           MSEEKLKMSFEPTVIEHLGVKMYSHTVPAIAELIANAYDACATEVEVRLFDKPEHKIVIK
Sbjct:   1 MSEEKLKMSFEPTVIEHLGVKMYSHTVPAIAELIANAYDACATEVEVRLFDKPEHKIVIK  60

Query:  61 DNGIGMSFDEINDFYLRIGRNRREEKQASPCGRIPTGKKGLGKLALFRLGNKIEISTIQG 120
           DNGIGMSFDEINDFYLRIGRNRREEKQASPCGRIPTGKKGLGKLALF LGNKIEISTIQG
Sbjct:  61 DNGIGMSFDEINDFYLRIGRNRREEKQASPCGRIPTGKKGLGKLALFGLGNKIEISTIQG 120

Query: 121 NERVTFTLDYAEIKKSERIYQPEFQKESVKPNTENGTTITLTELTKKQGYPLDNYVGHLS 180
           NERVTFTLDYAEI++S+ IYQPEF+KESV+ N E+GTTITLTELTKKQGYPLDNYV HLS
Sbjct: 121 NERVTFTLDYAEIRRSKGIYQPEFRKESVESNIESGTTITLTELTKKQGYPLDNYVEHLS 180

Query: 181 RLFDFPAQDFKIKVSLNGSEPRIIDGNLKYNLVTPQFEWEYQDLATNISSLSSKFEQYEY 240
           RLFDFPAQDFKIKVSLNGSEP+IIDGNLKY+LVTPQFEWEYQDLATNISSLSSKFEQYEY
Sbjct: 181 RLFDFPAQDFKIKVSLNGSEPKIIDGNLKYDLVTPQFEWEYQDLATNISSLSSKFEQYEY 240

Query: 241 SGLIQGKFITTEKPLKNNMKGITLFANGRMVNMPEFFTDSESSHF 285
           SGLIQGKFITTEKPLKNNMKGITLFANGRMVNMPEFFTDSESSHF
Sbjct: 241 SGLIQGKFITTEKPLKNNMKGITLFANGRMVNMPEFFTDSESSHF 285

>emb|CAC22276.1|(AJ302030) putative heat shock protein [Listeria
monocytogenes]
Length = 181

Score = 70.2 bits (171), Expect = 2e-11
Identities = 57/173 (32%), Positives = 90/173 (51%), Gaps = 10/173 (5%)

Query:   1 MSEEKLKMSFEPTVIEHLGVKMYSHTVPAIAELIANAYDACATEVEVRLFDKPEHKIVIK  60
           MSE++  +  +P ++E LG  +Y++     + ELIANAYDA A   V V      E+K++++
Sbjct:   1 MSEKEYNLDIDPRILELLGPHLYTNIYYILGELIANAYDADAKNVYVIDRIDEENKLIVE  60

Query:  61 DNGIGMSFD--EINDFYLRIGRNNREEKQASPC---GRIPTGKKGLGKLALFRLGNKIEI 115
           D+G GMS++  ++ +F L + +  R     S     R   G+KG+GKLA   +  + I
Sbjct:  61 DDGSGMSYENKDVKNF-LSVAKESRTNAINSYTKLNNRRKMGRKGVGKLASLSVSENVNI 119

Query: 116 STIQGNERVTFTLDYAEI-KKSERIYQPEFQKESVKPNTENGTTITLTELTKK 167
              TI+  E+   F L   I KK E I +         +K    +GT I +T  T K
Sbjct: 120 KTIKDGEKSGFVLSRKVINKKLEAINEDTISFIKIK---NHGTAIEMTNPTYK 169
```

As a homolog was found in serogroup A *N. meningitidis* but not in serogroup B, NGS51 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 52

A DNA sequence was identified in *N. gonorrhoeae* <SEQ ID 103> which encodes amino acid sequence <SEQ ID 104; NGS52>. Analysis of this protein sequence reveals the following:

GvH: Examining signal sequence (von Heijne)
Signal Score (-7.5): -3.5
Possible cleavage site: 49

>>> Seems to have no N-terminal signal seq.
Amino Acid Composition of Predicted Mature Form:
calculated from 1
ALOM: Finding transmembrane regions (Klein et al.)
count: 0 value: 7.64 threshold: 0.0

PERIPHERAL    Likelihood = 7.64
modified ALOM score: -2.03
Rule: cytoplasmic protein

*** Reasoning Step: 2
Final Results bacterial cytoplasm --- Certainty =           0.213(Affirmative) < succ>
bacterial periplasmic space --- Certainty =   0.000(Not Clear) < succ>
bacterial outer membrane --- Certainty =      0.000(Not Clear) < succ>
bacterial inner membrane --- Certainty =      0.000(Not Clear) < succ>

The protein has homology with the following sequences in the databases:

```
2.1.1.73) NMA0427 [imported] - Neisseria meningitidis
(group A strain Z2491)
gi|7379177|emb|CAB83726.1|(AL162753) modification methylase
(cytosine-specific DNA methylase)
[Neisseria meningitidis Z2491]
Length = 351

Score = 310 bits (794), Expect = 8e-84
Identities = 152/154 (98%), Positives = 153/154 (98%)

Query:   1 LGMENGFPKIMAGHQDETDFMHSCAGLSDINLKRLALIPKNGGNRLAFAHIPELQLECFI  60
           LGMENGFPKI+AGHQDETDFMHSCAGLSDINLKRLALIPKNGGNRLAFAHIPELQLECFI
Sbjct: 198 LGMENGFPKIIAGHQDETDFMHSCAGLSDINLKRLALIPKNGGNRLAFAHIPELQLECFI 257
```

```
-continued
Query:  61 GKDNSFKDTFGRLWWDKPAPTITTKFFSISNGRFAHPEEDRALSLREGATLQSFPRNYVF  120
           GKDNSFKDTFGRLWWDKPAPTITTKFFSISNGRFAHPEEDRALSLREGATLQSFPRNYVF
Sbjct: 258 GKDNSFKDTFGRLWWDKPAPTITTKFFSISNGRFAHPEEDRALSLREGATLQSFPRNYVF  317

Query: 121 KAGSRDKIARLIGNAVPPMYTEKIGRAIVDNIEC  154
           KAGSRDKIARLIGNAVPPMY EKIGRAIVDNIEC
Sbjct: 318 KAGSRDKIARLIGNAVPPMYAEKIGRAIVDNIEC  351

>gi|127441|sp|P25265|MTD2_HERAU MODIFICATION METHYLASE HGIDII
(CYTOSINE-SPECIFIC METHYLTRANSFESASE HGIDII) (M. HGIDII)
gi|538661|pir||JT0594 site-specific DNA-methyltransferase
(cytosine-specific)
(EC 2.1.1.73) - Herpetosiphon aurantiacus
gi|48773|emb|CAA38941.1|(X55141) methyltransferase
[Herpetosiphon aurantiacus]
Length = 354

Score = 95.6 bits (237), Expect = 3e-19
Identities = 62/142 (43%), Positives = 82/142 (57%), Gaps = 9/142 (6%)

Query:  12 AGHQDETDFMHSCAGLSDINLKRLALIPKNGGNRLAFAHIP-ELQLECFIGKD-NSFKDT   69
           +G    E D MH+ + L DINL+R+      G    +A P EL  EC   +    S+
Sbjct: 200 SGGHWEGDSMHAASRLEDINLRRIQHSVPGG----TWADWPEELIAECHKKESGESYGSV 255

Query:  70 FGRLWWDKPAPTITTKFFSISNGRFAHPEEDRALSLREGATLQSFPRNYVFKAGSRDK-- 127
           +GR+ WDK APTITT+     NGRF HPE+DRA+SLRE A LQ+FPR+Y F    + K
Sbjct: 256 YGRMEWDKVAPTITTQCNGYGNGRFGHPEQDRAISLREAALLQTFPRSYQFAPEGQLKFK 315

Query: 128 -IARLIGNAVPPMYTEKIGRAI 148
            ++R IGNAVP    I ++I
Sbjct: 316 TVSRQIGNAVPVALGRVIAKSI 337
```

As a homolog was found in serogroup A *N. meningitidis* but not in serogroup B, NGS52 protein and nucleic acid are useful for distinguishing between gonococcus and serogroup B. *N. meningitidis*.

Based on this analysis, it was predicted that this protein from *N. gonorrhoeae*, and its epitopes, could be useful antigens for vaccines or diagnostics.

Example 53

A DNA sequence was identified in *N. gonorrhoeae* <SEQ ID 105> which encodes amino acid sequence <SEQ ID 106; NGS53>. Analysis of this protein sequence reveals the following:

GvH: Examining signal sequence (von Heijne)
Signal Score (−7.5): −7.56
Possible cleavage site: 31

-continued

>>> Seems to have no N-terminal signal seq.
Amino Acid Composition of Predicted Mature Form:
calculated from 1
ALOM: Finding transmembrane regions (Klein et al.)
count: 0 value: 5.36 threshold: 0.0

PERIPHERAL Likelihood = 5.36
modified ALOM score: −1.57
Rule: cytoplasmic protein

*** Reasoning Step: 2
Final Results

| | |
|---|---|
| bacterial cytoplasm --- Certainty = | 0.189(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

>gi|11256915|pir||F81959 site-specific DNA-methyltransferase (cytosine-specific)
(EC2.1.1.73) NMA0427 [imported] - *Neisseria meningitidis* (group A strain Z2491)
gi|7379177|emb|CAB83726.1|(AL162753) modification methylase (cytosine-specific DNA methylase)
[*Neisseria meningitidis* Z2491]
Length = 351

Score = 247 bits (606), Expect = 5e-65
Identities = 124/149 (83%), Positives = 127/149 (85%)

```
Query:   1 LQPETLEKELGLKKNDDDLILIGCSPCQYWSVIQTDKRKSEKSKSLLLEFQRFVEYFNPG   60
           LQPETLEKELGLKKNDDDLILIGCSPCQYWSVIQTDKRKSEKSKSLLLEFQRFVEYFNPG
Sbjct:  59 LQPETLEKELGLKKNDDDLILIGCSPCQYWSVIQTDKRKSEKSKSLLLEFQRFVEYFNPG  118

Query:  61 YVVVENVPGILSRMKESGLDNFIKLLEEKGFTVHFGIHNTADYGIPQSRKRFTLIANRIT  120
           YVVVENVPGILSRMKES LDNFIKLLEEKGFTVHFGIHNTADYGIPQSRKRFTLIANRIT
Sbjct: 119 YVVVENVPGILSRMKESRLDNFIKLLEEKGFTVHFGIHNTADYGIPQSRKRFTLIANRIT  178
```

```
-continued
Query:    121 KKSWNQSSIRANGLRYAMFWEWKTAFPKL       149
              K+           L         + FPK+
Sbjct:    179 KEKLEPVKYSGKRLTVRDVLGMENGFPKI       207

>gi|127441|sp|P25265|MTD2_HERAU MODIFICATION METNYLASE HGIDII
(CYTOSINE-SPECIFIC METHYLTRANSFERASE HGIDII) (M. HGIDII)

gi|538661|pir||J0594 site-specific DNA-methyltransferase (cytosine-specific)
(EC
2.1.1.73) - Herpetosiphon aurantiacus
gi|48773|emb|CAA38941.1|(X55141) methyltransferase [Herpetosiphon aurantiacus]
Length = 354

Score = 71.9 bits (169), Expect = 4e-12
Identities = 39/105 (37%), Positives = 57/105 (54%), Gaps = 1/105 (0%)

Query:     12 LKKNDDDLILIGCSPCQYWSVIQTDKRKSEKSKSLLLEFQRFVEYFNPGYVVVENVPGIL    71
              L   N+    IL+GC+PCQ  +S      T K ++      LL EF R +    P  + +ENVP +
Sbjct:     64 LYPNNQHKILVGCAPCQDFSQY-TKKSRTGTKWQLLTEFSRLIREIEPDIISMENVPEVR    122

Query:     72 SRMKESGLDNFIKLLEEKGFTVHFGIHNTADYGIPQSRKRFTLIA   116
               +    +    +NFI+ LE+ G+ V    + +  DYGIPQ  R R   L A
Sbjct:    123 TFNRGEVFNNFIQSLEQLGYHVSHSVVHCPDYGIPQQRDRLVLFA   167
```

As a homolog was found in serogroup A *N. meningitidis* but not in serogroup B, NGS53 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 54

A DNA sequence was identified in *N. gonorrhoeae* <SEQ ID 107> which encodes amino acid sequence <SEQ ID 108; NGS54>. Analysis of this protein sequence reveals the following:

GvH: Examining signal sequence (von Heijne)
Signal Score (-7.5): -6.82
Possible cleavage site: 50
>>> Seems to have no N-terminal signal seq.
Amino Acid Composition of Predicted Mature Form:
calculated from 1
ALOM: Finding transmembrane regions (Klein et al.)
count: 0 value: 6.89 threshold: 0.0

| PERIPHERAL | Likelihood = 6.89 |
|---|---|
| modified ALOM score: -1.88 | |
| Rule: cytoplasmic protein | |

*** Reasoning Step: 2
Final Results

| | |
|---|---|
| bacterial cytoplasm --- Certainty = | 0.253(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
gi|1074456|pir||D64155 hypothetical protein H10597 - Haemophilus influenzae
(strain Rd KW20)
gi|1573586|gb|AAC22254.1|(U32741) conserved hypothetical protein
[Haemophilus influenzae Rd]
Length = 272

Score = 188 bits (459), Expect = 2e-47
Identities = 95/100 (95%), Positives = 97/100 (97%)

Query:      1 MNLPFRAMVSDLGGTLLTPEHLVGDLTIDTLRVLEQKGVDIILATGRNHTDMSSILGKIG    60
              MNLPFRAMVSDL GTLLTPEHLVGDLTIDTLR LEQKGVDIILATGRNHTD+SSILGKIG
Sbjct:      1 MNLPFRAMVSDLDGTLLTPEHLVGDLTIDTLRALEQKGVDIILATGRNHTDVSSILGKIG    60

Query:     61 AERAVMITSNGARVRDLQGNLLYSNSLPEELVLELYKTSY                      100
              AERAVMITSNGARVRDLQGNLLYSNSLPEELVLELYKT +
Sbjct:     61 AERAVMITSNGARVRDLQGNLLYSNSLPEELVLELYKTPF                      100
```

A homolog was found in serogroup A *N. meningitidis* but not in serogroup B, so NGS54 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 55

A DNA sequence was identified in *N. gonorrhoeae* <SEQ ID 109> which encodes amino acid sequence <SEQ ID 110; NGS55>. Analysis of this protein sequence reveals the following:

GvH: Examining signal sequence (von Heijne)
Signal Score (-7.5): -4.46
Possible cleavage site: 37
>>> Seems to have no N-terminal signal seq.
Amino Acid Composition of Predicted Mature Form:
calculated from 1
ALOM: Finding transmembrane regions (Klein et al.)
count: 0 value: 3.02 threshold: 0.0

| PERIPHERAL | Likelihood = 3.02 |
|---|---|
| modified ALOM score: -1.10 | |
| Rule: cytoplasmic protein | |

*** Reasoning Step: 2
Final Results

| bacterial cytoplasm --- Certainty = | 0.311(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
aeruginosa (strain PAO1)
gi|9948791|gb|AAG06104.1|AE004699_9 (AE004699) probable FMN oxidoreductase
[Pseudomonas aeruginosa]
Length = 411

Score = 279 bits (686), Expect = 2e-74
Identities = 157/375 (41%), Positives = 228/375 (59%), Gaps = 10/375 (2%)

Query:   1 MEEQLAQNDQ-PSEKLVRLYGAWAEGGAGVLVTGNVMVAESGKGSINDVLISDDRALEML    59
           MEE +A   Q PSE+L+RLY AWA+GGAG+L++GNVMV      V++ DD  LE
Sbjct:  24 MEENMADAAQAPSERLMRLYQAWADGGAGLLISGNVMVDSRAMTGPGGVVLEDDAQLEKF  83

Query:  60 KKWAKARTQNDTLLIMQINHAGKQSPAVVNKTPLAPSAVPLV--GMNGFINPPRELSADE  117
           ++WA+        +QINH G+Q A + +  APSAVPL    GM+    P+  +
Sbjct:  84 RRWARIGRSAGAQFWLQINHPGRQMQANLGQQAWAPSAVPLELGGMSRHFATPKAMDEAM  143

Query: 118 INGLIQQFVQTAKIAEQAGFSGVQIYAVHGYLISQFLSPHHNRRQDQWGGSLENRMRFLL  177
           I  +IQ+F ++A +AE+AGFSGV+I+A HGYL+SQFLSP  NRR D WGGSLENR R LL
Sbjct: 144 IAEVIQRFARSAGLAERAGFSGVEIHAAHGYLLSQFLSPLSNRRSDAWGGSLENRARLLL  203

Query: 178 ETYTAIRAAAGKDFLVGVKLNSADFQKGGFDESESVQVVQKLSEMGIDFIEVSGGNYESP  237
           E     A+RA    F V VKLNSADFQ+GGF   ++ +VV+ L  +G+D +E+SGG+YE+P
Sbjct: 204 EIVRAVRAEVAPGFAVAVKLNSADFQRGGFSADDAREVVRMLDGLGVDLVELSGGSYEAP  263

Query: 238 QMLA-AKDS-TRKREAFFIDYAEKARAASQAPLIITGGFRSQTAMEDALSSGHLDLVGIA  295
            M   A+D  T  REA+F+++A   RAA++ P+++TGG R +    E  L+SG +D+VGI
Sbjct: 264 AMQGEARDGRTLAREAYFVEFARDIRAAARMPVMVTGGIRRRPVAEQVLASG-VDMVGIG  322

Query: 296 RPFALVPDLANKMQNRTYQTVQADRIQTGVAFVDKKAGAMLEMNWYMTQMDLIGQGKQSN  355
            A+ P+L  +      Q  I   + +K  ++   M   Q+  + +G+  +N
Sbjct: 323 TALAIEPNLPRDWRAGKDSAPQLRPI----TWRNKPLASLANMAAVKFQLRKLSRGRATN  378

Query: 356 PKIVGVESIAENFAG                                               370
           P++   + ++      AG
Sbjct: 379 PRVSPLCALLAQQAG                                               393
```

Based on this analysis, it was predicted that this protein from *N. gonorrhoeae*, and its epitopes, could be useful antigens for vaccines or diagnostics.

Example 56

A DNA sequence was identified in *N. gonorrhoeae* <SEQ ID 111> which encodes amino acid sequence <SEQ ID 112; NGS56>. Analysis of this protein sequence reveals the following:

GvH: Examining signal sequence (von Heijne)
Signal Score (-7.5): -4.69
Possible cleavage site: 54
>>> Seems to have an uncleavable N-term signal seq
Amino Acid Composition of Predicted Mature Form:
calculated from 1
ALOM: Finding transmembrane regions (Klein et al.)
count: 0 value: 4.29 threshold: 0.0

| PERIPHERAL | Likelihood = 4.29 |
|---|---|
| modified ALOM score: -1.36 | |

*** Reasoning Step: 2
Final Results

| bacterial inner membrane --- Certainty = | 0.042(Affirmative) < succ> |
|---|---|
| bacterial periplasmic space --- Certainty = | 0.000(Not Clear) < succ> |

-continued

| bacterial outer membrane --- Certainty = | 0.000(Not Clear) < succ> |
|---|---|
| bacterial cytoplasm --- Certainty = | 0.000(Not Clear) < succ> |

The protein has homology with the following sequences in the databases:

```
>gi|7444004|pir||D70029 transcription regulator ArsR family homolog yvbA -
Bacillus subtilis
gi|2635892|emb|CAB15384.1|(Z99121) similar to transcriptional regulator
(ArsR family)
[Bacillus subtilis]
```

Length = 90

Score = 51.3 bits (118), Expect = 3e-06
Identities = 24/65 (36%), Positives = 42/65 (63%), Gaps = 1/65 (1%)

```
Query:  15 IFTVLSDENRHQILHVLWKHGRMNVNELTEHLHLSRPAVSHHLKIMLQAGAVAVEQVGKE    74
           +F  +SD  R +IL +L K G M   ++ EH ++S+P++SHHL I+ QA  ++  + G+

Sbjct:   4 VFKAISDPTRRKILDLL-KGGDMTAGDIAEHFNISKPSISHHLNILKQAEVISDHRKGQF    62

Query:  75 RFYSI    79
           +YS+

Sbjct:  63 IYYSL    67
```

Based on this analysis, it was predicted that this protein from *N. gonorrhoeae*, and its epitopes, could be useful antigens for vaccines or diagnostics.

Example 57

A DNA sequence was identified in *N. gonorrhoeae* <SEQ ID 113> which encodes amino acid sequence <SEQ ID 114; NGS57>. Analysis of this protein sequence reveals the following:

GvH: Examining signal sequence (von Heijne)
Signal Score (-7.5): -2.57
Possible cleavage site: 55
>>> Seems to have no N-terminal signal seq.
Amino Acid Composition of Predicted Mature Form: calculated from 1
ALOM: Finding transmembrane regions (Klein et al.)
count: 0 value: 5.67 threshold: 0.0

| PERIPHERAL | Likelihood = 5.67 |
|---|---|
| modified ALOM score: -1.63 | |
| Rule: cytoplasmic protein | |

*** Reasoning Step: 2
Final Results bacterial cytoplasm --- Certainty =            0.160(Affirmative) < succ>
bacterial periplasmic space --- Certainty =    0.000(Not Clear) < succ>
bacterial outer membrane --- Certainty =       0.000(Not Clear) < succ>
bacterial inner membrane --- Certainty =       0.000(Not Clear) < succ>

The protein has homology with the following sequences in the databases:

```
>gi|10444407|gb|AAG17897.1|AF297971_1 (AF297971) restriction endonuclease
R. NgoMIII [Neisseria gonorrhoeae]
Length = 213

Score = 319 bits (818), Expect = 1e-86
Identities = 156/156 (100%), Positives = 156/156 (100%)

Query:    1 LYKQYADWNRLSYNAPIYVGKAVPKGWRQARNSDNALNQSTELFHRLKEHSRSIAAVSDL    60
            LYKQYADWNRLSYNAPIYVGKAVPKGWRQARNSDNALNQSTELFHRLKEHSRSIAAVSDL
Sbjct:   58 LYKQYADWNRLSYNAPIYVGKAVPKGWRQARNSDNALNQSTELFHRLKEHSRSIAAVSDL   117

Query:   61 DPSDFMCRFVIFEGAGSDMIGTIEAALIKLHKPLWNSCVDGFGNHDPGKGRYEQAKSDWD   120
            DPSDFMCRFVIFEGAGSDMIGTIEAALIKLHKPLWNSCVDGFGNHDPGKGRYEQAKSDWD
Sbjct:  118 DPSDFMCRFVIFEGAGSDMIGTIEAALIKLHKPLWNSCVDGFGNHDPGKGRYEQAKSDWD   177

Query:  121 VLHSGRVWADRLNGIPNSYESILENINTHLEIIKRK   156
            VLHSGRVWADRLNGIPNSYESILENINTHLEIIKRK
Sbjct:  178 VLHSGRVWADRLNGIPNSYESILENINTHLEIIKRK   213
```

Based on this analysis, it was predicted that this protein from *N. gonorrhoeae*, and its epitopes, could be useful antigens for vaccines or diagnostics.

Example 58

A DNA sequence was identified in *N. gonorrhoeae* <SEQ ID 115> which encodes amino acid sequence <SEQ ID 116; NGS58>. Analysis of this protein sequence reveals the following:

GvH: Examining signal sequence (von Heijne)
Signal Score (-7.5): -1.92
Possible cleavage site: 16
>>> Seems to have no N-terminal signal seq.
Amino Acid Composition of Predicted Mature Form: calculated from 1
ALOM: Finding transmembrane regions (Klein et al.)
count: 0 value: 5.41 threshold: 0.0

| PERIPHERAL | Likelihood = 5.41 |
|---|---|
| modified ALOM score: -1.58 | |
| Rule: cytoplasmic protein | |

*** Reasoning Step: 2
Final Results bacterial cytoplasm --- Certainty =            0.107(Affirmative) < succ>
bacterial periplasmic space --- Certainty =    0.000(Not Clear) < succ>
bacterial outer membrane --- Certainty =       0.000(Not Clear) < succ>
bacterial inner membrane --- Certainty =       0.000(Not Clear) < succ>

The protein has homology with the following sequences in the databases:

```
>gi|10444408|gb|AAG17898.1|AF297971_2 (AF297971)
DNA cytosine methyltransferase
M. NgoMIII [Neisseria gonorrhoeae]
Length = 377

Score = 759 bits (1960), Expect = 0.0
Identities = 377/377 (100%), Positives = 377/377 (100%)

Query:    1 MKSLEIFSGAGGLAKGLELAGFQHASFIELNKDACNSLRSNFNPKLVYQGDVADFDLSSQ   60
            MKSLEIFSGAGGLAKGLELAGFQHASFIELNKDACNSLRSNFNPKLVYQGDVADFDLSSQ
Sbjct:    1 MKSLEIFSGAGGLAKGLELAGFQHASFIELNKDACNSLRSNFNPKLVYQGDVADFDLSSQ   60

Query:   61 EGIEVIAGGPPCQPFSLGGKHLAHEDRRDMFPHAVRYVEYYRPKAFIFENVKGLLRKSFA  120
            EGIEVIAGGPPCQPFSLGGKHLAHEDRRDMFPHAVRYVEYYRPKAFIFENVKGLLRKSFA
Sbjct:   61 EGIEVIAGGPPCQPFSLGGKHLAHEDRRDMFPHAVRYVEYYRPKAFIFENVKGLLRKSFA  120

Query:  121 DYFEYILLRLTYPNLGILQNEDWKGHLTRLKEIEFNLYKGIKYKVSYQLLNAADYGVPQK  180
            DYFEYILLRLTYPNLGILQNEDWKGHLTRLKEIEFNLYKGIKYKVSYQLLNAADYGVPQK
Sbjct:  121 DYFEYILLRLTYPNLGILQNEDWKGHLTRLKEIEFNLYKGIKYKVSYQLLNAADYGVPQK  180

Query:  181 RERVVIVGIRADLDIDWKFPKRTHSEDRLNWEKYVTGEYWEKHNEPKRFNKDIAEKLQKK  240
            RERVVIVGIRADLDIDWKFPKRTHSEDRLNWEKYVTGEYWEKHNEPKRFNKDIAEKLQKK
Sbjct:  181 RERVVIVGIRADLDIDWKFPKRTHSEDRLNWEKYVTGEYWEKHNEPKRFNKDIAEKLQKK  240

Query:  241 YGIFEPEKKPWQTVRDTLSDIPHPLGNHKITGHEYRDGARIYPGHTGSGIDEPSKTIKAG  300
            YGIFEPEKKPWQTVRDTLSDIPHPLGNHKITGHEYRDGARIYPGHTGSGIDEPSKTIKAG
Sbjct:  241 YGIFEPEKKPWQTVRDTLSDIPHPLGNHKITGHEYRDGARIYPGHTGSGIDEPSKTIKAG  300

Query:  301 GHGVPGGENMIRYDDGTVRYFTSYEAKLLQTFPEEFVISGAWGEAMRQIGNAVPVKLSEI  360
            GHGVPGGENMIRYDDGTVRYFTSYEAKLLQTFPEEFVISGAWGEAMRQIGNAVPVKLSEI
Sbjct:  301 GHGVPGGENMIRYDDGTVRYFTSYEAKLLQTFPEEFVISGAWGEAMRQIGNAVPVKLSEI  360

Query:  361 LGKHLMGVLSEKSSLHN                                             377
            LGKHLMGVLSEKSSLHN
Sbjct:  361 LGKHLMGVLSEKSSLHN                                             377
```

Based on this analysis, it was predicted that this protein from *N. gonorrhoeae*, and its epitopes, could be useful antigens for vaccines or diagnostics.

Example 59

A DNA sequence was identified in *N. gonorrhoeae* <SEQ ID 117> which encodes amino acid sequence <SEQ ID 118; NGS59>. Analysis of this protein sequence reveals the following:

GvH: Examining signal sequence (von Heijne)
Signal Score (−7.5): −3.82
Possible cleavage site: 60
>>> Seems to have no N-terminal signal seq.
Amino Acid Composition of Predicted Mature Form:

-continued calculated from 1
ALOM: Finding transmembrane regions (Klein et al.)
count: 0 value: 2.86 threshold: 0.0

| PERIPHERAL | Likelihood = 2.86 |
|---|---|
| modified ALOM score: −1.07 | |
| Rule: cytoplasmic protein | |

*** Reasoning Step: 2
Final Results bacterial cytoplasm --- Certainty =         0.197(Affirmative) < succ>
bacterial periplasmic space --- Certainty = 0.000(Not Clear) < succ>
bacterial outer membrane --- Certainty =    0.000(Not Clear) < succ>
bacterial inner membrane --- Certainty =    0.000(Not Clear) < succ>

The protein has homology with the following sequences in the databases:

```
>gi|11353338|pir||F81882 hypothetical protein NMA1155 [imported] -
Neisseria meningitidis
(group A strain Z2491)
gi|7379848|emb|CAB84417.1|(AL162755) hypothetical protein NMA1155
[Neisseria meningitidis Z2491]

Length = 120
Score = 131 bits (329), Expect = 2e-30
Identities = 64/68 (94%), Positives = 67/68 (98%)

Query:    1 LSDISASRAAYMDVQKQYPFETVAVCVLPNHIHAIWTLPPDDADYSLLRRLIKTKFSAYS   60
            +S+ISASRAAYMDVQKQYPFETVAVCVLPNHIHAIWTLPPDDADYSLLRRLIKTKFSAYS
Sbjct:    1 MSNISASRAAYMDVQKQYPFETVAVCVLPNHIHAIWTLPPDDADYSLLRRLIKTKFSAYS   60

Query:   61 PHTKNLGA   68
            P+TKNL A
Sbjct:   61 PYTKNLSA   68
```

Example 60

A DNA sequence was identified in *N. gonorrhoeae* <SEQ ID 119> which encodes amino acid sequence <SEQ ID 120; NGS60>. Analysis of this protein sequence reveals the following:

| | |
|---|---|
| GvH: Examining signal sequence (von Heijne) | |
| Signal Score (-7.5): -3.14 | |
| Possible cleavage site: 16 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 2.76 threshold: 0.0 | |
| PERIPHERAL    Likelihood = 2.76 | |
| modified ALOM score: -1.05 | |
| Rule: cytoplasmic protein | |
| *** Reasoning Step: 2 Final Results | |
| bacterial cytoplasm --- Certainty = | 0.330(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

Based on this analysis, it was predicted that this protein from *N. gonorrhoeae*, and its epitopes, could be useful antigens for vaccines or diagnostics.

As a homolog was found in serogroup A *N. meningitidis* but not in serogroup B, NGS60 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 61

A DNA sequence was identified in *N. gonorrhoeae* <SEQ ID 121> which encodes amino acid sequence <SEQ ID 122; NGS61>. Analysis of this protein sequence reveals the following:

| | |
|---|---|
| GvH: Examining signal sequence (von Heijne) | |
| Signal Score (-7.5): -6.88 | |
| Possible cleavage site: 32 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 5.52 threshold: 0.0 | |
| PERIPHERAL    Likelihood = 5.52 | |
| modified ALOM score: -1.60 | |
| Rule: cytoplasmic protein | |
| *** Reasoning Step: 2 Final Results | |
| bacterial cytoplasm --- Certainty = | 0.300(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>gi|11281269|pir||D81804 hypothetical protein NMA1789 [imported] -
Neisseria meningitidis (group A strain Z2491)
gi|7380430|emb|CAB85016.1|(AL162757) hypothetical protein [Neisseria
meningitidis Z2491]
Length = 243

Score = 154 bits (389), Expect = 5e-37
Identities = 82/85 (96%), Positives = 82/85 (96%)

Query:  12 MNTKTELQKLLEEDISTLKETLIRVDALPPRYVRSIATPIVRRWLIDKQLNILAKEIGLT  71
           MNTKTELQKLLEEDISTL ETLI  DALPPRYVRSIATPIVRRWLIDKQLNILAKEIGLT Sbjct:   1 MNTKTELQKLLEEDISTLTETLICADALPPRYVRSIATPIVRRWLIDKQLNILAKEIGLT  60

Query:  72 IELPILDTSLVFEKLSTLENKVNFY  96
           IELPILDTSLVFEKLSTLENKVNFY

Sbjct:  61 IELPILDTSLVFEKLSTLENKVNFY  85
```

```
>gi|11281269|pir||D81804 hypothetical protein NMA1789 [imported] -
Neisseria meningitidis (group A strain Z2491)
gi|7380430|emb|CAB85016.1|(AL162757) hypothetical protein [Neisseria
meningitidis Z2491]
Length = 243

Score = 193 bits (491), Expect = 5e-49
Identities = 96/101 (95%), Positives = 97/101 (95%)

Query:     1  MAGGVYLGGKIISPIYHSSQEFSGEPIIYAETNIILCPAEKFLTLKRVFHNGNIFNMNQI    60
              MAGGVYLGG+ IS IYHSSQEFSGEPIIYAE NIILCPAEKFLTLKRVFHNGNIFNMNQI
Sbjct:    86  MAGGVYLGGEFISSIYHSSQEFSGEPIIYAEPNIILCPAEKFLTLKRVFHNGNIFNMNQI   145

Query:    61  ITFLSNKQGGVRFDKNYDKYKTWQVAIEKAANFLKLGNPYN                     101
              ITFLSNKQGGV FDKNYDKYKTWQVAIEKAANFLKLGNPYN
Sbjct:   146  ITFLSNKQGGVHFDKNYDKYKTWQVAIEKAANFLKLGNPYN                    186)
```

As a homolog (amino acids 1-96) was found in serogroup A *N. meningitidis* but not in serogroup B, NGS61 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 62

A DNA sequence was identified in *N. gonorrhoeae* <SEQ ID 123> which encodes amino acid sequence <SEQ ID 124; NGS62>. Analysis of this protein sequence reveals the following:

---

GvH: Examining signal sequence (von Heijne)
Signal Score (-7.5): -2.43
Possible cleavage site: 44
>>> Seems to have no N-terminal signal seq.
Amino Acid Composition of Predicted Mature Form:
calculated from 1
ALOM: Finding transmembrane regions (Klein et al.)
count: 0 value: 4.72 threshold: 0.0

PERIPHERAL          Likelihood = 4.72
modified ALOM score: -1.44
Rule: cytoplasmic protein

*** Reasoning Step: 2
Final Results

| | |
|---|---|
| bacterial cytoplasm --- Certainty = | 0.324(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

---

A homolog was found in serogroup A *N. meningitidis* but not in serogroup B, so NGS62 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 63

A DNA sequence was identified in *N. gonorrhoeae* <SEQ ID 125> which encodes amino acid sequence <SEQ ID 126; NGS63>. Analysis of this protein sequence reveals the following:

---

GvH: Examining signal sequence (von Heijne)
Signal Score (-7.5): 0.74
Possible cleavage site: 24
>>> Seems to have a cleavable N-term signal seq.
Amino Acid Composition of Predicted Mature Form:
calculated from 25
ALOM: Finding transmembrane regions (Klein et al.)
count: 0 value: 10.72 threshold: 0.0

PERIPHERAL          Likelihood = 10.72
modified ALOM score: -2.64
Score for OM-PP discrimination: -22.14
Rule: outer membrane or periplasmic protein
Score for OM-PP discrimination: -22.14
Rule: outer membrane or periplasmic protein

*** Reasoning Step: 2
Periplasmic space?   Score: 2.21378
Periplasmic space?   Score: 2.21378
Final Results

| | |
|---|---|
| bacterial periplasmic space --- Certainty = | 0.931(Affirmative) < succ> |
| bacterial outer membrane --- Certainty = | 0.237(Affirmative) < succ> |
| bacterial inner membrane --- Certainty = | 0.000(Not Clear) < succ> |
| bacterial cytoplasm --- Certainty = | 0.000(Not Clear) < succ> |

---

The protein has homology with the following sequences in the databases:

```
>gi|11284146|pir||B81142 hypothetical protein NMB0912 [imported] -
Neisseria meningitidis
(group B strain MD58)
gi|7226150|gb|AAF41320.1|(AE002443) hypothetical protein [Neisseria
meningitidis MC58]
Length = 208

Score = 51.7 bits (119), Expect = 3e-06
Identities = 30/72 (41%), Positives = 40/72 (54%)

Query:     5  LLKNWKPLLILSAIAFFAVSWQLDRAAQYRRGYGAAVSEVSERLKAAAVEHAEHARKSSA    64
              LLK WKP+ +L  I    +W   DRA +YR G  AA +E+S RLK    +E A+ AR +
Sbjct:    43  LLKYWKPVGVLLLIVLIFTAWHFDRAEKYRMGREAAAAEISNRLKDGYIEQAKQARSAEQ   102
```

```
Query:   65  AYQAQKAAREEK                                           76
             A   A R+ K
Sbjct:  103  KAAAAFAERQTK                                          114
```

Based on this analysis, it was predicted that this protein from *N. gonorrhoeae*, and its epitopes, could be useful antigens for vaccines or diagnostics.

Example 64

A DNA sequence was identified in *N. gonorrhoeae* <SEQ ID 127> which encodes amino acid sequence <SEQ ID 128; NGS64>. Analysis of this protein sequence reveals the following:

McG: Examining signal sequence (McGeoch)
Length of UR: 0
Peak Value of UR: 2.99
Net Charge of CR: 4
Discriminant Score: 5.35
GvH: Examining signal sequence (von Heijne)
Signal Score (-7.5): -2.53
Possible cleavage site: 33
>>> Seems to have an uncleavable N-term signal seq
Amino Acid Composition of Predicted Mature Form: calculated from 1
ALOM: Finding transmembrane regions (Klein et al.)
count: 0 value: 3.23 threshold: 0.0

| PERIPHERAL | Likelihood = 3.23 |
|---|---|
| modified ALOM score: -1.15 | |

*** Reasoning Step: 2
Final Results

| bacterial inner membrane --- Certainty = | 0.054(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 65

A DNA sequence was identified in *N. gonorrhoeae* <SEQ ID 129> which encodes amino acid sequence <SEQ ID 130; NGS65>. Analysis of this protein sequence reveals the following:

GvH: Examining signal sequence (von Heijne)
Signal Score (-7.5): -5.61
Possible cleavage site: 61
>>> Seems to have no N-terminal signal seq.
Amino Acid Composition of Predicted Mature Form: calculated from 1
ALOM: Finding transmembrane regions (Klein et al.)
count: 0 value: 3.34 threshold: 0.0

| PERIPHERAL | Likelihood = 3.34 |
|---|---|
| modified ALOM score: -1.17 | |
| Rule: cytoplasmic protein | |

*** Reasoning Step: 2
Final Results

| bacterial cytoplasm --- Certainty = | 0.236(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>gi|1175791|sp|P44189|YE18_HAEIN HYPOTHETICAL PROTEIN HI1418
gi|1074769|pir||A64029 hypothetical protein HI1418 - Haemophilus influenzae
(strain Rd KW20)
gi|1574254|gb|AAC23068.1|(U32821) H. influenzae predicted coding region
HI1418
[Haemophilus influenzae Rd]
Length = 201

Score = 104 bits (251), Expect = 1e-21
Identities = 58/119 (48%), Positives = 72/119 (59%), Gaps = 4/119 (3%)

Query:   51  LKMQNTISVFSFKSQNVRTQI-LGAEPWFCLGDVAEILQIQNAR---QLPLKDQGIQKSS  106
             +K Q   S F+FK  VR +    E WFC DV  IL    N+R    Q   K G+ K
Sbjct:   14  MKNQIQFSTFNFKDLPVRVILDPKGEFWFCGTDVCHILGYTNSRKALQDHCKQGGVTKRY  73

Query:  107  VATKKGNQELLFINEPNLYRVIFRSRKAEAVKFQDWIFEEVIPQIRKTGGYQITPKTTA   165
                  TK  +QE+ FINEPNLYR+I +SRK EA   F+ W+FEEV+PQIRKTG YQ+ P+  A
Sbjct:   74  TPTKSADQEMTFINEPNLYRLIIKSRKPEAEPFEAWVFEEVLPQIRKTGKYQLQPQQLA   132

>gi|11281012|pir||A81144 hypothetical protein NMB0900 [imported] - Neisseria
meningitidis
(group B strain MD58)
gi|7226137|gb|AAF41308.1|(AE002442) hypothetical protein [Neisseria
meningitidis MC58]
Length = 305

Score = 104 bits (249), Expect = 2e-21
Identities = 73/137 (53%), Positives = 93/137 (67%), Gaps = 2/137 (1%)

Query:  190  YSMIHQRFNVEAVEGIPADKLPEAVAYVHALTLHTG-LAGEVPDREPLPAPQPALPISGN  248
             +S +  +F    E  +PA++  PE  +      +   G L GEV DREPLPAPQPALPISGN
Sbjct:  164  WSAVKSKFGCSYKE-VPAEQFPEVLSVMGRVAVENGVLYGEVLDREPLPAPQPALPISGN  222
```

-continued

```
Query:  249 ALADIAAMVYYGTRMIELGKDVSAPLKQLGCKQAVTMWTVWHETRSILKRSVAALEVLRG  308
            AL D+A  V YG   I++G+DVS PLKQLGCKQAVTMWTVW ETRS LK +  ALE L
Sbjct:  223 ALYDLAVAVRYGAWAIQMGRDVSLPLKQLGCKQAVTMWTVWAETRSRLKAAANALEALNA  282

Query:  309 YADKDASGRIAACLEGI  325
            +AD + + +I   L  I
Sbjct:  283 HADAEHAAKIRPMLPEI  299
```

>gi|7460273|pir||T13267 hypothetical protein - *Lactococcus lactis* phage BK5-T
gi|928839|gb|AAA98590.1|(L44593) ORF266; putative [*Lactococcus* phage BK5-T]
Length = 266

Score = 75.9 bits (179), Expect = 6e-13
Identities = 42/111 (37%), Positives = 63/111 (55%), Gaps = 3/111 (2%)

```
Query:   55 NTISVFSFKSQNVRTQILGAEPWFCLGDVAEILQIQNAR---QLPLKDQGIQKSSVATKK  111
            N + F+F +  VRT ++  EPWF   DVA +  +N R      +KD+  ++S + T
Sbjct:    2 NELQNFNFNNLPVRTVLINDEPWFVGKDVAIAIGYKNFRDALKSHVKDKYKRESRITTPS   61

Query:  112 GNQELLFINEPNLYRVIFRSRKAEAVKFQDWIFEEVIPQIRKTGGYQITPK  162
            G Q +  I+EP LY++    S+   A  FQDW++EEV+P IRK G Y   K
Sbjct:   62 GVQSVTVISEPGLYQLAGESKLPSAEPFQDWVYEEVLPTIRKHGAYMTDAK  112
```

Based on this analysis, it was predicted that this protein from *N. gonorrhoeae*, and its epitopes, could be useful antigens for vaccines or diagnostics.

Example 66

A DNA sequence was identified in *N. gonorrhoeae* <SEQ ID 131> which encodes amino acid sequence <SEQ ID 132; NGS66>. Analysis of this protein sequence reveals the following:

GvH: Examining signal sequence (von Heijne)
Signal Score (-7.5): -3.12
Possible cleavage site: 53
>>> Seems to have no N-terminal signal seq.
Amino Acid Composition of Predicted Mature Form:
calculated from 1
ALOM: Finding transmembrane regions (Klein et al.)
count: 0 value: 8.96 threshold: 0.0

PERIPHERAL   Likelihood = 8.96
modified ALOM score: -2.29
Rule: cytoplasmic protein

*** Reasoning Step: 2
Final Results

| | |
|---|---|
| bacterial cytoplasm --- Certainty = | 0.402(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology with sequences in the databases.

Based on this analysis, it was predicted that this protein from *N. gonorrhoeae*, and its epitopes, could be useful antigens for vaccines or diagnostics.

Example 67

A DNA sequence was identified in *N. gonorrhoeae* <SEQ ID 133> which encodes amino acid sequence <SEQ ID 134; NGS67>. Analysis of this protein sequence reveals the following:

GvH: Examining signal sequence (von Heijne)
Signal Score (-7.5): 5.71
Possible cleavage site: 22
>>> Seems to have a cleavable N-term signal seq.
Amino Acid Composition of Predicted Mature Form:
calculated from 23
ALOM: Finding transmembrane regions (Klein et al.)
count: 0 value: 2.81 threshold: 0.0

PERIPHERAL   Likelihood = 2.81
modified ALOM score: -1.06
Score for OM-PP discrimination: -32.34
Rule: outer membrane or periplasmic protein
Score for OM-PP discrimination: -32.34
Rule: outer membrane or periplasmic protein

*** Reasoning Step: 2
Periplasmic space?  Score: 3.23391
Periplasmic space?  Score: 3.23391
Final Results

| | |
|---|---|
| bacterial periplasmic space --- Certainty = | 0.928(Affirmative) < succ> |
| bacterial outer membrane --- Certainty = | 0.199(Affirmative) < succ> |
| bacterial inner membrane --- Certainty = | 0.000(Not Clear) < succ> |
| bacterial cytoplasm --- Certainty = | 0.000(Not Clear) < succ> |

The protein has homology with the following sequences in the databases:

>gi|7475078|pir||H69834 hypothetical protein yhjQ - *Bacillus subtilis*
gi|2226189|emb|CAA74479.1|(Y14081) hypothetical protein [*Bacillus subtilis*]
gi|2633396|emb|CAB12900.1|(Z99109) yhjQ [*Bacillus subtilis*]
Length = 108

Score = 32.9 bits (74), Expect = 2.1
Identities = 27/98 (27%), Positives = 44/98 (44%), Gaps = 4/98 (4%)

```
Query:   54 CLDAGQVCLTHCLSLLTQGDTSMSDCAVAVRQMLALCGAVHDLAAQNSPLTRDAAKVCLE  113
            C+ A    C T CL   Q    +S C   R+    +C        +SP  ++   +C +
```

-continued

```
Sbjct:    15 CMKACNHCFTKCLEESVQ--HHLSGCIRLDRECADICALAVKAMQTDSPFMKEICALCAD    72

Query:   114 ACKQCAKACKEHSAHHAECKACYESCLDCIKECEKLAA                          151
             C+ C    C +H    H  C+AC ++C   C ++C  +AA
Sbjct:    73 ICEACGTECGKHD--HDHCQACAKACFTCAEQCRSMAA                          108
```

>gi|7479923|pir||T36241 hypothetical protein SCE39.31c -
Streptomyces coelicolor
gi|4582392|emb|CAB40339.1|(AL049573) hypothetical protein [Streptomyces
coelicolor A3(2)]
Length = 136

Score = 30.9 bits (69), Expect = 7.7
Identities = 27/102 (26%), Positives = 43/102 (41%), Gaps = 6/102 (5%)

```
Query:    54 CLDAGQVCLTHCLSLLTQGDTSMSDCAVAVRQMLALCGAVHDLAAQ----NSPLTRDAAK    109
             C  A    C   CLS  T  D  ++ C          +C A   + ++     ++ +TR    +
Sbjct:    34 CAQACTACADACLSEPTVAD--LTKCIRTDMDCADVCTATAAVLSRHTGYDANVTRAVLQ     91

Query:   110 VCLEACKQCAKACKEHSAHHAECKACYESCLDCIKECEKLAA                     151
             C     C    C   C H+  H   C+  C E+C    C  + C++L A
Sbjct:    92 ACATVCAACGDECARHAGMHEHCRVCAEACRSCEQACQELLA                     133
```

The protein was expressed in *E. coli* as a soluble 14.19 kDa His-fusion product and then purified.

Based on this analysis, it was predicted that this protein from *N. gonorrhoeae*, and its epitopes, could be useful antigens for vaccines or diagnostics.

Example 68

A DNA sequence was identified in *N. gonorrhoeae* <SEQ ID 135> which encodes amino acid sequence <SEQ ID 136; NGS68>. Analysis of this protein sequence reveals the following:

GvH: Examining signal sequence (von Heijne)
Signal Score (-7.5): -4.05
Possible cleavage site: 38
>>> Seems to have no N-terminal signal seq.
Amino Acid Composition of Predicted Mature Form:

calculated from 1
ALOM: Finding transmembrane regions (Klein et al.)
count: 0 value: 5.25 threshold: 0.0

PERIPHERAL         Likelihood = 5.25
modified ALOM score: -1.55
Rule: cytoplasmic protein

*** Reasoning Step: 2
Final Results bacterial cytoplasm --- Certainty =         0.220(Affirmative) < succ>
bacterial periplasmic space --- Certainty = 0.000(Not Clear) < succ>
bacterial outer membrane --- Certainty =    0.000(Not Clear) < succ>
bacterial inner membrane --- Certainty =    0.000(Not Clear) < succ>

The protein has homology with the following sequences in the databases:

>gi|11353493|pir||A81795 hypothetical protein NMA2214 [imported] -
Neisseria meningitidis
(group A strain Z2491)
gi|7380833|emb|CAB85425.1|(AL162758) hypothetical protein [Neisseria
meningitidis Z2491]
Length = 208

Score = 263 bits (673), Expect = 3e-69
Identities = 140/145 (96%), Positives = 143/145 (98%)

```
Query:     1 LDWRGNKPLGAAELADLKPLYKDFMYWERGLHMYKASAVVPTGYVRVGNTAPLCGEDTQR     60
             LDW+GNKPLGAAELADLKPLYKDFMYWERGLHMYKASAVVPTGYVRVGNTAPL GEDTQR
Sbjct:    44 LDWQGNKPLGAAELADLKPLYKDFMYWERGLHMYKASAVVPTGYVRVGNTAPLVGEDTQR    103

Query:    61 YASFWGDGYDVYRQLRWRQIPEKQRKAFKKAAKSKNTVMFAGREYGISKQNLSDVWDDFE    120
             YASFWGDGYDVYRQLRW+QIPEKQRKAFKKAAKSK TVMFAGREYGISKQNLSDVWDDFE
Sbjct:   104 YASFWGDGYDVYRQLRWQQIPEKQRKAFKKAAKSKKTVMFAGREYGISKQNLSDVWDDFE    163

Query:   121 DAMELKAFPCLSSLFLTKWHKNLYE                                       145
             DAMELKAFPCLSSLFLTKWHKNLY+
Sbjct:   164 DAMELKAFPCLSSLFLTKWHKNLYD                                       188
```

>gi|11280955|pir||B81219 hypothetical protein NMB0273 [imported] -
Neisseria meningitidis
(group B strain MD58)
gi|7225497|gb|AAF40727.1|(AE002383) hypothetical protein [Neisseria
meningitidis MC58]
Length = 141

```
Score = 216 bits (550), Expect = 5e-55
Identities = 117/121 (96%), Positives = 119/121 (97%)

Query:    25 MYWERGLHMYKASAVVPTGYVRVGNTAPLCGEDTQRYASFWGDGYDVYRQLRWRQIPEKQ      84
             MYWERGLHMYKASAVVPTGYVRVGNTAPL GEDTQRYASFWGDGYDVYRQLRW+QIPEKQ
Sbjct:     1 MYWERGLHMYKASAVVPTGYVRVGNTAPLVGEDTQRYASFWGDGYDVYRQLRWRQQIPEKQ     60

Query:    85 RKAFKKAAKSKNTVMFAGREYGISKQNLSDVWDDFEDAMELKAFPCLSSLFLTKWHKNLY    144
             RKAFKKAAKSK TVMFAGREYGISKQNLSDVWDDFEDAMELKAFPCLSSLFLTKWHKNLY
Sbjct:    61 RKAFKKAAKSKKTVMFAGREYGISKQNLSDVWDDFEDAMELKAFPCLSSLFLTKWHKNLY    120

Query:   145 E                                                                145
             +
Sbjct:   121 D                                                                121
```

Based on this analysis, it was predicted that this protein from *N. gonorrhoeae*, and its epitopes, could be useful antigens for vaccines or diagnostics.

Example 69

A DNA sequence was identified in *N. gonorrhoeae* <SEQ ID 137> which encodes amino acid sequence <SEQ ID 138; NGS69>. Analysis of this protein sequence reveals the following:

---

GvH: Examining signal sequence (von Heijne)
Signal Score (−7.5): −5.63
Possible cleavage site: 43
>>> Seems to have no N-terminal signal seq.
Amino Acid Composition of Predicted Mature Form:
calculated from 1
ALOM: Finding transmembrane regions (Klein et al.)
count: 0 value: 6.84 threshold: 0.0

---

PERIPHERAL         Likelihood = 6.84
modified ALOM score: −1.87
Rule: cytoplasmic protein

---

*** Reasoning Step: 2
Final Results

--- bacterial cytoplasm --- Certainty =          0.361(Affirmative) < succ>
bacterial periplasmic space --- Certainty =  0.000(Not Clear) < succ>
bacterial outer membrane --- Certainty =     0.000(Not Clear) < succ>
bacterial inner membrane --- Certainty =     0.000(Not Clear) < succ>

---

The protein has homology with the following sequences in the databases:

A homolog was found in serogroup A *N. meningitidis* but not in serogroup B, so NGS69 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 70

A DNA sequence was identified in *N. gonorrhoeae* <SEQ ID 139> which encodes amino acid sequence <SEQ ID 140; NGS70>. Analysis of this protein sequence reveals the following:

---

GvH: Examining signal sequence (von Heijne)
Signal Score (−7.5): −1.18
Possible cleavage site: 22
>>> Seems to have a cleavable N-term signal seq.
Amino Acid Composition of Predicted Mature Form:
calculated from 23
ALOM: Finding transmembrane regions (Klein et al.)
count: 0 value: 4.19 threshold: 0.0

---

PERIPHERAL         Likelihood = 4.19
modified ALOM score: −1.34
Score for OM-PP discrimination: −5.89
Rule: outer membrane or periplasmic protein
Score for OM-PP discrimination: −5.89
Rule: outer membrane or periplasmic protein

---

```
>gi|7464552|pir||C64707 hypothetical protein HP1499 - Helicobacter pylori
(strain 26695)
gi|2314683|gb|AAD08545.1|(AE000648) H. pylori predicted coding region HP1499
[Helicobacter pylori 26695]
Length = 272

Score = 38.2 bits (88), Expect = 0.13
Identities = 34/123 (27%), Positives = 58/123 (46%), Gaps = 10/123 (8%)

Query:     3 EFKFIFGQDFGLSKKEAIRKVLKWLPSHLKFTLMVAQGIQG------FHPKAVFWKNDKN      56
             EF+ I G DF +  ++IR +L    ++ K       +           FHPK  + N K
Sbjct:    54 EFEIIVGLDFKTTDSKSIRFLLDLNKTYKKLRFYCYGDKENNKTDIVFHPKIYMFDNGK-    112

Query:    57 EYYALIGSSNLTHAAFNSNYEAN-ILTKISEQDFIKVKSWADEI--AMKSIPVSEDWLEE    113
             E  ++IGS+NLT    +N+E N I T+      + ++  + I A       +E++L+
Sbjct:   113 EKTSIIGSTNLTKGGLENNFEVNTIFTEKKPLYYTQLNAIYNSIKYADSLFTPNEEYLQN    172

Query:   114 YQE                                                              116
             Y E
Sbjct:   173 YNE                                                              175
```

-continued

```
            *** Reasoning Step: 2
         Periplasmic space? Score: 0.588927
         Periplasmic space? Score: 0.588927
                    Final Results
```

| | |
|---|---|
| bacterial periplasmic space --- Certainty = | 0.849(Affirmative) < succ> |
| bacterial outer membrane --- Certainty = | 0.106(Affirmative) < succ> |
| bacterial inner membrane --- Certainty = | 0.000(Not Clear) < succ> |
| bacterial cytoplasm --- Certainty = | 0.000(Not Clear) < succ> |

The protein has homology with the following sequences in the databases:

```
>gi|11353344|pir||A81886 hypothetical protein NMA1183
[imported] - Neisseria meningitidis
(group A strain Z2491)
gi|7379875|emb|CAB84445.1|(AL162755) hypothetical protein
NMA1183 [Neisseria meningitidis Z2491]
Length = 74

Score = 58.7 bits (141), Expect = 2e-08
Identities = 30/43 (69%), Positives = 32/43 (73%)

Query:   62  IGGFGGVGGFGGLKPALVYRNFRIIATNRPAATRARPRQTTVA   104
             +G   G+ G GGLKP LVY N  IIATNRPAATRA PR TTVA
Sbjct:   32  MGNIDGIDGSGGLKPTLVYWNHCIIATNRPAATRAHPRHTTVA    74
```

Based on this analysis, it was predicted that this protein from N. gonorrhoeae, and its epitopes, could be useful antigens for vaccines or diagnostics.

Example 71

A DNA sequence was identified in N. gonorrhoeae <SEQ ID 141> which encodes amino acid sequence <SEQ ID 142; NGS71>. Analysis of this protein sequence reveals the following

| | |
|---|---|
| GvH: Examining signal sequence (von Heijne) | |
| Signal Score (-7.5): -1.98 | |
| Possible cleavage site: 28 | |
| >>> Seems to have a cleavable N-term signal seq. | |
| Amino Acid Composition of Predicted Mature Form: calculated from 29 | |
| ALOM: Finding transmembrane regions (Klein et al.) | |
| count: 0 value: 5.04 threshold: 0.0 | |

| | |
|---|---|
| PERIPHERAL | Likelihood = 5.04 |
| modified ALOM score: -1.51 | |
| Score for OM-PP discrimination: -9.17 | |
| Rule: outer membrane or periplasmic protein | |
| Score for OM-PP discrimination: -9.17 | |
| Rule: outer membrane or periplasmic protein | |

```
            *** Reasoning Step: 2
         Periplasmic space? Score: 0.916744
         Periplasmic space? Score: 0.916744
                    Final Results
```

| | |
|---|---|
| bacterial periplasmic space --- Certainty = | 0.923(Affirmative) < succ> |
| bacterial outer membrane --- Certainty = | 0.146(Affirmative) < succ> |
| bacterial inner membrane --- Certainty = | 0.000(Not Clear) < succ> |
| bacterial cytoplasm --- Certainty = | 0.000(Not Clear) < succ> |

The protein has no homology with sequences in the databases.

Based on this analysis, it was predicted that this protein from N. gonorrhoeae, and its epitopes, could be useful antigens for vaccines or diagnostics.

Example 72

A DNA sequence was identified in N. gonorrhoeae <SEQ ID 143> which encodes amino acid sequence <SEQ ID 144; NGS72>. Analysis of this protein sequence reveals the following:

| | |
|---|---|
| GvH: Examining signal sequence (von Heijne) | |
| Signal Score (-7.5): -3.18 | |
| Possible cleavage site: 42 | |
| >>> Seems to have an uncleavable N-term signal seq | |
| Amino Acid Composition of Predicted Mature Form: calculated from 1 | |
| ALOM: Finding transmembrane regions (Klein et al.) | |
| count: 4 value: -8.76 threshold: 0.0 | |

| | | | |
|---|---|---|---|
| INTEGRAL | Likelihood = -8.76 | Transmembrane | 11-27 |
| | | | (8-37) |
| INTEGRAL | Likelihood = -6.90 | Transmembrane | 80-96 |
| | | | (75-102) |
| INTEGRAL | Likelihood = -2.39 | Transmembrane | 98-114 |
| | | | (98-114) |
| INTEGRAL | Likelihood = -1.12 | Transmembrane | 47-63 |
| | | | (47-64) |
| PERIPHERAL | Likelihood = 3.55 | | |
| modified ALOM score: 2.25 | | | |
| Rule: cytoplasmic membrane protein | | | |

```
            *** Reasoning Step: 2
                    Final Results
```

| | |
|---|---|
| bacterial inner membrane --- Certainty = | 0.450(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology with the following sequences in the databases:

```
>gi|11354095|pir||H81995 probable transmembrane transport protein NMA0047
[imported] - Neisseria meningitidis (group A strain Z2491)
gi|7378822|emb|CAB83364.1| (AL162752) putative transmembrane transport protein
[Neisseria meningitidis Z2491]
Length = 405

Score = 257 bits (658), Expect = 5e-68
Identities = 152/162 (93%), Positives = 154/162 (94%)

Query:    1  MTHTASKTPKLWAVIAAAAFILLITIGMRMTLGLFVQPVVNTTELNIAQFSLIITVFQLM    60
             MTHTASKTPK W  I AAAAFILLITIGMRMTLGLFVQPVVNTTEL+IAQFSLII VFQLM
Sbjct:    1  MTHTASKTPKFWLTITAAAFILLITIGMRMTLGLFVQPVVNTTELSIAQFSLIIAVFQLM    60

Query:   61  WGVLQPLSGALADRFGAFRVLSGGALLLVCACLIASNIPTYWGLMIAVGLLLAFGTGSGG   120
             WGV QPLSGALADRFGAFRVLSGGA+LLVCACLIA NIPTYWGLMIAVGLLLAFGTGSGG
Sbjct:   61  WGVSQPLSGALADRFGAFRVLSGGAVLLVCACLIAPNIPTYWGLMIAVGLLLAFGTGSGG   120

Query:  121  FSIIMGQVAAQVPTHKRGLASGLVNAGGSAGQFLFAPLVQGL                    162
             FSIIMGQVAAQVP HKRGLASGLVNAGGSAGQFLFAPLVQGL
Sbjct:  121  FSIIMGQVAAQVPAHKRGLASGLVNAGGSAGQFLFAPLVQGL                    162

>gi|11351469|pir||F83484 probable MFS transporter PA1286 [imported] -
Pseudomonas aeruginosa
(strain PAO1)
gi|9947221|gb|AAG04675.1|AE004558_4 (AE004558) probable MFS transporter
[Pseudomonas aeruginosa]
Length = 399

Score = 72.5 bits (177), Expect = 3e-12
Identities = 53/149 (35%), Positives = 81/149 (53%)

Query:   14  VIAAAAFILLITIGMRMTLGLFVQPVVNTTELNIAQFSLIITVFQLMWGVLQPLSGALAD    73
             ++ + A IL +++G+R   GLF+ P+          F+  I +  L+WG+ QP +GALAD
Sbject:   8  ILLSGALILALSLGVRHGFGLFLAPMSADFGWGREVFAFAIALQNLVWGLAQPFTGALAD    67

Query:   74  RFGAFRVLSGGALLLVCACLIASNIPTYWGLMIAVGLLLAFGTGSGGFSIIMGQVAAQVP   133
             R+GA R + G LL    ++      + GL ++ GLL+  G     FS+I+G V   VP
Sbjct:   68  RYGAARAVLVGGLLYALGLVLMGLSQSASGLSLSAGLLIGLGLSGTSFSVILGAVGRAVP   127

Query:  134  THKRGLASGLVNAGGSAGQFLFAPLVQGL                                 162
             +R +A G+ +A GS GQF   P   GL
Sbjct:  128  AEQRSMAMGISSAAGSFGQFAMLPGTLGL                                 156
```

As a homolog was found in serogroup A *N. meningitidis* but not in serogroup B, NGS72 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 73

A DNA sequence was identified in *N. gonorrhoeae* <SEQ ID 145> which encodes amino acid sequence <SEQ ID 146; NGS73>. Analysis of this protein sequence reveals the following:

GvH: Examining signal sequence (von Heijne)
Signal Score (-7.5): -4.26
Possible cleavage site: 52
>>> Seems to have no N-terminal signal seq.
Amino Acid Composition of Predicted Mature Form: calculated from 1
ALOM: Finding transmembrane regions (Klein et al.)
count: 3 value: -3.72 threshold: 0.0

| | | | |
|---|---|---|---|
| INTEGRAL | Likelihood = -3.72 | Transmembrane | 172-188 (171-190) |
| INTEGRAL | Likelihood = -2.97 | Transmembrane | 119-135 (114-137) |
| INTEGRAL | Likelihood = -1.86 | Trensmembrane | 209-225 (205-225) |
| PERIPHERAL | Likelihood = 4.88 | | | modified ALOM score: 1.24
Rule: cytoplasmic membrane protein

*** Reasoning Step: 2
Final Results

| | |
|---|---|
| bacterial inner membrane --- Certainty = | 0.249(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology with the following sequences in the databases:

```
>gi|11354095|pir||H81995 probable transmembrane transport protein NMA0047
[imported] - Neisseria meningitidis (group A strain Z2491)
gi|7378822|emb|CAB83364.1|(AL162752) putative trasmembrane transport protein
[Neisseria meningitidis Z2491]
Length = 405

Score = 222 bits (567), Expect = 3e-57
Identities = 116/123 (94%), Positives = 117/123 (94%), Gaps = 4/123 (3%)

Query:  103  QGLVVLPEVGWTGTFYVWGAIALLILPVSWWLAGGNNGGNNAAHTQHTQATHGQSLGEAV   162
             QGLVVLPEVGWTGTFYVWGAIALL LPVSWWLA    GGNNAAHTQH QATHGQSLGEAV
Sbjct:  160  QGLVVLPEVGWTGTFYVWGAIALLTLPVSWWLA----GGNNAAHTQHAQATHGQSLGEAV   215

Query:  163  KTAFKTPSYILLHLSFFACGFHIAFLVTHLPTEVALCGLPATVASTSIAIIGLANIAGCV   222
             KTAFKTPSYILLHLSFFACGFHIAFLVTHLPTEVALCGLPATVASTSIAIIGLANIAGC+
Sbjct:  216  KTAFKTPSYILLHLSFFACGFHIAFLVTHLPTEVALCGLPATVASTSIAIIGLANIAGCI   275

Query:  223  FSG   225
             FSG
Sbjct:  276  FSG   278

>gi|11351469|pir||F83484 probable MFS transporter PA1286 [imported] -
Pseudomonas aeruginosa
(strain PAO1)
gi|9947221|gb|AAG04675.1|AE004558_4 (AE004558) probable MFS transporter
[Pseudomonas aeruginosa]
Length = 399

Score = 54.4 bits (130), Expect = 1e-06
Identities = 37/115 (32%), Positives = 56/115 (48%), Gaps = 10/115 (8%)

Query:  111  VGWTGTFYVWGAIALLILPVSWWLAGGNNGGNNAAHTQHTQATHGQSLGEAVKTAFKTPS   170
             +GW+      G +  LI+P++   +              H QSLGEA++ A
Sbjct:  160  LGWSSALLALGLLVALIVPLAGLM---------KDRPLPPQGHEQSLGEALREACAHSG   209

Query:  171  YILLHLSFFACGFHIAFLVTHLPTEVALCGLPATVASTSIAIIGLANIAGCVFSG      225
             +  LL L FF CGF + F+  HLP      LPA V +T +A++GL N+ G    +G
Sbjct:  210  FWLLALGFFVCGFQVVFIGVHLPAYLVDQHLPAQVGTTVLALVGLFNVFGTYIAG     264
```

As a homolog was found in serogroup A *N. meningitidis* but not in serogroup B, so NGS73 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 74

A DNA sequence was identified in *N. gonorrhoeae* <SEQ ID 147> which encodes amino acid sequence <SEQ ID 148; NGS74>. Analysis of this protein sequence reveals the following:

GvH: Examining signal sequence (von Heijne)
Signal Score (−7.5): 0.41
Possible cleavage site: 30
>>> Seems to have no N-terminal signal seq.

Amino Acid Composition of Predicted Mature Form:
calculated from 1
ALOM: Finding transmembrane regions (Klein et al.)
count: 2 value: −1.49 threshold: 0.0

| INTEGRAL | Likelihood = −1.49 | Transmembrane | 15-31 (15-31) |
| INTEGRAL | Likelihood = −1.28 | Transmembrane | 83-99 (83-99) |
| PERIPHERAL | Likelihood = 1.59 | | | modified ALOM score: 0.80
Rule: cytoplasmic membrane protein

*** Reasoning Step: 2
Final Results bacterial inner membrane --- Certainty = 0.160(Affirmative) < succ>
bacterial periplasmic space --- Certainty = 0.000(Not Clear) < succ>
bacterial outer membrane --- Certainty = 0.000(Not Clear) < succ>
bacterial cytoplasm --- Certainty = 0.000(Not Clear) < succ>

The protein has homology with the following sequences in the databases:

```
>pir||H81995 probable transmembrane transport protein NmA0047 [imported] -
Neisseria meningitidis (group A strain Z2491)
emb|CAB83364.1|(AL162752) putative transmembrane transport protein
[Neisseria meningitidis Z2491]
Length = 405

Score = 148 bits (374), Expect = 2e-35
Identities = 97/106 (91%), Positives = 103/106 (96%)

Query:  1   MVLIYIFSPKTDLNFYIFAAALGFTWLATVAPTAAVTGKLFGTRYLATLFGLVMLTHQIG   60
            M+LIYIFSPKTDLNFYIFAAALGFTWLATV PTA++TGKLFGTRYLATLFGL ML+HQIG
```

```
-continued
Sbjct:  300  MILIYIFSPKTDLNFYIFAAALGFTWLATVTPTASITGKLFGTRYLATLFGLTMLSHQIG  359

Query:   61  GFLGSYIGGIVITQFGDYGWMWYADAVLAGTAALLVLPVREPRTAA              106
             GFLGSYIGGIVITQFGDYGWMWYADA+LAGTAALL LP+REPRTAA
Sbjct:  360  GFLGSYIGGIVITQFGDYGWMWYADALLAGTAALLNLPIREPRTAA              405

>pir||F83484 probable MFS transporter PA1286 [imported] -
Pseudomonas aeruginosa (strain PAO1)
gb|AAG04675.1|AE004558_4 (AE004558) probable MFS transporter [Pseudomonas
aeruginosa]
Length = 399

Score = 59.0 bits (142), Expect = 2e-08
Identities = 40/101 (39%), Positives = 61/101 (59%)

Query:    1  MVLIYIFSPKTDLNFYIFAAALGFTWLATVAPTAAVTGKLFGTRYLATLFGLVMLTHQIG   60
             ++++++++ P  +  + Y F  A+G  WL+TV   T     LFG R L+ L G+V L HQ+G
Sbjct:  286  VIVLFLWLPLSVYSAYAFGVAMGLLWLSTVPLTNGTVATLFGVRNLSMLGGIVFLFHQLG  345

Query:   61  GFLGSYIGGIVITQFGDYGWMWYADAVLAGTAALLVLPVRE                    101
              FLG ++GG+V  + G Y  +W     +L+  AALL  PVRE
Sbjct:  346  AFLGGWLGGVVYDRTGSYDLVWQLSILLSLLAALLNWPVRE                   386
```

As a homolog was found in serogroup A *N. meningitidis* but not in serogroup B, NGS74 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 75

A DNA sequence was identified in *N. gonorrhoeae* <SEQ ID 149> which encodes amino acid sequence <SEQ ID 150; NGS75>. Analysis of this protein sequence reveals the following:

GvH: Examining signal sequence (von Heijne)
Signal Score (-7.5): -5.2
Possible cleavage site: 22

-continued

>>> Seems to have no N-terminal signal seq.
Amino Acid Composition of Predicted Mature Form:
calculated from 1
ALOM: Finding transmembrane regions (Klein et al.)
count: 0 value: 4.45 threshold: 0.0

| PERIPHERAL | Likelihood = 4.45 |
|---|---|
| modified ALOM score: -1.39 | |
| Rule: cytoplasmic protein | |

*** Reasoning Step: 2
Final Results

| bacterial cytoplasm --- Certainty = | 0.237(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
pir||S04419 type II site-specific deoxyribonuclease (EC 3.1.21.4) NgoPII -
Neisseria gonorrhoeae
emb|CAA36887.1|(X52661) NgoPII restriction and modification [N. gonorrhoeae]
prf||1613419A NgoPII endonuclease [Neisseria gonorrhoeae]
Length = 278

Score = 240 bits (614), Expect = 4e-63
Identities = 128/129 (99%), Positives = 128/129 (99%)

Query:    1  MNIIDAIINLANNPVVGVNSHSQSNNRANQAGDALEEYVKDLFSGSFNLNETQRIARHAK   60
             MNIIDAIINLANNPVVGV SHSQSNNRANQAGDALEEYVKDLFSGSFNLNETQRIARHAK
Sbjct:    1  MNIIDAIINLANNPVVGVESHSQSNNRANQAGDALEEYVKDLFSGSFNLNETQRIARHAK   60

Query:   61  VFSYLGNNSNPPDAMLRNGDAIEVKKIESKDSALALNSSHPKSKLSVDDSMLTKACKDAE  120
             VFSYLGNNSNPPDAMLRNGDAIEVKKIESKDSALALNSSHPKSKLSVDDSMLTKACKDAE
Sbjct:   61  VFSYLGNNSNPPDAMLRNGDAIEVKKIESKDSALALNSSHPKSKLSVDDSMLTKACKDAE  120

Query:  121  KWEEKDIIY                                                    129
             KWEEKDIIY
Sbjct:  121  KWEEKDIIY                                                    129
```

Based on this analysis, it was predicted that this protein from *N. gonorrhoeae*, and its epitopes, could be useful antigens for vaccines or diagnostics.

Example 76

A DNA sequence was identified in *N. gonorrhoeae* <SEQ ID 151> which encodes amino acid sequence <SEQ ID 152; NGS76>. Analysis of this protein sequence reveals the following:

GvH: Examining signal sequence (von Heijne)
Signal Score (-7.5): -1.73
Possible cleavage site: 13
>>> Seems to have no N-terminal signal seq.
Amino Acid Composition of Predicted Mature Form: calculated from 1
ALOM: Finding transmembrane regions (Klein et al.)
count: 0 value: 9.39 threshold: 0.0

| PERIPHERAL | Likelihood = 9.39 |
|---|---|
| modified ALOM score: -2.38 | |
| Rule: cytoplasmic protein | |

*** Reasoning Step: 2
Final Results

| bacterial cytoplasm --- Certainty = | 0.272(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

Based on this analysis, it was predicted that this protein from *N. gonorrhoeae*, and its epitopes, could be useful antigens for vaccines or diagnostics.

Example 77

A DNA sequence was identified in *N. gonorrhoeae* <SEQ ID 153> which encodes amino acid sequence <SEQ ID 154; NGS77>. Analysis of this protein sequence reveals the following:

GvH: Examining signal sequence (von Heijne)
Signal Score (-7.5): -4.51
Possible cleavage site: 58
>>> Seems to have no N-terminal signal seq.
Amino Acid Composition of Predicted Mature Form: calculated from 1
ALOM: Finding transmembrane regions (Klein et al.)
count: 0 value: 3.18 threshold: 0.0

| PERIPHERAL | Likelihood = 3.18 |
|---|---|
| modified ALOM score: -1.14 | |
| Rule: cytoplasmic protein | |

*** Reasoning Step: 2
Final Results

| bacterial cytoplasm --- Certainty = | 0.127(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
pir||s04419 type II site-specific deoxyribonuclease (Ec 3.1.21.4) NgoPII -
Neisseria gonorrhoeae
emb|CAA36887.1|(x52661) NgoPII restriction and modification [N. gonorrhoeae]
prf||1613419A NgoPII endonuclease [Neisseria gonorrhoeae]
Length = 278

Score = 268 bits (687), Expect = 2e-71
Identities = 136/136 (100%), Positives = 136/136 (100%)

Query:    1 LAMVYGIDYCADAECYLKIKNQIKEGIGNIGGIQFAETKELGRVNRIDPLNITYLRVRGM    60
            LAMVYGIDYCADAECYLKIKNQIKEGIGNIGGIQFAETKELGRVNRIDPLNITYLRVRGM Sbjct:  143 LAMVYGIDYCADAECYLKIKNQIKEGIGNIGGIQFAETKELGRVNRIDPLNITYLRVRGM   202

Query:   61 WGIENPWFVFNYIYQRNMEKSFNFMAIINEDKWNSFNNTDKLLAIQDSKLAISDIKIKNP   120
            WGIENPWFVFNYIYQRNMEKSFNFMAIINEDKWNSFNNTDKLLAIQDSKLAISDIKIKNP Sbjct:  203 WGIENPWFVFNYIYQRNMEKSFNFMAIINEDKWNSFNNTDKLLAIQDSKLAISDIKIKNP   262

Query:  121 NNPARLRNAKLITYHL                                              136
            NNPARLRNAKLITYHL Sbjct:  263 NNPARLRNAKLITYHL                                              278
```

```
>pir||CTNHP2 site-specific DNA-methyltransferase (cytosine-specific) (EC
2.1.1.73) NgoPII - Neisseria gonorrhoeae
emb|CAA30038.1|(X06965) NgoPII methylase (AA 1-341) [Neisseria gonorrhoeae]
emb|CAA36888.1|(X52661) NgoPII restriction and modification [Neisseria
gonorrhoeae]
gb|AAA17019.1|(L14564) cytosine methylase [Neisseria gonorrhoeae]
prf||1613419B NgoPII methylase [Neisseria gonorrhoeae]
Length = 341

Score = 682 bits (1761), Expect = 0.0
Identities = 341/341 (100%), Positives = 341/341 (100%)

Query:    1 MQNSSPTTYNPMKIISLFSGCGGLDLGFEKAGFEIPAANEYDKTIWATFKANHPKTHLIE    60
            MQNSSPTTYNPMKIISLFSGCGGLDLGFEKAGFEIPAANEYDKTIWATFKANHPKTHLIE
Sbjct:    1 MQNSSPTTYNPMKIISLFSGCGGLDLGFEKAGFEIPAANEYDKTIWATFKANHPKTHLIE    60

Query:   61 GDIRKIKEEDFPEEIDGIIGGPPCQSWSEAGALRGIDDARGQLFFDYIRILKSKQPKFFL   120
            GDIRKIKEEDFPEEIDGIIGGPPCQSWSEAGALRGIDDARGQLFFDYIRILKSKQPKFFL
Sbjct:   61 GDIRKIKEEDFPEEIDGIIGGPPCQSWSEAGALRGIDDARGQLFFDYIRILKSKQPKFFL   120

Query:  121 AENVSGMLANRHNGAVQNLLKMFDGCGYDVTLTMANAKDYGVAQERKRVFYIGFRKDLEI   180
            AENVSGMLANRHNGAVQNLLKMFDGCGYDVTLTMANAKDYGVAQERKRVFYIGFRKDLEI
Sbjct:  121 AENVSGMLANRHNGAVQNLLKMFDGCGYDVTLTMANAKDYGVAQERKRVFYIGFRKDLEI   180

Query:  181 KFSFPKGSTVEDKDKITLKDVIWDLQDTAVPSAPQNKTNPDAVNNNEYFTGSFSPIFMSR   240
            KFSFPKGSTVEDKDKITLKDVIWDLQDTAVPSAPQNKTNPDAVNNNEYFTGSFSPIFMSR
Sbjct:  181 KFSFPKGSTVEDKDKITLKDVIWDLQDTAVPSAPQNKTNPDAVNNNEYFTGSFSPIFMSR   240

Query:  241 NRVKAWDEQGFTVQASGRQCQLHPQAPKMEKHGANDYRFAAGKETLYRRMTVREVARIQG   300
            NRVKAWDEQGFTVQASGRQCQLHPQAPKMEKHGANDYRFAAGKETLYRRMTVREVARIQG
Sbjct:  241 NRVKAWDEQGFTVQASGRQCQLHPQAPKMEKHGANDYRFAAGKETLYRRMTVREVARIQG   300

Query:  301 FPDNFKFIYQNVNDAYKMIGNAVPVNLAYEIAAAIKKTLER                     341
            FPDNFKFIYQNVNDAYKMIGNAVPVNLAYEIAAAIKKTLER
Sbjct:  301 FPDNFKFIYQNVNDAYKMIGNAVPVNLAYEIAAAIKKTLER                     341
```

Based on this analysis, it was predicted that this protein from *N. gonorrhoeae*, and its epitopes, could be useful antigens for vaccines or diagnostics.

Example 78

A DNA sequence was identified in *N. gonorrhoeae* <SEQ ID 155> which encodes amino acid sequence <SEQ ID 156; NGS78>. Analysis of this protein sequence reveals the following:

GvH: Examining signal sequence (von Heijne)
Signal Score (-7.5): -8.33
Possible cleavage site: 24
>>> Seems to have no N-terminal signal seq.
Amino Acid Composition of Predicted Mature Form:

-continued calculated from 1
ALOM: Finding transmembrane regions (Klein et al.)
count: 0 value: 2.17 threshold: 0.0

| PERIPHERAL | Likelihood = 2.17 |
|---|---|
| modified ALOM score: –0.93 | |
| Rule: cytoplasmic protein | |

*** Reasoning Step: 2
Final Results

| | |
|---|---|
| bacterial cytoplasm --- Certainty = | 0.220(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||H82000 hypothetical protein NMA0089 [imported] -
Neisseria meningitidis (group A strain Z2491)
emb|CAB83405.1|(AL162752) hypothetical protein NMA0089
[Neisseria meningitidis Z2491]
Length = 226

Score = 422 bits (1085), Expect = e-117
Identities = 217/228 (95%), Positives = 220/228 (96%), Gaps = 2/228 (0%)

Query:    1 MERYKNAVRKDKAAELYLLNLSLSRELFHVVSIFEIVLRNKIDICFRQEFKDRNRLYDSI    60
            MERYKNAV KDKAAELYLLNLSLSRELFHVVSIFEIVLNKIDIC +Q FKD N LY+SI
Sbjct:    1 MERYKNAVGKDKAAELYLLNLSLSRELFHVVSIFEIVLNKIDICLQQAFKDGNWLYNSI    60

Query:   61 QPQTNPALKYQGCFLRNGTKESAELIKVALSKIQNNSGGKFDHNQLVAGLGFGFWRYLFA   120
            QPQTNPALKYQGCFLRNGTKESAELIKVALSKIQNNSGGKFDHNQLVAGLGFGFWRYLFA
Sbjct:   61 QPQTNPALKYQGCFLRNGTKESAELIKVALSKIQNNSGGKFDHNQLVAGLGFGFWRYLFA   120

Query:  121 GGKDAQFDAAGKVLMKVFPKKPKSTPSVQYNQKWIFRELSNINNFRNRLAHHEPICFSFK   180
            GGKDAQFDA GKVLMKVFPKKPKSTPSVQ+NQKWIFRELSNINNFRNRLAHHEPIC FK
```

```
                          -continued
Sbjct:  121  GGKDAQFDATGKVLMKVFPKKPKSTPSVQHNQKWIFRELSNINNFRNRLAHHEPIC--FK  178

Query:  181  GAIKDTGYARNIHQSIFELLNYMDVDTASVFSHFSDQVIAVCDEIDKL              228
             GAIKDTGYARNIHQSIFELLNYMDVDTASVFSHFSDQVIAVCDEIDKL
Sbjct:  179  GAIKDTGYARNIHQSIFELLNYMDVDTASVFSHFSDQVIAVCDEIDKL              226

>ref|NP_053274.1|Hypothetical gene [Agrobacterium tumefaciens]
 bj|BAA87659.1|(AB016260) Hypothetical gene [Agrobacterium tumefaciens]
Length = 380

Score = 43.6 bits (102), Expect = 0.002
Identities = 53/215 (24%), Positives = 86/215 (39%), Gaps = 42/215 (19%)

Query:    5  KNAVRKDKAAELYLLNLSLSRELFHVVSIFEIVLRNKIDICFRQEFKDRNRLYDSIQPQT   64
             K     ++ A  LYL N +++    +  +++ E+ LRN +D        F
Sbjct:   55  KGGNHEEYAMALYLYNARVAKAFLYPLNVAEVTLRNAVDGILVARFG-------------  101

Query:   65  NPALKYQGCFLRNGTKESAELIKVALSKIQNNSGGKFDHNQLVAGLGFGFWRYLFAGGKD  124
                  A  +Q   R+ T    L   L K   +G      +Q+VA L F FW  LF
Sbjct:  102  --ANWHQDATFRDQTLTGNGL--ATLDKAIQRAGAGAARDQIVATLTFDFWSNLFR----  153

Query:  125  AQFDAAGKVLMKVFPKPKSTPSVQYNQKWIFRELSN----INNFRNRLAHHEPICFSFK  180
             ++    +   + +       + P +Q+ +     +E+ N    IN FRNR+AHHEP+
Sbjct:  154  PEYGGLWRTTVNI------AFPHLQHGESR--QEIQNLVKPINVFRNRVAHHEPVL----  201

Query:  181  GAIKDTGYARNIHQSIFELLNYMDVDTASVFSHFS                           215
                   D    +IH  I  L+       +TA+   H S
Sbjct:  202  ----DLNVT-DIHAKIVRLIELRCAETATWMKHHS                           231
```

As a homolog was found in serogroup A *N. meningitidis* but not in serogroup B, so NGS78 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 79

A DNA sequence was identified in *N. gonorrhoeae* <SEQ ID 157> which encodes amino acid sequence <SEQ ID 158; NGS79>. Analysis of this protein sequence reveals the following:

---

GvH: Examining signal sequence (von Heijne)
Signal Score (−7.5): 2.07
Possible cleavage site: 17
>>> Seems to have a cleavable N-term signal seq.
Amino Acid Composition of Predicted Mature Form:
calculated from 18
ALOM: Finding transmembrane regions (Klein et al.)
count: 0 value: 9.49 threshold: 0.0

---

PERIPHERAL          Likelihood = 9.49
modified ALOM score: −2.40
Score for OM-PP discrimination: −11.72
Rule: outer membrane or periplasmic protein
Score for OM-PP discrimination: −11.72
Rule: outer membrane or periplasmic protein

---

*** Reasoning Step: 2
Periplasmic space? Score: 1.17242
Periplasmic space? Score: 1.17242
Final Results

---

| | |
|---|---|
| bacterial periplasmic space --- Certainty = | 0.932(Affirmative) < succ> |
| bacterial outer membrane --- Certainty = | 0.240(Affirmative) < succ> |
| bacterial inner membrane --- Certainty = | 0.000(Not Clear) < succ> |
| bacterial cytoplasm --- Certainty = | 0.000(Not Clear) < succ> |

A homolog (amino acids 23-85) was found in serogroup A *N. meningitidis* but not in serogroup B, so NGS79 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 80

A DNA sequence was identified in *N. gonorrhoeae* <SEQ ID 159> which encodes amino acid sequence <SEQ ID 160; NGS80>. Analysis of this protein sequence reveals the following:

---

GvH: Examining signal sequence (von Heijne)
Signal Score (−7.5): −8.49
Possible cleavage site: 57
>>> Seems to have no N-terminal signal seq.
Amino Acid Composition of Predicted Mature Form:
calculated from 1
ALOM: Finding transmembrane regions (Klein et al.)
count: 0 value: 4.98 threshold: 0.0

---

PERIPHERAL          Likelihood = 4.98
modified ALOM score: −1.50
Rule: cytoplasmic protein

---

*** Reasoning Step: 2
Final Results

---

| | |
|---|---|
| bacterial cytoplasm --- Certainty = | 0.428(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

```
>pir||E81080 conserved hypothetical protein NMB1466 [imported] - Neisseria
meningitidis (group B strain MD58)
gb|AAF41823.1|(AE002496) conserved hypothetical protein
[Neisseria meningitidis MC58]
Length = 243

Score = 148 bits (375), Expect = 7e-35
Identities = 82/189 (43%), Positives = 109/189 (57%)

Query:  120 VDRMFNMAGNHFARLGISGSGVHYWNARDFSEQAFHAEVGYRYRNSRLEWGFRPFVKQNR   179
            + R N   +HF  GISG GVHYW+ +DFSEQ+     GY+ R+   +G  PFV+QN
Sbjct:    1 MSREINAGRHHFLYGGISGGGVHYWDNKDFSEQSLRLSFGYKNRSVTRSFGIVPFVEQNL    60

Query:  180 LGNNRYTANTGIVLDYSRRLNEKWRSTQSFQYGRKQYHDEYLAKRYNSKTISVSGTFSYY   239
            LG +RY    G   D+S+RL+E+WR T +     K Y ++ A RY+S      T Y
Sbjct:   61 LGGSRYNFVGGFNADFSQRLSERWRLTLNAGNMWKHYQEDRTAARYDSHMPLAGATLMYS   120

Query:  240 AMSAWQLYGGISGMFDNTVEKEQASRRYGVSLGTVKILDGGLGLKLGAGYTKRIFKAPAT   299
            A   W LYGG    + T E EQAS R G+ +G VK  DGGLGL+     YT+R+F AP T
Sbjct:  121 APKDWLLYGGADWSHNITKEAEQASIRKGLRVGAVKTFDGGLGLRANLRYTRRMFDAPGT   180

Query:  300 LIYNFTRRD   308
            ++Y F R+D
Sbjct:  181 IVYRFPRKD   189

>gb|AAD11779.1|(AF118122) putative outer membrane protein OmpU [Neisseria
meningitidis]
Length = 488

Score = 72.1 bits (176), Expect = 7e-12
Identities = 71/300 (23%), Positives = 128/300 (42%), Gaps = 17/300 (5%)

Query:    3 EAADLYRELLSERPDLVYPRFDLGVMLFEDKQYREALVQLHRAE-EVLPPDMRQLAREYI    61
            EA   YREL++ +PD   R L   LF+++Q    A Q  R + ELPP + +      Y
Sbjct:  136 EAISHYRELIAAQPDAPAVRMRLAAALFDNRQNEAAADQFDRLKAENLPPQLMEQVELYR   195

Query:   62 RQAEAVQAWHPSFNMNYEQTDNVNNASLSRDIVINGRKWIKSEDSLPKRANG--IRYELG   119
            +    AW   +   +   N+N A   +     KW   + PK+ +G  + Y LG
Sbjct:  196 KALRERDAWKVNGGFSVTREHNINQAPKRQQY----GKW-----TFPKQVDGTAVNYRLG   246

Query:  120 VDRMFNMAGNHFARLGISGSGVHYWNARDFSEQAFHAEVGYRYRNSRLEWGFRPFVKQNR   179
            ++ +++     +   G   SG   Y    + F++      G  + +R + G    F ++
Sbjct:  247 AEKKWSLKNGWYTTAGGDVSGRVYPGNKKFNDMTAGVSGGIGFADRRKDAGLAVFHERRT   306

Query:  180 LGNNRYTANTGIVLDYSRRLNEKWRSTQSFQYGRKQYHDEYLAKRYNSKTISVSGTFSYY   239
               GN+ Y+    G  L ++R    KW++  S ++GR +       R ++  +S +  +Y
Sbjct:  307 YGNDAYSYTNGARLYFNRWQTPKWQTLSSAEWGRLK---NTRRARSDNTHLQISNSLVFY   363

Query:  240 AMSAWQLYGGISGMFD-NTVEKEQASRRYGVSLGTVKILDG-GLGLKLGAGYTKRIFKAP   297
            +     GG+   + N ++     RYG+   +   G GL  L  G KR ++ P
Sbjct:  364 RNARQYWMGGLDFYRERNPADRGDNFNRYGLRFAWGQEWGGSGLSSLLRLGAAKRHYEKP   423
```

Based on this analysis, it was predicted that this protein from *N. gonorrhoeae*, and its epitopes, could be useful antigens for vaccines or diagnostics.

Example 81

A DNA sequence was identified in *N. gonorrhoeae* <SEQ ID 161> which encodes amino acid sequence <SEQ ID 162; NGS81>. Analysis of this protein sequence reveals the following:

GvH: Examining signal sequence (von Heijne)
Signal Score (-7.5): -6.25
Possible cleavage site: 15
>>> Seems to have no N-terminal signal seq.

Amino Acid Composition of Predicted Mature Form: calculated from 1
ALOM: Finding transmembrane regions (Klein et al.)
count: 0 value: 7.05 threshold: 0.0

| PERIPHERAL | Likelihood = 7.05 |
|---|---|
| modified ALOM score: -1.91 | |
| Rule: cytoplasmic protein | |

\*\*\* Reasoning Step: 2
Final Results bacterial cytoplasm --- Certainty =   0.232(Affirmative) < succ>

The protein has homology with the following sequences in the databases:

```
gi|10803654|ref|NP_046052.1|putative ISH4 transposase
[Halobacterium sp. NRC-1]
gi|7484109|pir||T08324 probable transposase H1306 - Halobacterium sp. (strain
NRC-1]
insertion sequence ISH4 plasmid pNRC100
```

-continued

```
gi|2822385|gb|AAC82891.1|(AF016485) putative ISH4 transposase [Halobacterium
sp. NRC-1]
gi|10580476|gb|AAG19350.1|(AE005029) Vng0918h [Halobacterium sp. NRC-1]
Length = 294

Score = 52.1 bits (124), Expect = 4e-06
Identities = 36/139 (25%), Positives = 63/139 (44%), Gaps = 7/139 (5%)

Query:   31 CPHCQSTHFVKNGKDCGNQRFLCRDCKKSFVEQTGTILYNTQKDIEVWEKYIHCMIE-KY    89
            CP C++     ++ G     QR+LC+DC ++F +QTGT+   ++    +  W    ++   I
Sbjct:   28 CPSCRAESVIRYGSYRVFQRYLCKDCDRTFNDQTGTVFEHSAVALRKWFLAVYTYIRLNT   87

Query:   90 PLRKCAEICKINLATAFTWRHKILDALQNMMNEVELDGIVQADETYSTISYKGHHKNFNL  149
            +R+       ++ T +    + L AL          L+G V+ DE Y      KG    ++
Sbjct:   88 SIRQLDAEIDVSYKTVYRRVQRFLRALD--APRPHLEGPVEIDEFYVKAGLKGRERD---  142

Query:  150 PRPAHKRGTRATKRGISKE                                          168
            +P+   RG    RG    E
Sbjct:  143 -QPSRSRGLSTRGRGTYAE                                          160
```

Based on this analysis, it was predicted that this protein from *N. gonorrhoeae*, and its epitopes, could be useful antigens for vaccines or diagnostics.

Example 82

A DNA sequence was identified in *N. gonorrhoeae* <SEQ ID 163> which encodes amino acid sequence <SEQ ID 164; NGS82>. Analysis of this protein sequence reveals the following:

GvH: Examining signal sequence (von Heijne)
Signal Score (-7.5): -4.66
Possible cleavage site: 57
>>> Seems to have no N-terminal signal seq.

Amino Acid Composition of Predicted Mature Form:
calculated from 1
ALOM: Finding transmembrane regions (Klein et al.)
count: 1 value: -0.85 threshold: 0.0

| | | | |
|---|---|---|---|
| INTEGRAL | Likelihood = -0.85 | Transmembrane | 76-92 (76-92) |
| PERIPHERAL | Likelihood = 1.75 | | |
| | modified ALOM score: 0.67 | | |
| | Rule: cytoplasmic membrane protein | | |

*** Reasoning Step: 2
Final Results bacterial inner membrane --- Certainty =   0.134(Affirmative) < succ>

The protein has homology with the following sequences in the databases:

```
>gi|586070|sp|Q07605|T4BA_BACCO RESTRICTION ENZYME BGCI ALPHA SUBUNIT
[INCLUDES: ADENINE-SPECIFIC METHYLTRANSFERASE ACTIVITY]
gi|1075788|pir||A53125 restriction enzyme BcgI alpha chain -
Bacillus coagulans
gi|304140|gb|AAA16626.1|(L17341) restriction endonuclease alpha subunit
[Bacillus coagulans]
Length = 637

Score = 91.4 bits (226), Expect = 1e-17
Identities = 78/256 (30%), Positives = 123/256 (47%), Gaps = 42/256 (16%)

Query:    1 MFALAASNMILRGDGKANLHQSSCFMTDFQDLIKNPKPETGLKRPNVGFLNPPYAQSKSD   60
            +F +A +NMILRGDGK+NL + +C    F + N      G+  N   +NPPY+Q+K+D
Sbjct:  394 LFTIATTNMILRGDGKSNLIRDNCLT--FDNTIMN---GYGI---NKILMNPPYSQAKND  445

Query:   61 AELH--ELYFVKENLDMLAEGGTGIAIIPVSCVIAPSK----AKSEIVKYHRLKAVMSMP  114
               H    EL F+++ L+ML  GG    AI+P S  ++       K  +I+K H L+ V+++
Sbjct:  446 QTQHLSELSFIQQALEMLVVGGKLCAIVPQSTMVGKNRHDKARKKQILKQHTLETVITLN  505

Query:  115 SELFYPVGTVTCIVVFEAHKPHFQTVVIDPDTQEEISTKKACRKTWFGYWRDDGFEKTKH  174
             + F+ VG   CIV+F+A  H +                 ++  F   DDG    KH
Sbjct:  506 KDTFHGVGVNPCIVIFKAGIKHPEN----------------KRVSFVNFEDDGHVVRKH  548

Query:  175 LGRIDLYDRWQGIKARWLEHYL-----NNEVHTGESVTAFVTDNDEWVAEAYLETDYSKI  229
            +G +      G +    EH L      + +  T V   + D DEW+    Y   D
Sbjct:  549 VGLVG-----DGTEKGKREHLLAVLAGDEDDGTDLIVKTAIKDTDEWLHSFYYFND-GIP  602

Query:  230 TRADFEQVVREFALFQ                                             245
            +  DF + V +   FQ
Sbjct:  603 SEDDFYKTVANYLTFQ                                             618
```

Based on this analysis, it was predicted that this protein from *N. gonorrhoeae*, and its epitopes, could be useful antigens for vaccines or diagnostics.

Based on this analysis, it was predicted that this protein from *N. gonorrhoeae*, and its epitopes, could be useful antigens for vaccines or diagnostics.

Example 83

A DNA sequence was identified in *N. gonorrhoeae* <SEQ ID 165> which encodes amino acid sequence <SEQ ID 166; NGS83>. Analysis of this protein sequence reveals the following:

GvH: Examining signal sequence (von Heijne)
Signal Score (−7.5): −8.04
Possible cleavage site: 43
>>> Seems to have no N-terminal signal seq.
Amino Acid Composition of Predicted Mature Form:
calculated from 1
ALOM: Finding transmembrane regions (Klein et al.)
count: 1 value: −1.44 threshold: 0.0

| | | | |
|---|---|---|---|
| INTEGRAL | Likelihood = −1.44 | Transmembrane | 55-71 (55-71) |
| PERIPHERAL | Likelihood = 4.03 | | | modified ALOM score: 0.79
Rule: cytoplasmic membrane protein

*** Reasoning Step: 2
Final Results bacterial inner membrane --- Certainty =    0.157(Affirmative) < succ>

Example 84

A DNA sequence was identified in *N. gonorrhoeae* <SEQ ID 167> which encodes amino acid sequence <SEQ ID 168; NGS84>. Analysis of this protein sequence reveals the following:

Signal Score (−7.5): 3.15
Possible cleavage site: 33
>>> Seems to have no N-terminal signal seq.
Amino Acid Composition of Predicted Mature Form:
calculated from 1
ALOM: Finding transmembrane regions (Klein et al.)
count: 0 value: 1.22 threshold: 0.0

| | | |
|---|---|---|
| PERIPHERAL | | Likelihood = 1.22 | modified ALOM score: −0.74
Rule: cytoplasmic protein

*** Reasoning Step: 2
Final Results bacterial cytoplasm --- Certainty =    0.072(Affirmative) < succ>

The protein has homology with the following sequences in the databases:

The protein has homology with the following sequences in the databases:

```
>gi|586071|sp|Q07606|T4BB_BACCO RESTRICTION ENZYME BGCI BETA SUBUNIT
gi|1075789|pir||B53125 restriction enzyme BcgI beta chain - Bacillus coagulans
gi|304141|gb|AAA16627.1|(L17341) restriction endonuclease beta subunit
[Bacillus coagulans]
Length = 341

Score = 44.0 bits (103), Expect = 0.002
Identities = 46/195 (23%), Positives = 79/195 (39%), Gaps = 23/195 (11%)

Query:    4 LQEIFDVSYGSKLDLNKMSSFNPTINFVGRSGKNNGVTASVDLLKNTKPYPAGLLTVALG     63
              + ++FDV  G  +D NK        ++ R   NG   +D  K  KY   L   + +G
Sbjct:   12 ISDLFDVVIGKTIDGNKAQRNENGTPYITRKATRNGFEFMIDGEKE-KLYSGKLPVITIG     70

Query:   64 GSVLSTFLQNKPFYTAQNVAVLNPKTEMTEQQKLFYCAAIFANAYRFSACGREANRT-LR    122
                        F+Q    F+T   V +  PK ++      L Y    + NA +   +    N T L+
Sbjct:   71 NETSKPFVQEFHFFTGTKVNICIPKLDLNRNH-LLYITTMIENATKMFSYSYTINSTRLK    129

Query:  123 QL--FVPSLDEIPSW--------------VESVNLNPSAGVTEPKLKESLDLPVVRQSKR    166
               L   +P   E P W                     ++  ++   + GV++  +   + L              +
Sbjct:  130 SLKILLPIKGEEPDWDYMNTYISKILSNMEKNFDVQQNDGVSDLRSLKDLSW----SQFK    185

Query:  167 LDEIFTIQNGIAATK                                               181
              +DEIF+I +G+   TK
Sbjct:  186 MDEIFSINSGVRLTK                                               200
```

```
>gi|2495432|sp|P55409|Y4DJ_RHISN HYPOTHETICAL TRANSCRIPTIONAL REGULATOR Y4DJ
gi|7465604|pir||T02773 y4dJ protein - Rhizobium sp. plasmid pNGR234a
gi|2182353|gb|AAB91639.1|(AE000069) Y4dJ [Rhizobium sp. NGR234]
Length = 77

Score = 44.4 bits (104), Expect = 7e-04
Identities = 25/61 (40%), Positives = 36/61 (58%)

Query:    92 KAGGETFVSLRMKKGFTQSELATAAGLPQPYLSRIENSKQSLQDKTVQKLANALGVSPLE    151
             K   G   F  LR +KG TQ E+    +G   Q YLS +E   +++      T+ +LA ALGVS +E
Sbjct:     5 KLVGSNFARLRREKGLTQEEVEARSGFSQQYLSSLERGRRNPTVITLYELAQALGVSHVE     64

Query:   152 V                                                             152
             +
Sbjct:    65 L                                                              65
```

Based on this analysis, it was predicted that this protein from *N. gonorrhoeae*, and its epitopes, could be useful antigens for vaccines or diagnostics.

Example 85

A DNA sequence was identified in *N. gonorrhoeae* <SEQ ID 169> which encodes amino acid sequence <SEQ ID 170; NGS85>. Analysis of this protein sequence reveals the following:

Signal Score (–7.5): –6.09
Possible cleavage site: 15
>>> Seems to have no N-terminal signal seq.
Amino Acid Composition of Predicted Mature Form: calculated from 1
ALOM: Finding transmembrane regions (Klein et al.)
count: 0 value: 2.92 threshold: 0.0

PERIPHERAL   Likelihood = 2.92
modified ALOM score: –1.08
Rule: cytoplasmic protein

*** Reasoning Step: 2
Final Results bacterial cytoplasm --- Certainty =   0.480(Affirmative) < succ>

The protein has no homology with sequences in the databases.

Based on this analysis, it was predicted that this protein from *N. gonorrhoeae*, and its epitopes, could be useful antigens for vaccines or diagnostics.

Example 86

A DNA sequence was identified in *N. gonorrhoeae* <SEQ ID 171> which encodes amino acid sequence <SEQ ID 172; NGS86>. Analysis of this protein sequence reveals the following:

Signal Score (–7.5): –2.92
Possible cleavage site: 21
>>> Seems to have no N-terminal signal seq.
Amino Acid Composition of Predicted Mature Form: calculated from 1
ALOM: Finding transmembrane regions (Klein et al.)
count: 1 value: –2.76 threshold: 0.0

INTEGRAL    Likelihood = –2.76    Transmembrane    179-195
                                                   (179-195)
PERIPHERAL  Likelihood = 2.17
modified ALOM score: 1.05
Rule: cytoplasmic membrane protein

*** Reasoning Step: 2
Final Results bacterial inner membrane --- Certainty =   0.210(Affirmative) < succ>

The protein has homology with the following sequences in the databases:

```
>sp|Q05205|PPB_LYSEN ALKALINE PHOSPHATASE PRECURSOR (APASE)
pir||A42467 alkaline phosphatase (EC 3.1.3.1) phoA precursor - Lysobacter
enzymogenes
emb|CAA39978.1|(X56656) alkaline phosphatase [Lysobacter enzymogenes]
Length = 539

Score = 37.5 bits (86), Expect = 0.40
Identities = 28/82 (34%), Positives = 43/82 (52%), Gaps = 8/82 (9%)

Query:   189 VALGLQAYWDVAGANNGATGQSPNIKTAQVPAKITRRNADGTTDTFGGGSARKSAAASVS    248
             V   GL A W+V+ A             +  AQV +++ R+  GT D +  G+A    A AS S
Sbjct:   458 VLRGLMA-WNVSSA------AGKTLTGAQVKLQVSDRST-GTYDLYRAGAAWTEANASYS    509

Query:   249 GIEAGKKVTAVIPAVRGAVAYA                                         270
             G+   G K+ +V+P+   GA + A
Sbjct:   510 GVSLGSKIGSVVPSATGAQSIA                                         531
```

Based on this analysis, it was predicted that this protein from *N. gonorrhoeae*, and its epitopes, could be useful antigens for vaccines or diagnostics.

Example 87

A DNA sequence was identified in *N. gonorrhoeae* <SEQ ID 173> which encodes amino acid sequence <SEQ ID 174; NGS87>. Analysis of this protein sequence reveals the following:

Signal Score (−7.5): 0.18
Possible cleavage site: 35
>>> Seems to have no N-terminal signal seq.
Amino Acid Composition of Predicted Mature Form: calculated from 1
ALOM: Finding transmembrane regions (Klein et al.)
count: 0 value: 1.70 threshold: 0.0

PERIPHERAL    Likelihood = 1.70
modified ALOM score: −0.84
Rule: cytoplasmic protein

*** Reasoning Step: 2
Final Results bacterial cytoplasm --- Certainty =    0.138(Affirmative) < succ>

The protein has homology with the following sequences in the databases:

```
>gi|12514207|gb|AAG55499.1|AE005289_17 (AE005289) unknown protein
encoded by cryptic prophage CP-933M
[Escherichia coli O157:H7]
gi|12514720|gb|AAG55907.1|AE005324_10 (AE005324) unknown protein
encoded by prophage CP-933N
[Escherichia coli O157:H7]
Length = 108

Score = 30.9 bits (69), Expect = 9.1
Identities = 21/55 (38%), Positives = 28/55 (50%), Gaps = 3/55 (5%)

Query:  1 MAAPVSLEEFKQRIGVEHDRRDDFFLSVIDGVSAAAEAYIGRSLLAADYVGRYDG   55
          M A ++LEE K  + V+HD  DD +  +   +A   AYI  S    D V R DG
Sbjct:  1 MTALLTLEEIKAHLRVDHDADDDMLMDKVRQATAVLLAYIQGS---RDKVIREDG  52
```

Based on this analysis, it was predicted that this protein from *N. gonorrhoeae*, and its epitopes, could be useful antigens for vaccines or diagnostics.

Example 88

A DNA sequence was identified in *N. gonorrhoeae* <SEQ ID 175> which encodes amino acid sequence <SEQ ID 176; NGS88>. Analysis of this protein sequence reveals the following:

Signal Score (−7.5): −3.69
Possible cleavage site: 43
>>> Seems to have no N-terminal signal seq.
Amino Acid Composition of Predicted Mature Form: calculated from 1
ALOM: Finding transmembrane regions (Klein et al.)
count: 0 value: 6.05 threshold: 0.0

PERIPHERAL    Likelihood = 6.05
modified ALOM score: −1.71
Rule: cytoplasmic protein

*** Reasoning Step: 2
Final Results bacterial cytoplasm --- Certainty =    0.227(Affirmative) < succ>

The protein has no homology with sequences in the databases.

Based on this analysis, it was predicted that this protein from *N. gonorrhoeae*, and its epitopes, could be useful antigens for vaccines or diagnostics.

Example 89

A DNA sequence was identified in *N. gonorrhoeae* <SEQ ID 177> which encodes amino acid sequence <SEQ ID 178; NGS89>. Analysis of this protein sequence reveals the following:

Signal Score (−7.5): −4.77
Possible cleavage site: 26
>>> Seems to have no N-terminal signal seq.
Amino Acid Composition of Predicted Mature Form: calculated from 1
ALOM: Finding transmembrane regions (Klein et al.)
count: 0 value: 1.38 threshold: 0.0

PERIPHERAL    Likelihood = 1.38
modified ALOM score: −0.78
Rule: cytoplasmic protein

*** Reasoning Step: 2
Final Results bacterial cytoplasm --- Certainty =    0.284(Affirmative) < succ>

The protein has homology with the following sequences in the databases:

```
>gi|9634142|ref|NP_037684.1|gp24 [Enterobacteria phage HK022]
gi|6863134|gb|AAF30375.1|AF069308_23 (AF069308) gp24 [Enterobacteria phage
HK022]
Length = 1183

Score = 44.9 bits (102), Expect = 0.006
Identities = 38/127 (29%), Positives = 64/127 (49%), Gaps = 11/127 (8%)

Query:   851  NKALRDKINLIDGNGAGSVNERVEAVRSTADGNAAAVQTHARSI---NG-LEAQYTVK--   904
              NKA  + +N    +   +   ++  + +T +GN +A+ T+A  I   NG L A Y +K
Sbjct:   989  NKASINSLNQTFSDYQQATATQINGITATVNGNTSAITTNAQAIANVNGDLSAMYNIKVG  1048

Query:   905  VDANGK--VAGFGLATTPKNGTPESKFIVNADRFGI-GAAGKADVFPFVVDTQKNRVGIN   961
              V +NG+    AG G+       +S+ I  ADRF + AAG +    PFV+ Q + I
Sbjct  : 1049  VSSNGQYYAAGMGIGVENTPSGMQSQVIFLADRFAVTTAAGNSVALPFVI--QNGQTFIR  1106

Query:   962  GELVVNG                                                       968
              + +G
Sbjct:  1107  ASFIQDG                                                      1113
```

Based on this analysis, it was predicted that this protein from *N. gonorrhoeae*, and its epitopes, could be useful antigens for vaccines or diagnostics.

Example 90

A DNA sequence was identified in *N. gonorrhoeae* <SEQ ID 179> which encodes amino acid sequence <SEQ ID 180; NGS90>. Analysis of this protein sequence reveals the following:

---

Signal Score (−7.5): −2.82
Possible cleavage site: 24
>>> Seems to have no N-terminal signal seq.
Amino Acid Composition of Predicted Mature Form:
calculated from 1
ALOM: Finding transmembrane regions (Klein et al.)
count: 4 value: −9.66 threshold: 0.0

-continued

| INTEGRAL | Likelihood = −9.66 | Transmembrane | 321-337 (317-349) |
| INTEGRAL | Likelihood = −6.48 | Transmembrane | 351-367 (340-371) |
| INTEGRAL | Likelihood = −5.73 | Transmembrane | 907-923 (903-926) |
| INTEGRAL | Likelihood = −0.00 | Transmembrane | 430-446 (430-446) |
| PERIPHERAL | Likelihood = 2.17 | | |
| | modified ALOM score: 2.43 | | |
| | Rule: cytoplasmic membrane protein | | |

*** Reasoning Step: 2
Final Results bacterial inner membrane --- Certainty =   0.486(Affirmative) < succ>

---

The protein has homology with the following sequences in the databases:

```
>gi|12514839|gb|AAG56002.1|AE005332_9 (AE005332) putative tail component of
prophage CP-933X [Escherichia coli O157:H7]
Length = 1026

Score = 111 bits (279), Expect = 3e-23
Identities = 78/274 (28%), Positives = 146/274 (52%), Gaps = 10/274 (3%)

Query:   69  AAGNQAQQASEKVRAEVGKIGSGLSGLTKLLAGLATADFAKSVLDTADAMQSINSQVRQV   128
             AA  + ++A ++ +++ +I +    G+T   AG   A       ++ AD   S+N++++Q
Sbjct:   45  AAAREQRRALAELHSQLTEIRASAVGMTGAFAG---AFATGHLISLADEWSSVNARLKQA   101

Query:  129  TSSETEYLAVQQQLLDTANRTRASLESTANLYVSTSRALKDYGYTQQEILKFTEAANNAM   188
             + S  E++ + Q+ L+D + RT     A L+  ++  ++++YGY+   ++LK TEA + +
Sbjct:  102  SQSSDEFASSQKVLMDISQRTGTAFSDNAALFARSAASMREYGYSADDVLKVTEAISTGL   161

Query:  189  TIGGVGAQQQAAALMQLSQALGSGVLQGDEFKSISEAAPILLDTIAEYMGKSRDEIKKLG   248
               I G     + + + Q SQAL  GVL+G+EF S++E+     ++  +A  MG +R ++K +
Sbjct:  162  KISGASTAEAGSVITQFSQALAQGVLRGEEFNSVNESGDRIVRALAAGMGVARKDLKAMA   221

Query:  249  SEGKLTADVIFKAISGASEKFGEQAAKMPVTMGQALTVFSNNWQSMVSKLLNDSGTMSGI   308
              +GKLTAD + A+         ++ A MP T+    ++T   N + V         G   +
Sbjct:  222  DDGKLTADKVVPALISQLGILRDEYAAMPETVSSSITKVENAFMAWV-------GGANEA   274

Query:  309  AAVIKLIADNLNLVVPIVAGFAVAVAAAVAPTLA                           342
             + V K ++  LN V   +   A AV AVA  +A
Sbjct:  275  SGVTKTLSGMLNGVAGQIDNVATAVGALVAVGVA                           308
```

Based on this analysis, it was predicted that this protein from *N. gonorrhoeae*, and its epitopes, could be useful antigens for vaccines or diagnostics.

Example 91

A DNA sequence was identified in *N. gonorrhoeae* <SEQ ID 181> which encodes amino acid sequence <SEQ ID 182; NGS91>. Analysis of this protein sequence reveals the following:

---

Signal Score (−7.5): −0.63
Possible cleavage site: 36
>>> Seems to have no N-terminal signal seq.
Amino Acid Composition of Predicted Mature Form: calculated from 1
ALOM: Finding transmembrane regions (Klein et al.)
count: 0 value: 0.16 threshold: 0.0

---

| PERIPHERAL | Likelihood = 0.16 |
|---|---|
| modified ALOM score: −0.53 | |
| Rule: cytoplasmic protein | |

---

*** Reasoning Step: 2
Final Results

--- bacterial cytoplasm --- Certainty =      0.250(Affirmative) < succ>

---

The protein has homology with the following sequences in the databases:

```
(AF237934) putative integrase/recombinase
[Pasteurella multocida]
Length = 329

Score = 449 (206.9 bits), Expect = 4.4e-91, Sum P(2) = 4.4e-91
Identities = 93/196 (47%), Positives = 129/196 (65%)

Query:    56 IFADLIRRYLSEVTPSKRGAREESYRIGRALKTPLAKVRLADLRPQDFADWRDQRLQEVS   115
             IF D+I RY +EV+ +K+GAR E  R+ R L+  ++ + + DLR +DF +W   RL EVS
Sbjct:    55 IFRDVIERYQNEVSITKKGARNEIIRLNRFLRYDISNLYIRDLRKEDFEEWIRIRLTEVS   114

Query:   116 PTSVGRELTTLSAVCEHAMKEWGLLRENPVRKISKPKKSRARTRRPTEQEIADICAALLY   175
                SV REL T+S+V   A+ +WG +   +P+   I KPK  S   R    R +EQ+I  I          Y
Sbjct:   115 DASVRRELVTISSVLTTAINKWGYISRHPMTGIEKPKNSAERKERYSEQDIKTILETARY   174

Query:   176 RPNEKPKMAVQRVAVAVLFAIETAMRAGEICGLKWADVNMRRRIAHLPITKNGDSRDVPL   235
             ++ P     QRVA+A+LFAIETAMRAGEI  +KW +V + +RI HLP TKNG SRDVPL
Sbjct:   175 CEDKLPITLKQRVAIAMLFAIETAMRAGEIASIKWDNVFLEKRIVHLPTTKNGHSRDVPL   234

Query:   236 SLRAAELIEQLRGIDD                                               251
             S RA   LI +++ +++
Sbjct:   235 SQRAVALILKMKEVEN                                               250

Score = 248 (114.3 bits), Expect = 4.4e-91, Sum P(2) = 4.4e-91
Identities = 48/76 (63%), Positives = 57/76 (75%)

Query:   254 VFSLDAKSLDVLFRRARDNCGIQGLHFHDTRREALTRLSKKVPVEVLAKISGHRDLRILL   313
             VF    +SL    FR   +  CG++ LHFHDTRREALTRLSKKV V  LAKISGHRDLRIL
Sbjct:   254 VFQTTPESLSTTFRVLKKECGLEHLHFHDTRREALTRLSKKVDVMTLAKISGHRDLRILQ   313

Query:   314 NVYYRPDMADIAKMLD                                               329
             N YY P+M+++A +LD
Sbjct:   314 NTYYAPNMSEVANLLD                                               329
```

Based on this analysis, it was predicted that this protein from *N. gonorrhoeae*, and its epitopes, could be useful antigens for vaccines or diagnostics.

Example 92

A DNA sequence was identified in *N. gonorrhoeae* <SEQ ID 183> which encodes amino acid sequence <SEQ ID 184; NGS92>. Analysis of this protein sequence reveals the following:

---

Signal Score (−7.5): −7.85
Possible cleavage site: 25
>>> Seems to have an uncleavable N-term signal seq
Amino Acid Composition of Predicted Mature Form: calculated from 1
ALOM: Finding transmembrane regions (Klein et al.)
count: 1 value: −8.33 threshold: 0.0

---

| INTEGRAL | Likelihood = −8.33 | Transmembrane 6-22 (1-25) |
|---|---|---|
| PERIPHERAL | Likelihood = 5.99 | |
| modified ALOM score: 2.17 | | |
| Rule: cytoplasmic membrane protein | | |

---

*** Reasoning Step: 2
Final Results

--- bacterial inner membrane --- Certainty =      0.433(Affirmative) < succ>

---

The protein has homology with the following sequences in the databases:

```
>gi|9632051|ref|NP_048840.1|A484L [Paramecium bursaria Chlorella virus 1]
gi|7461623|pir||T17986 hypothetical protein A484L - Chlorella virus PBCV-1
gi|1620155|gb|AAC96851.1|(U42580) A484L
[Paramecium bursaria Chlorella virus 1]
Length = 155

Score = 31.6 bits (70), Expect = 3.5
Identities = 20/72 (27%), Positives = 36/72 (49%)
Frame = +1

Query:   52 LQINLKMLEKRIDFLVENIDKYYQQYGSYPNNFDFISTKTDFTTESYCDFWDKNIAGYGN   231
            + +NLKM    I F    +DKY +QY +Y  N  F  T+ +    +    ++ + +I    N
Sbjct:   23 IAVNLKMNGVSIPF----VDKYSKQYPTYTKNALFHVTRFNNAYQKTFEYKNISIDTINN    78

Query:  232 CYFVKNDKDYTI                                                  267
             + +++D  Y I
Sbjct:   79 LFSIRDDVLYNI                                                   90
```

Based on this analysis, it was predicted that this protein from *N. gonorrhoeae*, and its epitopes, could be useful antigens for vaccines or diagnostics.

Example 93

A DNA sequence was identified in *N. gonorrhoeae* <SEQ ID 185> which encodes amino acid sequence <SEQ ID 186; NGS93>. Analysis of this protein sequence reveals the following:

| |
|---|
| GvH: Examining signal sequence (von Heijne)<br>Signal Score (−7.5): −5.08<br>Possible cleavage site: 14<br>>>> Seems to have no N-terminal signal seq. |

-continued

| | |
|---|---|
| Amino Acid Composition of Predicted Mature Form:<br>calculated from 1<br>ALOM: Finding transmembrane regions (Klein et al.)<br>count: 0 value: 0.79 threshold: 0.0 | |
| PERIPHERAL<br>modified ALOM score: −0.66<br>Rule: cytoplasmic protein | Likelihood = 0.79 |
| *** Reasoning Step: 2<br>Final Results | |
| bacterial cytoplasm --- Certainty = | 0.320(Affirmative) < succ> |

The protein has homology with the following sequences in the databases:

```
>gb|AAG22017.1|AF288038_2 (AF288038) putative HsdR
[Streptococcus thermophilus]
Length = 740

Score = 674 bits (1738), Expect = 0.0
Identities = 364/746 (48%), Positives = 489/746 (64%), Gaps = 40/746 (5%)

Query:   14 NENSRVKIPAVLHLMRLGYDYLSLKNANW---DRQTNIFPEIFVDSLCRINPDLPPDDAR    70
            +E +RV+IPA  HLMRLGY YL           D +TNI   IF +   + N      D
Sbjct:    8 SELTRVQIPAAFHLMRLGYTYLPHNGKEIMGRDPETNILISIFREQFLKFNNYATDLDVE    67

Query:   71 RLLADIRLELDNEDLGQKFYERLTNQSGGKKLIDFQNFDNNSFHVVTELPCINGDEAFRP   130
            R L +I++ELD  DLG+ FY R+ + SG    +D++N +NN+FH+  E+ C NG + FRP
Sbjct:   68 RELNNIKIELDQNDLGRAFYNRIVSDSG-PTYVDWENPENNTFHLALEVTCQNGGDEFRP   126

Query:  131 DIALLVNGMPLVFIEVKKPN----NKGGIGEERERMGKRAKNPKFRRFINITQFMIFSNN   186
            DI + +NG+PL +IEVK+PN      K  I  E+ R   R +N +FRRF NITQ + FS+N
Sbjct:  127 DIVIFINGLPLSYIEVKQPNAIRDGKTAIQSEQSRTAVRFENRRFRRFNNITQLISFSDN   186

Query:  187 MEYDDGATEPAQGAFYASSACGKPVFNYFREEHKXXXXXXXXXXXXXXXXXVLQDNNLPV   246
            + Y  G  +  QG+FY S+A  K  FN F+EE +                   VL+D N
Sbjct:  187 LPYISGQGQQKQGSFYCSNAFSKTKFNAFKEEREEELIYSIRSLGEEEIDAVLKDVNRFA   246

Query:  247 IKHSPEFISNKSPDTPTNRILTSLLCRERLSFLLQHGLTYVK--ASQGLVQ--KHIMRYP   302
            +K  PEF +N+ P TP N  ++SL  ++RL FLL++GL YV+  +  G +Q  KH+MRYP
Sbjct:  247 LKSQPEFKTNQDPSTPCNTFISSLYQKKRLLFLLRYGLAYVEEHSKDGTIQLQKHVMRYP   306

Query:  303 QLFATLAIEKHLANGGKKGVIWHTQGSGKTALAYYNTRYLTHYYAKQGIVPKFYFIVDRL   362
            Q FAT AIE  +   G +KGVIWHTQGSGKTAL+Y+N RYLT+Y++KQGIVP+FYF+VDRL
Sbjct:  307 QFFATKAIEDAIGKGVRKGVIWHTQGSGKTALSYFNIRYLTNYFSKQGIVPQFYFVVDRL   366

Query:  363 DLLKQAQREFTARDLVVHTIDSREAFAADIKSAQTLHNHAGKAEITVVNIQKFQDDPDVV   422
            DL  QA REFT R L V  I+S           Q L+      ++ VVNIQKF+D+ D+
Sbjct:  367 DLADQATREFTKRGLKVKRINS----------PQELNEKHDAYQVAVVNIQKFKDNSDLT   416
```

```
Query:  423  ARNDYDLAIQRVYFLDEVHRSYNPKGSFLANLNQSDVNAVKIGLTGTPLI-----GVTA-    476
             + YDL Q +YF+DE HRSYN KGS+L NL +D NA+KI LTGTPLI    G T
Sbjct:  417  DHSGYDLNRQNIYFIDEAHRSYNEKGSYLPNLYNADKNAIKIALTGTPLITYKKDGKTKE    476

Query:  477  GNVNTRELFGDYIHKYYYNASIADGYTLRLIREEIGSRYKAQLQEALAQLEIEKGSFDRK    536
             +  TR++FGDYIHKYYYN SI DG+TLRL+RE+I + YK LQ      EI +G   +
Sbjct:  477  SHATTRDIFGDYIHKYYYNQSIDDGFTLRLMREDIETSYKETLQTI--NEEILRGDLSKD    534

Query:  537  EIYAHPHFVHPMLDYILDDFAKFRKTN-QDESLGAMVVCDSAEQARQL---FEHFQTASD    592
             +I+AHP +V PMLD+IL+DF + R     D+S+G M+VCDS++QAR++       E ++ +
Sbjct:  535  DIFAHPRYVSPMLDFILEDFNRARDVVFDDDSIGGMIVCDSSKQAREIEKQLEERRSGE    594

Query:  593  HNFTAALILHDVGTKEERDQWVKDFKAGKIDILFVYNMLLTGFDAPRLKKLYLGRLIKAH    652
             N T+ALILHD G KE +   V+ ++ GKID++ VY+MLLTGFDAPRLK+LYLGR IKAH
Sbjct:  595  TNITSALILHDEGDKEYKKDRVESYREGKIDLVIVYSMLLTGFDAPRLKRLYLGRKIKAH    654

Query:  653  NLLQTLTRVNRTYKSYRYGYVVDFADIEREFDKTNRAYWDELSNE-----LGDEIGS-YS    706
             NLLQTLTRVNR YK Y++GYV+DFADI +EFDKTNRAY +EL+ E        G+++ + +
Sbjct:  655  NLLQTLTRVNRPYKDYQFGYVIDFADISKEFDKTNRAYLEELNQEYDPKNTGEDVENVFG    714

Query:  707  QLFKTAEEIEQEIADIKNALFDFDTE                                    732
             LF +A+EI +++   + L ++ TE
Sbjct:  715  SLFVSADEISKQLEKSETILMNYPTE                                    740
```

Based on this analysis, it was predicted that this protein from *N. gonorrhoeae*, and its epitopes, could be useful antigens for vaccines or diagnostics.

Example 94

A DNA sequence was identified in *N. gonorrhoeae* <SEQ ID 187> which encodes amino acid sequence <SEQ ID 188; NGS94>. Analysis of this protein sequence reveals the following:

---

Signal Score (−7.5): −3.19
Possible cleavage site: 35
>>> Seems to have no N-terminal signal seq.

---

-continued

Amino Acid Composition of Predicted Mature Form:
calculated from 1
ALOM: Finding transmembrane regions (Klein et al.)
count: 0 value: 5.73 threshold: 0.0

| PERIPHERAL | Likelihood = 5.73 |
|---|---|
| modified ALOM score: −1.65 | |
| Rule: cytoplasmic protein | |

*** Reasoning Step: 2
Final Results bacterial cytoplasm --- Certainty =    0.302(Affirmative) < succ>

---

The protein has homology with the following sequences in the databases:

```
>gi|10717100|gb|AAG22014.1|AF288037_3 (AF288037) putative Hsds [Streptococcus
thermophilus]
Length = 402

Score = 154 bits (389), Expect = 2e-36
Identities = 123/348 (35%), Positives = 168/348 (47%), Gaps = 48/348 (13%)

Query:   73  GKTAFVDILDDGEVAFGSTEFIVLRAKNET--NPEFLYYFAISPDFRKRAIECMEGTSGR    130
             GKT     ++ DGE ++      IV    +E+      +FLYYF   +  F        G++ +
Sbjct:   74  GKT----VIFDGEDSYFQDSNIVWIENDESKVTNQFLYYFLQTNPFIT-----TNGSTIK    124

Query:  131  QRVNENALKTLELPIPEPQIQQSIAAVLSALDKKIALNKQINARLEEMAKTLYDYWFVQF    190
             +  N+N   T    +P  Q Q  I  +L  LDKKI +N QIN  LE  MAKTLYDYWFVQF
Sbjct:  125  RLYNDNLRDTKIPNVPSIQQQNQITDILGTLDKKIQINNQINQELEAMAKTLYDYWFVQF    184

Query:  191  DFPDANGKPYKSSGGDMVFDETLKREIPKGWGSIELQSCL---AKIPNTTKILNKDIKDF    247
             DFPD NGKPYKSSGG MV++   LKREIP+GWG+  +L S L    + N  K  N++ K +
Sbjct:  185  DFPDQNGKPYKSSGGKMVYNPELKREIPEGWGAEKLSSLLKIGKETTNPKKFPNEEFKYY    244

Query:  248  --------GKYPVVD----QSQDFICGFTNDEKSILNPQDAHIIFGDHTRIVKLVNFQYA    295
                     G Y +       +S  F      +  S LNP  +I+   +      F
Sbjct:  245  SIPEFDTTGTYSLERGESIKSNKFKVEKNDLLVSKLNPWFNRVIYNLEENAIASTEF---    301

Query:  296  RGADGTQVILSNNERMPNYLFYQIINQIDLSSY------GYARHFK-----FLKEFKIIL    344
                 ++         R        YQ+     +  Y     G +     K      + F+I
Sbjct:  302  -------IVWKTFNRFEKNFLYQVATGKEFIEYCTRFATGTSNSHKRVSPDIMVGFQIPF    354

Query:  345  PSKDISQKYNEIANTFFVKVRNNLKQNHHLTQLRDFLLPMLMNGQVSV              392
             I QK+ EI ++    +V N +QN LTQLRD++LPMLMNGQV V
Sbjct:  355  EKTHI-QKFGEIIDSIRTQVLQNNEQNQELTQLRDWILPMLMNGQVKV              401
```

Based on this analysis, it was predicted that this protein from *N. gonorrhoeae*, and its epitopes, could be useful antigens for vaccines or diagnostics.

Example 95

A DNA sequence was identified in *N. gonorrhoeae* <SEQ ID 189> which encodes amino acid sequence <SEQ ID 190; NGS95>. Analysis of this protein sequence reveals the following:

GvH: Examining signal sequence (von Heijne)
Signal Score (-7.5): -6.12
Possible cleavage site: 19
>>> Seems to have an uncleavable N-term signal seq
Amino Acid Composition of Predicted Mature Form: calculated from 1
ALOM: Finding transmembrane regions (Klein et al.)
count: 3 value: -10.51 threshold: 0.0

| | | | |
|---|---|---|---|
| INTEGRAL | Likelihood = -10.51 | Transmembrane | 112-128 (109-132) |
| INTEGRAL | Likelihood = -4.46 | Transmembrane | 50-66 (46-70) |
| INTEGRAL | Likelihood = -2.23 | Transmembrane | 7-23 (7-23) |
| PERIPHERAL | Likelihood = 4.19 | | | modified ALOM score: 2.60
Rule: cytoplasmic membrane protein

\*\*\* Reasoning Step: 2
Final Results bacterial inner membrane --- Certainty = 0.520(Affirmative) < succ>

The protein has homology with the following sequences in the databases:

```
>pir||G69096 hypothetical protein MTH1717 -
Methanobacterium thermoautotrophicum
(strain Delta H)
gb|AAB86189.1|(AE000928) unknown [Methanothermobacter thermautotrophicus]
Length = 557

Score = 35.4 bits (80), Expect = 0.50
Identities = 25/80 (31%), Positives = 47/80 (58%), Gaps = 5/80 (6%)

Query:   52 LLFYFLIPFIATATVLWLSKYLGKDEFKQGEVKELEYVNDNFLPSYLGYFFVALSIPDNN   111
            L+F+F+  P + TATVL + K + ++ F++ EV  L     + +PS++    ++ IP++
Sbjct:   92 LVFFFISPLLGTATVLVIYK-VARETFEREEVALLSAFLFSMVPSFVAR--TSVFIPESM  148

Query:  112 LFLLFVMYGIIFLLVSCSKS   131
            LL    GI+++LV    K+
Sbjct:  149 GLLL--TSGILYMLVKYLKT   166
```

Based on this analysis, it was predicted that this protein from *N. gonorrhoeae*, and its epitopes, could be useful antigens for vaccines or diagnostics.

Example 96

A DNA sequence was identified in *N. gonorrhoeae* <SEQ ID 191> which encodes amino acid sequence <SEQ ID 192; NGS96>. Analysis of this protein sequence reveals the following:

GvH: Examining signal sequence (von Heijne)
Signal Score (-7.5): -7.76
Possible cleavage site: 28

>>> Seems to have no N-terminal signal seq.
Amino Acid Composition of Predicted Mature Form: calculated from 1
ALOM: Finding transmembrane regions (Klein et al.)
count: 0 value: 6.15 threshold: 0.0

| | |
|---|---|
| PERIPHERAL | Likelihood = 6.15 | modified ALOM score: -1.73
Rule: cytoplasmic protein

\*\*\* Reasoning Step: 2
Final Results bacterial cytoplasm --- Certainty = 0.362(Affirmative) < succ>

The protein has no homology with sequences in the databases.

Based on this analysis, it was predicted that this protein from *N. gonorrhoeae*, and its epitopes, could be useful antigens for vaccines or diagnostics.

Example 97

A DNA sequence was identified in *N. gonorrhoeae* <SEQ ID 193> which encodes amino acid sequence <SEQ ID 194; NGS97>. Analysis of this protein sequence reveals the following:

GvH: Examining signal sequence (von Heijne)
Signal Score (-7.5): -0.48
Possible cleavage site: 13
>>> Seems to have no N-terminal signal seq.
Amino Acid Composition of Predicted Mature Form: calculated from 1
ALOM: Finding transmembrane regions (Klein et al.)
count: 0 value: 8.86 threshold: 0.0

| | |
|---|---|
| PERIPHERAL | Likelihood = 8.86 | modified ALOM score: -2.27
Rule: cytoplasmic protein

\*\*\* Reasoning Step: 2
Final Results bacterial cytoplasm --- Certainty = 0.127(Affirmative) < succ>

The protein has homology with the following sequences in the databases:

```
>ref|NP_052265.1|P2 J homolog; baseplate or base of tail fibre
[Enterobacteria phage 186]
gb|AAC34162.1|(U32222) P2 J homolog; baseplate or base of tail fibre
[Enterobacteria phage 186]
Length = 302

Score = 112 bits (280), Expect = 3e-24
Identities = 65/151 (43%), Positives = 85/151 (56%), Gaps = 1/151 (0%)

Query:     1 MGNSRLSQLPAPAAIEETDFEGIFARKKAALTALCPESIRETVAQTLELESEPLTIDLQQ    60
             M   LS LP P +EE DFE I A + A L +L PE  +E VA+TL LESEP+   LQ+
Sbjct:     1 MATVDLSLLPVPDVVEELDFETILAERIATLISLYPEDQQEAVARTLALESEPIVKLLQE    60

Query:    61 QAYQELLVRNRINEAVKANLLAYAQGSDLDHIAAQYGLSRKTIRXXXXXXXXXXXXXEYET   120
             AY+E++ R R+NEA +A +LAYA+ SDLD++ A + + R   +R              E E
Sbjct:    61 NAYREVIWRQRVNEAARAGMLAYARDSDLDNLGANFNVERLVVRPADDTTIPPTPAEMEL   120

Query:   121 DDAFRARV-QAHPEKYAAGPRTAYEAHAIDA                              150
             D  FR R+ QA      AG   AYE H  A
Sbjct:   121 DADFRLRIQQAFEGMSVAGSTGAYEFHGRSA                              151
```

Based on this analysis, it was predicted that this protein from *N. gonorrhoeae*, and its epitopes, could be useful antigens for vaccines or diagnostics.

Example 98

A DNA sequence was identified in *N. gonorrhoeae* <SEQ ID 195> which encodes amino acid sequence <SEQ ID 196; NGS98>. Analysis of this protein sequence reveals the following:

Signal Score (-7.5): -3.68
Possible cleavage site: 33
>>> Seems to have no N-terminal signal seq.
Amino Acid Composition of Predicted Mature Form:
calculated from 1
ALOM: Finding transmembrane regions (Klein et al.)
count: 0 value: 4.61 threshold: 0.0

PERIPHERAL          Likelihood = 4.61
modified ALOM score: -1.42
Rule: cytoplasmic protein

*** Reasoning Step: 2
Final Results bacterial cytoplasm --- Certainty =     0.182(Affirmative) < succ>

The protein has no homology with sequences in the databases.

Based on this analysis, it was predicted that this protein from *N. gonorrhoeae*, and its epitopes, could be useful antigens for vaccines or diagnostics.

Example 99

A DNA sequence was identified in *N. gonorrhoeae* <SEQ ID 197> which encodes amino acid sequence <SEQ ID 198; NGS99>. Analysis of this protein sequence reveals the following:

Signal Score (-7.5): -4.87
Possible cleavage site: 19
>>> Seems to have no N-terminal signal seq.
Amino Acid Composition of Predicted Mature Form:
calculated from 1
ALOM: Finding transmembrane regions (Klein et al.)
count: 0 value: 4.93 threshold: 0.0

PERIPHERAL          Likelihood = 4.93
modified ALOM score: -1.49
Rule: cytoplasmic protein

*** Reasoning Step: 2
Final Results bacterial cytoplasm --- Certainty =     0.189(Affirmative) < succ>

The protein has homology with the following sequences in the databases:

```
>gi|10172952|dbj|BAB04058.1|(AP001508) BH0339~unknown conserved protein
in others [Bacillus halodurans]
Length = 283

Score = 83.7 bits (206), Expect = 1e-15
Identities = 59/156 (37%), Positives = 87/156 (54%), Gaps = 8/156 (5%)

Query:    10 VRGPVQLAFAQSIDPIVPPEVSITRMAVTNEKDLEKERTMGRKYIVPYVVYRVHGFISAN    69
             VRGPV + A SIDPI      IT+   +   D    TMG K+ V + VY    G I+
Sbjct:   129 VRGPVSIHTATSIDPIDIVSTQITKSVNSVTGDKRSSDTMGMKHRVDFGVYVFKGSINTQ   188

Query:    70 LAAKTGFSDDDLAKLWQALTLMFEHDRSAAR--GEMAARKLVVFKHDSALGSQPAHKLFD   127
             LA KTGF+++D K+ +AL +FE+D S AR  G M    K+  ++H S LG    + K+
Sbjct:   189 LAEKTGFTNEDAEKIKRALITLFENDSSSARPDGSMEVHKVYWWEHSSKLGQYSSAKVHR   248

Query:   128 AVKVERVNGESGTPASGFGDYKISVVSDGLNGVSVE                          163
             ++K+E    ++ TP S F DY + +    L+G+ VE
Sbjct:   249 SLKIE---SKTDTPKS-FDDYAVELYE--LDGLGVE                          278
```

Example 100

A DNA sequence was identified in *N. gonorrhoeae* <SEQ ID 199> which encodes amino acid sequence <SEQ ID 200; NGS100>. Analysis of this protein sequence reveals the following:

Signal Score (−7.5): −3.03

Possible cleavage site: 18

>>> Seems to have no N-terminal signal seq.

Amino Acid Composition of Predicted Mature Form:

calculated from 1

ALOM: Finding transmembrane regions (Klein et al.)

count: 0 value: 6.63 threshold: 0.0

PERIPHERAL  Likelihood = 6.63
modified ALOM score: −1.83
Rule: cytoplasmic protein

*** Reasoning Step: 2
Final Results bacterial cytoplasm --- Certainty =    0.185(Affirmative) < succ>

The protein has homology with the following sequences in the databases:

```
>gi|1175791|sp|P44189|YE18_HAEIN HYPOTHETICAL PROTEIN HI1418
gi|1074769|pir||A64029 hypothetical protein HI1418 - Haemophilus influenzae
(strain Rd KW20)
gi|1574254|gb|AAC23068.1|(U32821) H. influenzae predicted coding region
HI1418 [Haemophilus influenzae Rd]
Length = 201

Score = 144 bits (364), Expect = 1e-33
Identities = 71/109 (65%), Positives = 79/109 (72%)

Query:    8 NFQQNSVRTVADNKGELWFLANDVCEILGYTNPRRTVDLHCKSRGVTKRYTPTTSGEQEM    67
            NF+   VR + D KGE WF   DVC ILGYTN R+ +  HCK  GVTKRYTPT S +QEM
Sbjct:   24 NFKDLPVRVILDPKGEFWFCGTDVCHILGYTNSRKALQDHCKQGGVTKRYTPTKSADQEM   83

Query:   68 TYINEPNLYRLIIKSRKPAAEAFEEWVMETVLPAIRKTGGCQVGPKTTA             116
            T+INEPNLYRLIIKSRKP AE FE WV E VLP IRKTG  Q+ P+  A
Sbjct:   84 TFINEPNLYRLIIKSRKPEAEPFEAWVFEEVLPQIRKTGKYQLQPQQLA             132
```

Based on this analysis, it was predicted that this protein from *N. gonorrhoeae*, and its epitopes, could be useful antigens for vaccines or diagnostics.

Example 101

A DNA sequence was identified in *N. gonorrhoeae* <SEQ ID 201> which encodes amino acid sequence <SEQ ID 202; NGS101>. Analysis of this protein sequence reveals the following:

Signal Score (−7.5): −1.23

Possible cleavage site: 47

>>> Seems to have no N-terminal signal seq.

Amino Acid Composition of Predicted Mature Form:

calculated from 1

ALOM: Finding transmembrane regions (Klein et al.)

count: 0 value: 3.55 threshold: 0.0

PERIPHERAL  Likelihood = 3.55
modified ALOM score: −1.21
Rule: cytoplasmic protein

*** Reasoning Step: 2
Final Results bacterial cytoplasm --- Certainty =    0.126(Affirmative) < succ>

The protein has homology with the following sequences in the databases:

Based on this analysis, it was predicted that this protein from *N. gonorrhoeae*, and its epitopes, could be useful antigens for vaccines or diagnostics.

```
>gi|9632520|ref|NP_0495142.1|hypothetical protein [Bacteriophage 933W]
gi|9633449|ref|NP_050552.1|hypothetical protein [Bacteriophage VT2-Sa]
gi|4585431|gb|AAD25459.1|AF125520_54 (AF125520) hypothetical protein
[Bacteriophage 933W]
gi|5881645|dbj|BAA84336.1|(AP000363) hypothetical protein [Bacteriophage
VT2-Sa]
gi|7649882|dbj|BAA94160.1|(AP000422) hypothetical protein [Escherichia coli
O157:H7]
Length = 404

Score = 177 bits (449), Expect = 3e-43
Identities = 130/425 (30%), Positives = 204/425 (47%) , Gaps = 27/425 (6%)

Query:    7 TAYGDPQAMMKQAAGLFAMHMQRNSTLNRLAGKMPAGTA-GAEATLRKQTTQHMPVVRCQ     65
            T     QA         LF    + S +N L  + A A   +   KQT+    PVVR
Sbjct:    2 TTVTSAQANKLYQVALFTAANRNRSMVNILTEQQEAPKAVSPDKKSTKQTSAGAPVVRIT    61

Query:   66 DLTRGMGDEIRFNLVNPVSALPIMGDNTAEGRGVGMSLSEAGLRVNQARFPVDGGGTMTN    125
            DL +   GDE+ F++++ +S  P MGD    EGRG +S ++  L++NQ R  VD GG M+
sbjct:   62 DLNKQAGDEVTFSIMHKLSKRPTMGDERVEGRGEDLSHADFSLKINQGRHLVDAGGRMSQ   121

Query:  126 QRSPADYRALIRPAAQSLMDRYADQTLLVHMAGARGFHDNIEWGVPLAGDPKFNDYAVNP    185
               QR+  +   +  R      + +    DQ +VH+AGARG      +P A  P+F   +N
Sbjct:  122 QRTKFNLASSARTLLGTYFNDLQDQCAIVHLAGARGDFVADDTILPTAEHPEFKKIMIND   181

Query:  186 VKAPSKNRHFTASGDAVTGVGDNGGELKIASTDLFTMDTVDSMRTVLDQIPLPPPIVKFE    245
            V  P+ +RHF         GD     +I + D+F++   VD++   +D++   P  V+
Sbjct:  182 VLPPTHDRHFFG--------GDATSFEQIEAADIFSIGLVDNLSLFIDEMAHPLQPVRLS   233

Query:  246 GDKAAGDSPLRVWLLSPAQYNRF---AADPKFRQLQASAIARASQANQNPLFLGDAGLWN    302
            GD+   G+ P  V  ++P Q+N +     +  + Q+   A+ RA   N +PLF G+   +W
Sbjct:  234 GDELHGEDPYYVLYVTPRQWNDWYTSTSGKDWNQMMVRAVNRAKGFN-HPLFKGECAMWR   292

Query:  303 GFILVKMP-RPIRFYAGDEMKYCADKFSEAESGLKIPASFADKFAVDRSVILGGQAVLEA    361
             ++   K     PIRFY G ++     + +           A    +DR+++LG QA+  A
Sbjct:  293 NILVRKYAGMPIRFYQGSKVLVSENNLTATTK------EVAAATNIDRAMLLGAQALANA   346

Query:  362 FANTGKHGGMPFFWSEKELDHGNRVETLVGTIRGVAKTRFAVDVGGGAKEITDYGVTVVD    421
              +    G+    G F    EK+ D  NR E  +  I G+ K RF      G     ++ D+GV  VD
Sbjct:  347 Y---GQKAGGHFNMVEKKTDMDNRTEIAISWINGLKKIRFPEKSG----KMQDHGVIAVD   399

Query:  422 TVVPL    426
            T V L
Sbjct:  400 TAVKL    404
```

Based on this analysis, it was predicted that this protein from *N. gonorrhoeae*, and its epitopes, could be useful antigens for vaccines or diagnostics.

Example 102

A DNA sequence was identified in *N. gonorrhoeae* <SEQ ID 203> which encodes amino acid sequence <SEQ ID 204; NGS102>. Analysis of this protein sequence reveals the following:

Signal Score (−7.5): −6.09
Possible cleavage site: 15
>>> Seems to have no N-terminal signal seq.
Amino Acid Composition of Predicted Mature Form:
calculated from 1
ALOM: Finding transmembrane regions (Klein et al.)
count: 0 value: 2.92 threshold: 0.0

| PERIPHERAL | Likelihood = 2.92 |
|---|---|
| modified ALOM score: −1.08 | |
| Rule: cytoplasmic protein | |

*** Reasoning Step: 2
Final Results bacterial cytoplasm --- Certainty =    0.480(Affirmative) < succ The protein has no homology with sequences in the databases.

Based on this analysis, it was predicted that this protein from *N. gonorrhoeae*, and its epitopes, could be useful antigens for vaccines or diagnostics.

Example 103

A DNA sequence was identified in *N. gonorrhoeae* <SEQ ID 205> which encodes amino acid sequence <SEQ ID 206; NGS103>. Analysis of this protein sequence reveals the following:

Signal Score (−7.5): −1.29
Possible cleavage site: 34
>>> Seems to have no N-terminal signal seq.
Amino Acid Composition of Predicted Mature Form:
calculated from 1
ALOM: Finding transmembrane regions (Klein et al.)
count: 1 value: −0.00 threshold: 0.0

| INTEGRAL | Likelihood = −0.00 | Transmembrane 22-38 (22-38) |
|---|---|---|
| PERIPHERAL | Likelihood = 4.88 | |
| modified ALOM score: 0.50 | | |
| Rule: cytoplasmic membrane protein | | |

*** Reasoning Step: 2
Final Results bacterial inner membrane --- Certainty =    0.100(Affirmative) < succ>

The protein has homology with the following sequences in the databases:

```
>gi|11277848|pir||E81145 replicative DNA helicase NMB0885 [imported] -
Neisseria meningitidis (group B strain MD58)
gi|7226124|gb|AAF41296.1|(AE002441) replicative DNA helicase [Neisseria
meningitidis MC58]
Length = 468

Score = 233 bits (594), Expect = 5e-60
Identities = 158/456 (34%), Positives = 245/456 (53%), Gaps = 34/456 (7%)

Query:  15 SVGAEQNILGGILIEPTAIARCA-ILTPEKFYQAQHRIIFRALLDMAAANEPIDIITLND    73
           S+ AEQ++LGG+++E  A  R A +++ E FY+ +HR+IFR++ +   + P D+IT+ +
Sbjct:  23 SMEAEQSVLGGLMLENPAWDRIADVVSGEDFYRHEHRLIFRSIAKLINESRPADVITVQE   82

Query:  74 KLEARGEAENAGGLAYLIDLNQNTPSAKNISRYVGIVNDRFVERGLLKASAAIEKIAVSK  133
           +L+    E E AGG  YLI L QNTPSA NI RY  IV +R +  R L +   I + A +
Sbjct:  83 DLQRNEELEAAGGFEYLITLAQNTPSAANIRRYAEIVRERSIMRQLAEVGTEIARSAYNP  142

Query: 134 DGGTVAEKLSKAADELAAVGKDAVKRETKTFGQTVEDLIGGLDKRLDGVR--------FG  185
           G  +  L +A +++  + + K +K    + DL+  + +R+D +          G
Sbjct: 143 QGRDAGQLLDEAENKVFQIAESTAK--SKQGFLEMPDLLKEVVQRIDMLYSRDNPDEVTG  200

Query: 186 LPTGLMKLDGMTGGLPDGNLIVIAARPSMGKTVLAENIARFLAKQGK-AVHFQSYEMSAV  244
           +PTG + LD  T GL  G+LI++A RPSMGKT + NIA     +G+ V   S EM
Sbjct: 201 VPTGFIDLDKKTSGLQPGDLIIVAGRPSMGKTAFSINIAEHVAVEGRLPVAVFSMEMGGA  260

Query: 245 ELARRGMAAECNIPMQNLKTGNLTQSDYANM----------PIYVSQAKEWKFDVNCDLL  294
           +L R ++ +    LKTG L +   +           P+Y+ +
Sbjct: 261 QLVMRMLGSVGRLDQSVLKTGRLEDEHWGRLNEAVVKLSDAPVYIDETPGLTALELRARA  320

Query: 295 NVDELCFLAKEKKLTTGLDLLVVDHLHIMPRAGRDE--VAELGNISRRLKNLAAELNTPV  352
              F  K   L L+V+D+L +M +GR +   +ELG ISR LK  LA EL   P+
Sbjct: 321 RRLARQFNNK-------LGLIVIDYLQLMAGSGRSDNRASELGEISRSLKALAKELQVPI  373

Query: 353 VLVAQLNRGNTKQADKRPNMADIRGSGAIEQDANIIIMPHRESYYDGNENP--SIAELII  410
           + ++QL+R  +  DKRP M+D+R SGAIEQDA++I+  +R+ YY+  ++P   +AE II
Sbjct: 374 IALSQLSRTVESRTDKRPMMSDLRESGAIEQDADLIMFMYRDEYYN-QDSPMKGLAECII  432

Query: 411 AKNRDGEMGTVVCGWKGQFMKFEEEPDLAWQAPKHD                          446
           K+R+G +G +   W GQF KF+    + +A    D
Sbjct: 433 GKHRNGPVGKIFLTWTGQFTKFDNAAYIPEEAKIED                          468

>gi|11277846|pir||E81876 probable replicative DNA helicase (EC 3.6.1.-)
NMA1105 [imported] -
Neisseria meningitidis (group A strain Z2491)
gi|7379799|emb|CAB84367.1|(AL162755) putative replicative DNA helicase
[Neisseria meningitidis Z2491]
Length = 468

Score = 230 bits (588), Expect = 2e-59
Identities = 158/456 (34%), Positives = 244/456 (52%), Gaps = 34/456 (7%)

Query:  15 SVGAEQNILGGILIEPTAIARCA-ILTPEKFYQAQHRIIFRALLDMAAANEPIDIITLND    73
           S+ AEQ++LGG+++E  A  R A +++ E FY+ +HR+IFR++ +   + P D+IT+ +
Sbjct:  23 SMEAEQSVLGGLMLENPAWDRIADVVSGEDFYRHEHRLIFRSIAKLINESRPADVITVQE   82

Query:  74 KLEARGEAENAGGLAYLIDLNQNTPSAKNISRYVGIVNDRFVERGLLKASAAIEKIAVSK  133
           +L+    E E AGG  YLI L QNTPSA NI RY  IV +R +  R L +   I + A +
Sbjct:  83 DLQRNEELEAAGGFEYLITLAQNTPSAANIRRYAEIVRERSIMRQLAEVGTEIARSAYNP  142

Query: 134 DGGTVAEKLSKAADELAAVGKDAVKRETKTFGQTVEDLIGGLDKRLDGVR--------FG  185
           G  +  L +A +++  + + K +K    + DL+  + +R+D +          G
Sbjct: 143 QGRDAGQLLDEAENKVFQIAESTAK--SKQGFLEMPDLLKEVVQRIDMLYSRDNPDEVTG  200

Query: 186 LPTGLMKLDGMTGGLPDGNLIVIAARPSMGKTVLAENIARFLAKQGK-AVHFQSYEMSAV  244
           + TG + LD  T GL  G+LI++A RPSMGKT + NIA     +GK V   S EM
Sbjct: 201 VSTGFIDLDKKTSGLQPGDLIIVAGRPSMGKTAFSINIAEHVAVEGKLPVAVFSMEMGGA  260

Query: 245 ELARRGMAAECNIPMQNLKTGNLTQSDYANM----------PIYVSQAKEWKFDVNCDLL  294
           +L R ++ +    LKTG L +   +           P+Y+ +
Sbjct: 261 QLVMRMLGSVGRLDQSVLKTGRLEDEHWGRLNEAVVKLSDAPVYIDETPGLTALELRARA  320

Query: 295 NVDELCFLAKEKKLTTGLDLLVVDHLHIMPRAGRDE--VAELGNISRRLKNLAAELNTPV  352
              F  K   L L+V+D+L +M +GR +   +ELG ISR LK  LA EL   P+
Sbjct: 321 RRLARQFNNK-------LGLIVIDYLQLMAGSGRSDNRASELGEISRSLKALAKELQVPI  373

Query: 353 VLVAQLNRGNTKQADKRPNMADIRGSGAIEQDANIIIMPHRESYYDGNENP--SIAELII  410
           + ++QL+R  +  DKRP M+D+R SGAIEQDA++I+  +R+ YY+  ++P   +AE II
Sbjct: 374 IALSQLSRTVESRTDKRPMMSDLRESGAIEQDADLIMFMYRDEYYN-QDSPMKGLAECII  432
```

```
                                    -continued
Query: 411 AKNRDGEMGTVVCGMKGQFMKFEEEPDLAWQAPKHD             446
           K+R+G +G +   W GQF KF+        +   +A   D
Sblct: 433 GKHRNGPVGKIFLTWTGQFTKFDNAAYIPEEAKIED             468
```

Based on this analysis, it was predicted that this protein from *N. gonorrhoeae*, and its epitopes, could be useful antigens for vaccines or diagnostics.

Example 104

A DNA sequence was identified in *N. gonorrhoeae* <SEQ ID 207> which encodes amino acid sequence <SEQ ID 208; NGS104>. Analysis of this protein sequence reveals the following:

---

Signal Score (−7.5): −2.11
Possible cleavage site: 15
>>> Seems to have no N-terminal signal seq.
Amino Acid Composition of Predicted Mature Form:
calculated from 1
ALOM: Finding transmembrane regions (Klein et al.)
count: 0 value: 5.04 threshold: 0.0

---

PERIPHERAL            Likelihood = 5.04
modified ALOM score: −1.51
Rule: cytoplasmic protein

---

*** Reasoning Step: 2
Final Results bacterial cytoplasm --- Certainty =    0.220(Affirmative) < succ

---

The protein has homology with the following sequences in the databases:

```
>gi|7515458|pir||T13296 hypothetical protein 8 - Streptococcus phage
phi-O1205 gi|2444088|gb|AAC79524.1|(U88974) ORF8
[Streptococcus thermophilus temperate bacteriophage O1205]
Length = 157

Score = 62.1 bits (150), Expect = 3e-09
Identities = 53/161 (32%), Positives = 86/161 (52%), Gaps = 8/161 (4%)

Query:   5 TLYRCAADVQAGLDYYFDSETEREDTLEAV--IGQFEVKAQSVIAYIKNQEITEKMLEGH   62
           TLY    +    + D ET + DTLEA+     +E K +  + IK+ E    +   +
Sbjct:   3 TLYELTDQLLEIYNMDVDDET-KLDTLEAIDWTTDYENKVEGYVKVIKSLEADIEARKNE  61

Query:  63 IRQMTGKLKAAKARNQSLKDYLARNMQAAGITEIKADDGTFKASFRKSEAVVILDEAQIP  122
           +++ G  K+ +++   LK  LA +M    G T + D    FK   FRKSEAVV+ +E ++P
Sbjct:  62 KKRLDGLNKSDQSKIDKLKTALAVSMAETGQTRV--DTTLFKVGFRKSEAVVV-NEEKLP  118

Query: 123 AEFMREAVKTEPDKTAIRKAIESGRQVAGAKIEGRKNLQIR                    163
           E+      K   PDK  +++ ++SG+ + GA +E R+NL IR
Sbjct: 119 KEYQIATYK--PDKKTLKELLKSGKHIEGATLEERRNLNIR                    157
```

Based on this analysis, it was predicted that this protein from *N. gonorrhoeae*, and its epitopes, could be useful antigens for vaccines or diagnostics.

Example 105

A DNA sequence was identified in *N. gonorrhoeae* <SEQ ID 209> which encodes amino acid sequence <SEQ ID 210; NGS105>. Analysis of this protein sequence reveals the following:

---

Signal Score (−7.5): −5.52
Possible cleavage site: 31

---

>>> Seems to have no N-terminal signal seq.
Amino Acid Composition of Predicted Mature Form:
calculated from 1
ALOM: Finding transmembrane regions (Klein et al.)
count: 0 value: 2.60 threshold: 0.0

---

PERIPHERAL            Likelihood = 2.60
modified ALOM score: −1.02
Rule: cytoplasmic protein

---

*** Reasoning Step: 2
Final Results bacterial cytoplasm --- Certainty =    0.135(Affirmative) < succ

---

The protein has no homology with sequences in the databases.

Based on this analysis, it was predicted that this protein from *N. gonorrhoeae*, and its epitopes, could be useful antigens for vaccines or diagnostics.

Example 106

A DNA sequence was identified in *N. gonorrhoeae* <SEQ ID 211> which encodes amino acid sequence <SEQ ID 212; NGS106>. Analysis of this protein sequence reveals the following:

---

Signal Score (−7.5): 4.8
Possible cleavage site: 26
>>> Seems to have a cleavable N-term signal seq.
Amino Acid Composition of Predicted Mature Form:
calculated from 27
ALOM: Finding transmembrane regions (Klein et al.)
count: 0 value: 7.80 threshold: 0.0

---

PERIPHERAL            Likelihood = 7.80
modified ALOM score: −2.06
Score for OM-PP discrimination: 4.38
Rule: outer membrane or periplasmic protein
Score for OM-PP discrimination: 4.38
Rule: outer membrane or periplasmic protein -continued

```
        *** Reasoning Step: 2
    Outer membrane? Score: 0.437687
    Outer membrane? Score: 0.437687
              Final Results
``` bacterial outer membrane --- Certainty =     0.768(Affirmative) < succ>

The protein has no homology with sequences in the databases, although it is similar to HMBW1 from *Haemophilus influenzae*.

The protein was expressed in *E. coli* as an insoluble 43.56 kDa His-fusion product and then purified.

Based on this analysis, it was predicted that this protein from *N. gonorrhoeae*, and its epitopes, could be useful antigens for vaccines or diagnostics.

Example 107

A DNA sequence was identified in *N. gonorrhoeae* <SEQ ID 213> which encodes amino acid sequence <SEQ ID 214; NGS107>. Analysis of this protein sequence reveals the following:

```
Signal Score (-7.5): -3.83
Possible cleavage site: 51
>>> Seems to have no N-terminal signal seq.
Amino Acid Composition of Predicted Mature Form:
  calculated from 1
ALOM: Finding transmembrane regions (Klein et al.)
  count: 0 value: 4.61 threshold: 0.0

PERIPHERAL              Likelihood = 4.61
modified ALOM score: -1.42
Rule: cytoplasmic protein

*** Reasoning Step: 2
                Final Results
``` bacterial cytoplasm --- Certainty =     0.146(Affirmative) < succ>

The protein has no homology with sequences in the databases.

Based on this analysis, it was predicted that this protein from *N. gonorrhoeae*, and its epitopes, could be useful antigens for vaccines or diagnostics.

Example 108

A DNA sequence was identified in *N. gonorrhoeae* <SEQ ID 215> which encodes amino acid sequence <SEQ ID 216; NGS108>. Analysis of this protein sequence reveals the following:

```
GvH: Examining signal sequence (von Heijne)
Signal Score (-7.5): -6.14
Possible cleavage site: 19
>>> Seems to have no N-terminal signal seq.
Amino Acid Composition of Predicted Mature Form:
  calculated from 1
ALOM: Finding transmembrane regions (Klein et al.)
  count: 0 value: 8.43 threshold: 0.0

PERIPHERAL              Likelihood = 8.43
modified ALOM score: -2.19
Rule: cytoplasmic protein

*** Reasoning Step: 2
                Final Results
``` bacterial cytoplasm --- Certainty =         0.574(Affirmative) < succ>
bacterial periplasmic space --- Certainty = 0.000(Not Clear) < succ>
bacterial outer membrane --- Certainty =    0.000(Not Clear) < succ>
bacterial inner membrane --- Certainty =    0.000(Not Clear) < succ>

The protein has homology with the following sequences in the databases:

```
>pir||G81977 probable lipoprotein NMA0586 [imported] - Neisseria
meningitidis (group A strain Z2491)
emb|CAB83877.1|(AL162753) putative lipoprotein [Neisseria meningitidis
Z2491]
Length = 280

Score = 52.9 bits (126), Expect = 5e-06
Identities = 43/134 (32%), Positives = 63/134 (46%),
Gaps = 23/134 (17%)

Query: 174 LGDIRGVATDEDKLPKAGSFQYEGRAFGGNGVLSKESLDNHNGVFRYTIDFDRRKGSGSI 233
           +GDI G  T  DKLP+ G   Y G AFG          D+ +G   YTIDF  ++G G I
Sbjct: 156 IGDIAGEHTSFDKLPEGGRATYRGTAFGS---------DDASGKLTYTIDFAAKQGHGKI 206

Query: 234 EGMEQYGKIKLEEAAIERIPYRESGSSLGLKDRVSYFGVNEGVAMLEKDNEIKKYHLGIF 293
           E ++    ++ ++ AA +   P ++  +                 ++L    E   Y LGIF
Sbjct: 207 EHLKS-PELNVDLAASDIKPDKKRHAVI-------------SGSVLYNQAEKGSYSLGIF 252

Query: 294 GEAANEVAGAVSQE 307
           G  A EVAG+  E
Sbjct: 253 GGQAQEVAGSAEVE 266

>pir||D81032 hypothetical protein NMB1870 [imported] - Neisseria
meningitidis (group B strain MD58)
gb|AAF42204.1|(AE002537) hypothetical protein [Neisseria meningitidis
MC58]
Length = 320
```

-continued

```
Score = 50.6 bits (120), Expect = 3e-05
Identities = 50/168 (29%), Positives = 76/168 (44%),
Gaps = 28/168 (16%)

Query: 136 VYEQPYSVVRGYFGYSRKDGNPIEGDGQNPEEIPFDLYLGDIRGVATDEDKLPKAGSFQY 195
            VY+Q +S + +      +D    E  G+    + F  +GDI G  T  DKLP+ G   Y
Sbjct: 163 VYKQSHSALTAFQTEQIQDS---EHSGKMVAKRQFR--IGDIAGEHTSFDKLPEGGRATY 217

Query: 196 EGRAFGGNGVLSKESLDNHNGVFRYTIDFDRRKGSGSIEGMEQYGKIKLEEAAIERIPYR 255
            G  AFG           D+  G    YTIDF  ++G+G IE ++      ++ ++ AA + P
Sbjct: 218 RGTAFGS---------DDAGGKLTYTIDFAAKQGNGKIEHLKS-PELNVDLAAADIKPDG 267

Query: 256 ESGSSLGLKDRVSYFGVNEGVAMLEKDNEIKKYHLGIFGEAANEVAGA 303
            +  + + +              ++L   E   Y LGIFG  A EVAG+
Sbjct: 268 KRHAVI------------SGSVLYNQAEKGSYSLGIFGGKAQEVAGS 302
```

Based on this analysis, it was predicted that this protein from *N. gonorrhoeae*, and its epitopes, could be useful antigens for vaccines or diagnostics.

Example 109

A DNA sequence was identified in *N. gonorrhoeae* <SEQ ID 217> which encodes amino acid sequence <SEQ ID 218; NGS109>. Analysis of this protein sequence reveals the following:

| | |
|---|---|
| GvH: Examining signal sequence (von Heijne) | |
| Signal Score (-7.5): -5.39 | |
| Possible cleavage site: 25 | |
| >>> Seems to have no N-terminal signal seq. | |
| Amino Acid Composition of Predicted Mature Form: calculated from 1 | |
| ALOM: Finding transmembrane regions (Klein et al.) | |
| count: 0 value: 7.00 threshold: 0.0 | |
| PERIPHERAL  Likelihood = 7.00 modified ALOM score: -1.90 | |
| Rule: cytoplasmic protein | |

*** Reasoning Step: 2
Final Results

| | |
|---|---|
| bacterial cytoplasm --- Certainty = | 0.353(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

As a homolog was found in serogroup A *N. meningitidis* but not in serogroup B, NGS109 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 110

A DNA sequence was identified in *N. gonorrhoeae* <SEQ ID 219> which encodes amino acid sequence <SEQ ID 220; NGS110>. Analysis of this protein sequence reveals the following:

| | | | |
|---|---|---|---|
| GvH: Examining signal sequence (von Heijne) | | | |
| Signal Score (-7.5): -2.76 | | | |
| Possible cleavage site: 41 | | | |
| >>> Seems to have no N-terminal signal seq. | | | |
| Amino Acid Composition of Predicted Mature Form: calculated from 1 | | | |
| ALOM: Finding transmembrane regions (Klein et al.) | | | |
| count: 1 value: -0.00 threshold: 0.0 | | | |
| INTEGRAL | Likelihood = -0.00 | Transmembrane | 88-104 (88-104) |
| PERIPHERAL | Likelihood = 7.69 | | |
| modified ALOM score: 0.50 | | | |
| Rule: cytoplasmic membrane protein | | | |

*** Reasoning Step: 2
Final Results

| | |
|---|---|
| bacterial inner membrane --- Certainty = | 0.100(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

```
>pir||A82012 hypothetical protein NMA0179 [imported] - Neisseria
meningitidis (group A strain Z2491)
emb|CAB83494.1|(AL162752) hypothetical protein NMA0179 [Neisseria
meningitidis Z2491]
Length = 97

Score = 183 bits (464), Expect = 1e-45
Identities = 92/97 (94%), Positives = 95/97 (97%)

Query:  44 MKANDKLNRQIDVLQKQSAAIHNEAYIEMNTLLYRHREVVSIHNRKADYAEKGKERIALF 103
           MK NDKLNRQIDVLQKQSAAIHNEAYIEMNTLLYRHREVVS+HNRKADYAEKGKE+IALF
Sbjct:   1 MKTNDKLNRQIDVLQKQSAAIHNEAYIEMNTLLYRHREVVSVHNRKADYAEKGKEQIALF 60

Query: 104 PRGLNGITKLPAAVLLPERPYHFDMKEVLYIFSRIPR 140
           PRGLNGITKLPAAVLLPERPYHFDMKEVL+IFS IPR
Sbjct:  61 PRGLNGITKLPAAVLLPERPYHFDMKEVLHIFSWIPR 97
```

The protein has no homology with sequences in the databases.

Based on this analysis, it was predicted that this protein from *N. gonorrhoeae*, and its epitopes, could be useful antigens for vaccines or diagnostics.

Example 111

A DNA sequence was identified in *N. gonorrhoeae* <SEQ ID 221> which encodes amino acid sequence <SEQ ID 222; NGS111>. Analysis of this protein sequence reveals the following:

GvH: Examining signal sequence (von Heijne)
Signal Score (-7.5): -5.89
Possible cleavage site: 21
>>> Seems to have no N-terminal signal seq.
Amino Acid Composition of Predicted Mature Form: calculated from 1
ALOM: Finding transmembrane regions (Klein et al.)
count: 0 value: 2.44 threshold: 0.0

PERIPHERAL         Likelihood = 2.44
modified ALOM score: -0.99
Rule: cytoplasmic protein

*** Reasoning Step: 2
Final Results

| | |
|---|---|
| bacterial cytoplasm --- Certainty = | 0.293(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology with the following sequences in the databases:

Based on this analysis, it was predicted that this protein from *N. gonorrhoeae*, and its epitopes, could be useful antigens for vaccines or diagnostics.

Example 112

A DNA sequence was identified in *N. gonorrhoeae* <SEQ ID 223> which encodes amino acid sequence <SEQ ID 224; NGS112>. Analysis of this protein sequence reveals the following:

GvH Examining signal sequence (von Heijne)
Signal Score (-7.5): -9.08
Possible cleavage site: 54
>>> Seems to have no N-terminal signal seq.
Amino Acid Composition of Predicted Mature Form: calculated from 1
ALOM: Finding transmembrane regions (Klein et al.)
count: 1 value: -1.22 threshold: 0.0

| | | | |
|---|---|---|---|
| INTEGRAL | Likelihood = -1.22 | Transmembrane | 160-176 (160-177) |
| PERIPHERAL | Likelihood = 0.58 | | | modified ALOM score: 0.74
Rule: cytoplasmic membrane protein

*** Reasoning Step: 2
Final Results

| | |
|---|---|
| bacterial inner membrane --- Certainty = | 0.149(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
>gb|AAC45840.1|(AF001598) restriction endonuclease [Neisseria gonorrhoeae]
Length = 374

Score = 539 bits (1390), Expect = e-152
Identities = 285/285 (100%), Positives = 285/285 (100%)

Query:    1 MGFIEPFLSSYTPLSRDYVQARTNRKRQTLLSKIVYTHSGFQRSVTENSNIRQINFLIKT   60
            MGFIEPFLSSYTPLSRDYVQARTNRKRQTLLSKIVYTHSGFQRSVTENSNIRQINFLIKT
Sbjct:   90 MGFIEPFLSSYTPLSRDYVQARTNRKRQTLLSKIVYTHSGFQRSVTENSNIRQINFLIKT  149

Query:   61 LVEHPQGKLNKKEIAAMMLVDLKTFQQDYLTETELNDYFQQGIESGFIERKYNQISYLWN  120
            LVEHPQGKLNKKEIAAMMLVDLKTFQQDYLTETELNDYFQQGIESGFIERKYNQISYLWN
Sbjct:  150 LVEHPQGKLNKKEIAAMMLVDLKTFQQDYLTETELNDYFQQGIESGFIERKYNQISYLWN  209

Query:  121 LLDKLDDLKRVGDDLYFAEDAQRIFGNLDEITVRKRDPYLHRLYKNQLQEESEEHYGNVK  180
            LLDKLDDLKRVGDDLYFAEDAQRIFGNLDEITVRKRDPYLHRLYKNQLQEESEEHYGNVK
Sbjct:  210 LLDKLDDLKRVGDDLYFAEDAQRIFGNLDEITVRKRDPYLHRLYKNQLQEESEEHYGNVK  269

Query:  181 CMLEKLAYPVLIASHIKPFILSDDTEAYDPNNGLLLSRTLDSLFDLKYISFDDEGNMVKS  240
            CMLEKLAYPVLIASHIKPFILSDDTEAYDPNNGLLLSRTLDSLFDLKYISFDDEGNMVKS
Sbjct:  270 CMLEKLAYPVLIASHIKPFILSDDTEAYDPNNGLLLSRTLDSLFDLKYISFDDEGNMVKS  329

Query:  241 KRLSDDVWRRWCDVKLDNNLLNDKRKSYLAYHRELMLQEDQEFHI                285
            KRLSDDVWRRWCDVKLDNNLLNDKRKSYLAYHRELMLQEDQEFHI
Sbjct:  330 KRLSDDVWRRWCDVKLDNNLLNDKRKSYLAYHRELMLQEDQEFHI                374
```

```
^ **gbp_12644572 gi|12644572|sp|Q505973|T2B1_NEIGO TYPE II RESTRICTION
ENZYME NGOBI (ENDONUCLEASE NGOBI) (R. NGOBI) (R. NGOI)
gb|AAB03207.2|(U42459) NgoI restriction endonuclease R. NgoI
[N. gonorrhoeae]
Length = 350

Score = 694 bits (1791), Expect = 0.0
Identities = 349/350 (99%), Positives = 349/350 (99%)

Query:    1 MTLEEQQAKEALDGIIKKSRVHLYKPIQIAEILYHDRCIKQLDFLNLDTYRNQSKRWRDE    60
            MTLEEQQAKEALDGIIKKSRVHLYKPIQIAEILYHDRCIKQLDFLNLDTYRNQSKRWRDE
Sbjct:    1 MTLEEQQAKEALDGIIKKSRVHLYKPIQIAEILYHDRCIKQLDFLNLDTYRNQSKRWRDE    60

Query:   61 ICRRFLGRISTSSAKFQDNLFEKNAIPPEKLAVLGTLNRQSDGGVESYIYKQFFNRFSQM   120
            ICRRFLGRISTSSAKFQDNLFEKNAIPPEKLAVLGTLNRQSDGGVESYIYKQFFNRFSQM
Sbjct:   61 ICRRFLGRISTSSAKFQDNLFEKNAIPPEKLAVLGTLNRQSDGGVESYIYKQFFNRFSQM   120

Query:  121 SEALAYVGNTDRYSFQLSEFLNLFWLEPGLKRSIDKIYEIVVYALFDALVSELGITVSID   180
            SE LAYVGNTDRYSFQLSEFLNLFWLEPGLKRSIDKIYEIVVYALFDALVSELGITVSID
Sbjct:  121 SERLAYVGNTDRYSFQLSEFLNLFWLEPGLKRSIDKIYEIVVYALFDALVSELGITVSID   180

Query:  181 FPKENLFLWEEYQDFAEKIITMPKNEHLKLPAKIHRVGVTNAADRGLDMWSNFGLAIQVK   240
            FPKENLFLWEEYQDFAEKIITMPKNEHLKLPAKIHRVGVTNAADRGLDMWSNFGLAIQVK
Sbjct:  181 FPKENLFLWEEYQDFAEKIITMPKNEHLKLPAKIHRVGVTNAADRGLDMWSNFGLAIQVK   240

Query:  241 HLSLDEELAEDIVSSISADRIVIVCKKAEQSVIVSLLTQIGWKSRIQNIVTEDDLISWYE   300
            HLSLDEELAEDIVSSISADRIVIVCKKAEQSVIVSLLTQIGWKSRIQNIVTEDDLISWYE
Sbjct:  241 HLSLDEELAEDIVSSISADRIVIVCKKAEQSVIVSLLTQIGWKSRIQNIVTEDDLISWYE   300

Query:  301 KALRGQYPIAEALLENIKTEIMREFPAVNEANEFLDFAQNRGYDITVTHF            350
            KALRGQYPIAEALLENIKTEIMREFPAVNEANEFLDFAQNRGYDITVTHF
Sbjct:  301 KALRGQYPIAEALLENIKTEIMREFPAVNEANEFLDFAQNRGYDITVTHF            350
```

Based on this analysis, it was predicted that this protein from *N. gonorrhoeae*, and its epitopes, could be useful antigens for vaccines or diagnostics.

Example 113

A DNA sequence was identified in *N. gonorrhoeae* <SEQ ID 225> which encodes amino acid sequence <SEQ ID 226; NGS113>. Analysis of this protein sequence reveals the following:

---

GVH Examining signal sequence (von Heijne)
Signal Score (−7.5): −1.7
Possible cleavage site: 43
>>> Seems to have no N-terminal signal seq.
Amino Acid Composition of Predicted Mature Form:
calculated from 1
ALOM: Finding transmembrane regions (Klein et al.)
count: 4 value: −9.77 threshold: 0.0

---

| | | | |
|---|---|---|---|
| INTEGRAL | Likelihood = −9.77 | Transmembrane | 187-203 (183-208) |
| INTEGRAL | Likelihood = −7.22 | Transmembrane | 25-41 (19-46) |
| INTEGRAL | Likelihood = −4.14 | Transmembrane | 139-155 (138-155) |
| INTEGRAL | Likelihood = −2.87 | Transmembrane | 86-102 (85-102) |
| PERIPHERAL | Likelihood = 1.27 modified ALOM score: 2.45 Rule: cytoplasmic membrane protein | | |

*** Reasoning Step: 2
Final Results

| | |
|---|---|
| bacterial inner membrane --- Certainty = | 0.491(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_15902668 gi|15902668|ref|NP_358218.1|\(NC_003098) ABC
transporter membrane-spanning permease - glutamine
transport [Streptococcus pneumoniae R6]
gb|AAK99428.1|(AE008440) ABC transporter membrane-spanning permease -
glutamine transport [Streptococcus pneumoniae R6]
Length = 226

Score = 218 bits (556), Expect = 7e-56
Identities = 113/218 (51%), Positives = 155/218 (70%)

Query:    1 MNWPYLIDAVPKFADAAKLTLELSVYGVVLSLLFGLPVAVVTAYRIRPFYALARAYIELS    60
            M+W   +P + A  LTL ++V+G++ S L GL V+++  YRI    +A AYIELS
Sbjct:    1 MDWSIVEQYLPLYQKAFFLTLHIAVWGILGSFLLGLIVSIIRHYRIPVLAQVATAYIELS    60

Query:   61 RNTPLLIQLFFLYYGLPKMGIKWDGFTCGVIALVFLGASYMAEAVRAGILAVPKGQVGAG   120
            RNTPLLIQLFFLY+GLP++GI     C + LVFLG SYMAE+ R+G+ A + Q   G
Sbjct:   61 RNTPLLIQLFFLYFGLPRIGIVLSSEVCATLGLVFLGGSYMAESFRSGLEAISQTQQEIG   120
```

-continued
```
Query: 121 KAIGLSRFQVFRYVELPQVWAVAVPAIGANILFLMKETSVVSTVGIAELLFVTKDVIGMD 180
           AIGL+   QVFRYV LPQ  AVA+P+   AN++FL+KETSV S V +A+L++V KD+IG+
Sbjct: 121 LAIGLTPLQVFRYVVLPQATAVALPSFSANVIFLIKETSVFSAVALADLMYVAKDLIGLY 180

Query: 181 YKTNEALFLLPAAYLIILLPVSLLARRIENRVRSAKYG                       218
           Y+T+ AL +L  AYLI+LLP+SL+    IE R+R A +G
Sbjct: 181 YETDIALAMLVVAYLIMLLPISLVFSWIERRIRHAGFG                       218
```

Based on this analysis, it was predicted that this protein from *N. gonorrhoeae*, and its epitopes, could be useful antigens for vaccines or diagnostics.

Example 114

A DNA sequence was identified in *N. gonorrhoeae* <SEQ ID 227> which encodes amino acid sequence <SEQ ID 228; NGS114>. Analysis of this protein sequence reveals the following:

| | |
|---|---|
| GvH Examining signal sequence (von Heijne) | |
| Signal Score (−7.5): −0.46 | |
| Possible cleavage site: 17 | |
| >>> Seems to have a cleavable N-term signal seq. | |
| Amino Acid Composition of Predicted Mature Form: calculated from 18 | |
| ALOM: Finding transmembrane regions (Klein et al.) | |
| count: 3 value: −5.36 threshold: 0.0 | |

| | | | |
|---|---|---|---|
| INTEGRAL | Likelihood = −5.36 | Transmembrane | 50-66 (47-67) |
| INTEGRAL | Likelihood = −4.83 | Transmembrane | 183-199 (176-200) |
| INTEGRAL | Likelihood = −1.81 | Transmembrane | 72-88 (72-88) |
| PERIPHERAL | Likelihood = 0.26 | | |
| modified ALOM score: 1.57 | | | |
| Rule: cytoplasmic membrane protein | | | |

*** Reasoning Step: 2
Final Results

| | |
|---|---|
| bacterial inner membrane --- Certainty = | 0.314(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_15902667 gi|15902667|ref|NP_358217.1|\(NC_003098) ABC
transporter membrane-spanning permease - glutamine
transport [Streptococcus pneumoniae R6]
gb|AAK99427.1|(AE008440) ABC transporter membrane-spanning permease -
glutamine transport [Streptococcus pneumoniae R6]
Length = 225

Score = 218 bits (555), Expect = 9e-56
Identities = 111/206 (53%), Positives = 151/206 (72%)

Query:   3 EGLLLTAQISLISVAASCVLGTLFGLVLRSRNRLVRFVGRFYLETIRIVPILVWLFGLYF  62
           +GL +T   IS++SV  S + GT+ G+++  S +R++RF+ R YLE IRI+P LV LF +YF
Sbjct:  20 QGLGVTIGISILSVLLSMMFGTVMGIIMTSHSRIIRFLTRLYLEFIRIMPQLVLLFIVYF  79

Query:  63 GLSVWTGIHIGGFWVCVWVFSLWGVAEMGDLVRGALESIEKHQVESGLAPGLSRGQVFRC 122
           GL+      I+I G   + VF+LWG AEMGDLVRGA+  S+ KHQ  ESG A GL+   Q++
Sbjct:  80 GLARNFNINISGETSAIIVFTLWGTAEMGDLVRGAITSLPKHQFESGQALGLTNVQLYYH 139

Query: 123 IELPQSIRRVLPGAVNLFTRMIKTSSLAWLIGIVIEVVKVGQQIIENSLLTQPNASFWVYG 182
           I +PQ +RR+LP A+NL TRMIKT+SL   LIGV+EV KVGQQII+++  LT P ASFW+YG
Sbjct: 140 IIIPQVLRRLLPQAINLVTRMIKTTSLVVLIGVVEVTKVGQQIIDSNRLTIPTASFWIYG 199

Query: 183 LIFMLYFFCCWPLSLLAAKLEQKWEH                                   208
           I +LYF  C+P+S L  LE+ W +
Sbjct: 200 TILVLYFAVCYPISKLSTHLEKHWRN                                   225
```

Based on this analysis, it was predicted that this protein from *N. gonorrhoeae*, and its epitopes, could be useful antigens for vaccines or diagnostics.

Example 115

A DNA sequence was identified in *N. gonorrhoeae* <SEQ ID 229> which encodes amino acid sequence <SEQ ID 230; NGS115>. Analysis of this protein sequence reveals the following:

| | |
|---|---|
| GvH Examining signal sequence (von Heijne) | |
| Signal Score (−7.5): −0.639999 | |
| Possible cleavage site: 38 | |
| >>> May be a lipoprotein | |
| Amino Acid Composition of Predicted Mature Form: calculated from 23 | |
| ALOM: Finding transmembrane regions (Klein et al.) | |
| count: 0 value: 5.25 threshold: 0.0 | |

| | |
|---|---|
| PERIPHERAL | Likelihood = 5.25 |
| modified ALOM score: −1.55 | |
| Rule: inner or outer membrane protein | |
| Rule: inner or outer membrane protein | |

*** Reasoning Step: 2
Lipoprotein?
Inner membrane?
Final Results

| | |
|---|---|
| bacterial outer membrane --- Certainty = | 0.790(Affirmative) < succ> |
| bacterial inner membrane --- Certainty = | 0.700(Affirmative) < succ> |
| bacterial periplasmic space --- Certainty = | 0.000(Not Clear) < succ> |
| bacterial cytoplasm --- Certainty = | 0.000(Not Clear) < succ> |

The protein has homology to the following sequences in the databases:

^ **gbp_4588485 gi|4588485|gb|AAD26123.1|\(AF109148) antigenic protein
[Actinobacillus pleuropneumoniae]
Length = 278

Score = 407 bits (1045), Expect = e-112
Identities = 212/282 (75%), Positives = 242/282 (85%), Gaps = 7/282 (2%)

```
Query:    1 MKLNAKLKALLASAAIAVGLTACGGGSGDAQSSQSSGAA-TVAAIKEKGVIRIGVFGDKP    59
            MKL+ LK LLA+A A LTAC     +A ++QSS A +VA IKEKGVIRIGVFGDKP
Sbjct:    1 MKLSTTLKTLLATAITAFALTACD----NANNAQSSTAKDSVAQIKEKGVIRIGVFGDKP   56

Query:   60 PFGYVDANGKNQGFDVEIAKDLAKDLLGSPDKVEFVLTEAANRVEYVRSGKVDLILANFT  119
            PFGYVDANGK+QGFDVEIAK++A DLLGS DKVEFVLTEAANRVEY++S KVDLILANFT
Sbjct:   57 PFGYVDANGKSQGFDVEIAKEIANDLLGSSDKVEFVLTEAANRVEYLKSNKVDLILANFT  116

Query:  120 QTPERAEAVDFADPYMKVALGVVSPKNKPITDMAQLKDQTLLVNKGTTADAFFTKSHPEV  179
            +TPERAE VDFA PYM VALGVVSPK + I+D+ QL+ +TLLVNKGTTADA+FTK+HPE+
Sbjct:  117 KTPERAEVVDFAAPYMNVALGVVSPKVRLISDLKQLEGKTLLVNKGTTADAYFTKNHPEI  176

Query:  180 KLLKFDQNTETFDALKDGRGVALAHDNALLWAWAKENPNFEVAIGNLGPAEFIAPAVQKG  239
            LLKFDQNTETFDALKDGRGVALAHDNAL+WAWAKENP F+VAIG++GPAE IAPAVQKG
Sbjct:  177 NLLKFDQNTETFDALKDGRGVALAHDNALVWAWAKENPTFDVAIGSVGPAEQIAPAVQKG  236

Query:  240 NADLLNWVNGEIAAMKKDGRLKAAYEKTLLPVYGEKVKPEAL                   281
            N  LL+ +N EIA  K +G+LKAAYEKTL+PVYG+  KPE L
Sbjct:  237 NQALLDVINKEIAEFKTNGKLKAAYEKTLVPVYGD--KPELL                   276
```

The protein was expressed in *E. coli* as a soluble 28.16 kDa His-fusion product, lacking its leader peptide and its polyglycine sequence (GGGSG), and then purified.

Based on this analysis, it was predicted that this protein from *N. gonorrhoeae*, and its epitopes, could be useful antigens for vaccines or diagnostics.

Example 116

A DNA sequence was identified in *N. gonorrhoeae* <SEQ ID 231> which encodes amino acid sequence <SEQ ID 232; NGS116>. Analysis of this protein sequence reveals the following:

| |
|---|
| GvH Examining signal sequence (von Heijne) |
| Signal Score (−7.5): −7.13 |
| Possible cleavage site: 61 |
| >>> Seems to have no N-terminal signal seq. |
| Amino Acid Composition of Predicted Mature Form: |
| calculated from 1 |
| ALOM: Finding transmembrane regions (Klein et al.) |
| count: 1 value: −1.86 threshold: 0.0 |

| | | | |
|---|---|---|---|
| INTEGRAL | Likelihood = −1.86 | Transmembrane | 51-67 (51-67) |
| PERIPHERAL | Likelihood = 1.54 | | |
| | modified ALOM score: 0.87 | | |
| | Rule: cytoplasmic membrane protein | | |

*** Reasoning Step: 2
Final Results

| | |
|---|---|
| bacterial inner membrane --- Certainty = | 0.174(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has no homology to sequences in the databases.

Based on this analysis, it was predicted that this protein from *N. gonorrhoeae*, and its epitopes, could be useful antigens for vaccines or diagnostics.

Example 117

A DNA sequence was identified in *N. gonorrhoeae* <SEQ ID 233> which encodes amino acid sequence <SEQ ID 234; NGS117>. Analysis of this protein sequence reveals the following:

| |
|---|
| GvH Examining signal sequence (von Heijne) |
| Signal Score (−7.5): 0.25 |
| Possible cleavage site: 40 |
| >>> Seems to have a cleavable N-term signal seq. |
| Amino Acid Composition of Predicted Mature Form: |
| calculated from 41 |
| ALOM: Finding transmembrane regions (Klein et al.) |
| count: 2 value: −4.57 threshold: 0.0 |

| | | | |
|---|---|---|---|
| INTEGRAL | Likelihood = −4.57 | Transmembrane | 100-116 (99-118) |
| INTEGRAL | Likelihood = −1.59 | Transmembrane | 54-70 (54-70) |
| PERIPHERAL | Likelihood = 0.53 | | |
| | modified ALOM score: 1.41 | | |
| | Rule: cytoplasmic membrane protein | | |

*** Reasoning Step: 2
Final Results

| | |
|---|---|
| bacterial inner membrane --- Certainty = | 0.283(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

^ **gbp_15793413 gi|15793413|ref|NP_283235.1|\(NC_003116) putative
integral membrane protein [*Neisseria meningitidis* Z2491]
pir||C81957 probable integral membrane protein NMA0408 [imported] -
*Neisseria meningitidis* (group A strain Z2491)
emb|CAB83707.1|(AL162753) putative integral membrane protein [*Neisseria meningitidis* Z2491]
Length = 550

-continued

```
Score = 1115 bits (2885), Expect = 0.0
Identities = 539/550 (98%), Positives = 545/550 (99%)

Query:    1 MVAYAFLFLFVTAAVLLIVRSHYRWTYFFASALFVFLAGGMLMLTAQWQRALNFASVWFV   60
            MVAY FLFLFVTAA++LI+RSHYRWTYFFASALFVFLAGGMLMLTAQWQRALNFASVWFV
Sbjct:    1 MVAYVFLFLFVTAALVLIIRSHYRWTYFFASALFVFLAGGMLMLTAQWQRALNFASVWFV   60

Query:   61 VLILFHRLKIHYYKQPLLISDFLLIADWRNWETLFHYKEAVIGMAGLLALAGYAVFGWSG  120
            VLILFHRLKIHYYKQPLLISDFLLIADWRNWETLFHYKEAVIGMAGLLALA YAVFGWSG
Sbjct:   61 VLILFHRLKIHYYKQPLLISDFLLIADWRNWETLFHYKEAVIGMAGLLALAAYAVFGWSG  120

Query:  121 ADSLGMPWRWAGAVLFAAAFVSVRHFSKHPGAVKTWLDSLPDDGRDVFLNLPMSCRAVFF  180
            ADSL +PWRWAGAVLFAAAFVS+RHFSKHPGAVKTWLDSLPDDGRDVFLNLPMSCRAVFF
Sbjct:  121 ADSLDVPWRWAGAVLFAAAFVSMRHFSKHPGAVKTWLDSLPDDGRDVFLNLPMSCRAVFF  180

Query:  181 QVPVFEGDGEAFARQMPSETRPYGMSDEKPDIVVTLMESTLDPHCFDFAAAKIPDLKMFG  240
            QVPVFEGDGEAFARQMPSETRP GMSDEKPDIVVTLMESTLDPHCFDFAAAKIPDLKMFG
Sbjct:  181 QVPVFEGDGEAFARQMPSETRPCGMSDEKPDIVVTLMESTLDPHCFDFAAAKIPDLKMFG  240

Query:  241 RQEDTVFSSPLRVHTFGGATWKSEFAFLAGVPSTDFGALASGVFYSVVPHLQTGFVRNLR  300
            RQEDTVFSSPLRVHTFGGATWKSEFAFLAGVPSTDFGALASGVFYSVVPHLQTGFVRNLR
Sbjct:  241 RQEDTVFSSPLRVHTFGGATWKSEFAFLAGVPSTDFGALASGVFYSVVPHLQTGFVRNLR  300

Query:  301 EHGYFCVALSPFTKGNYNAKAAYDHFGFNLMFQPQDLGYPAPMGKNLWHISSEEMMQYAR  360
            EHGYFCVALSPFTKGNYNAKAAYDHFGFNLMFQPQDLGYPAPMGKNLWHISSEEMMQYAR
Sbjct:  301 EHGYFCVALSPFTKGNYNAKAAYDHFGFNLMFQPQDLGYPAPMGKNLWHISSEEMMQYAR  360

Query:  361 MILEKRHPDLENVRQPMFVYVLTMKEHGPYRTDTDNVFDLDAPDLNAKTVSALNDYIGRI  420
            MILEKRHPDLENVRQPMFVYVLTMKEHGPYRTDTDNVFDLDAPDLNAKTVSALNDYIGRI
Sbjct:  361 MILEKRHPDLENVRQPMFVYVLTMKEHGPYRTDTDNVFDLDAPDLNAKTVSALNDYIGRI  420

Query:  421 ADLDKAVESFDRYLHERGKPFVFGYFGDHQVPFEGVSVRKKWDYAQPDYVTQFAVRSNIA  480
            ADLDKAVESFDRYLHERGKPFVFGYFGDHQVPFEGVSVRKKWDYAQPDYVTQFAVRSNIA
Sbjct:  421 ADLDKAVESFDRYLHERGKPFVFGYFGDHQVPFEGVSVRKKWDYAQPDYVTQFAVRSNIA  480

Query:  481 GGFVQRQDFLDLAFAGGVLMEAAGLEAKDGFMRANMAMRGLCGGGLEDCPNRELVGNYRN  540
            GGFVQRQ+FLDLAFAGGVLMEAAGLEAKDGFMRANMAMRGLCGGGLEDCPN ELVGNYRN
Sbjct:  481 GGFVQRQNFLDLAFAGGVLMEAAGLEAKDGFMRANMAMRGLCGGGLEDCPNWELVGNYRN  540

Query:  541 YLYDVLKIAR  550
            YLYDVLKIAR
Sbjct:  541 YLYDVLKIAR  550
```

A homolog was found in serogroup A *N. meningitidis* but not in serogroup B, so NGS117 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 118

A DNA sequence was identified in *N. gonorrhoeae* <SEQ ID 235> which encodes amino acid sequence <SEQ ID 236; NGS118>. Analysis of this protein sequence reveals the following:

---

GvH Examining signal sequence (von Heijne)
Signal Score (−7.5): 0.59
Possible cleavage site: 19
>>> May be a lipoprotein
Amino Acid Composition of Predicted Mature Form:
calculated from 22
ALOM: Finding transmembrane regions (Klein et al.)
count: 0 value: 8.33 threshold: 0.0

---

PERIPHERAL    Likelihood = 8.33
modified ALOM score: −2.17
Rule: inner or outer membrane protein
Rule: inner or outer membrane protein

---

*** Reasoning Step: 2
Lipoprotein?

-continued

Inner membrane?
Final Results

| | |
|---|---|
| bacterial outer membrane --- Certainty = | 0.790(Affirmative) < succ> |
| bacterial inner membrane --- Certainty = | 0.700(Affirmative) < succ> |
| bacterial periplasmic space --- Certainty = | 0.000(Not Clear) < succ> |
| bacterial cytoplasm --- Certainty = | 0.000(Not Clear) < succ> |

The protein has no homology to sequences in the databases.

The protein was expressed in *E. coli* as a soluble 12.98 kDa His-fusion product and then purified.

Based on this analysis, it was predicted that this protein from *N. gonorrhoeae*, and its epitopes, could be useful antigens for vaccines or diagnostics.

Example 119

A DNA sequence was identified in *N. gonorrhoeae* <SEQ ID 237> which encodes amino acid sequence <SEQ ID 238; NGS119>. Analysis of this protein sequence reveals the following:

---

GvH Examining signal sequence (von Heijne)
Signal Score (−7.5): −4.75
Possible cleavage site: 47
>>> Seems to have no N-terminal signal seq.
Amino Acid Composition of Predicted Mature Form:

-continued calculated from 1
ALOM: Finding transmembrane regions (Klein et al.)
count: 0 value: 7.69 threshold: 0.0

| PERIPHERAL | Likelihood = 7.69 |
|---|---|
| modified ALOM score: −2.04 | |
| Rule: cytoplasmic protein | |

*** Reasoning Step: 2
Final Results

| bacterial cytoplasm --- Certainty = | 0.213(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^**gbp_2625122 gi|2625122|gb|AAB86635.1|\(AF031495) putative
hemoglobin receptor component precursor HpuA [Neisseria gonorrhoeae]
Length = 360

Score = 668 bits (1724), Expect = 0.0
Identities = 331/331 (100%), Positives = 331/331 (100%)

Query:   1 VSIPTATPLPAGEVTLSSDNGNIENINTAGAGSASDAPSRSRRSLDAAPQNTSGISIRQR    60
           VSIPTATPLPAGEVTLSSDNGNIENINTAGAGSASDAPSRSRRSLDAAPQNTSGISIRQR
Sbjct:  30 VSIPTATPLPAGEVTLSSDNGNIENINTAGAGSASDAPSRSRRSLDAAPQNTSGISIRQR    89

Query:  61 EVEKDYFGYKSKETSFIFKTPGGAQYALSSYADPITVSYSSPDFKIPDRHAGQRLADGSR   120
           EVEKDYFGYKSKETSFIFKTPGGAQYALSSYADPITVSYSSPDFKIPDRHAGQRLADGSR
Sbjct:  90 EVEKDYFGYKSKETSFIFKTPGGAQYALSSYADPITVSYSSPDFKIPDRHAGQRLADGSR   149

Query: 121 IFICCSDSGATSYAEITKQDYMKFGAWIGPNGEIDLFAGGFPVGKTPPPAFSYGSSTPET   180
           IFICCSDSGATSYAEITKQDYMKFGAWIGPNGEIDLFAGGFPVGKTPPPAFSYGSSTPET
Sbjct: 150 IFICCSDSGATSYAEITKQDYMKFGAWIGPNGEIDLFAGGFPVGKTPPPAFSYGSSTPET   209

Query: 181 ALSKGKITYQVWGIRVRNGQFVTSSYTPPKSGSYYGTLANTPVLSFITANFNSNTLAGKI   240
           ALSKGKITYQVWGIRVRNGQFVTSSYTPPKSGSYYGTLANTPVLSFITANFNSNTLAGKI
Sbjct: 210 ALSKGKITYQVWGIRVRNGQFVTSSYTPPKSGSYYGTLANTPVLSFITANFNSNTLAGKI   269

Query: 241 LGNSDYGPDVDIQNATITGPTFSGDATSGGKSGKLEGKFFGKFASTRSSEVSIGGKITFD   300
           LGNSDYGPDVDIQNATITGPTFSGDATSGGKSGKLEGKFFGKFASTRSSEVSIGGKITFD
Sbjct: 270 LGNSDYGPDVDIQNATITGPTFSGDATSGGKSGKLEGKFFGKFASTRSSEVSIGGKITFD   329

Query: 301 GDRSLDTVFGGVSYEKKLDDTSQDTNHLTKQ                               331
           GDRSLDTVFGGVSYEKKLDDTSQDTNHLTKQ
Sbjct: 330 GDRSLDTVFGGVSYEKKLDDTSQDTNHLTKQ                               360
```

Based on this analysis, it was predicted that this protein from *N. gonorrhoeae*, and its epitopes, could be useful antigens for vaccines or diagnostics.

Example 120

A DNA sequence was identified in *N. gonorrhoeae* <SEQ ID 239> which encodes amino acid sequence <SEQ ID 240; NGS120>. Analysis of this protein sequence reveals the following:

GvH Examining signal sequence (von Heijne)
Signal Score (−7.5): −7.24
Possible cleavage site: 38
>>> Seems to have no N-terminal signal seq.
Amino Acid Composition of Predicted Mature Form:
calculated from 1
ALOM: Finding transmembrane regions (Klein et al.)
count: 0 value: 6.42 threshold: 0.0

| PERIPHERAL | Likelihood = 6.42 |
|---|---|
| modified ALOM score: −1.78 | |
| Rule: cytoplasmic protein | |

*** Reasoning Step: 2
Final Results

| bacterial cytoplasm --- Certainty = | 0.280(Affirmative) < succ> |
|---|---|
| bacterial periplasmic space --- Certainty = | 0.000(Not Clear) < succ> |

-continued

| bacterial outer membrane --- Certainty = | 0.000(Not Clear) < succ> |
|---|---|
| bacterial inner membrane --- Certainty = | 0.000(Not Clear) < succ> |

The protein has homology to the following sequences in the databases:

```
^**gsa_AAR91313 N. gonorrhoeae glycosyltransferase LgtC
|WO9610086-A1|09-JUL-1996
Length = 306

Score = 535 bits (1379), Expect = e-151
Identities = 252/253 (99%), Positives = 252/253 (99%)

Query:   8 GGGNIRFIDVNPEDFAGFPLNIRHISITTYARLKLGEYIADCDKVLYLDTDVLVRDGLKP    67
           GGGNIRFIDVNPEDFAGFPLNIRHISITTYARLKLGEYIADCDKVLYLDTDVLVRDGLKP
Sbjct:  54 GGGNIRFIDVNPEDFAGFPLNIRHISITTYARLKLGEYIADCDKVLYLDTDVLVRDGLKP   113
```

-continued
```
Query:   68 LWDTDLGGNWVGACIDLFVERQEGYKQKIGMADGEYYFNAGVLLINLKKWRRHDIFKMSC 127
            LWDTDLGGNWVGACIDLFVERQEGYKQKIGMADGEYYFNAGVLLINLKKWRRHDIFKMSC
Sbjct:  114 LWDTDLGGNWVGACIDLFVERQEGYKQKIGMADGEYYFNAGVLLINLKKWRRHDIFKMSC 173

Query:  128 EWVEQYKDVMQYQDQDILNGLFKGGVCYANSRFNFMPTNYAFMANGFASRHTDPLYLDRT 187
            EWVEQYKDVMQYQDQDILNGLFKGGVCYANSRFNFMPTNYAFMANGFASRHTDPLYLDRT
Sbjct:  174 EWVEQYKDVMQYQDQDILNGLFKGGVCYANSRFNFMPTNYAFMANGFASRHTDPLYLDRT 233

Query:  188 NTAMPVAVSHYCGSAKPWHRDCTVWGAERFTELAGSLTTVPEEWRGKLAVPPTKRMLQRW 247
            NTAMPVAVSHYCGSAKPWHRDCTVWGAERFTELAGSLTTVPEEWRGKLAVPPTK MLQRW
Sbjct:  234 NTAMPVAVSHYCGSAKPWHRDCTVWGAERFTELAGSLTTVPEEWRGKLAVPPTKCMLQRW 293

Query:  248 RKKLSARFLRKIY                                                260
            RKKLSARFLRKIY
Sbjct:  294 RKKLSARFLRKIY                                                306
```

Based on this analysis, it was predicted that this protein from *N. gonorrhoeae*, and its epitopes, could be useful antigens for vaccines or diagnostics.

Example 121

A DNA sequence was identified in *N. gonorrhoeae* <SEQ ID 241> which encodes amino acid sequence <SEQ ID 242; NGS121>. Analysis of this protein sequence reveals the following:

GvH Examining signal sequence (von Heijne)
Signal Score (-7.5): -6.22
Possible cleavage site: 37
>>> Seems to have no N-terminal signal seq.
Amino Acid Composition of Predicted Mature Form: calculated from 1
ALOM: Finding transmembrane regions (Klein et al.)
count: 0 value: 3.23 threshold: 0.0

PERIPHERAL    Likelihood = 3.23
modified ALOM score: -1.15
Rule: cytoplasmic protein

*** Reasoning Step: 2
Final Results

| | |
|---|---|
| bacterial cytoplasm --- Certainty = | 0.402(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

Based on this analysis, it was predicted that this protein from *N. gonorrhoeae*, and its epitopes, could be useful antigens for vaccines or diagnostics.

Example 122

A DNA sequence was identified in *N. gonorrhoeae* <SEQ ID 243> which encodes amino acid sequence <SEQ ID 244; NGS122>. Analysis of this protein sequence reveals the following:

GvH Examining signal sequence (von Heijne)
Signal Score (-7.5): -2.55
Possible cleavage site: 23
>>> May be a lipoprotein
Amino Acid Composition of Predicted Mature Form: calculated from 15
ALOM: Finding transmembrane regions (Klein et al.)
count: 0 value: 11.46 threshold: 0.0

PERIPHERAL    Likelihood = 11.46
modified ALOM score: -2.79
Rule: inner or outer membrane protein

*** Reasoning Step: 2
Lipoprotein?
Inner membrane?
Final Results

| | |
|---|---|
| bacterial outer membrane --- Certainty = | 0.790(Affirmative) < succ> |
| bacterial inner membrane --- Certainty = | 0.700(Affirmative) < succ> |
| bacterial periplasmic space --- Certainty = | 0.000(Not Clear) < succ> |
| bacterial cytoplasm --- Certainty = | 0.000(Not Clear) < succ> |

```
^ **gbp_15281345 gi|15281345|dbj|BAB63435.1|\(AB058945) DNA adenine
methylase M.Ssu4109IB [Streptococcus suis]
Length = 271

Score = 269 bits (687), Expect = 4e-71
Identities = 127/211 (60%), Positives = 158/211 (74%), Gaps = 1/211 (0%)

Query:    1 MIFADPPYFLSNDGFSCQNGQMVSVNKGNWDKSKGMAADLEFYEEWLRLCYALLKPNGTI   60
            MIFADPPYFLSN G S   GQ+VSV+KG+WDK     EF  +W+RL    +LKPNGTI
Sbjct:   44 MIFADPPYFLSNGGISNSGGQVVSVDKGDWDKVNSLEEKHEFNRKWIRLAKNVLKPNGTI  103

Query:   61 WVCGTFHNIYLIGYLMQTVGYHILNNITWEKPNPPPNLSCRFFTHSTETILWAKK-NKKA  119
            W+ G+FHNIY +G  ++  G+ ILNNITW+K NP PNLSCR+FTHSTETILWA+K +KKA
Sbjct:  104 WISGSFHNIYSVGMALEQEGFKILNNITWQKTNPAPNLSCRYFTHSTETILWARKDDKKA  163

Query:  120 KHTFHYEMMKAQNNGKQMKCVWTFAPPNKTEKTFGKHPTQKPLPLLERCILSASNIGDLI  179
            +H  ++YE+MK  N+GKQMK VW     K+EK GKHPTQKP  LLER IL+++  GD I
Sbjct:  164 RHYYNYELMKELNDGKQMKDVWVGGLTKKSEKWAGKHPTQKPEYLLERIILASTREGDYI  223

Query:  180 FDPFMGSGTTGVAALKHGRRFCGCELEEDFL                              210
            DPF+GSGTTGV A + GR F G + E D+L
Sbjct:  224 LDPFVGSGTTGVVAKRLGRKFIGIDAERDYL                              254
```

The protein has no homology to sequences in the databases:

The protein was expressed in E. coli as an insoluble 14.85 kDa His-fusion product and then purified.

Based on this analysis, it was predicted that this protein from N. gonorrhoeae, and its epitopes, could be useful antigens for vaccines or diagnostics.

Example 123

A DNA sequence was identified in N. gonorrhoeae <SEQ ID 245> which encodes amino acid sequence <SEQ ID 246; NGS123>. Analysis of this protein sequence reveals the following:

GvH Examining signal sequence (von Heijne)
Signal Score (–7.5): –5.65
Possible cleavage site: 20
>>> Seems to have no N-terminal signal seq.
Amino Acid Composition of Predicted Mature Form: calculated from 1
ALOM: Finding transmembrane regions (Klein et al.)
count: 0 value: 4.24 threshold: 0.0

| PERIPHERAL | Likelihood = 4.24 |
|---|---|
| modified ALOM score: –1.35 | |
| Rule: cytoplasmic protein | |

*** Reasoning Step: 2
Final Results

| bacterial cytoplasm --- Certainty = | 0.404(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to the sequences in the databases.

Based on this analysis, it was predicted that this protein from N. gonorrhoeae, and its epitopes, could be useful antigens for vaccines or diagnostics.

Example 124

A DNA sequence was identified in N. gonorrhoeae <SEQ ID 247> which encodes amino acid sequence <SEQ ID 248; NGS124>. Analysis of this protein sequence reveals the following:

GvH Examining signal sequence (von Heijne)
Signal Score (–7.5): –5
Possible cleavage site: 18
>>> Seems to have no N-terminal signal seq.
Amino Acid Composition of Predicted Mature Form: calculated from 1
ALOM: Finding transmembrane regions (Klein et al.)
count: 1 value: –1.59 threshold: 0.0

| INTEGRAL | Likelihood = –1.59 | Transmembrane | 289-305 |
|---|---|---|---|
| | | | (289-305) |
| PERIPHERAL | Likelihood = 3.76 | | |
| | modified ALOM score: 0.82 | | |
| | Rule: cytoplasmic membrane protein | | |

*** Reasoning Step: 2
Final Results

| bacterial inner membrane --- Certainty = | 0.164(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_1617515 gi|1617515|gb|AAC82509.1|\(U65994) pilin gene inverting
  protein homolog PivNG [Neisseria gonorrhoeae]
  Length = 320

Score = 614 bits (1584), Expect = e-175
  Identities = 311/320 (97%), Positives = 316/320 (98%)

Query:    1 MRNTVGLDISKLTFDATAMVGKTEHSAKFDNDSKGLDQFSDRLKSLGYQNLHICMEATGS    60
              MRN VGLDISKLTF+A+AMVGKTEHSAKFDNDSKGLDQFSDRLKSLG QNLHICMEATG+
  Sbjct:    1 MRNAVGLDISKLTFNASAMVGKTEHSAKFDNDSKGLDQFSDRLKSLGCQNLHICMEATGN    60

Query:   61 YYEEVADYFAQYYSVYVVNPLKISKYAESRFKRTKTDKQDAKLIAQYCRSAQESELVKRQ   120
              YYEEVADYFAQYYSVYVVNPLKISKYAESRFKRTKTDKQDAKLIAQYCR A+ESELVKRQ
  Sbjct:   61 YYEEVADYFAQYYSVYVVNPLKISKYAESRFKRTKTDKQDAKLIAQYCRLAKESELVKRQ   120

Query:  121 KPTDEQYRLSRMTAAYAQIKSECAAMKNRHHAAKDEEAAKAYAEIIKAMNEQLEVLKEKI   180
              KPTDEQYRL RMTAAYAQIKSECAAMKNRHHAAKDEEAAKAYA+IIKAMNEQLEVLKEKI
  Sbjct:  121 KPTDEQYRLLRMTAAYAQIKSECAAMKNRHHAAKDEEAAKAYAQIIKAMNEQLEVLKEKI   180

Query:  181 KEQTEKPNCKEGVKRLETIPAIGRMTAAVLFHHLTSSKFETSNKFAAFAGLSPQQKESGT   240
              KEQTEKPNCKEGVKRLETIPAIGRMTAAVLFHHLTSSKFETSNKFAAFAGLSPQQKESGT
  Sbjct:  181 KEQTEKPNCKEGVKRLETIPAIGRMTAAVLFHHLTSSKFETSNKFAAFAGLSPQQKESGT   240

Query:  241 SVRGKGKLTKFGNRKLRAVLFMPAMVAYRIRAFPDFIKRLEEKKKPKKVIIAALMRKLAV   300
              SVRGKGKLTKFGNRKLRAVLFMPAMVAYRIRAFPDFIKRLEEKKKPKKVIIAALMRKLAV
  Sbjct:  241 SVRGKGKLTKFGNRKLRAVLFMPAMVAYRIRAFPDFIKRLEEKKKPKKVIIAALMRKLAV   300

Query:  301 IAYHVHKKGGDYDPSRYKSA                                          320
              IAYHVHKKGGDYDPSRYKSA
  Sbjct:  301 IAYHVHKKGGDYDPSRYKSA                                          320
```

Based on this analysis, it was predicted that this protein front *N. gonorrhoeae*, and its epitopes, could be useful antigens for vaccines or diagnostics.

Example 125

A DNA sequence was identified in *N. gonorrhoeae* <SEQ ID 249> which encodes amino acid sequence <SEQ ID 250; NGS127>. Analysis of this protein sequence reveals the following:

---

GvH Examining signal sequence (von Heijne)
Signal Score (−7.5): −5.8
Possible cleavage site: 52
>>> Seems to have no N-terminal signal seq.
Amino Acid Composition of Predicted Mature Form:

--- calculated from 1
ALOM: Finding transmembrane regions (Klein et al.)
count: 0 value: 1.70 threshold: 0.0

| | |
|---|---|
| PERIPHERAL | Likelihood = 1.70 |
| modified ALOM score: −0.84 | |
| Rule: cytoplasmic protein | |

*** Reasoning Step: 2
Final Results

| | |
|---|---|
| bacterial cytoplasm --- Certainty = | 0.383(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

---

The protein has homology to the following sequences in the databases:

```
^ **gbp_1076012 gi|1076012|pir||B55225 stress-sensitive restriction
system protein 2 - Corynebacterium glutamicum (ATCC 13032)
gb|AAC00044.1|(U13922) This orf may encode a typeI or typeIII restriction
endonuclease which is stress-sensitive and
ATP-dependent. It contains a typical ATP binding region
(Walker motif) [Corynebacterium glutamicum]
Length = 632

Score = 298 bits (764), Expect = 2e-79
Identities = 199/633 (31%), Positives = 321/633 (50%), Gaps = 32/633 (5%)

Query:    2 LRTYLNQLTP-PELADSVKNTVDGFMEKLSQTEPKIA-QNVLLLGNVQSGKTAQVLGVLS    59
            L Y+  L+    +L + V TVD F   +      I+ Q VLL G+VQSGKT+ +LG+++
Sbjct:    7 LNNYITSLSDNADLREKVTATVDAFRHTVMDDFDYISDQQVLLYGDVQSGKTSHMLGIIA   66

Query:   60 ALADDGDHKVFLYLTTDSVDLQDQTVKRAKANLKNFIVLSEADDRSFMEVMKAENP--IL  117
                 D   H + +LT+ +   L QT R         + +V           F  K+ P +
Sbjct:   67 DCLDSTFHTIVI-LTSPNTRLVQQTYDRVAQAFPDTLVCDRDGYNDFRANQKSLTPRKSI  125

Query:  118 VVIKKNARVLKRWRNLFASQSSLKGYPLVIVDDEADAASLNTNSDKPAKDASTINKLLND  177
            VV+ K    VL W +F     +L G+P++I+DDEADA SLNT ++    D STIN  L
Sbjct:  126 VVVGKIPAVLGNWLRVFNDSGALSGHPVLIIDDEADATSLNTKVNQ--SDVSTINHQLTS  183

Query:  178 IKNSCCQSLFIQLTATPQSLLLQHEESDWQPEFIHFFEAGEKYIGGNFVFSDPPS-YIVR  236
            I++      +++Q+T TPQ++LLQ ++S+W E +  F  GE YIGG   FS+  + Y+
Sbjct:  184 IRDLATGCIYLQVTGTPQAVLLQSDDSNWAAEHVLHFAPGESYIGGQLFFSELNNPYLRL  243

Query:  237 FIDSELDDMKDESGEIAEGAKQALLSFLTCAEFALCDKANCNFALHPSYKIQDHQAFSK   296
            F +++ D+      S        A+ ++L+T A F L ++  C   +HPS+    H+ F++
Sbjct:  244 FANTQFDEDSRFS--------DAIYTYLLTAALFKLRGESLCTMLIHPSHTASSHRDFAQ  295

Query:  297 KIQAFLNDLVQAVNNGEDLAGSFKESYLDLQKTKPDIHHFDEIYEKLTALLENKQISTLV  356
            + +  L    +         +   +F+ +Y  L +T ++    +I   L + ++ I    +
Sbjct:  296 EARLQLTFAFERFYEPM-IQHNFQRAYEQLAQTDSNLPPLRKILNILGGMEDDFSIH--I  352

Query:  357 VNSQTET-DFDLEKGFNIIGGNVIGRGLTIPKLQTVYYSRTAKKPNADTFWQHSRIFGY   415
            VNS   T + D    G+NII+GGN +GRGLT    LQTV+Y R  +K+P  ADT WQH+R+FGY
Sbjct:  353 VNSDNPTVEEDWADGYNIIVGGNSLGRGLTFNNLQTVFYVRESKRPQADTLWQHARMFGY  412

Query:  416 DRDKSLLRLYIPFDVYYFFVQLNQANNLIIGQAKNSG--GNIQVIYPKNINPTRKNVLKF  473
               R K  +R+++P  +    F ++  N I Q   +      +I+VI    + PTR NVL
Sbjct:  413 KRHKDTMRVFMPATIAQTFQEVYLGNEAIKNQLDHGTHINDIRVILGDGVAPTRANVLDK  472

Query:  474 DSINQIVGGVNYFPLHPNEDNLSEINKILPSILKDEIQSDLYQIDIEDLFLVLDKLGRYV  533
             + +  GGVNYF    P   N+    ++K L + L     + I +    +L+
Sbjct:  473 RKVGNLSGGVNYFAADPRIKNVEALDKKLLAYLDKHGEDS--TIGMRAIITILNAF-TVD  529

Query:  534 PDDWNKEKFIAGVEALKAQRPSFKTYVLIKTGRKLSRATGTMLSEDDRKLGEKYPNDLFL  593
            P+D +   F A +    +P          ++++T RK+++ TG +LS   D+ L          L
Sbjct:  530 PNDLDLATFKAALLDFERNQPHLTARMVLRTNRKVNQGTGALLSPTDQALSRAEVAHPLL  589

Query:  594 TLYQVVGNKDKG-------WQGKDFWLPNIKLP                             619
             LY++  G  D        W      W+PNIKLP
Sbjct:  590 ILYRIEGVNDAAAQRGEPTWSSDPIWVPNIKLP                             622
```

Example 126

A DNA sequence was identified in *N. gonorrhoeae* <SEQ ID 251> which encodes amino acid sequence <SEQ ID 252; NGS128>. Analysis of this protein sequence reveals the following:

GvH Examining signal sequence (von Heijne)
Signal Score (−7.5): −4.98
Possible cleavage site: 20
>>> Seems to have no N-terminal signal seq.
Amino Acid Composition of Predicted Mature Form: calculated from 1
ALOM: Finding transmembrane regions (Klein et al.)
count: 0 value: 7.37 threshold: 0.0

| PERIPHERAL | Likelihood = 7.37 |
|---|---| modified ALOM score: −1.97
Rule: cytoplasmic protein

*** Reasoning Step: 2
Final Results

| | |
|---|---|
| bacterial cytoplasm --- Certainty = | 0.225(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_11387195 gi|11387195|sp|Q50976|T2F7_NEIGO TYPE II RESTRICTION
ENZYME NGOFVII (ENDONUCLEASE NGOFVII) (R. NGOFVII)
(R. NGOVII)
pir||T10166 restriction endonuclease (EC 3.1.21.—) NgoVII - N. gonorrhoeae
gb|AAA86271.1|(U43736) R. NgoVII [Neisseria gonorrhoeae]
Length = 326

Score = 651 bits (1679), Expect = 0.0
Identities = 317/326 (97%), Positives = 320/326 (97%)

Query:   1 MNTVFSNIANAKITEKSLNAVWMDLFKSADEVLMATGYVSNDAVVELHKILELNDHIQKI    60
           MNTVFSNIANAKITEKSLNAVWMDLFKSADEVLMATGYVSNDAVVELHKILELNDHIQKI
Sbjct:   1 MNTVFSNIANAKITEKSLNAVWMDLFKSADEVLMATGYVSNDAVVELHKILELNDHIQKI    60

Query:  61 DLLVGMHYLEGFSHLQYDSLCKLNDFLRHEKRGAVYVSPFVKFHGKMYSFKNYQKINGLI   120
           DLLVGMHYLEGFSHLQYDSLCKLNDFLRHEKRGAVYVSPFVKFHGKMYSFKNYQKINGLI
Sbjct:  61 DLLVGMHYLEGFSHLQYDSLCKLNDFLRHEKRGAVYVSPFVKFHGKMYSFKNYQKINGLI   120

Query: 121 GSANLTCFWDSTERTYETMLHLNGKPAQILQADIQSTIHKLGKNIQEVERPSKFIEHNSH   180
           GSANLTCFWDSTERTYETMLHLNGKPAQILQADIQSTIHKLGKNIQEVERPSKFIEHNSH
Sbjct: 121 GSANLTCFWDSTERTYETMLHLNGKPAQILQADIQSTIHKLGKNIQEVERPSKFIEHNSH   180

Query: 181 LENCLGVQKIAPEQIRQLFAQTSEYHFSIPAKTEEKSNLNVFFGEGRRDKRGFVKPRPWY   240
           LENCLGVQKIAPEQIRQLFAQTSEYHFSIPAKTEEKSNLNVFFGEGRRDKRGFVKPRPWY
Sbjct: 181 LENCLGVQKIAPEQIRQLFAQTSEYHFSIPAKTEEKSNLNVFFGEGRRDKRGFVKPRPWY   240

Query: 241 EVELIVSKDITSQEGYPVLKSFTVITDDGWQFQCKTSGDYSKNFRSENDLKTLGKWIKGR   300
           EVELIVSKDITSQEGYPVLKSFTVITDDGWQFQCKTSGDYSK  + +LKTLGKWIKGR
Sbjct: 241 EVELIVSKDITSQEGYPVLKSFTVITDDGWQFQCKTSGDYSKTSTQKMNLKTLGKWIKGR   300

Query: 301 LESHGCLQNNEKITHETLREYGNDHF   326
           LESHGCLQNNEKITHETLREYGN+ F
Sbjct: 301 LESHGCLQNNEKITHETLREYGNESF   326
```

Based on this analysis, it was predicted that this protein from *N. gonorrhoeae*, and its epitopes, could be useful antigens for vaccines or diagnostics.

Example 127

A DNA sequence was identified in *N. gonorrhoeae* <SEQ ID 253> which encodes amino acid sequence <SEQ ID 254; NGS129>. Analysis of this protein sequence reveals the following:

GvH Examining signal sequence (von Heijne)
Signal Score (−7.5): −5.5
Possible cleavage site: 48
>>> Seems to have no N-terminal signal seq.
Amino Acid Composition of Predicted Mature Form: calculated from 1
ALOM: Finding transmembrane regions (Klein et al.)
count: 0 value: 10.03 threshold: 0.0

| PERIPHERAL | Likelihood = 10.03 |
|---|---| modified ALOM score: −2.51
Rule: cytoplasmic protein

*** Reasoning Step: 2
Final Results

| | |
|---|---|
| bacterial cytoplasm --- Certainty = | 0.545(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_15804186 gi|15804186|ref|NP_290225.1|\(NC_002655)
DNA-damage-inducible protein [Escherichia coli O157:H7
EDL933]
ref|NP_312547.1|(NC_002695) DNA-damage-inducible protein [Escherichia coli
O157:H7]
gb|AAG58789.1|AE005591_13 (AE005591) DNA-damage-inducible protein
[Escherichia coli O157:H7
EDL933]
dbj|BAB37943.1|(AP002566) DNA-damage-inducible protein [Escherichia coli
O157:H7]
Length = 278
Score = 340 bits (872), Expect = 2e-92
Identities = 161/266 (60%), Positives = 197/266 (73%)

Query:   1 MTTENNAFENAKHIDETGNEYWSARTLQQILEYSEWRNFQRAIDKAITACETSGNDKNHH  60
           M   +  FE  +H    G E+WSAR L  +L+Y +WRNFQ+  +A  ACE S    + H
Sbjct:   5 MNEHHQPFEEIRHYGTEGQEFWSARELAPLLDYRDWRNFQKVLARATQACEASNQAASDH  64

Query:  61 FVETNKMIALGKGGQREVADYRLSRYACYLIVQNGDPSKSVIAAGQTYFAVQARRQELQD 120
           FVET KM+ LG G QRE+ D  LSRYACYL+VQNGDP+K VIAAGQTYFA+Q RRQEL D
Sbjct:  65 FVETTKMVVLGSGAQRELEDVHLSRYACYLVVQNGDPAKPVIAAGQTYFAIQTRRQELAD 124

Query: 121 EAAFRSLGEDKQRLLLRRQLREHNTDLAAAAKDAGVEKPVEYAVFQNHGYRGLYGGLDKQ 180
           + AF+ L ED++RL LR +L+EHN   L  AA+ A V    ++A+FQNHGY+GLYGGLD++
Sbjct: 125 DEAFKQLREDEKRLFLRNELKEHNKQLVEAAQQAAVATATDFAIFQNHGYQGLYGGLDQK 184

Query: 181 GIHSRKGLKKSQRILDHMNASEPAANLFRATQTEEKLRRKNIQGKTQANRVHFEVGQKVR 240
            IH  KGLKKSQ+ILDHM ++E AANLFRATQTEEKL+R  +  K QAN  HF+VG KVR
Sbjct: 185 AIHQLKGLKKSQKILDHMGSTELAANLFRATQTEEKLKRDGVNSKQQANTTHFDVGSKVR 244

Query: 241 QTIEELGGIMPENQPVPEKSIKQLEN                                    266
           QTI+ELGG MPE P P+ SIKQLEN
Sbjct: 245 QTIQELGGTMPEELPTPQVSIRQLEN                                    270
```

Based on this analysis, it was predicted that this protein from *N. gonorrhoeae*, and its epitopes, could be useful antigens for vaccines or diagnostics.

Example 128

A DNA sequence was identified in *N. gonorrhoeae* <SEQ ID 255> which encodes amino acid sequence <SEQ ID 256; NGS130>. Analysis of this protein sequence reveals the following:

GvH Examining signal sequence (von Heijne)
Signal Score (−7.5): −3.68
Possible cleavage site: 14
>>> Seems to have an uncleavable N-term signal seq
Amino Acid Composition of Predicted Mature Form:
calculated from 1

-continued

| ALOM: Finding transmembrane regions (Klein et al.) count: 3 value: −3.45 threshold: 0.0 | | | |
|---|---|---|---|
| INTEGRAL | Likelihood = −3.45 | Transmembrane | 68-84 (68-92) |
| INTEGRAL | Likelihood = −1.59 | Transmembrane | 10-26 (10-26) |
| INTEGRAL | Likelihood = −1.44 | Transmembrane | 46-62 (45-62) |
| PERIPHERAL | Likelihood = 1.48 modified ALOM score: 1.19 Rule: cytoplasmic membrane protein | | |

*** Reasoning Step: 2
Final Results

| bacterial inner membrane --- Certainty = | 0.238(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_17988861 gi|17988861|ref|NP_541494.1|\(NC_003318) hypothetical
protein [Brucella melitensis]
gb|AAL53758.1|(AE009687) hypothetical protein [Brucella melitensis]
Length = 99

Score = 108 bits (270), Expect = 3e-23
Identities = 59/91 (64%), Positives = 69/91 (74%)

Query:  11 LLFSCMLAVTCPTRLIGFFALRNRTLSRRAQTVMEAAPGCVLISVIAPYFVSDKPHELIA  70
              L   M +VT TR+ G+  LRNRTLS RA VMEAAPGCVLISVIAP FVSDKP  LIA
Sbjct:   8 LTILAMASVTYLTRIGGYVLLRNRTLSNRAMAVMEAAPGCVLISVIAPDFVSDKPANLIA  67

Query:  71 IALTAFAACRFSMLFTVLIGVGSSGISGWLM                              101
           +A+T FAA RFSML TVLIG+G++ I  +L+
Sbjct:  68 LAVTVFAATRFSMLPTVLIGMGAASICRYLI                               98
```

Based on this analysis, it was predicted that this protein from *N. gonorrhoeae*, and its epitopes, could be useful antigens for vaccines or diagnostics.

Example 129

A DNA sequence was identified in *N. gonorrhoeae* <SEQ ID 257> which encodes amino acid sequence <SEQ ID 258; NGS131>. Analysis of this protein sequence reveals the following:

GvH Examining signal sequence (von Heijne)
Signal Score (-7.5): -1.65
Possible cleavage site: 43
>>> Seems to have no N-terminal signal seq.
Amino Acid Composition of Predicted Mature Form: calculated from 1
ALOM: Finding transmembrane regions (Klein et al.)
count: 0 value: 7.05 threshold: 0.0

| PERIPHERAL | Likelihood = 7.05 |
|---|---|
| modified ALOM score: -1.91 | |
| Rule: cytoplasmic protein | |

*** Reasoning Step: 2
Final Results

| bacterial cytoplasm --- Certainty = | 0.152(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_16760390 gi|16760390|ref|NP_456007.1|\(NC_003198) hypothetical
protein [Salmonella enterica subsp. enterica serovar
Typhi]
emb|CAD01841.1|(AL627270) hypothetical protein [Salmonella enterica subsp.
enterica serovar Typhi]
Length = 227

Score = 104 bits (259), Expect = 2e-21
Identities = 68/221 (30%), Positives = 115/221 (51%), Gaps = 11/221 (4%)

Query:    2 DKEKVLDKIKKCLALGRSVNEHEAAQALRQAQALMEKYKVNAEDIALSKVSEQKAD--RK   59
            D++K ++K+KK LAL  S N HEAA ALR+A+ LM+ + +   DIA+S + E    +
Sbjct:    3 DQDKHIEKLKKLLALAASGNPHEAALALRRARKLMDVHGITHSDIAMSDIDETISHYWPT  62

Query:   60 MAFKLAGWQWGVANMIADIFGCKSYQRGKT---MMFYGIGNRAETSAYAFDVVYRQISAD  116
             + +    + G+ N+I + FG  S    T   + FYG  RA  +AY ++V+ RQ+
Sbjct:   63 GSLRPPRYMLGLMNIIREAFGVNSIIHPGTYPGVGFYGNRERAALAAYTWEVLARQLKKA 122

Query:  117 RRKFLKT-CRAGKPSHRTYLADRFCGGWIASAWETVKKFEMSDEEKAIMDGYKKKEYPDM  175
            R++++      + K + RT   D+F  GW+ +    ++ F ++D+E+ +M  + + +YP
Sbjct:  123 RQQYISAQNKRIKTATRTSRGDQFAEGWVLAVISEIQSFALTDDERELMQQWLEHKYPQT 182

Query:  176 AEARTRDAKSSILQGSKMEYEALTRGMESGKQVKLHYAVNG                    216
               R R   S   G   Y    G   G+ V+LH V+G
Sbjct:  183 QTTRARKPGRS-RNGDASRY----AGFREGQNVRLHRPVSG                    218
```

Based on this analysis, it was predicted that this protein from *N. gonorrhoeae*, and its epitopes, could be useful antigens for vaccines or diagnostics.

Example 130

A DNA sequence was identified in *N. gonorrhoeae* <SEQ ID 259> which encodes amino acid sequence <SEQ ID 260; NGS132>. Analysis of this protein sequence reveals the following:

GvH Examining signal sequence (von Heijne)
Signal Score (-7.5): -4.06
Possible cleavage site: 30
>>> Seems to have no N-terminal signal seq.
Amino Acid Composition of Predicted Mature Form: calculated from 1
ALOM: Finding transmembrane regions (Klein et al.)
count: 0 value: 2.49 threshold: 0.0

| PERIPHERAL | Likelihood = 2.49 |
|---|---|
| modified ALOM score: -1.00 | |
| Rule: cytoplasmic protein | |

*** Reasoning Step: 2
Final Results

| bacterial cytoplasm --- Certainty = | 0.075(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to sequences in the databases.

Based on this analysis, it was predicted that this protein from *N. gonorrhoeae*, and its epitopes, could be useful antigens for vaccines or diagnostics.

Example 131

A DNA sequence was identified in *N. gonorrhoeae* <SEQ ID 261> which encodes amino acid sequence <SEQ ID 262; NGS133>. Analysis of this protein sequence reveals the following:

GvH Examining signal sequence (von Heijne)
Signal Score (-7.5): 1.64
Possible cleavage site: 53
>>> Seems to have no N-terminal signal seq.
Amino Acid Composition of Predicted Mature Form: calculated from 1
ALOM: Finding transmembrane regions (Klein et al.)
count: 0 value: 3.82 threshold: 0.0

|  |  |
|---|---|
| PERIPHERAL | Likelihood = 3.82 |
| modified ALOM score: −1.26 | |
| Rule: cytoplasmic protein | |

*** Reasoning Step: 2
Final Results

| | |
|---|---|
| bacterial cytoplasm --- Certainty = | 0.068(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to the following sequences in the databases:

Based on this analysis, it was predicted that this protein from *N. gonorrhoeae*, and its epitopes, could be useful antigens for vaccines or diagnostics.

Example 132

A DNA sequence was identified in *N. gonorrhoeae* <SEQ ID 263> which encodes amino acid sequence <SEQ ID 264; NGS135>. Analysis of this protein sequence reveals the following:

GvH Examining signal sequence (von Heijne)
Signal Score (−7.5): −4.67
Possible cleavage site: 39
>>> Seems to have no N-terminal signal seq.
Amino Acid Composition of Predicted Mature Form:
calculated from 1
ALOM: Finding transmembrane regions (Klein et al.)
count: 0 value: 5.52 threshold: 0.0

| | |
|---|---|
| PERIPHERAL | Likelihood = 5.52 |
| modified ALOM score: −1.60 | |
| Rule: cytoplasmic protein | |

*** Reasoning Step: 2
Final Results

| | |
|---|---|
| bacterial cytoplasm --- Certainty = | 0.475(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to sequences in the databases:

Based on this analysis, it was predicted that this protein from *N. gonorrhoeae*, and its epitopes, could be useful antigens for vaccines or diagnostics.

Example 133

A DNA sequence was identified in *N. gonorrhoeae* <SEQ ID 265> which encodes amino acid sequence <SEQ ID 266; NGS136>. Analysis of this protein sequence reveals the following:

GvH Examining signal sequence (von Heijne)
Signal Score (−7.5): −3.97
Possible cleavage site: 15
>>> Seems to have no N-terminal signal seq.
Amino Acid Composition of Predicted Mature Form:
calculated from 1
ALOM: Finding transmembrane regions (Klein et al.)
count: 0 value: 11.35 threshold: 0.0

| | |
|---|---|
| PERIPHERAL | Likelihood = 11.35 |
| modified ALOM score: −2.77 | |
| Rule: cytoplasmic protein | |

*** Reasoning Step: 2
Final Results

| | |
|---|---|
| bacterial cytoplasm --- Certainty = | 0.523(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to sequences in the databases:

Based on this analysis, it was predicted that this protein from *N. gonorrhoeae*, and its epitopes, could be useful antigens for vaccines or diagnostics.

Example 134

A DNA sequence was identified in *N. gonorrhoeae* <SEQ ID 267> which encodes amino acid sequence <SEQ ID 268; NGS137>. Analysis of this protein sequence reveals the following:

GvH Examining signal sequence (von Heijne)
Signal Score (−7.5): −8.52
Possible cleavage site: 51
>>> Seems to have no N-terminal signal seq.
Amino Acid Composition of Predicted Mature Form:
calculated from 1
ALOM: Finding transmembrane regions (Klein et al.)
count: 0 value: 2.81 threshold: 0.0

| | |
|---|---|
| PERIPHERAL | Likelihood = 2.81 |
| modified ALOM score: −1.06 | |
| Rule: cytoplasmic protein | |

*** Reasoning Step: 2
Final Results

| | |
|---|---|
| bacterial cytoplasm --- Certainty = | 0.374(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has no homology to sequences in the databases.

Based on this analysis, it was predicted that this protein from *N. gonorrhoeae*, and its epitopes, could be useful antigens for vaccines or diagnostics.

Example 135

A DNA sequence was identified in *N. gonorrhoeae* <SEQ ID 269> which encodes amino acid sequence <SEQ ID 270; NGS138>. Analysis of this protein sequence reveals the following:

GvH Examining signal sequence (von Heijne)
Signal Score (−7.5): −7
Possible cleavage site: 36
>>> Seems to have no N-terminal signal seq.
Amino Acid Composition of Predicted Mature Form:
calculated from 1
ALOM: Finding transmembrane regions (Klein et al.)
count: 0 value: 10.66 threshold: 0.0

| | |
|---|---|
| PERIPHERAL | Likelihood = 10.66 |
| modified ALOM score: −2.63 | |
| Rule: cytoplasmic protein | |

\*\*\* Reasoning Step: 2
Final Results

| | |
|---|---|
| bacterial cytoplasm --- Certainty = | 0.415(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_13559865 gi|13559865|ref|NP_112075.1|\(NC_002730) terminase
small subunit [Bacteriophage HK620]
gb|AAK28890.1|AF335538_42 (AF335538) terminase small subunit [Bacteriophage
HK620]
Length = 140

Score = 125 bits (313), Expect = 5e-28
Identities = 56/122 (45%), Positives = 85/122 (68%)

Query:   4 TKRKLGRPTDYTKDMADKICEKIANGRSLRSICAEDGVPPMKTIYRWLEANEEFRHQYAR    63
           T+ K GRP+DY ++AD IC +++G SL  +C   G+P   T++RWL  +E+FR +YA+
Sbjct:   3 TEPKAGRPSDYMPEVADDICSLLSSGESLLKVCKRPGMPDKSTVFRWLAKHEDFRDKYAK   62

Query:  64 AREKQADYFAEEIIEIADSAQAESAAVSKAKLQIDARKWAASKIAPKKYGDKSELDVKSGDG  125
           A E +AD   EEI EIAD+A  ++A V+KA+L++D RKWA +++ P+KYGDK  ++   DG
Sbjct:  63 ATEARADSIFEEIFEIADNAIPDAAEVAKARLRVDTRKWALARMNPRKYGDKVTNELVGKDG  124
```

Based on this analysis, it was predicted that this protein from *N. gonorrhoeae*, and its epitopes, could be useful antigens for vaccines or diagnostics.

Example 136

A DNA sequence was identified in *N. gonorrhoeae* <SEQ ID 271> which encodes amino acid sequence <SEQ ID 272; NGS139>. Analysis of this protein sequence reveals the following:

| |
|---|
| GvH Examining signal sequence (von Heijne) |
| Signal Score (−7.5): −1.49 |
| Possible cleavage site: 32 |
| >>> Seems to have no N-terminal signal seq. |
| Amino Acid Composition of Predicted Mature Form: calculated from 1 |
| ALOM: Finding transmembrane regions (Klein et al.) |
| count: 0 value: 8.65 threshold: 0.0 |

| | |
|---|---|
| PERIPHERAL | Likelihood = 8.65 |
| modified ALOM score: −2.23 | |
| Rule: cytoplasmic protein | |

\*\*\* Reasoning Step: 2
Final Results

| | |
|---|---|
| bacterial cytoplasm --- Certainty = | 0.301(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_16127009 gi|16127009|ref|NP_421573.1|\(NC_002696) hypothetical
protein [Caulobacter crescentus]
gb|AAK24741.1|(AE005943) hypothetical protein [Caulobacter crescentus]
Length = 184

Score = 59.7 bits (143), Expect = 4e-08
Identities = 50/164 (30%), Positives = 74/164 (44%), Gaps = 20/164 (12%)

Query:  30 ASGREFRTAYYTYPQWRFSLSFEVLRTKASVNELEKLAGFFNARKGSFESFLYEDPAD--   87
           ASG E RT+ ++  + R+ ++            ++E+ +L  FF AR+G   F + DPAD
Sbjct:   5 ASGHERRTSPWSQSRRRYLIA----TAPRPLDEIAELVAFFEARRGRLHGFRFRDPADFK   60
```

```
Query:   88 -------NAVTDQPVGNTVQGVAR-YQLVRSMGGFIEPVSAVKERP-----AVKVGGTAL   134
                    A  DQ +G T   GV + +QL ++ G    E V+     +P      V V G  L Sbjct:   61 SCAPSVQPAAGDQAIG-TGDGVRKAFQLRKTYGAGGEAVARTIAKPVAGTVTVAVAGVVL   119

Query:  135 AYGRDYTVTDKGVLVFNTPQPPGRPITWTGGFYFRVRFTSDTVD                   178
                A G          G++ NT P G  +T      F   VRF D +D Sbjct:  120 APGAFAVDVTTGLITLNTAPPAGAAVTAGFAFDTPVRFDLDRLD                   163
```

Based on this analysis, it was predicted that this protein from *N. gonorrhoeae*, and its epitopes, could be useful antigens for vaccines or diagnostics.

Example 137

A DNA sequence was identified in *N. gonorrhoeae* <SEQ ID 273> which encodes amino acid sequence <SEQ ID 274; NGS140>. Analysis of this protein sequence reveals the following:

| | |
|---|---|
| GvH Examining signal sequence (von Heijne) | |
| Signal Score (−7.5): −3.86 | |
| Possible cleavage site: 31 | |
| >>> Seems to have no N-terminal signal seq. | |
| Amino Acid Composition of Predicted Mature Form: | |
| calculated from 1 | |
| ALOM: Finding transmembrane regions (Klein et al.) | |
| count: 1 value: −4.94 threshold: 0.0 | |
| INTEGRAL Likelihood = −4.94 Transmembrane 34-50 (31-54) | |
| PERIPHERAL Likelihood = 8.01 | |
| modified ALOM score: 1.49 | |
| Rule: cytoplasmic membrane protein | |
| *** Reasoning Step: 2 Final Results | |
| bacterial inner membrane --- Certainty = | 0.297(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

Based on this analysis, it was predicted that this protein from *N. gonorrhoeae*, and its epitopes, could be useful antigens for vaccines or diagnostics.

Example 138

A DNA sequence was identified in *N. gonorrhoeae* <SEQ ID 275> which encodes amino acid sequence <SEQ ID 276; NGS141>. Analysis of this protein sequence reveals the following:

| | |
|---|---|
| GvH Examining signal sequence (von Heijne) | |
| Signal Score (−7.5): 5.35 | |
| Possible cleavage site: 28 | |
| >>> Seems to have a cleavable N-term signal seq. | |
| Amino Acid Composition of Predicted Mature Form: | |
| calculated from 29 | |
| ALOM: Finding transmembrane regions (Klein et al.) | |
| count: 0 value: 8.86 threshold: 0.0 | |
| PERIPHERAL Likelihood = 8.86 | |
| modified ALOM score: −2.27 | |
| Score for OM-PP discrimination: 1.53 | |
| Rule: outer membrane or periplasmic protein | |
| Score for OM-PP discrimination: 1.53 | |
| Rule: outer membrane or periplasmic protein | |
| *** Reasoning Step: 2 | |
| Outer membrane?Score: 0.152929 | |
| Outer membrane?Score: 0.152929 | |
| Final Results | |
| bacterial outer membrane --- Certainty = | 0.512(Affirmative) < succ> |
| bacterial periplasmic space --- Certainty = | 0.320(Affirmative) < succ> |
| bacterial inner membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_17987625 gi|17987625|ref|NP_540259.1|\(NC_003317) Hypothetical
  Phage Protein [Brucella melitensis]
gb|AAL52523.1|(AE009572) Hypothetical Phage Protein [Brucella melitensis]
Length = 144

Score = 72.4 bits (176), Expect = 5e-12
Identities = 43/119 (36%), Positives = 64/119 (53%), Gaps = 7/119 (5%)

Query:   10 RIVEEARSWLGTPYHHHAMVKGAGVDCAMLLVAVYGAV-GLLPEGFDPRPYPQDWHLHRD   68
             R++  EA  W+GTPY H A   G   DC  L+  ++ A+ G+ PE  +P   Y  DW
Sbjct:    6 RVLAEAHRWIGTPYRHGASTLGVSCDCLGLVRGIWRALYGVEPE--NPGVYAPDWAEVSQ   63

Query:   69 CERYLGFVTQFC--RETESPQAGDIAV--WRFGRSFSHGGILAGGGKVIHSYIGRGVVS   123
               +  L   ++     RE  +PQ GD+  V    W+ G  +   H GI+A   G+ IH+Y  G GV++
Sbjct:   64 GDPMLEAAVRYMVRREEHAPQPGDLLVFRWKPGFAAKHMGIMAREGRFIHAYQGHGVLA   122
```

```
^ **gbp_5915870 gi|5915870|sp|Q50940|CAH_NEIGO Carbonic anhydrase
precursor (Carbonate dehydratase)
emb|CAA72038.1|(Y11152) carbonic anhydrase [Neisseria gonorrhoeae]
Length = 252

Score = 523 bits (1347), Expect = e-147
Identities = 252/252 (100%), Positives = 252/252 (100%)

Query:    1 MPRFPRTLPRLTAVLLLACTAFSAAAHGNHTHWGYTGHDSPESWGNLSEEFRLCSTGKNQ   60
            MPRFPRTLPRLTAVLLLACTAFSAAAHGNHTHWGYTGHDSPESWGNLSEEFRLCSTGKNQ
Sbjct:    1 MPRFPRTLPRLTAVLLLACTAFSAAAHGNHTHWGYTGHDSPESWGNLSEEFRLCSTGKNQ   60

Query:   61 SPVNITETVSGKLPAIKVNYKPSMVDVENNGHTIQVNYPEGGNTLTVNGRTYTLKQFHFH  120
            SPVNITETVSGKLPAIKVNYKPSMVDVENNGHTIQVNYPEGGNTLTVNGRTYTLKQFHFH
Sbjct:   61 SPVNITETVSGKLPAIKVNYKPSMVDVENNGHTIQVNYPEGGNTLTVNGRTYTLKQFHFH  120

Query:  121 VPSENQIKGRTFPMEAHFVHLDENKQPLVLAVLYEAGKTNGRLSSIWNVMPMTAGKVKLN  180
            VPSENQIKGRTFPMEAHFVHLDENKQPLVLAVLYEAGKTNGRLSSIWNVMPMTAGKVKLN
Sbjct:  121 VPSENQIKGRTFPMEAHFVHLDENKQPLVLAVLYEAGKTNGRLSSIWNVMPMTAGKVKLN  180

Query:  181 QPFDASTLLPKRLKYYRFAGSLTTPPCTEGVSWLVLKTYDHIDQAQAEKFTRAVGSENNR  240
            QPFDASTLLPKRLKYYRFAGSLTTPPCTEGVSWLVLKTYDHIDQAQAEKFTRAVGSENNR
Sbjct:  181 QPFDASTLLPKRLKYYRFAGSLTTPPCTEGVSWLVLKTYDHIDQAQAEKFTRAVGSENNR  240

Query:  241 PVQPLNARVVIE                                                 252
            PVQPLNARVVIE
Sbjct:  241 PVQPLNARVVIE                                                 252
```

Based on this analysis, it was predicted that this protein from *N. gonorrhoeae*, and its epitopes, could be useful antigens for vaccines or diagnostics.

Example 139

A DNA sequence was identified in *N. gonorrhoeae* <SEQ ID 277> which encodes amino acid sequence <SEQ ID 278; NGS142>. Analysis of this protein sequence reveals the following:

GvH Examining signal sequence (von Heijne)
Signal Score (-7.5): -0.49
Possible cleavage site: 22
>>> Seems to have no N-terminal signal seq.
Amino Acid Composition of Predicted Mature Form:

-continued calculated from 1
ALOM: Finding transmembrane regions (Klein et al.)
count: 0 value: 1.22 threshold: 0.0

| PERIPHERAL | Likelihood = 1.22 |
|---|---|
| modified ALOM score: -0.74 | |
| Rule: cytoplasmic protein | |

*** Reasoning Step: 2
Final Results

| bacterial cytoplasm --- Certainty = | 0.145(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_15794480 gi|15794480|ref|NP_284302.1|\(NC_003116) hypothetical
protein [Neisseria meningitidis Z2491]
pir||F81851 hypothetical protein NMA1587 [imported] - Neisseria meningitidis
(group A strain Z2491)
emb|CAB84814.1|(AL162756) hypothetical protein [Neisseria meningitidis Z2491]
Length = 181

Score = 358 bits (919), Expect = 6e-98
Identities = 173/181 (95%), Positives = 178/181 (97%)

Query:    1 LKTDTARMNNLIPEHLAAYAHSDNLQIEGGHRCFSLSCQGRDTFHIRYYGEPFDGLITDT   60
            +KTDTA+MNNLIPEHLAAYAHSD+LQIEG HRCFSLSCQGRDTFHIRYYGEPFDGL+TDT
Sbjct:    1 MKTDTAKMNNLIPEHLAAYAHSDSLQIEGVHRCFSLSCQGRDTFHIRYYGEPFDGLMTDT   60

Query:   61 DKAPVKIVAVEAVSGDEIVLFDGAEHGYNAMFCDKYSQNQKQNRTLTDLDEYTYRVPIHL  120
            DKAPVKIVAVEAVSGDEIVLFDGAEHGYNAMFCDKYS NQKQNRTLTDLDEYTYRV IHL
Sbjct:   61 DKAPVKIVAVEAVSGDEIVLFDGAEHGYNAMFCDKYSPNQKQNRTLTDLDEYTYRVLIHL  120

Query:  121 YYNIDYEDEYEDFVNSEGQVPLIDGRIISFDSLKRNGFDAISIDLIDEKHSVRELLNEELS  181
            YYNIDYEDEYEDFVNSEGQVPLIDGRIISFDSLKRNGFDAIS+DLIDEKHSVRELLNEELS
Sbjct:  121 YYNIDYEDEYEDFVNSEGQVPLIDGRIISFDSLKRNGFDAISVDLIDEKHSVRELLNEELS  181
```

A homolog was found in serogroup A *N. meningitidis* but not in serogroup B, so NGS142 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 140

A DNA sequence was identified in *N. gonorrhoeae* <SEQ ID 279> which encodes amino acid sequence <SEQ ID 280; NGS143>. Analysis of this protein sequence reveals the following:

GvH Examining signal sequence (von Heijne)
Signal Score (−7.5): −2.51
Possible cleavage site: 57
>>> Seems to have no N-terminal signal seq.
Amino Acid Composition of Predicted Mature Form: calculated from 1

ALOM: Finding transmembrane regions (Klein et al.)
count: 4 value: −15.23 threshold: 0.0

| INTEGRAL | Likelihood = −15.23 | Transmembrane | 84-100 (79-107) |
|---|---|---|---|
| INTEGRAL | Likelihood = −8.12 | Transmembrane | 259-275 (250-281) |
| INTEGRAL | Likelihood = −4.14 | Transmembrane | 159-175 (153-176) |
| INTEGRAL | Likelihood = −3.88 | Transmembrane | 216-232 (216-235) |
| PERIPHERAL | Likelihood = 1.11 | | |
| | modified ALOM score: 3.55 | | |
| | Rule: cytoplasmic membrane protein | | |

*** Reasoning Step: 2
Final Results

| bacterial inner membrane --- Certainty = | 0.709(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_5764059 gi|5764059|emb|CAB53350.1|\(AJ010260) NosR protein
[Paracoccus denitrificans]
Length = 724

Score = 393 bits (1009), Expect = e-108
Identities = 191/379 (50%), Positives = 249/379 (65%), Gaps = 22/379 (5%)

Query:    1 LMVQRVLSVNDKAFVTADLDYELPQAYYVDDPKAPPVEISAPVEAVPAAASDTASDGIAE    60
            L+VQR +   +K F T DL Y+LPQ Y       AP      A PAA +D
Sbjct:  358 LLVQREVGPIEKVFHTFDLGYQLPQKYLRSIAPAPEA-------AAPAAQAD--------  402

Query:   61 DASAENGVSNQLWKQIWKAKQGQIVVVGIALTILLLVFLFQDWIVRYEKWYDRFRFAFLT  120
               E+    QLWK+IW  + +I +   L +L VF FQ +  RYE+ +  FR A+LT
Sbjct:  403 ----ESQAQAQLWKRIWLDSKPKIAGLAAMLLVLTGVFFFQSFTTRYERAFYVFRMAYLT  458

Query:  121 FTLFYIGWYAQAQLSVVNTLTLFSAILTEFHWEFFLMDPIVFILWLFTAATMLLWNRGTF  180
             TL ++GWYA AQLSVVN + LF +++   F W+ FL+DP+ FILW  AA +L W RG +
Sbjct:  459 VTLVFLGWYANAQLSVVNLMALFGSLVNGFSWQAFLLDPLTFILWFAVAAALLFWGRGAY  518

Query:  181 CGWLCPFGSLQELTNRIAKKLGVKQITVPHMLHTRLNVIKYLILFGFLAISLYDLGTAEK  240
            CGWLCPFG+LQELTN++A+KL + Q T+P  LH RL  +KY+I  G   +SL   + AE
Sbjct:  519 CGWLCPFGALQELTNQVARKLRIPQWTLPWGLHERLWPVKYMIFLGLFGVSLMSVEQAEH  578

Query:  241 FAEVEPFKTAIILKFMCDWWFVAFAVALLIAGLFIERFFCRYLCPLGAGIALPGRFRVFD  300
             AEVEPFKTAIILKF+  W FVA+A ALLIAGLF+ERF+CRYLCPLGA +A+P R R+FD
Sbjct:  579 LAEVEPFKTAIILKFIRAWPFVAYAAALLIAGLFVERFYCRYLCPLGAALAIPARMRMFD  638

Query:  301 WLRRYKMCGNPCQICTHECPVQAIAPEGDIHPNECIQCLHCQVMYHHDTRCPQVVAENKK  360
            WL+RY  CGNPCQ C  +CPVQ+I P G+I+PNECI CLHCQV+Y  +T CP V+   KK
Sbjct:  639 WLKRYHECGNPCQTCARQCPVQSIHPTGEINPNECINCLHCQVLYQSETTCPVVI---KK  695

Query:  361 KQKQAAAKSGELENVSKQP                                           379
            +++  A  +G +  + + P
Sbjct:  696 LKRREAVAAGSMPKLGQPP                                           714
```

Based on this analysis, it was predicted that this protein from *N. gonorrhoeae*, and its epitopes, could be useful antigens for vaccines or diagnostics.

Example 141

A DNA sequence was identified in *N. gonorrhoeae* <SEQ ID 281> which encodes amino acid sequence <SEQ ID 282; NGS144>. Analysis of this protein sequence reveals the following:

GvH Examining signal sequence (von Heijne)
Signal Score (-7.5): 1.23
Possible cleavage site: 21
>>> May be a lipoprotein
Amino Acid Composition of Predicted Mature Form: calculated from 20
ALOM: Finding transmembrane regions (Klein et al.)
count: 1 value: -0.37 threshold: 0.0

| | | | |
|---|---|---|---|
| INTEGRAL | Likelihood = -0.37 | Transmembrane | 90-106 (89-106) |
| PERIPHERAL | Likelihood =10.82 | | | modified ALOM score: 0.57
Rule: inner or outer membrane protein
Rule: inner or outer membrane protein
Rule: cytoplasmic membrane protein

*** Reasoning Step: 2
Lipoprotein?
Inner membrane?
Final Results bacterial outer membrane --- Certainty =   0.790(Affirmative) < succ>
bacterial inner membrane --- Certainty =   0.734(Affirmative) < succ>
bacterial periplasmic space --- Certainty =   0.000(Not Clear) < succ>
bacterial cytoplasm --- Certainty =   0.000(Not Clear) < succ>

The protein has homology no to sequences in the databases.

Based on this analysis, it was predicted that this protein from *N. gonorrhoeae*, and its epitopes, could be useful antigens for vaccines or diagnostics.

Example 142

A DNA sequence was identified in *N. gonorrhoeae* <SEQ ID 283> which encodes amino acid sequence <SEQ ID 284; NGS145>. Analysis of this protein sequence reveals the following:

GvH Examining signal sequence (von Heijne)
Signal Score (-7.5): 1.5
Possible cleavage site: 19
>>> Seems to have a cleavable N-term signal seq.
Amino Acid Composition of Predicted Mature Form: calculated from 20
ALOM: Finding transmembrane regions (Klein et al.)
count: 0 value: 8.70 threshold: 0.0

PERIPHERAL    Likelihood = 8.70
modified ALOM score: -2.24
Score for OM-PP discrimination: -9.24
Rule: outer membrane or periplasmic protein
Score for OM-PP discrimination: -9.24
Rule: outer membrane or periplasmic protein

*** Reasoning Step: 2
Periplasmic space?   Score: 0.924443
Periplasmic space?   Score: 0.924443
Final Results bacterial periplasmic space --- Certainty =   0.931(Affirmative) < succ>
bacterial outer membrane --- Certainty =   0.231(Affirmative) < succ>
bacterial inner membrane --- Certainty =   0.000(Not Clear) < succ>
bacterial cytoplasm --- Certainty =   0.000(Not Clear) < succ>

The protein has homology to the following sequences in the databases:

```
^ **gbp_5051426 gi|5051426|emb|CAB45007.1|\(AJ242839) OpcA protein
[Neisseria gonorrhoeae]
Length = 263

Score = 531 bits (1369), Expect = e-150
Identities = 262/263 (99%), Positives = 263/263 (99%)

Query:    1 MKKALLALTIAAISGTAMAQLPDFLGKGEYTVRTDISKQTLKNADLKEKHKVQKNIGFRA    60
            MKKALLALTIAAISGTAMAQLPDFLGKGEYTVRTDISKQTLKNADLKEKHKVQKNIGFRA
Sbjct:    1 MKKALLALTIAAISGTAMAQLPDFLGKGEYTVRTDISKQTLKNADLKEKHKVQKNIGFRA    60

Query:   61 DMPFDDIHHGMRFEVSHSRDKKDMYVVTESTTKPFGKDVEEKRTDVYAGYTYTQPISEAT   120
            DMPFDDIHHGMRFEVSHSRDKKDMYVVTESTTKPFGKDV+EKRTDVYAGYTYTQPISEAT
Sbjct:   61 DMPFDDIHHGMRFEVSHSRDKKDMYVVTESTTKPFGKDVKEKRTDVYAGYTYTQPISEAT   120

Query:  121 KLRAGLGLGYEKYKDAVANEKGTVSTEREAFYTKAHADLTSDLGGGWYLNPWAEVKVDLD   180
            KLRAGLGLGYEKYKDAVANEKGTVSTEREAFYTKAHADLTSDLGGGWYLNPWAEVKVDLD
Sbjct:  121 KLRAGLGLGYEKYKDAVANEKGTVSTEREAFYTKAHADLTSDLGGGWYLNPWAEVKVDLD   180

Query:  181 AKLKHNATVAGVSADINAKTRGWGVGVGANIGKQITDTVGIEAGPFYKHRHFKASGSFVL   240
            AKLKHNATVAGVSADINAKTRGWGVGVGANIGKQITDTVGIEAGPFYKHRHFKASGSFVL
Sbjct:  181 AKLKHNATVAGVSADINAKTRGWGVGVGANIGKQITDTVGIEAGPFYKHRHFKASGSFVL   240

Query:  241 DGGNIRVDPTKINEYGVRVGVKF                                       263
            DGGNIRVDPTKINEYGVRVGVKF
Sbjct:  241 DGGNIRVDPTKINEYGVRVGVKF                                       263
```

Based on this analysis, it was predicted that this protein from *N. gonorrhoeae*, and its epitopes, could be useful antigens for vaccines or diagnostics.

Example 143

A DNA sequence was identified in *N. gonorrhoeae* <SEQ ID 285> which encodes amino acid sequence <SEQ ID 286; NGS146>. Analysis of this protein sequence reveals the following:

GvH Examining signal sequence (von Heijne)

Signal Score (−7.5): 0.1

Possible cleavage site: 51

>>> Seems to have a cleavable N-term signal seq.

Amino Acid Composition of Predicted Mature Form:

calculated from 52

ALOM: Finding tranemembrane regions (Klein et al.)

count: 0 value: 3.50 threshold: 0.0

PERIPHERAL   Likelihood = 3.50
modified ALOM score: −1.20
Score for OM-PP discrimination: −15.70
Rule: outer membrane or periplasmic protein
Score for OM-PP discrimination: −15.70
Rule: outer membrane or periplasmic protein

*** Reasoning Step: 2
Periplasmic space?   Score: 1.56979
Periplasmic space?   Score: 1.56979
Final Results bacterial periplasmic space --- Certainty =   0.944(Affirmative) < succ>
bacterial outer membrane --- Certainty =      0.375(Affirmative) < succ>
bacterial inner membrane --- Certainty =      0.000(Not Clear) < succ>
bacterial cytoplasm --- Certainty =           0.000(Not Clear) < succ>

The protein has homology to the following sequences in the databases:

Based on this analysis, it was predicted that this protein from *N. gonorrhoeae*, and its epitopes, could be useful antigens for vaccines or diagnostics.

Example 144

A DNA sequence was identified in *N. gonorrhoeae* <SEQ ID 287> which encodes amino acid sequence <SEQ ID 288; NGS147>. Analysis of this protein sequence reveals the following:

GvH Examining signal sequence (von Heijne)

Signal Score (−7.5): −4.09

Possible cleavage site: 40

>>> Seems to have no N-terminal signal seq.

Amino Acid Composition of Predicted Mature Form:

calculated from 1

ALOM: Finding transmembrane regions (Klein et al.)

count: 1 value: −2.28 threshold: 0.0

INTEGRAL   Likelihood = −2.28   Transmembrane   36-52 (36-52)
PERIPHERAL   Likelihood = 5.20
modified ALOM score: 0.96
Rule: cytoplasmic membrane protein

*** Reasoning Step: 2
Final Results bacterial inner membrane --- Certainty =      0.191(Affirmative) < succ>
bacterial periplasmic space --- Certainty =   0.000(Not Clear) < succ>
bacterial outer membrane --- Certainty =      0.000(Not Clear) < succ>
bacterial cytoplasm --- Certainty =           0.000(Not Clear) < succ>

The protein has homology to the following sequences in the databases:

```
^ **gbp_5051429 gi|5051429|emb|CAB45013.1|\(AJ242839) hypothetical
protein [Neisseria gonorrhoeae]
Length = 109

Score = 216 bits (549), Expect = 2e-55
Identities = 109/109 (100%), Positives = 109/109 (100%)

Query:    1 MFKRPEEIIVLILAVLWIAGTYFLAALFGADAYTVLKITALTLLWSAASFLLWQKKPQPA   60
            MFKRPEEIIVLILAVLWIAGTYFLAALFGADAYTVLKITALTLLWSAASFLLWQKKPQPA Sbjct:    1 MFKRPEEIIVLILAVLWIAGTYFLAALFGADAYTVLKITALTLLWSAASFLLWQKKPQPA   60

Query:   61 YLAAAARLPDHLLVAVSESIGRTRFFTLACIMDVQNHLSPDSRNRRLSV            109
            YLAAAARLPDHLLVAVSESIGRTRFFTLACIMDVQNHLSPDSRNRRLSV Sbjct:   61 YLAAAARLPDHLLVAVSESIGRTRFFTLACIMDVQNHLSPDSRNRRLSV            109
```

```
^ **gbp_6606516 gi|6606516|gb|AAF19189.1|AF200716_2\(AF200716)
trafficking protein B [Neisseria gonorrhoeae]
Length = 139

Score = 274 bits (700), Expect = 7e-73
Identities = 139/139 (100%), Positives = 139/139 (100%)

Query:    2 MILLDTNVISEPLRPQPNERVVAWLDSLILEDVYLSAITVAELRLGVALLLNGKKKNVLH   61
            MILLDTNVISEPLRPQPNERVVAWLDSLILEDVYLSAITVAELRLGVALLLNGKKKNVLH
Sbjct:    1 MILLDTNVISEPLRPQPNERVVAWLDSLILEDVYLSAITVAELRLGVALLLNGKKKNVLH   60

Query:   62 ERLEQSILPLFAGRILPFDEPVAAIYAQIRSYAKTHGKEIAAADGYIAATAKQHSLTVAT  121
            ERLEQSILPLFAGRILPFDEPVAAIYAQIRSYAKTHGKEIAAADGYIAATAKQHSLTVAT
Sbjct:   61 ERLEQSILPLFAGRILPFDEPVAAIYAQIRSYAKTHGKEIAAADGYIAATAKQHSLTVAT  120

Query:  122 RDTGSFFAADVAVFNPWHD                                           140
            RDTGSFFAADVAVFNPWHD
Sbjct:  121 RDTGSFFAADVAVFNPWHD                                           139
```

Based on this analysis, it was predicted that this protein from *N. gonorrhoeae*, and its epitopes, could be useful antigens for vaccines or diagnostics.

Example 145

A DNA sequence was identified in *N. gonorrhoeae* <SEQ ID 289> which encodes amino acid sequence <SEQ ID 290; NGS148>. Analysis of this protein sequence reveals the following:

```
GvH Examining signal sequence (von Heijne)
Signal Score (-7.5): 0.86
Possible cleavage site: 47
>>> Seems to have a cleavable N-term signal seq.
Amino Acid Composition of Predicted Mature Form:
calculated from 48
ALOM: Finding transmembrane regions (Klein et al.)
count: 5 value: -15.44 threshold: 0.0
```

-continued

| INTEGRAL | Likelihood = −15.44 | Transmembrane | 157-173 (142-181) |
|---|---|---|---|
| INTEGRAL | Likelihood = −12.15 | Transmembrane | 62-78 (56-83) |
| INTEGRAL | Likelihood = −6.32 | Transmembrane | 194-210 (191-212) |
| INTEGRAL | Likelihood = −4.30 | Transmembrane | 87-103 (85-104) |
| INTEGRAL | Likelihood = −2.60 | Transmembrane | 121-137 (121-142) |
| PERIPHERAL | Likelihood = 2.92 | | |
| | modified ALOM score: 3.59 | | |
| | Rule: cytoplasmic membrane protein | | |

*** Reasoning Step: 2
Final Results

| bacterial inner membrane --- Certainty = | 0.718(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

```
^ **gbp_15777859 gi|15777859|gb|AAL05955.1|\(AY048756) putative cadmium
binding protein [Staphylococcus aureus]
Length = 209

Score = 354 bits (908), Expect = 1e-96
Identities = 177/208 (85%), Positives = 194/208 (93%)

Query:   14 MRCFMFSTVITAAVLYIATAVDLLVILLIFFARANTRKEYRDIYIGQYLGSVILILVSLF   73
            MRC M  TV+ AAVLYIATAVDLLVILLIFFARA TRKEYRDIY+GQYLGS+ILILVSLF
Sbjct:    1 MRCIMIQTVVAAAVLYIATAVDLLVILLIFFARAKTRKEYRDIYVGQYLGSIILILVSLF   60

Query:   74 LAFVLNYVPEKWVLGLLGLIPIYLGIKVAIYDDCEGEKRAKKELDEKGLSKLVGIVALVT  133
            LAFVLNYVPEKW+LGLLGLIPIYLGIKVAIYDDCEGEKRAKKEL+EKGLSKLVG VA+VT
Sbjct:   61 LAFVLNYVPEKWILGLLGLIPIYLGIKVAIYDDCEGEKRAKKELNEKGLSKLVGTVAIVT  120

Query:  134 VASCGADNIGLFVPYFVTLDLVDLLVTLLVFLILIFVLVYTAQRLANISGVGEIVEKFSR  193
            +ASCGADNIGLFVPYFVTL + +LL+TL VFLILIF LV+TAQ+LANI G+GEIVEKFSR
Sbjct:  121 IASCGADNIGLFVPYFVTLSVTNLLLTLFVFLILIFFLVFTAQKLANIPGIGEIVEKFSR  180

Query:  194 WIMAVIYIGLGLFIIIENNTIRTIISII                                  221
            WIMA+IYI LGLFIIIEN+TI+TI+  I
Sbjct:  181 WIMAIIYIALGLFIIIENDTIQTILGFI                                  208
```

Based on this analysis, it was predicted that this protein from *N. gonorrhoeae*, and its epitopes, could be useful antigens for vaccines or diagnostics.

Example 146

A DNA sequence was identified in *N. gonorrhoeae* <SEQ ID 291> which encodes amino acid sequence <SEQ ID 292; NGS149>. Analysis of this protein sequence reveals the following:

GvH Examining signal sequence (von Heijne)
Signal Score (−7.5): −0.63
Possible cleavage site: 43
>>> Seems to have no N-terminal signal seq.
Amino Acid Composition of Predicted Mature Form:
calculated from 1
ALOM: Finding transmembrane regions (Klein et al.)
count: 0 value: 2.12 threshold: 0.0

PERIPHERAL   Likelihood = 2.12
modified ALOM score: −0.92
Rule: cytoplasmic protein

*** Reasoning Step: 2
Final Results bacterial cytoplasm --- Certainty =         0.122(Affirmative) < succ>
bacterial periplasmic space --- Certainty = 0.000(Not Clear) < succ>
bacterial outer membrane --- Certainty =    0.000(Not Clear) < succ>
bacterial inner membrane --- Certainty =    0.000(Not Clear) < succ>

The protein has homology to the following sequences in the databases:

```
^ **gbp_15675455 gi|15675455|ref|NP_269629.1|\(NC_002737) conserved
hypothetical protein [Streptococcus pyogenes]
[Streptococcus pyogenes M1 GAS]
gb|AAK34350.1|(AE006588) conserved hypothetical protein [Streptococcus pyogenes
M1 GAS]
Length = 224

Score = 106 bits (264), Expect = 3e-22
Identities = 63/151 (41%), Positives = 85/151 (55%), Gaps = 12/151 (7%)

Query:  20 LSALQHYAFCPRQCALIHNEQAWAENYLTAQGKALHERVDSDE-PETCKGVRFEWTVHVL    78
           LS +QH+ FC RQ ALIH EQ W +N  TA G+ LH + D+    E  K +      + +
Sbjct:  11 LSGIQHFQFCKRQWALIHIEQQWLDNEATAHGQVLHTKADNPYIKEKRKELLVSRAMPIS   70

Query:  79 ADKLGISGILDLVE---------VDTKTGRLKP--VEYKRGKPKPDPGDEIQLCAQGLCL  127
           + +LG+SGI+D+VE          +  K G+  P   VEYKRGKPK  D  D +QL AQ +CL
Sbjct:  71 SAELGLSGIMDVVEFYKDDQGVSLRGKRGKWLPKVVEYKRGKPKKDTRDIVQLVAQTMCL  130

Query: 128 EEMTGQTVSEGALWYMQTRHRVPVVFSDGLR                              158
           EE     ++EG L+Y     RV V  +  LR
Sbjct: 131 EETLDCDINEGCLYYHSVNQRVIVPMTSALR                              161
```

Based on this analysis, it was predicted that this protein from *N. gonorrhoeae*, and its epitopes, could be useful antigens for vaccines or diagnostics.

Example 147

A DNA sequence was identified in *N. gonorrhoeae* <SEQ ID 293> which encodes amino acid sequence <SEQ ID 294; NGS150>. Analysis of this protein sequence reveals the following:

GvH Examining signal sequence (von Heijne)
Signal Score (−7.5): −0.71
Possible cleavage site: 19
>>> Seems to have no N-terminal signal seq.
Amino Acid Composition of Predicted Mature Form:
calculated from 1
ALOM: Finding transmembrane regions (Klein et al.)
count: 1 value: −0.85 threshold: 0.0

INTEGRAL     Likelihood = −0.85    Transmembrane   79-95 (79-96)
PERIPHERAL   Likelihood = 6.52
             modified ALOM score: 0.67
             Rule: cytoplasmic membrane protein

*** Reasoning Step: 2
Final Results bacterial inner membrane --- Certainty =    0.134(Affirmative) < succ>
bacterial periplasmic space --- Certainty = 0.000(Not Clear) < succ>
bacterial outer membrane --- Certainty =    0.000(Not Clear) < succ>
bacterial cytoplasm --- Certainty =         0.000(Not Clear) < succ>

The protein has no homology to sequences in the databases.

Based on this analysis, it was predicted that this protein from *N. gonorrhoeae*, and its epitopes, could be useful antigens for vaccines or diagnostics.

Example 148

A DNA sequence was identified in *N. gonorrhoeae* <SEQ ID 295> which encodes amino acid sequence <SEQ ID 296; NGS151>. Analysis of this protein sequence reveals the following:

GvH Examining signal sequence (von Heijne)
Signal Score (−7.5): 3.47
Possible cleavage site: 23
>>> Seems to have a cleavable N-term signal seq.
Amino Acid Composition of Predicted Mature Form:
calculated from 24
ALOM: Finding transmembrane regions (Klein et al.)
count: 0 value: 14.32 threshold: 0.0

PERIPHERAL   Likelihood = 14.32
modified ALOM score: −3.36
Score for OM-PP discrimination: −32.29
Rule: outer membrane or periplasmic protein -continued Score for OM-PP discrimination: −32.29
Rule: outer membrane or periplasmic protein \*\*\* Reasoning Step: 2
Periplasmic space? Score: 3.22889
Periplasmic space? Score: 3.22889
Final Results bacterial periplasmic space --- Certainty = 0.933(Affirmative) < succ>
bacterial outer membrane --- Certainty = 0.253(Affirmative) < succ>
bacterial inner membrane --- Certainty = 0.000(Not Clear) < succ>
bacterial cytoplasm --- Certainty = 0.000(Not Clear) < succ>

The protein has homology to the following sequences in the databases:

```
^ **gsa_AAY75310 Neisseria gonorrheae ORF 649 protein sequence SEQ ID
NO: 2094|WO9957280-A2|21-MAR-2000
Length = 103

Score = 35.4 bits (80), Expect = 0.32
Identities = 25/85 (29%), Positives = 38/85 (44%), Gaps = 5/85 (5%)

Query:   7 ILTGILLATALPASAHGMHKSKPLAMDELPPICQQYFKRAETCYNKAGNKADFARN-NTK  65
           + T    T+ PA  H  SK     L P C++Y +R    Y  GN +   N    +
Sbjct:  13 VSTTAAAGTSEPAHRHTKHISKA-NKQMLHPECRKYLERRAAWYRSQGNVQELRENKKAR  71

Query:  66 FLFQALPAADLGQRKQMCQIAMDSF  90
           F+ LP A   ++K  C+ A ++F
Sbjct:  72 KAFRTLPYA---EQKIQCRAAYEAF  93
```

The protein was expressed in *E. coli* as a soluble 9.35 kDa His-fusion product and then purified.

Based on this analysis, it was predicted that this protein from *N. gonorrhoeae*, and its epitopes, could be useful antigens for vaccines or diagnostics.

Example 149

A DNA sequence was identified in *N. gonorrhoeae* <SEQ ID 297> which encodes amino acid sequence <SEQ ID 298; NGS152>. Analysis of this protein sequence reveals the following:

GvH Examining signal sequence (von Heijne)
Signal Score (−7.5): −5.46
Possible cleavage site: 18
>>> Seems to have an uncleavable N-term signal seq
Amino Acid Composition of Predicted Mature Form:
calculated from 1
ALOM: Finding transmembrane regions (Klein et al.)
count: 1 value: −3.19 threshold: 0.0

INTEGRAL     Likelihood = −3.19   Transmembrane   368-384
                                                  (367-384)
PERIPHERAL   Likelihood = 0.53
             modified ALOM score: 1.14
             Rule: cytoplasmic membrane protein \*\*\* Reasoning Step: 2
Final Results bacterial inner membrane --- Certainty = 0.227(Affirmative) < succ>
bacterial periplasmic space --- Certainty = 0.000(Not Clear) < succ>
bacterial outer membrane --- Certainty = 0.000(Not Clear) < succ>
bacterial cytoplasm --- Certainty = 0.000(Not Clear) < succ>

The protein has homology to the following sequences in the databases:

```
^ **gsa_AAY81609 Streptococcus pneumoniae type 4 protein sequence
#109|WO200006737-A2|24-MAY-2000
Length = 1237

Score = 48.1 bits (113), Expect = 4e-04
Identities = 80/312 (25%), Positives = 142/312 (44%), Gaps = 59/312 (18%)

Query:   57 RRQARIRVGNLITDSLEHIRVKALLPLPL----KLPVKRI---NLPRNLPALPVRLRKTI   109
            RRQ R +   ++  L+H RV L   P+    ++PV+++     +PR   A    RL++ +
Sbjct:  941 RRQVR-QPQQVLVHQLQHQRVHRLRRQPVHQSQQVPVRQLPHQQVPRLQQAPVRRLQQVL   999

Query:  110 SPRQIGDALPILKLQRI--RLTLHLKPLPLHPQLGLLHIKRPVRIPLRHLAVQRTLVRLN   167
            +P+      P+ + Q++  RL  H +  PL  L     +P R  + L   QR  VRLN
Sbjct: 1000 APQP--QPQPVRQPQQVSQRLNRHQRVRPLQQVLA----PQPQRQQVHRL--QRQRVRLN  1051

Query:  168 RRIKPPLLQHRLTVRRILRRSRRQPFPAQFPDRRIFIMFRHNPARRIKLCRRQLTVQGPR   227
            R  +    LQ L             A P R+   +H     +R++ ++  L  Q   R
Sbjct: 1052 RHQRVRPLQQVL---------------APQPQRQQVHRLQH---QRVRPLQQVLAPQPQR  1093

Query:  228 IRRSRPLIKLPLLRRQRIRPGRHQRTLRVKITHRLAAPIHIPVKSQRRRPSARIRRARI   287
            + R      L+RQR+R  +HQR + +  H+L    +H PV+ Q + R ++++ +
Sbjct: 1094 QQVHR------LQRQRVRLSQHQRVRQPQQAHQL-LNLHQPVR-QPQHRQAPQLQQVPV  1144
```

```
                         -continued
Query:    288 APREIRPGPRIGGKRLIAARKP-QTGIRTPFESTRPAQPPRPI-LNIVTAQIHHIPITRR    345
              + R    R+    + +   R+P Q   +R P     R   + P+P+ LN       H P+ R+
Sbjct:   1145 RQPQRRQVRRL---QQVPVRQPQQVPVRQP--QRRQVRRPQPVHLN------RHQPV-RQ    1192

Query:    346 PGLIIRNGTPHR                                                     357
              P   ++ +   H+
Sbjct:   1193 PQQVLVHQLQHQ                                                     1204
```

Based on this analysis, it was predicted that this protein from *N. gonorrhoeae*, and its epitopes, could be useful antigens for vaccines or diagnostics.

Example 150

A DNA sequence was identified in *N. gonorrhoeae* <SEQ ID 299> which encodes amino acid sequence <SEQ ID 300; NGS153>. Analysis of this protein sequence reveals the following:

GvH Examining signal sequence (von Heijne)
Signal Score (−7.5): −5.48
Possible cleavage site: 13
>>> Seems to have no N-terminal signal seq.
Amino Acid Composition of Predicted Mature Form:
calculated from 1
ALOM: Finding transmembrane regions (Klein et al.)
count: 0 value: 6.31 threshold: 0.0

| PERIPHERAL | Likelihood = 6.31 |
|---|---|
| modified ALOM score: −1.76 | |
| Rule: cytoplasmic protein | |

*** Reasoning Step: 2
Final Results

| | |
|---|---|
| bacterial cytoplasm --- Certainty = | 0.150(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

Based on this analysis, it was predicted that this protein from *N. gonorrhoeae*, and its epitopes, could be useful antigens for vaccines or diagnostics.

Example 151

A DNA sequence was identified in *N. gonorrhoeae* <SEQ ID 301> which encodes amino acid sequence <SEQ ID 302; NGS154>. Analysis of this protein sequence reveals the following:

GvH Examining signal sequence (von Heijne)
Signal Score (−7.5): −6.98
Possible cleavage site: 28
>>> Seems to have no N-terminal signal seq.
Amino Acid Composition of Predicted Mature Form:
calculated from 1
ALOM: Finding transmembrane regions (Klein et al.)
count: 0 value: 8.12 threshold: 0.0

| PERIPHERAL | Likelihood = 8.12 |
|---|---|
| modified ALOM score: −2.12 | |
| Rule: cytoplasmic protein | |

*** Reasoning Step: 2
Final Results

| | |
|---|---|
| bacterial cytoplasm --- Certainty = | 0.423(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_15832758 gi|15832758|ref|NP_311531.1|\(NC_002695) hypothetical
protein [Escherichia coli O157:H7]
dbj|BAB36927.1|(AP002562) hypothetical protein [Escherichia coli O157:H7]
Length = 188

Score = 73.9 bits (180), Expect = 3e-12
Identities = 54/169 (31%), Positives = 79/169 (45%), Gaps = 15/169 (8%)

Query:    12 LTQEVLKELLRYDDNTGKLYWAERPRKYFNSGLHYKSWNTGFSGKEVFLYKGRLGYLKLK    71
             LT + + ELL +D +TG   W   +        +     GY       GY +
Sbjct:    16 LTVKRIFELLSFDKSTGVFRWKVPTQ----GRIALNSVAGAFDSN---------GYSMIM  62

Query:    72 IFKKQYNAHRLIWLFVYGKH-ASSIGHINRDKTDNRISNLRDVTHAENMKNRGKFKNNTS   130
             I   ++Y  H L++   + + A  I  H+N  +TDNR  NLR+     EN +N    KN+  S
Sbjct:    63 IDGRRYKTHVLVFYITHNRWPAGQIDHVNGIRTDNRPENLRECLPIENSRNIRIRKNSKS   122

Query:   131 GHTGVYFHKPSKKWQARIMVNRKNKILGLFEHIEDAA-KAREAASKDFG             178
             G   GV +HK   KKW    R+   + K+K  G F+  +E A    A EA   K  +G
Sbjct:   123 GCRGVTWHKRQKKWNVRLGFHGKSKHFGCFDDLELAVLVAEEARDKYYG             171
```

```
^ **gbp_15830449 gi|15830449|ref|NP_309222.1|\(NC_002695) hypothetical
protein [Escherichia coli O157:H7]
dbj|BAA94132.1|(AP000422) hypothetical protein [Escherichia coli O157:H7]
dbj|BAB34618.1|(AP002554) hypothetical protein [Escherichia coli O157:H7]
Length = 148

Score = 42.7 bits (99), Expect = 0.003
Identities = 27/99 (27%), Positives = 49/99 (49%), Gaps = 10/99 (10%)

Query:  37 IRPRKSKRSVEQNRRLWFLYREISEKVFIDGRRFSQDVWHE-----FLKRKFIGCIEMPN     91
            +  ++ KRS  QN R+W +  ++S +V   G+R + + W +       +LK K +     +P
Sbjct:  33 VHVKEPKRSKAQNDRMWPMLNDVSRQVLWHGQRLAPEDWKDLFTALWLKTKKLEQRSVPG    92

Query:  92 GQ----LMGISTTKLSVREMSEYQEKIISWASMEHGVLW                        126
            ++G+  T+K+      M+E   E I+ W    E   V W
Sbjct:  93 IDGGVVMLGVRTSKMRKASMTELIE-IMFWFGSERNVRW                        130
```

Based on this analysis, it was predicted that this protein from *N. gonorrhoeae*, and its epitopes, could be useful antigens for vaccines or diagnostics.

Example 152

A DNA sequence was identified in *N. gonorrhoeae* <SEQ ID 303> which encodes amino acid sequence <SEQ ID 304; NGS155>. Analysis of this protein sequence reveals the following:

| | |
|---|---|
| GvH Examining signal sequence (von Heijne) | |
| Signal Score (−7.5): −4 | |
| Possible cleavage site: 27 | |
| >>> Seems to have an uncleavable N-term signal seq | |
| Amino Acid Composition of Predicted Mature Form: | |
| calculated from 1 | |
| ALOM: Finding transmembrane regions (Klein et al.) | |
| count: 0 value: 4.98 threshold: 0.0 | |
| PERIPHERAL   Likelihood = 4.98 | |
| modified ALOM score: −1.50 | |

*** Reasoning Step: 2
Final Results

| | |
|---|---|
| bacterial inner membrane --- Certainty = | 0.046(Affirmative) < succ> |
| bacterial periplasmic space --- Certainty = | 0.000(Not Clear) < succ> |
| bacterial outer membrane --- Certainty = | 0.000(Not Clear) < succ> |
| bacterial cytoplasm --- Certainty = | 0.000(Not Clear) < succ> |

The protein has homology to the following sequences in the databases:

Based on this analysis, it was predicted that this protein from *N. gonorrhoeae*, and its epitopes, could be useful antigens for vaccines or diagnostics.

Example 153

A DNA sequence was identified in *N. gonorrhoeae* <SEQ ID 305> which encodes amino acid sequence <SEQ ID 306; NGS156>. Analysis of this protein sequence reveals the following:

| | |
|---|---|
| GvH Examining signal sequence (von Heijne) | |
| Signal Score (−7.5): −2.61 | |
| Possible cleavage site: 49 | |
| >>> Seems to have no N-terminal signal seq. | |
| Amino Acid Composition of Predicted Mature Form: | |
| calculated from 1 | |
| ALOM: Finding transmembrane regions (Klein et al.) | |
| count: 0 value: 7.96 threshold: 0.0 | |
| PERIPHERAL   Likelihood = 7.96 | |
| modified ALOM score: −2.09 | |
| Rule: cytoplasmic protein | |

*** Reasoning Step: 2
Final Results

| | |
|---|---|
| bacterial cytoplasm --- Certainty = | 0.307(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_15801502 gi|15801502|ref|NP_287519.1|\(NC_002655) putative
endonuclease of prophage CP-9330 [Escherichia coli
O157:H7 EDL933]
ref|NP_309804.1|(NC_002695) endonuclease [Escherichia coli O157:H7]
gb|AAG56131.1|AE005344_7 (AE005344) putative endonuclease of prophage CP-9330
[Escherichia coli O157:H7 EDL933]
dbj|BAB35200.1|(AP002556) endonuclease [Escherichia coli O157:H7]
Length = 119

Score = 47.4 bits (111), Expect = 2e-04
Identities = 38/122 (31%), Positives = 54/122 (44%), Gaps = 8/122 (6%)

Query:  71 LILPYPVSANRYWRIWRNRAVRSAEAAAYKETVRRIA-QGAGAMPSEGAVAVYVRLIPKA    129
            L+LPYP + N YWR +   S     Y+ V  I  Q    +  G +A+  +     P
Sbjct:   5 LVLPYPPTVNTYWRRRGSTYFVSKAGERYRRAVVLIVRQQRLKLSLSGRLAIKIIAEP--     62

Query: 130 NKDGGANKTVIDLDNALKVTLDALQGVAYHNDRQVRRIAAEYGGEPVTGGGLAVEVGELE    189
              +K    DLDN LK   LDAL      D +            G+PV+GG L V++ ++E
Sbjct:  63 -----PDKRRRDLDNILKAPLDALTHAGVLMDDEQFDEINIVRGQPVSGGRLGVKIYKIE    117

Query: 190 ME                                                             191
            E
Sbjct: 118 SE                                                             119
```

```
^ **gsa_AAG90098 C glutamicum protein fragment SEQ ID NO: 3852
|EP1108790-A2|26-SEP-2001
Length = 148

Score = 102 bits (253), Expect = 7e-21
Identities = 60/147 (40%), Positives = 88/147 (59%), Gaps = 18/147 (12%)

Query:    3 NAYDVADFFLSPFEEEDGEQISNLKLQKLLYYAQGYALAILNRPLFAENIEHWQHGPVVP      62
            +A ++A++F++   +E  D E +S LKLQKLLYY+QG  +A    R LF++  I  WQHGPV P
Sbjct:    5 SAREIAEWFVAWGDELDAE-VSPLKLQKLLYYSQGEHIAATGRKLFSDKILAWQHGPVTP     63

Query:   63 CIYRTYKKYGGSPLPAAHIEPDKYADEEL---------VVLNRVRKEQGCYTAWALRNKT    113
            +Y   K  YG +P         I+PD++   +E              L  V ++  G Y+AWALR KT
Sbjct:   64 GVYSDTKSYGRNP-----IDPDEFVSDEFNWDDYSDVSDELVTVWRKYGIYSAWALREKT    118

Query:  114 HQEAPWIQT-RQGEVIGI--ALMGEYF                                    137
            H E+PW+    QG+ I  I    A +  ++F
Sbjct:  119 HSESPWLDAWAQGQNIEITDAALKDFF                                    145
```

Based on this analysis, it was predicted that this protein from *N. gonorrhoeae*, and its epitopes, could be useful antigens for vaccines or diagnostics.

Example 154

A DNA sequence was identified in *N. gonorrhoeae* <SEQ ID 307> which encodes amino acid sequence <SEQ ID 308; NGS157>. Analysis of this protein sequence reveals the following:

GvH Examining signal sequence (von Heijne)
Signal Score (-7.5): -5.65
Possible cleavage site: 42
>>> Seems to have no N-terminal signal seq.

Amino Acid Composition of Predicted Mature Form: calculated from 1
ALOM: Finding transmembrane regions (Klein et al.)
count: 0 value: 3.98 threshold: 0.0

| PERIPHERAL | Likelihood = 3.98 |
|---|---|
| modified ALOM score: -1.30 | |
| Rule: cytoplasmic protein | |

*** Reasoning Step: 2
Final Results

| bacterial cytoplasm --- Certainty = | 0.291(Affirmative) < succ> |
|---|---|
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
^ **gbp_6274533 gi|6274533|gb|AAF06681.1|AF163663_6\(AF058689) Tou1
[Neisseria meningitidis]
Length = 272

Score = 546 bits (1408), Expect = e-154
Identities = 267/272 (98%), Positives = 271/272 (99%)

Query:   19 MKGMDKLRYQRDFLNIRPIFTAGEQEYLTELSDRLPLSVLTDSVRNIEEIGIDFVYSPAK     78
            MKGMDKLRYQ+DFLNIRPIFTAGEQEYLTELSDRLPLSVLTDSVRNIEEIGIDFVYS AK
Sbjct:    1 MKGMDKLRYQQDFLNIRPIFTAGEQEYLTELSDRLPLSVLTDSVRNIEEIGIDFVYSSAK     60

Query:   79 LEGNTYNQYDTQALLKLGQTAGGKLYSDAVMLINLRESYRHLLSGLDSPKPFDWLDFLKT    138
            LEGNTYNQYDTQALLKLGQTAGGKLYSDAVMLINLRESYRHLLSGLDSP+PFDWLDFLKT
Sbjct:   61 LEGNTYNQYDTQALLKLGQTAGGKLYSDAVMLINLRESYRHLLSGLDSPEPFDWLDFLKT    120

Query:  139 THSLISENLLEKGSGGVVRRDSVTISGTDYTPLSNPQSLDTELKWLLQEAPKIENPFDRA    198
            THSLISENLLEKGSGGVVRRDSVTISGTDYTPLSNPQSLDTELKWLLQEAPKIENPFDRA
Sbjct:  121 THSLISENLLEKGSGGVVRRDSVTISGTDYTPLSNPQSLDTELKWLLQEAPKIENPFDRA    180

Query:  199 VYLHNNLAYLRYFKDCNKRTARNCMTLSLMRSGFFPCVFSPDSYPAYAEAVVAYYETGDY    258
            VYLHNNLAYL+YFKDCNKRTARNCMTLSLMRSGFFPCVFSPDSYPAYAEAVVAYYETGDY
Sbjct:  181 VYLHNNLAYLQYFKDCNKRTARNCMTLSLMRSGFFPCVFSPDSYPAYAEAVVAYYETGDY    240

Query:  259 GLFKKYFISAYENTVNKYGPQPDVDIFRNFSI                              290
            GLFKKYFISAYENTVNKYGPQPDVDIFRNFS+
Sbjct:  241 GLFKKYFISAYENTVNKYGPQPDVDIFRNFSL                              272
```

A homolog was found in serogroup A *N. meningitidis* but not in serogroup B, so NGS157 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 155

A DNA sequence was identified in *N. gonorrhoeae* <SEQ ID 309> which encodes amino acid sequence <SEQ ID 310; NGS158>. Analysis of this protein sequence reveals the following:

---

GvH Examining signal sequence (von Heijne)
Signal Score (−7.5): −6.98
Possible cleavage site: 18
>>> Seems to have no N-terminal signal seq.
Amino Acid Composition of Predicted Mature Form:
calculated from 1
ALOM: Finding transmembrane regions (Klein et al.)
count: 0 value: 0.16 threshold: 0.0

---

| PERIPHERAL | Likelihood = 0.16 | modified ALOM score: −0.53
Rule: cytoplasmic protein

---

*** Reasoning Step: 2
Final Results

--- bacterial cytoplasm --- Certainty = 0.185(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

---

The protein has homology to the following sequences in the databases:

Based on this analysis, it was predicted that this protein from *N. gonorrhoeae*, and its epitopes, could be useful antigens for vaccines or diagnostics.

Example 156

A DNA sequence was identified in *N. gonorrhoeae* <SEQ ID 311> which encodes amino acid sequence <SEQ ID 312; NGS159>. Analysis of this protein sequence reveals the following:

---

GvH Examining signal sequence (von Heijne)
Signal Score (−7.5): −4.16
Possible cleavage site: 13
>>> Seems to have no N-terminal signal seq.
Amino Acid Composition of Predicted Mature Form:
calculated from 1
ALOM: Finding transmembrane regions (Klein et al.)
count: 0 value: 6.47 threshold: 0.0

---

| PERIPHERAL | Likelihood = 6.47 | modified ALOM score: −1.79
Rule: cytoplasmic protein

---

*** Reasoning Step: 2
Final Results

--- bacterial cytoplasm --- Certainty = 0.312(Affirmative) < succ>
bacterial periplasmic space --- Certainty = 0.000(Not Clear) < succ>
bacterial outer membrane --- Certainty = 0.000(Not Clear) < succ>
bacterial inner membrane --- Certainty = 0.000(Not Clear) < succ>

---

The protein has homology to the following sequences in the databases:

```
>  ^^ **gbp_15791833 gi|15791833|ref|NP_281656.1|\(NC_002163) amino-acid
ABC transporter ATP-binding protein [Campylobacter jejuni]
pir||H81391 amino-acid ABC transporter ATP-binding protein Cj0469 [imported] -
Campylobacter jejuni (strain NCTC 11168)
emb|CAB75107.1|(AL139075) amino-acid ABC transporter ATP-binding protein
[Campylobacter jejuni]
Length = 253

Score = 301 bits (772), Expect = 6e-81
Identities = 153/244 (62%), Positives = 195/244 (79%), Gaps = 2/244 (0%)

Query:    1 MALLSIRKLHKQYGSVTAIQSLDLDLEKGEVIVLLGPSGCGKSTLLRCVNGLEPHQGGSI    60
            M++L  I   L KYGS   A++ ++L+++   EV+V+LGPSGCGKSTLLRC+NGLE    G+I
Sbjct:    1 MSILKIENLQKYYGSHHALKDINLEVKAKEVVVILGPSGCGKSTLLRCINGLEEIASGNI   60

Query:   61 VMDGVGEFGKDVS-WQTARQKVGMVFQSYELFAHMTVIENILLGPVKVQNRDRAEAEAQA  119
             +D  +   KD   W   RQKVGMVFQSYELF H++V ENILLGP+KVQ R + E    +A
Sbjct:   61 YIDNE-KIDKDFKEWPRMRQKVGMVFQSYELFEHLSVEENILLGPMKVQRKKDEVLKEA  119

Query:  120 GKLLERVGLLDRKNAYPRELSGGQKQRIAIVRALCLNPEVILLDEITAALDPEMVREVLE  179
                LE+VGLL +  +AYPRELSGGQKQRIAIVR+LC+NPE++L DE+TAALDPE+VREVLE
Sbjct:  120 KIWLEKVGLLHKIHAYPRELSGGQKQRIAIVRSLCMNPELMLFDEVTAALDPEIVREVLE  179

Query:  180 VVLELAREGMSMLIVTHEMGFARKVADRIVFMDKGGIVESSDPETFFSAPKSERARQFLA  239
            V+L LA+EGM+MLIVTHEMGFA+ VAD+I+FMD G I+E +DP++FF  PKSERA++FL
Sbjct:  180 VMLNLAKEGMTMLIVTHEMGFAKAVADKIIFMDEGKIIEENDPKSFFKNPKSERAKKFLN  239

Query:  240 GMDY                                                         243
               DY
Sbjct:  240 LFDY                                                         243
```

```
>  ^^, **gbp_15794799 gi|15794799|ref|NP_284621.1|\(NC_003216)
hypothetical protein [Neisseria meningitidis Z2491]
pir||B81819 hypothetical protein NMA1914 [imported] -
Neisseria meningitidis (group A strain Z2491)
emb|CAB85135.1|(AL162757) hypothetical protein
[Neisseria meningitidis Z2491]
Length = 206

Score = 265 bits (678), Expect = 8e-70
Identities = 131/146 (89%), Positives = 138/146 (93%)

Query:   1 MTKLYAQIAKTEAQDDGTVKVWGYASSEAVDSDGEVVAAEAMKAAIPDYMKFGAVREMHG   60
           MTKLYA+IAK E QDDGTVKVWGYASSE +DSDGEV+AA AMKAAIPDYMKFGA REMHG
Sbjct:   1 MTKLYAEIAKMETQDDGTVKVWGYASSEEIDSDGEVIAAAAMKAAIPDYMKFGAGREMHG   60

Query:  61 SNAAGTAIEINVEDDGRTFFGAHIVDPVAVTKVKTGVYKGFSIGGSVTARNDLNKSQITG  120
           SNAAGTAIEINVEDDG TFFGAHI+DPV V+KVKTGVYKGFSIGGSVTAR+DLNKSQITG
Sbjct:  61 SNAAGTAIEINVEDDGITFFGAHIIDPVVVSKVKTGVYKGFSIGGSVTARDDLNKSQITG  120

Query: 121 LKLTEISLVDRPANPDAVFTCFKADK                                   146
           LKLTEISL+DRPANPDAV TCFKADK
Sbjct: 121 LKLTEISLIDRPANPDAVSTCFKADK                                   146
```

A homolog was found in serogroup A *N. meningitidis* but not in serogroup B, so NGS159 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 157

A DNA sequence was identified in *N. gonorrhoeae* <SEQ ID 313> which encodes amino acid sequence <SEQ ID 314; NGS160>. Analysis of this protein sequence reveals the following:

GvH Examining signal sequence (von Heijne)
Signal Score (−7.5): −8.3
Possible cleavage site: 33

>>> Seems to have no N-terminal signal seq.
Amino Acid Composition of Predicted Mature Form:
calculated from 1
ALOM: Finding transmembrane regions (Klein et al.)
count: 0 value: 7.85 threshold: 0.0

| PERIPHERAL | Likelihood = 7.85 |
|---|---|
| modified ALOM score: −2.07 | |
| Rule: cytoplasmic protein | |

*** Reasoning Step: 2
Final Results

| | |
|---|---|
| bacterial cytoplasm --- Certainty = | 0.407(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
>  ^^ **gbp_2126352 gi|2126352|pir||JC5218 type I site-specific
deoxyribonuclease (EC 3.1.21.3) Hsd chain S [validated] -
Pasteurella haemolytica
gb|AAC44667.1|(U46781) HSDS [Mannheimia haemolytica]
Length = 442

Score = 97.1 bits (240), Expect = 3e-19
Identities = 55/149 (36%), Positives = 81/149 (53%), Gaps = 3/149 (2%)

Query:  26 EVAEYSKNRICSDKLNEHNYVGVDNLLQNREGKKLSGYVPSEGKMTEYIVNDILIGNIRP   85
           ++ E   +I    L + NY+  DN+L N G   L+  +P+         DIL  NIR
Sbjct:  10 DIVELISEKIKIKDLKKENYISTDNMLPNFGGITLAENLPNSASCNRFAKKDILFSNIRT   69

Query:  86 YLKKIWQADCTGGTNGDVLVIRV--TDEKVNPKYLYQVLADDKFFAFNMKHAKGAKMPRG  143
           Y KK+W A+ +GG + DVLV+R   TD  +N +YL+ ++   D F  F +   A GAKMPRG
Sbjct:  70 YFKKVWLAEFSGGCSPDVLVMRSKNTDILLN-EYLFLLIRSDDFINFTVISANGAKMPRG  128

Query: 144 SKAAIMQYKIPIPPLPEQEKIVAILGKFD                                172
           K A+    IP +   Q+K +A    FD
Sbjct: 129 DKNAMKGFIFNIPSIEYQKKCIANYFAFD                                157
```

Based on this analysis, it was predicted that this protein from *N. gonorrhoeae*, and its epitopes, could be useful antigens for vaccines or diagnostics.

Example 158

A DNA sequence was identified in *N. gonorrhoeae* <SEQ ID 315> which encodes amino acid sequence <SEQ ID 316; NGS161>. Analysis of this protein sequence reveals the following:

|   |   |   |   |
|---|---|---|---|
| GvH Examining signal sequence (von Heijne) | | | |
| Signal Score (−7.5): −5.08 | | | |
| Possible cleavage site: 36 | | | |
| >>> Seems to have no N-terminal signal seq. | | | |
| Amino Acid Composition of Predicted Mature Form: | | | |
| calculated from 1 | | | |
| ALOM: Finding transmembrane regions (Klein et al.) | | | |
| count: 1 value: −1.59 threshold: 0.0 | | | |
| INTEGRAL | Likelihood = −1.59 | Transmembrane | 302-318 |
|  |  |  | (302-318) |
| PERIPHERAL | Likelihood = 3.76 | | |
| modified ALOM score: 0.82 | | | |
| Rule: cytoplasmic membrane protein | | | |
| *** Reasoning Step: 2 Final Results | | | |
| bacterial inner membrane --- Certainty = | 0.164(Affirmative) < succ> | | |
| bacterial periplasmic space --- Certainty = | 0.000(Not Clear) < succ> | | |
| bacterial outer membrane --- Certainty = | 0.000(Not Clear) < succ> | | |
| bacterial cytoplasm --- Certainty = | 0.000(Not Clear) < succ> | | |

The protein has homology to the following sequences in the databases:

```
pir||E81921 probable DNA-invertase NMA0772 [imported] -
Neisseria meningitidis (group A strain Z2491)
emb|CAB84055.1|(AL162754) putative DNA-invertase
[Neisseria meningitidis Z2491]
Length = 321

Score = 295 bits (755), Expect = 9e-79
Identities = 151/322 (46%), Positives = 216/322 (66%), Gaps = 3/322 (0%)

Query:   14 LRNAVGLDISKLTFDATAIVGNAEYSAKFDNDSKGLDQFSDRLKSLGCQNLHICMEATGN    73
            +RNAVGLDIS  TFD   I+     KF ND +G    + +   +++++CMEATGN
Sbjct:    1 MRNAVGLDISAKTFDVVTIINGETDYRKFSNDEQGCKNLKEWISAKREKDIYVCMEATGN    60

Query:   74 YYEEVADYFAQYYSVYVVNPLKISKYAESRFKRTKTDKQDAKLIAQYCRSAQESELVKRQ   133
            YYE+ AD  A+ Y V V+NPLKI  YA+ RF R K DKQDAKLIA++C++A   EL KR+
Sbjct:   61 YYEQAADCLAEEYHVSVINPLKIKAYAQKRFSRVKNDKQDAKLIAEFCQTALIEELPKRE   120

Query:  134 KPTDEQYRLSRMTAAYAQIKSECAAMKNRHHAAKDEEAAKAYAEIIKAMNEQLEVLKEKI   193
            KPT++QY L R+ +  +Q+  +  + KNR  AAKD   K + +K +  L  +K+KI
Sbjct:  121 KPTEQQYSLKRLLSLQSQLLEQQTSQKNRIKAAKDSFVQKIHEKQLKELENHLNAVKKKI   180

Query:  194 KEQTEKPN--CKEGVKRLETIPAIGRMTAAVLFHHLTSSKFETSNKPAAFAGLSPQQKES   251
              +QT K +    KE  KRLETIP++G+ TA  L   +L +S FE +  +F A+AGL+P Q   S
Sbjct:  181 -DQTIKSDKKMKELTKRLETIPSVGKTTAISLMSYLINSTFENAKQFTAYAGLNPHQNIS   239

Query:  252 GTSVRGKGKLTKFGNRKLRAVLFMPAMVAYRIRAFPDFIKRLEEKKKPKKVIIAALMRKL   311
            GTSV   K K+TK+GNR++R  LFM A+VA++   FP F  RL++ KKPK +II ALMRK+
Sbjct:  240 GTSVNKKSKMTKYGNRRIRGSLFMAALVAFKNNYFPAFTNRLKKAKKPKMLIIGALMRKI   299

Query:  312 AVIAYHVHKKGGDYDPSRYKSA                                        333
             V+A++++K    D+D +RY++A
Sbjct:  300 LVVAFNLYKTETDFDKTRYQTA                                        321
```

A homolog was found in serogroup A *N. meningitidis* but not in serogroup B, so NGS161 protein and nucleic acid are useful for distinguishing between gonococcus and serogroup B *N. meningitidis*.

Based on this analysis, it was predicted that this protein from *N. gonorrhoeae*, and its epitopes, could be useful antigens for vaccines or diagnostics.

Example 159

A DNA sequence was identified in *N. gonorrhoeae* <SEQ ID 983> which encodes amino acid sequence <SEQ ID 984; NGS162>. Analysis of this protein sequence reveals the following:

|   |   |
|---|---|
| GvH Examining signal sequence (von Heijne) | |
| Signal Score (−7.5): −0.86 | |
| Possible cleavage site: 33 | |
| >>> Seems to have no N-terminal signal seq. | |
| Amino Acid Composition of Predicted Mature Form: | |
| calculated from 1 | |
| ALOM: Finding transmembrane regions (Klein et al.) | |
| count: 0 value: 4.08 threshold: 0.0 | |
| PERIPHERAL | Likelihood = 4.08 |
| modified ALOM score: −1.32 | |
| Rule: cytoplasmic protein | |
| *** Reasoning Step: 2 Final Results | |
| bacterial cytoplasm --- Certainty = | 0.032(Affirmative) < succ> |
| bacterial periplasmic space --- Certainty = | 0.000(Not Clear) < succ> |
| bacterial outer membrane --- Certainty = | 0.000(Not Clear) < succ> |
| bacterial inner membrane --- Certainty = | 0.000(Not Clear) < succ> |

The protein has homology to the following sequences in the databases:

```
ref|NP_312507.1|(NC_002695) hypothetical protein [Escherichia coli O157:H7]
gb|AAG58749.1|AE005587_7 (AE005587) putative adhesin
[Escherichia coli O157:H7 EDL933]
dbj|BAB37903.1|(AP002566) hypothetical protein [Escherichia coli O157:H7]
Length = 1588

Score = 120 bits (302), Expect = 4e-26
Identities = 109/359 (30%), Positives = 170/359 (46%), Gaps = 65/359 (18%)

Query:  22 AVALGSSSTASGEYSYASGYNSVASGNKSYAAGYASVASAEGSVVIGDSRQVKPEADQGV   81
           + A+G   + A G+YS A G  + A G   SA G ++++  + S+ +G S      +    +
Sbjct:  93 STAVGYDAIAEGQYSSAIGSKTHAIGGASMAFGVSAISEGDRSIALGASSYSLGQYSMAL  152

Query:  82 AVGSKATVKNKAKQRVVVGSEAKVNAERGIAIGKEAKAGGKTTNTLLDGPAYYADAIAVG  141
              SKA    K  + +G  +K          IA+G   KA      T   +         +IA+G
Sbjct: 153 GRYSKAL----GKLSIAMGDSSKAEGANAIALGNATKA----TEIM---------SIALG  195

Query: 142 YQAEAGKGGAIALGKQAKATKQNGMALGVESEAAGDFSTAVGNESKAKGQGG--------  193
             A  A  K   ++ALG   + A+++N +A+G E+EAA +  +TA+GN +KAKG
Sbjct: 196 DTANASKAYSMALGASSVASEENAIAIGAETEAA-ENATAIGNNAKAKGTNSMAMGFGSL  254

Query: 194 ------VGLGNQSKAEADFAVAV--GNKAEATKE------------NSLVIGRYARANGN  233
                 + LGN S+A AD A+A+  GNKA+             N++ +G   + A G+
Sbjct: 255 ADKVNTIALGNGSQALADNAIAIGQGNKADGVDAIALGNGSQSRGLNTIALGTASNATGD  314

Query: 234 HSVSLGSRSEIKDGVSNSVAPGYGSVASENNVVSVAYKETPQSTELSYRKIVGVDDGV--  291
             S++LGS S   +G+ NSVA G  S+A  +N VSV         RKIV V +G
Sbjct: 315 KSLALGSNSS-ANGI-NSVALGADSIADLDNTVSVGNSSLK-------RKIVNVKNGAIK  365

Query: 292 -NDFDAVNVRQLKAMQGQNMAELFSVRSEVRGVAASSAALSALTPLSYDANNPTQFMVG   349
            + +DA+N  QL A+           SV   + G AA       +T  +Y+  N ++   VG
Sbjct: 366 SDSYDAINGSQLYAISD-------SVAKRLGGGAAVDVDDGTVTAPTYNLKNGSKNNVG   417

Score = 86.3 bits (212), Expect = 1e-15
Identities = 68/253 (26%), Positives = 118/253 (45%), Gaps = 39/253 (15%)

Query:  28 SSTASGEYSYASGYNSVASGNKSYAAGYASVASAEGSVVIGDSRQVKPEADQGVAVGSKA   87
           S+  +G   + G   + A   +     Y S  ++ +G V IG             G+KA
Sbjct:  38 SALVAGGMLSSFGALANAGNDNGQGVDYGSGSAGDGWVAIGK--------------GAKA   83

Query:  88 -TVKNKAKQRVVVGSEAKVNAERGIAIGKEAKAGGKTTNTLLDGPAYYADAIAVGYQAEA  146
             T   N +     VG +A    +   AIG + A G  +            +A G   A +
Sbjct:  84 NTFMNTSGSSTAVGYDAIAEGQYSSAIGSKTHAIGGAS-------------MAFGVSAIS  130

Query: 147 GKGGAIALGKQAKATKQNGMALGVESEAAGDFSTAVGNESKAKGQGGVGLGNQSKAEADF  206
               +IALG  +  +   Q  MALG  S+A  G   S A+G+   SKA+G     + LGN +KA
Sbjct: 131 EGDRSIALGASSYSLGQYSMALGRYSKALGKLSIAMGDSSKAEGANAIALGNATKATEIM  190

Query: 207 AVAVGNKAEATKENSLVIGRYARANGNHSVSLGSRSEIKDGV-----------SNSVAPG  255
             ++A+G+ A A+K  S+ +G   + A+   +++++G+ +E  +              +NS+A G
Sbjct: 191 SIALGDTANASKAYSMALGASSVASEENAIAIGAETEAAENATAIGNNAKAKGTNSMAMG  250

Query: 256 YGSVASENNVVSV                                                 268
            +GS+A + N +++
Sbjct: 251 FGSLADKVNTIAL                                                263
```

Based on this analysis, it was predicted that this protein from *N. gonorrhoeae*, and its epitopes, could be useful antigens for vaccines or diagnostics.

Example 160

Further open reading frames were identified in gonococcus <SEQ IDs 317/318 to 8621/8622>. These polypeptide and nucleotide sequences are useful for studying gonococcus, for diagnostic purposes, as antibiotic targets, and as vaccine antigens.

It will be understood that the invention has been described by way of example only and modifications may be made whilst remaining within the scope and spirit of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08642050B2). An electronic copy of the "Sequence Listing" will also be available from the USPTO upon request and payment of the fee set forth in 37 CFR 1.19(b)(3).

The invention claimed is:

1. An isolated protein comprising an amino acid sequence selected from the group consisting of (i) a fragment of SEQ ID NO: 4, wherein the fragment of SEQ ID NO: 4 includes 10 or more consecutive amino acids from SEQ ID NO: 4, and (ii) a sequence having 95% or greater sequence identity to SEQ ID NO: 4.

2. The isolated protein of claim 1, wherein the amino acid sequence is (i).

3. The isolated protein of claim 1, wherein the amino acid sequence is (ii).

4. A composition comprising an isolated protein according to any one of claims 1-3.

5. The composition of claim 4, further comprising an adjuvant.

6. The composition of claim 4, further comprising a pharmaceutically acceptable carrier.

7. The composition of claim 5, wherein the adjuvant is an aluminum salt.

8. A method of inducing an immune response to *N. gonorrhoeae* in a subject comprising administering to the subject the composition according to claim 1.

* * * * *